US012319657B1

(12) United States Patent
Bichler et al.

(10) Patent No.: US 12,319,657 B1
(45) Date of Patent: *Jun. 3, 2025

(54) SOLID STATE CRYSTALLINE FORMS OF A SELECTIVE POTASSIUM CHANNEL MODULATOR

(71) Applicant: Xenon Pharmaceuticals Inc., Burnaby (CA)

(72) Inventors: Paul Robert Bichler, Burnaby (CA); Jean-Jacques Alexandre Cadieux, Burnaby (CA); Matthew David Tandy, Burnaby (CA); Gregory N. Beatch, Burnaby (CA)

(73) Assignee: Xenon Pharmaceuticals Inc., Burnaby (CA)

( * ) Notice: Subject to any disclaimer, the term of this patent is extended or adjusted under 35 U.S.C. 154(b) by 0 days.

This patent is subject to a terminal disclaimer.

(21) Appl. No.: 19/094,370

(22) Filed: Mar. 28, 2025

Related U.S. Application Data

(63) Continuation of application No. 18/540,582, filed on Dec. 14, 2023, which is a continuation of application No. 17/368,766, filed on Jul. 6, 2021, now abandoned, which is a continuation of application No. 17/069,386, filed on Oct. 13, 2020, now Pat. No. 11,091,441.

(60) Provisional application No. 62/913,574, filed on Oct. 10, 2019.

(51) Int. Cl.
   *C07D 217/04* (2006.01)

(52) U.S. Cl.
   CPC ........ *C07D 217/04* (2013.01); *C07B 2200/13* (2013.01)

(58) Field of Classification Search
   CPC .................... C07D 217/04; C07B 2200/13
   See application file for complete search history.

(56) References Cited

U.S. PATENT DOCUMENTS

| | | |
|---|---|---|
| 3,639,385 A | 2/1972 | Weaver et al. |
| 3,845,770 A | 11/1974 | Theeuwes et al. |
| 4,181,803 A | 1/1980 | Morita et al. |
| 4,326,525 A | 4/1982 | Swanson et al. |
| 4,554,281 A | 11/1985 | vonBebenburg et al. |
| 4,668,684 A | 5/1987 | Tibes et al. |
| 4,778,799 A | 10/1988 | Tibes et al. |
| 4,923,858 A | 5/1990 | Engel et al. |
| 4,923,974 A | 5/1990 | Ueda et al. |
| 5,032,591 A | 7/1991 | Evans et al. |
| 5,162,346 A | 11/1992 | Lobisch et al. |
| 5,234,947 A | 8/1993 | Cherksey |
| 5,262,419 A | 11/1993 | Aberg et al. |
| 5,284,861 A | 2/1994 | Lobisch et al. |
| 5,384,330 A | 1/1995 | Dieter et al. |
| 5,428,039 A | 6/1995 | Cohen |
| 5,502,058 A | 3/1996 | Mayer et al. |
| 5,643,921 A | 7/1997 | Grover |
| 5,679,706 A | 10/1997 | D'Alonzo et al. |
| 5,760,007 A | 6/1998 | Shank |
| 5,800,385 A | 9/1998 | Demopulos et al. |
| 5,849,789 A | 12/1998 | Rostock et al. |
| 5,852,053 A | 12/1998 | Rostock et al. |
| 5,858,017 A | 1/1999 | Demopulos et al. |
| 5,860,950 A | 1/1999 | Demopulos et al. |
| 5,914,425 A | 6/1999 | Meisel et al. |
| 5,925,634 A | 7/1999 | Olney |
| 6,117,900 A | 9/2000 | Rundfeldt et al. |
| 6,211,171 B1 | 4/2001 | Sawynok et al. |
| 6,218,411 B1 | 7/2001 | Koga |
| 6,281,211 B1 | 8/2001 | Cai et al. |
| 6,265,417 B1 | 12/2001 | Carroll |
| 6,326,385 B1 | 12/2001 | Wickenden et al. |
| 6,348,486 B1 | 2/2002 | Argentieri et al. |
| 6,395,736 B1 | 5/2002 | Parks et al. |
| 6,451,857 B1 | 9/2002 | Hurtt et al. |
| 6,469,042 B1 | 10/2002 | Hewawasam et al. |
| 6,472,165 B1 | 10/2002 | Rundfeldt et al. |
| 6,495,550 B2 | 12/2002 | McNaughton-Smith et al. |
| 6,500,455 B1 | 12/2002 | Frantsits |
| 6,537,991 B1 | 3/2003 | Shaw et al. |
| 6,538,004 B2 | 3/2003 | Drizin |
| 6,538,151 B1 | 3/2003 | Meisel et al. |
| RE38,115 E | 5/2003 | Smith et al. |
| 6,589,986 B2 | 7/2003 | Bowlby et al. |
| 6,593,335 B1 | 7/2003 | Carroll |
| 6,642,209 B1 | 11/2003 | Fukunuga |

(Continued)

FOREIGN PATENT DOCUMENTS

| | | |
|---|---|---|
| CA | 2542434 A1 | 5/2005 |
| DE | 3337593 A1 | 5/1984 |

(Continued)

OTHER PUBLICATIONS

International Search Report and Written Opinion, mailed Dec. 23, 2021 for International Application No. PCT/US2020/055129.
International Preliminary Report on Patentability, mailed Apr. 21, 2022 for International Application No. PCT/US2020/055129.
[No Author Listed], Drugs for Treatment of Partial Onset Seizures: Full Extrapolation of Efficacy from Adults to Pediatric Patients 2 Years of Age and Older. FDA Federal Register. Sep. 2019; 84(173):46955-56.
[No Author Listed], Powder rheology. Anton Paar GmbH. 2024. Accessed at: https://wiki.anton-paar.com/ca-en/powder-rheology/ [last accessed: May 16, 2024].
[No Author Listed], Depression Assessment Instruments. American Psychological Association. Aug. 2019, last updated Jan. 2023. Accessed at: https://www.apa.org/depression-guideline/assessment. Last accessed: Jun. 20, 2024. 19 pages.

(Continued)

*Primary Examiner* — Timothy R Rozof
(74) *Attorney, Agent, or Firm* — Wolf, Greenfield & Sacks, P.C.

(57) ABSTRACT

The present disclosure provides solid state forms of a selective potassium channel modulator and pharmaceutical compositions comprising the solid state crystalline forms and pharmaceutically acceptable excipients, and methods for preparing and using the solid state forms and the pharmaceutical compositions thereof.

30 Claims, 29 Drawing Sheets

(56) References Cited

U.S. PATENT DOCUMENTS

| | | | |
|---|---|---|---|
| 6,645,521 | B2 | 11/2003 | Cassel |
| 6,737,422 | B2 | 5/2004 | McNaughton-Smith et al. |
| 7,045,551 | B2 | 5/2006 | Wu et al. |
| 7,160,684 | B2 | 1/2007 | Argentieri et al. |
| 7,250,511 | B2 | 7/2007 | Bavetsias |
| 7,309,713 | B2 | 12/2007 | Rundfeldt et al. |
| 7,419,981 | B2 | 9/2008 | Field et al. |
| 8,236,861 | B2 | 8/2012 | Anttila |
| 8,293,911 | B2 | 10/2012 | Vernier et al. |
| 8,993,593 | B2 | 3/2015 | Vernier et al. |
| 9,315,461 | B2 | 4/2016 | Kandula |
| 2002/0013349 | A1 | 1/2002 | Wickenden |
| 2002/0015730 | A1 | 2/2002 | Hoffmann et al. |
| 2002/0183395 | A1 | 12/2002 | Argentieri |
| 2004/0198724 | A1 | 10/2004 | McNaughton-Smith et al. |
| 2005/0070570 | A1 | 3/2005 | Garcia et al. |
| 2005/0089473 | A1 | 4/2005 | Black et al. |
| 2005/0089559 | A1 | 4/2005 | Szelenyi |
| 2005/0090547 | A1 | 4/2005 | Szelenyi |
| 2005/0202394 | A1 | 9/2005 | Dobson |
| 2005/0277579 | A1 | 12/2005 | Krishnan et al. |
| 2007/0066612 | A1 | 3/2007 | Khanzhin et al. |
| 2008/0139610 | A1* | 6/2008 | Vernier .............. A61P 43/00 514/307 |
| 2009/0018154 | A1 | 1/2009 | Kao et al. |
| 2009/0318507 | A2 | 12/2009 | Rundfeldt et al. |
| 2010/0256145 | A1 | 10/2010 | Bak-Jensen et al. |
| 2010/0297181 | A1 | 11/2010 | Hanada et al. |
| 2011/0003850 | A1 | 1/2011 | Vernier et al. |
| 2012/0046330 | A1 | 2/2012 | Alargova et al. |
| 2013/0131030 | A1 | 5/2013 | Belanoff et al. |
| 2014/0148478 | A1 | 5/2014 | Kühnert et al. |
| 2018/0000749 | A1 | 1/2018 | Mollard et al. |
| 2018/0177781 | A1 | 6/2018 | Wu |

FOREIGN PATENT DOCUMENTS

| | | |
|---|---|---|
| DE | 3604575 A1 | 8/1986 |
| EP | 1334972 A1 | 8/2003 |
| EP | 1407768 A2 | 4/2004 |
| EP | 1813285 A1 | 8/2007 |
| EP | 4074696 A1 | 10/2022 |
| JP | 2000-014350 A | 5/2000 |
| WO | WO 00/55137 A1 | 9/2000 |
| WO | WO 00/59487 A2 | 10/2000 |
| WO | WO 00/59508 A1 | 10/2000 |
| WO | WO 01/001970 A2 | 1/2001 |
| WO | WO 01/01972 A2 | 1/2001 |
| WO | WO 01/009612 A1 | 2/2001 |
| WO | WO 01/22953 A1 | 4/2001 |
| WO | WO 02/080898 A2 | 10/2002 |
| WO | WO 03/020706 A1 | 3/2003 |
| WO | WO 03/097586 A1 | 11/2003 |
| WO | WO 03/016454 A1 | 12/2003 |
| WO | WO 04/082677 A1 | 3/2004 |
| WO | WO 04/058739 A1 | 7/2004 |
| WO | WO 04/080950 A1 | 9/2004 |
| WO | WO 2004/096767 A1 | 11/2004 |
| WO | WO 04/105705 A1 | 12/2004 |
| WO | WO 05/087754 A1 | 3/2005 |
| WO | WO 2005/039576 A1 | 5/2005 |
| WO | WO 05/048975 A1 | 6/2005 |
| WO | WO 2005/058420 A1 | 6/2005 |
| WO | WO 05/100349 A1 | 10/2005 |
| WO | WO 06/029623 A1 | 3/2006 |
| WO | WO 06/092143 A1 | 9/2006 |
| WO | WO 2008/024398 A2 | 2/2008 |
| WO | WO 08/066900 A1 | 6/2008 |
| WO | WO 2009/015667 A1 | 2/2009 |
| WO | WO 2009/074594 A1 | 6/2009 |
| WO | WO 2011/089126 A2 | 7/2011 |
| WO | WO 2011/090923 A1 | 7/2011 |
| WO | WO 2011/094186 A1 | 8/2011 |
| WO | WO 2013/067591 A1 | 5/2013 |
| WO | WO 2013/130573 A1 | 9/2013 |
| WO | WO 2019/074908 A1 | 4/2019 |
| WO | WO 2019/161877 A1 | 8/2019 |

OTHER PUBLICATIONS

[No Author Listed], Guidance for Industry Food-Effect Bioavailability and Fed Bioequivalence Studies. U.S. Department of Health and Human Services, Food and Drug Administration, Center for Drug Evaluation and Research (CDER). Dec. 2002. 12 pages.

[No Author Listed], Guidance for Industry: Assessment of Abuse Potential of Drugs. Food and Drug Administration. (Jan. 2017) Accessed from <https://www.fda.gov/regulatory-information/search-fda-guidance-documents/assessment-abuse-potential-drugs>. 37 pages.

[No Author Listed], Guidance for Industry: Environmental Assessment of Human Drug and Biologics Applications. Food and Drug Administration. (Jul. 1998) Accessed from <https://www.fda.gov/media/70809/download>. 42 pages.

[No Author Listed], Guidance for Industry: Major Depressive Disorder: Developing Drugs for Treatment. Food and Drug Administration. (Jun. 2018) Accessed from <www.fda.gov/media/113988/download>. 11 pages.

[No Author Listed], Guideline on the Environmental Risk Assessment of Medicinal Products for Human Use. European Medicines Agency. (Jun. 1, 2006) Accessed from <https://www.ema.europa.eu/en/documents/scientific-guideline/guideline-environmental-risk-assessment-medicinal-products-human-use-first-version_en.pdf>. 12 pages.

[No Author Listed], NCT03796962: A Study to Evaluate XEN1101 as Adjunctive Therapy in Focal Epilepsy. First Submitted Jan. 8, 2019. Last Update Posted Nov. 1, 2021. 12 pages. Accessed May 17, 2022 from <https://clinicaltrials.gov/ct2/show/NCT03796962>.

[No Author Listed], Potiga (ezogabine) Tablets Full Prescribing Information. United States Food and Drug Administration. Last revised Jun. 2011. 27 pages.

[No Author Listed], Potiga (ezogabine) Tablets, CV. FDA Approved Labeling (2012) NDA 022345/S-001. 21 pages.

[No Author Listed], Submission PM-2011-04248-3-1. Extract from the Clinical Evaluation Report for Retigabine. Australian Government Department of Health. (Jul. 9, 2012) pp. 1-89.

[No Author Listed], Xenon Pharmaceuticals Announces Initiation of XEN1101 Phase 1 Clinical Trial. Xenon Pharmaceuticals Inc. (Oct. 17, 2017) Accessed from <https://investor.xenon-pharma.com/news-releases/news-release-details/xenon-pharmaceuticals-announces-initiation-xen1101-phase-1>. 4 pages.

Aaberg et al., Seizures, syndromes, and etiologies in childhood epilepsy: The International League Against Epilepsy 1981, 1989, and 2017 classifications used in a population-based cohort. Epilepsia. Nov. 2017;58(11):1880-1891. doi: 10.1111/epi.13913. Epub Sep. 26, 2017.

Ambrosino et al., Activation of Kv7 Potassium Channels Inhibits Intracellular Ca2+ Increases Triggered by TRPV1-Mediated Pain-Inducing Stimuli in F11 Immortalized Sensory Neurons. Int J Mol Sci. Sep. 4, 2019;20(18):4322. doi: 10.3390/ijms20184322.

Andreev et al., Analgesic Activity of Acid-Sensing Ion Channel 3 (ASIC3) Inhibitors: Sea Anemones Peptides Ugr9-1 and APETx2 versus Low Molecular Weight Compounds. Mar Drugs. (Dec. 12, 2018) 16(12):500. doi: 10.3390/md16120500.

Armand et al., Effects of retigabine (D-23129) on different patterns of epileptiform activity induced by 4-aminopyridine in rat entorhinal cortex hippocampal slices. Naunyn-Schmiedebera's Arch Pharmacol. Jan. 1999;359(1):33-9. doi: 10.1007/pl00005320.

Armijo et al., Ion channels and epilepsy. Curr Pharm Des. 2005;11(15):1975-2003. doi: 10.2174/1381612054021006.

Arzimanoglou et al., Pediatric Epilepsy Academic Consortium for Extrapolation (PEACE). A Review of the New Antiepileptic Drugs for Focal-Onset Seizures in Pediatrics: Role of Extrapolation. Paediatr Drugs. Jun. 2018;20(3):249-264. doi: 10.1007/s40272-018-0286-0.

Ashizawa, Iyakuhin Kessho no Bunshi Jotai ni Kansuru Bussei Hyoka (12) Shio Kesshokei no Saitekika to Kesshoka Gijutsu

(56) References Cited

OTHER PUBLICATIONS

[Physico-Chemical Studies on the Molecular Details of Drug Crystals]. Pharm Tech Japan. 2002;18(10): 1629 -1644.

Aycardi et al., A First-in-Human Study to Assess the Safety, Tolerability, Pharmacokinetics and Preliminary Pharmacodynamics of a Novel Small Molecule KV7.2/7.3 Positive Allosteric Modulator (XEN1101) in Healthy Subjects. Presented at the 72nd Annual Meeting of the American Epilepsy Society, New Orleans, LA (Nov. 30-Dec. 4, 2018). 1 page. Poster.

Barhanin et al., KvLQT1 and ISK (minK) proteins associate to form the IKs cardiac potassium current. Nature. Nov. 7, 1996;384(6604):78-80. doi: 10.1038/384078a0.

Barker et al., Clinical evaluation of conduction time measurements in central motor pathways using magnetic stimulation of human brain. Lancet. Jun. 7, 1986;1(8493):1325-6. doi: 10.1016/s0140-6736(86)91243-2.

Barrese et al., KCNQ-Encoded Potassium Channels as Therapeutic Targets. Annu Rev Pharmacol Toxicol. Jan. 6, 2018:58:625-648. doi: 10.1146/annurev-pharmtox-010617-052912. Epub Oct. 6, 2017.

Barry et al., The American Urological Association symptom index for benign prostatic hyperplasia. The Measurement Committee of the American Urological Association. J Urol. Nov. 1992;148(5):1549-57; discussion 1564. doi: 10.1016/s0022-5347(17)36966-5.

Beatch et al., A Phase 1 Study Utilizing Transcranial Magnetic Stimulation to Assess the Pharmacodynamic Effects of a Novel Potassium Channel Opener (XEN1101) on Human Cortical Excitability. Presented at the 72nd Annual Meeting of the American Epilepsy Society, New Orleans, LA (Dec. 3, 2018). 1 page. Poster.

Beck et al. An inventory for measuring clinical anxiety: psychometric properties. J Consult Clin Psychol. (1988) 56(6):893-897.

Beck et al., Comparison of Beck Depression Inventories -IA and -II in psychiatric outpatients. J Pers Assess. Dec. 1996;67(3):588-97. doi: 10.1207/s15327752jpa6703_13.

Beeby et al., The synthesis and properties of 2:7-Disubstituted 1:2:3:4-tetrahydroisoquinolines. J Chem Soc. 1949; 385:1799-1803.

Berge et al., Pharmaceutical salts. J Pharm Sci. Jan. 1977;66(1):1-19. doi: 10.1002/jps.2600660104.

Berton et al., Essential role of BDNF in the mesolimbic dopamine pathway in social defeat stress. Science. (Feb. 10, 2006) 311(5762):864-868. doi: 10.1126/science.1120972.

Bharmal et al., Validation of an abbreviated Treatment Satisfaction Questionnaire for Medication (TSQM-9) among patients on antihypertensive medications. Health Qual Life Outcomes. Apr. 27, 2009;7:36. doi: 10.1186/1477-7525-7-36.

Bi et al., Visceral hyperalgesia induced by forebrain-specific suppression of native Kv7/KCNQ/M-current in mice. Mol Pain. (Oct. 26, 2011) 7:84. doi: 10.1186/1744-8069-7-84.

Bialer et al, Progress report on new antiepileptic drugs: A summary of the Thirteenth Eilat Conference on New Antiepileptic Drugs and Devices (Eilat XIII). Epilepsia. (Feb. 2017) 58(2):181-221. doi: 10.1111/epi.13634.

Bialer et al., Progress report on new antiepileptic drugs: A summary of the Fourteenth Eilat Conference on New Antiepileptic Drugs and Devices (Eilat XIV). I. Drugs in preclinical and early clinical development. Epilepsia. (Oct. 2018) 59(10):1811-1841. doi: 10.1111/epi.14557.

Bialer et al., Progress report on new antiepileptic drugs: A summary of the Fourteenth Eilat Conference on New Antiepileptic Drugs and Devices (Eilat XIV). II. Drugs in more advanced clinical development. Epilepsia. 2018;59(10):1842-1866. doi:10.1111/epi.14555.

Bialer et al., Progress report on new antiepileptic drugs: a summary of the fourth Eilat conference (Eilat Iv). Epilepsy Res. Mar. 1999;34(1):1-41. doi: 10.1016/s0920- 1211(98)00108-9.

Bialer, Progress report on new antiepileptic drugs: a summary of the Seventh Eilat Conference (Eilat VII). Epilepsy Res. Sep.-Oct. 2004;61(1-3):1-48. doi: 10.1016/j.eplepsyres.2004.07.010.

Bialer, Progress report on new antiepileptic drugs: a summary of the Sixth Eilat Conference (Eilat VI). Epilepsy Res. Sep. 2002;51(1-2):31-71. doi: 10.1016/s0920-1211(02)00106-7.

Biervert et al., A potassium channel mutation in neonatal human epilepsy. Science. Jan. 16, 1998;279(5349):403-6. doi: 10.1126/science.279.5349.403.

Blackburn-Munro et al., The anticonvulsant retigabine attenuates nociceptive behaviours in rat models of persistent and neuropathic pain. Eur J Pharmacol. (Jan. 24, 2003) 460(2-3):109-116. doi: 10.1016/s0014-2999(02)02924-2.

Boylan et al. Depression but not seizure frequency predicts quality of life in treatment-resistant epilepsy. Neurology. Jan. 27, 2004;62(2):258-61. doi: 10.1212/01.wnl.0000103282.62353.85.

Braatz et al., Particle Size and Shape Control in Crystallization Processes. 2002; 307-327. Accessed at: https://folk.ntnu.no/skoge/prost/proceedings/cpc6-jan2002/braatz.pdf.

Brodie et al., Antiepileptic drug therapy: does mechanism of action matter? Epilepsy Behav. Aug. 2011;21(4):331-41. doi: 10.1016/j.yebeh.2011.05.025. Epub Jul. 16, 2011.

Brown et al., Muscarinic suppression of a novel voltage-sensitive K+ current in a vertebrate neurone. Nature. Feb. 14, 1980;283(5748):673-6. doi: 10.1038/283673a0.

Brown, Ion Channels. Plenum Press, Eds. 1988. pp. 55-94.

Byrn et al., Pharmaceutical solids: a strategic approach to regulatory considerations. Pharm Res. (Jul. 1995) 12(7):945-954. doi: 10.1023/a:1016241927429.

Cains, P.W., Classical Methods of Preparation of Polymorphs and Alternative Solid Forms. In: Polymorphism in Pharmaceutical Solids. Chapter 4. Second Edition. Brittain, Ed. (2009) pp. 76-138.

Caira, M., Crystalline Polymorphism of Organic Compounds. Top Curr Chem. (Feb. 26, 1999) 198;163-208. doi: 10.1007/3-540-69178-2_5.

Can et al., The mouse forced swim test. J Vis Exp. (Jan. 29, 2012) 59:e3638. 5 pages. doi: 10.3791/3638.

Carlisle et al., Estimation of total hepatic blood flow by duplex ultrasound. Gut. (Jan. 1992) 33(1):92-97. doi: 10.1136/gut.33.1.92.

Casaca-Carreira et al., Transependymal Cerebrospinal Fluid Flow: Opportunity for Drug Delivery? Mol Neurobiol. (Apr. 2018) 55(4):2780-2788. doi: 10.1007/s12035-017-0501-y. Epub Apr. 28, 2017.

Charlier et al., A pore mutation in a novel KQT-like potassium channel gene in an idiopathic epilepsy family. Nat Genet. Jan. 1998;18(1):53-5. doi: 10.1038/ng0198-53.

Chaudhury et al., Rapid regulation of depression-related behaviours by control of midbrain dopamine neurons. Nature. (Jan. 24, 2013) 493(7433):532-536. doi: 10.1038/nature11713.

Chaves et al., Seizure aggravation in idiopathic generalized epilepsies. Epilepsia. 2005:46 Suppl 9:133-9. doi: 10.1111/j.1528-1167.2005.00325.x.

Chen et al., Treatment Outcomes in Patients With Newly Diagnosed Epilepsy Treated With Established and New Antiepileptic Drugs: A 30-Year Longitudinal Cohort Study. JAMA Neurol. Mar. 1, 2018;75(3):279-286. doi: 10.1001/jamaneurol.2017.3949.

Chiesa et al., A systematic review of neurobiological and clinical features of mindfulness meditations. Psychol Med. (Aug. 2010) 40(8):1239-1252. doi: 10.1017/S0033291709991747.

Chourbaji et al., Learned helplessness: validity and reliability of depressive-like states in mice. Brain Res Protoc. Dec. 2005;16(1-3):70-8. doi: 10.1016/j.brainresprot.2005.09.002. Epub Nov. 23, 2005.

Chung et al., Segmental spinal nerve ligation model of neuropathic pain. Methods Mol Med. (2004) 99:35-45. doi: 10.1385/1-59259-770-X:035.

Cooper et al., Colocalization and coassembly of two human brain M-type potassium ctiannel subunits that are mutated in epilepsy. Proc Natl Acad Sci USA. Apr. 25, 2000;97(9):4914-9. doi: 10.1073/pnas.090092797.

Cramer et al., Development and cross-cultural translations of a 31-item quality of life in epilepsy inventory. Epilepsia. Jan. 1998;39(1):81-8. doi: 10.1111/j.1528-1157.1998.tb01278.x.

Cramer et al., Development of the Quality of Life in Epilepsy Inventory for Adolescents: the QOLIE-AD-48. Epilepsia. Aug. 1999;40(8):1114-21. doi: 10.1111/j.1528-1157.1999.tb00828.x.

Cryan et al., The tail suspension test as a model for assessing antidepressant activity: review of pharmacological and genetic studies in mice. Neurosci Biobehav Rev. 2005;29(4-5):571-625. doi: 10.1016/j.neubiorev.2005.03.009.

(56) References Cited

OTHER PUBLICATIONS

Darmani et al., Effects of the Selective α5-GABAAR Antagonist S44819 on Excitability in the Human Brain: A TMS-EMG and TMS-EEG Phase I Study. J Neurosci. Dec. 7, 2016;36(49):12312-12320. doi: 10.1523/JNEUROSCI.1689-16.2016.

Delmas et al., Pathways modulating neural KCNQ/M (Kv7) potassium channels. Nat Rev Neurosci. Nov. 2005;6(11):850-62. doi: 10.1038/nrn1785.

Di Nicola et al., Reduced hedonic capacity in euthymic bipolar subjects: A trait-like feature? J Affect Disord. May 2013;147(1-3):446-50. doi: 10.1016/j.jad.2012.10.004. Epub Nov. 2, 2012.

Dickenson et al., Neurobiology of neuropathic pain: mode of action of anticonvulsants. Eur J Pain. 2002:6 Suppl A:51-60. doi: 10.1053/eujp.2001.0323.

Dost et al., The anticonvulsant retigabine potently suppresses epileptiform discharges in the low Ca ++ and low Mg++ model in the hippocampal slice preparation. Epilepsy Res. Jan. 2000;38(1):53-66. doi: 10.1016/s0920-1211(99)00065-0.

Dost et al., The anti-hyperalgesic activity of retigabine is mediated by KCNQ potassium channel activation. Naunyn Schmiedebergs Arch Pharmacol. (Apr. 2004) 369(4):382-390. doi: 10.1007/s00210-004-0881-1.

Dulawa et al., Recent advances in animal models of chronic antidepressant effects: the novelty-induced hypophagia test. Neurosci Biobehav Rev. 2005;29(4-5):771-83. doi: 10.1016/j.neubiorev.2005.03.017.

Duru et al., The clinical relevance of changes in the Montgomery-Asberg Depression Rating Scale using the minimum clinically important difference approach. Curr Med Res Opin. (2008) 24(5):1329-1335.

Elger et al. Diagnosing and treating depression in epilepsy. Seizure. Jan. 2017:44:184-193. doi: 10.1016/j.seizure.2016.10.018. Epub Oct. 31, 2016.

Elger et al., Modern management of epilepsy: a practical approach. Epilepsy Behav. (May 2008) 12(4):501-539. doi: 10.1016/j.yebeh.2008.01.003. Erratum in: Epilepsy Behav. (Oct. 2008) 13(3):575.

Emery, Flow Properties of Selected Pharmaceutical Powders. University of Saskatchewan Graduate Thesis. Sep. 2008. 107 pages.

Enna et al., The GABA Receptors. In: Enna and Möhler, The GABA Receptors, Third Edition. (2007) Humana Press Inc, Totowa, NJ. 26 pages.

Faber, R.C., Section 57. In: Landis on Mechanics of Patent Claim Drafting. Third edition. Mar. 1990. p. 184.

Fang et al., Chapter II. Crystalline form and crystal habit. In: Pharmacy. China Pharmaceutical Science and Technology Press. 3rd edition, 1st printing. Mar. 2016. pp. 46-48.

Fava, M., Weight gain and antidepressants. J Clin Psychiatry. (2000) 61 Suppl 11:37-41.

Ferber et al., Concentration-effect modelling based on change from baseline to assess the prolonging effect of drugs on QTc together with an estimate of the circadian time course. J Clin Pharmacol. Dec. 2014;54(12):1400-6. doi: 10.1002/jcph.347. Epub Jun. 27, 2014.

Fisher et al., Operational classification of seizure types by the International League Against Epilepsy: Position Paper of the ILAE Commission for Classification and Terminology. Epilepsia. Apr. 2017;58(4):522-530. doi: 10.1111/epi.13670. Epub Mar. 8, 2017.

Fodor et al., Attempts to find new spasmolytics. VIII. The synthesis of 6,7-diethoxy-3-alkyl- and 6,7-diethyl-3-phenyl-isoquinolines. J Chem Soc. 1949; 1681-1682.

Foster, Deuterium isotope effects in the metabolism of drugs and xenobiotics: implications for drug design. Advances in Drug Research. Jan. 1985; 14: 1-40.

French et al., Effects of marketed antiepileptic drugs and placebo in the human photosensitivity screening protocol. Neurotherapeutics. Apr. 2014;11(2):412-8. doi: 10.1007/s13311-013-0243-0.

French et al., Perampanel for tonic-clonic seizures in idiopathic generalized epilepsy A randomized trial. Neurology. Sep. 15, 2015;85(11):950-7. doi: 10.1212/WNL.0000000000001930.

Friedel et al., Flupirtine: a review of its analgesic properties, and therapeutic efficacy in pain states. Drugs. Apr. 1993;45(4):548-69. doi: 10.2165/00003495-199345040-00007.

Friedman et al., Enhancing depression mechanisms in midbrain dopamine neurons achieves homeostatic resilience. Science. (Apr. 18, 2014) 344(6181):313-319. doi: 10.1126/science.1249240.

Friedman et al., Identifying depression in epilepsy in a busy clinical setting is enhanced with systematic screening. Seizure. Jul. 2009;18(6):429-33. doi: 10.1016/j.seizure.2009.03.001. Epub May 5, 2009.

Friedman et al., KCNQ channel openers reverse depressive symptoms via an active resilience mechanism. Nat Commun. (May 24, 2016) 24;7:11671. 7 pages. doi: 10.1038/ncomms11671.

Ganesan et al., Flowability and handling characteristics of bulk solids and powders—a review with implications for DDGS. Biosystems Engineering. Dec. 2008; 101(4): 425-435.

Garnett et al., Operational Characteristics of Linear concentration-QT models for assessing QTc interval in the thorough QT and Phase I clinical studies. Clin Pharmacol Ther. Aug. 2016;100(2):170-8. doi: 10.1002/cpt.361. Epub May 9, 2016.

GBD 2016 Epilepsy Collaborators, Global, regional, and national burden of epilepsy, 1990-2016: a systematic analysis for the Global Burden of Disease Study 2016. Lancet Neurol. Apr. 2019; 18(4):357-375. doi: 10.1016/S1474-4422(18)30454-X. Epub Feb. 14, 2019.

Ghareeb et al., HPLC-ESI-MS/MS Profiling of Polyphenolics of a Leaf Extract from Alpinia zerumbet (Zingiberaceae) and Its Anti-Inflammatory, Anti-Nociceptive, and Antipyretic Activities In Vivo. Molecules. (Dec. 7, 2018) 23(12):3238. doi: 10.3390/molecules23123238.

Gilliam et al., Rapid detection of major depression in epilepsy: a multicentre study. Lancet Neurol. May 2006;5(5):399-405. doi: 10.1016/S1474-4422(06)70415-X.

Goldberg, Y.P., XEN1101, a Novel Modulator of Kv7.2/3 for the Treatment of Epilepsy. Presented at the Epilepsy Foundation Pipeline Conference, San Francisco, CA (Feb. 22-23, 2018) 10 pages.

Goldberg, Y.P., XEN1101: A Novel, Next-Generation KCNQ2 Modulator for the Treatment of Epilepsy. Presented at the EILAT XIV Meeting, Madrid, Spain (May 15, 2018) 32 pages.

Gong et al., Targeting Cre recombinase to specific neuron populations with bacterial artificial chromosome constructs. J Neurosci. (Sep. 12, 2007) 27(37):9817-9823. doi: 10.1523/JNEUROSCI.2707-07.2007.

Greenberg et al., The economic burden of adults with major depressive disorder in the United States (2005 and 2010). J Clin Psychiatry. (Feb. 2015) 76(2):155-162. doi: 10.4088/JCP.14m09298.

Greene et al., Modulation of Kv7 channels and excitability in the brain. Cell Mol Life Sci. Feb. 2017;74(3):495-508. doi: 10.1007/s00018-016-2359-y. Epub Sep. 19, 2016.

Greenfield, L.J., Molecular mechanisms of antiseizure drug activity at GABAA receptors. Seizure. (2013) 22(8):589-600. doi: 10.1016/j.seizure.2013.04.015.

Groppa et al., A practical guide to diagnostic transcranial magnetic stimulation: report of an IFCN committee. Clin Neurophysiol. Author manuscript; available in PMC Jun. 2, 2016 Published in final edited form as: Clin Neurophysiol. May 2012; 123(5): 858-882. Published online Feb. 19, 2012. doi: 10.1016/j.clinph.2012.01.010.

Groseclose et al., An investigation into retigabine (ezogabine) associated dyspigmentation in rat eyes by MALDI imaging mass spectrometry. Chem Res Toxicol. Feb. 18, 2019;32(2):294-303. doi: 10.1021/acs.chemrestox.8b00313. Epub Jan. 31, 2019.

Grupp et al., Protection against hypoxia-reoxygenation in the absence of poly (ADP-ribose) synthetase in isolated working hearts. J Mol Cell Cardiol. Jan. 1999;31(1):297-303. doi: 10.1006/jmcc.1998.0864.

Gunthorpe et al., The mechanism of action of retigabine (ezogabine), a first-in-class K+ channel opener for the treatment of epilepsy. Epilepsia. Mar. 2012;53(3):412-24. doi: 10.1111/j.1528-1167.2011.03365.x. Epub Jan. 5, 2012.

Guy et al., BRIEF-SR: Behavior rating inventory of executive function—self-report version: Professional manual: Psychological Assessment Resources; 2004. Overview only.

(56) References Cited

OTHER PUBLICATIONS

Guy et al., Test Review: Behavior Rating Inventory of Executive Function-Self-Report version. Journal of Psychoeducational Assessment. 2006;24(4):394-8.
Hamilton, M., A rating scale for depression. J Neurol Neurosurg Psychiatry. (Feb. 1960) 23(1):56-62. doi: 10.1136/jnnp.23.1.56.
Hamilton, Rating depressive patients. J Clin Psychiatry. Dec. 1980;41(12 Pt 2):21-4.
Hansen et al., The KCNQ channel opener retigabine inhibits the activity of mesencephalic dopaminergic systems of the rat. J Pharmacol Exp Ther. (Sep. 2006) 318(3):1006-1019. doi: 10.1124/jpet.106.106757.
Harmer et al., How do antidepressants work? New perspectives for refining future treatment approaches. Lancet Psychiatry. (May 2017) 4(5):409-418. doi: 10.1016/S2215-0366(17)30015-9.
Harris et al., Retigabine (ezogabine) as add-on therapy for partial-onset seizures: an update for clinicians. Ther Adv Chronic Dis. (Nov. 2011) 2(6):371-376. doi: 10.1177/2040622311421542.
He et al., Multicomplex-based pharmacophore-guided 3D-QSAR studies of N-substituted 2'-(aminoaryl)benzothiazoles as Aurora-A inhibitors. Chem Biol Drug Des. Jun. 2012;79(6):960-71. doi: 10.1111/j.1747-0285.2012.01366.x. Epub Apr. 17, 2012.
Heimbach et al., Case studies for practical food effect assessments across BCS/BDDCS class compounds using in silico, in vitro, and preclinical in vivo data. AAPS J. (Jan. 2013) 15(1):143-158. doi: 10.1208/s12248-012-9419-5.
Hetka et al., Retigabine strongly reduces repetitive firing in rat entorhinal cortex. Eur J Pharmacol. (Dec. 15, 1999) 386(2-3):165-171. doi: 10.1016/s0014-2999(99)00786-4.
Hiller et al., Retigabine N-glucuronidation and its potential role in enterohepatic circulation. Drug Metab Dispos. May 1999;27(5):605-12.
Hino et al., Drug Interaction, 34. Drug Interactions of food and medicine. J Okayama Med Assoc. (Dec. 1, 2015) 127(3):245-249. doi: 10.4044/joma.127.245.
Hirano et al., Kv7.2-7.5 voltage-gated potassium channel (KCNQ2-5) opener, retigabine, reduces capsaicin-induced visceral pain in mice. Neurosci Lett. (Feb. 14, 2007) 413(2):159-162. doi: 10.1016/j.neulet.2006.11.043.
Hirtz et al., How common are the "common" neurologic disorders? Neurology. (Jan. 30, 2007) 68(5):326-337. doi: 10.1212/01.wnl.0000252807.38124.a3.
Hitiris et al., Mortality in epilepsy. Epilepsy Behav. (May 2007) 10(3):363-376. doi: 10.1016/j.yebeh.2007.01.005.
Hunt et al., The molecular dynamics of pain control. Nat Rev Neurosci. Feb. 2001;2(2):83-91. doi: 10.1038/35053509.
Ilmoniemi et al., Methodology for combined TMS and EEG. Brain Topogr. Jan. 2010;22(4):233-48. doi: 10.1007/s10548-009-0123-4. Epub Dec. 10, 2009.
Ilmoniemi et al., Neuronal responses to magnetic stimulation reveal cortical reactivity and connectivity. Neuroreport. Nov. 10, 1997;8(16):3537-40. doi: 10.1097/00001756-199711100-00024.
Jentsch, Neuronal KCNQ potassium channels; physiology and role in disease. Nat Rev Neurosci. Oct. 2000;1(1):21-30. doi: 10.1038/35036198.
Jiang et al., X-ray structure of a voltage-dependent K+ channel. Nature. May 1, 2003;423(6935):33-41. doi: 10.1038/nature01580.
Johannessen et al., Management of focal-onset seizures: an update on drug treatment. Drugs. (2006) 66(13):1701-1725. doi: 10.2165/00003495-200666130-00004.
Johnson et al., Psychometric Properties of the General Anxiety Disorder 7-Item (GAD-7) Scale in a Heterogeneous Psychiatric Sample. Front Psychol. Aug. 6, 2019:10:1713. doi: 10.3389/fpsyg.2019.01713. eCollection 2019.
Kahkonen et al., Transcranial magnetic stimulation: applications for neuropsychopharmacology. J Psychopharmacol. Jun. 2004;18(2):257-61. doi: 10.1177/0269881104042631.
Kaleem et al., An experimental investigation on accuracy of Hausner Ratio and Carr Index of powders in additive manufacturing processes. Metal Powder Report. Dec. 2021; 76(1): S50-S54.

Kanner et al. Depression and epilepsy: epidemiologic and neurobiologic perspectives that may explain their high comorbid occurrence. Epilepsy Behav. Jun. 2012;24(2):156-68. doi: 10.1016/j.yebeh.2012.01.007.
Kasteleijn-Nolst Trenité et al., Kv7 potassium channel activation with ICA-105665 reduces photoparoxysmal EEG responses in patients with epilepsy. Epilepsia. Aug. 2013;54(8):1437-43. doi: 10.1111/epi.12224. Epub May 20, 2013.
Keel et al., A safety screening questionnaire for transcranial magnetic stimulation. Clin Neurophys. Apr. 2001;112(4):720. doi: 10.1016/s1388-2457(00)00518-6.
Keren et al., Reward Processing in Depression: A Conceptual and Meta-Analytic Review Across fMRI and EEG Studies. Am J Psychiatry. Nov. 1, 2018;175(11):1111-1120. doi: 10.1176/appi.ajp.2018.17101124. Epub Jun. 20, 2018.
Kharkovets et al., Mice with altered KCNQ4 KT channels implicate sensory outer hair cells in human progressive deafness. Embo J. Feb. 8, 2006;25(3):642-52. doi: 10.1038/sj.emboj.7600951. Epub Jan. 26, 2006.
Kibbe, Handbook of Pharmaceutical Excipients (Pharmaceutical Press, London) (2000).
Krishnan et al., Molecular adaptations underlying susceptibility and resistance to social defeat in brain reward regions. Cell. (Oct. 19, 2007) 131(2):391-404. doi: 10.1016/j.cell.2007.09.018.
Kubisch et al., KCNQ4, a novel potassium channel expressed in sensory outer hair cells, is mutated in dominant deafness. Cell. Feb. 5, 1999;96(3):437-46. doi: 10.1016/s0092-8674(00)80556-5.
Kuo et al., Inhibition of Na(+) current by diphenhydramine and other diphenyl compounds: molecular determinants of selective binding to the inactivated channels. Mol Pharmacol. Jan. 2000;57(1):135-43.
Kupferberg, H., Antiepileptic drug development program: a cooperative effort of government and industry. Epilepsia. (1989) 30 Suppl 1:S51-S56; discussion S64-S68. doi: 10.1111/j.1528-1157.1989.tb05815.x.
Kushner et al., Pharmacological uses and perspectives of heavy water and deuterated compounds. Can J Physiol Pharmacol. Feb. 1999;77(2):79-88.
Kuzma et al., Progress in the development of ultra-long-acting local anesthetics. Reg Anesth. Nov.-Dec. 1997;22(6):543-51.
Kwan et al., Early identification of refractory epilepsy. N Engl J Med. Feb. 3, 2000;342(5):314-9. doi: 10.1056/NEJM200002033420503.
Lamas et al., Effects of a cognition-enhancer, linopirdine (DuP 996), on M-type potassium currents (IK(M)) and some other voltage- and ligand-gated membrane currents in rat sympathetic neurons. Eur J Neurosci. Mar. 1997;9(3):605-16. doi: 10.1111/j.1460-9568.1997.tb01637.x.
Lang et al., Effects of lacosamide and carbamazepine on human motor cortex excitability: a double-blind, placebo-controlled transcranial magnetic stimulation study. Seizure. (Nov. 2013) 22(9):726-730. doi: 10.1016/j.seizure.2013.05.010.
Lange et al., Refinement of the binding site and mode of action of the anticonvulsant Retigabine on KCNQ K+ channels. Mol Pharmacol. Feb. 2009;75(2):272-80. doi: 10.1124/mol.108.052282. Epub Nov. 17, 2008.
Large et al., The spectrum of anticonvulsant efficacy of retigabine (ezogabine) in animal models: implications for clinical use. Epilepsia. Mar. 2012;53(3):425-36. doi: 10.1111/j.1528-1167.2011.03364.x. Epub Jan. 5, 2012.
Lee et al., Structure of the KvAP voltage-dependent K+ channel and its dependence on the lipid membrane. Proc Natl Acad Sci USA. Oct. 25, 2005;102(43):15441-6. doi: 10.1073/pnas.0507651102. Epub Oct. 13, 2005.
Legoix et al., Characterizing powders in order to determine their flow behavior in a mixer: From small scale observations to macroscopic in-mixer rheology for powders of various flowabilities. Powder Technology. 2017; 322: 314-331. 10.1016/j.powtec.2017.07.075. hal-01617227.
Levenson et al., Statistical Review and Evaluation—Antiepileptic Drugs and Suicidality. United States Food and Drug Administration. May 2008.45 pages.

(56) References Cited

OTHER PUBLICATIONS

Long et al., Crystal structure of a mammalian voltage-dependent Shaker family K+ channel. Science. Aug. 5, 2005;309(5736):897-903. doi: 10.1126/science.1116269. Epub Jul. 7, 2005.
Lukyanetz et al., Selective blockade of N-type calcium channels by levetiracetam. Epilepsia. (Jan. 2002) 43(1):9-18. doi: 10.1046/j.1528-1157.2002.24501.x.
Luscher et al., The GABAergic deficit hypothesis of major depressive disorder. Mol Psychiatry. (2011) 16(4):383-406. doi: 10.1038/mp.2010.120. Author Manuscript, 41 pages.
Maguire, J., Neuroactive Steroids and GABAergic Involvement in the Neuroendocrine Dysfunction Associated With Major Depressive Disorder and Postpartum Depression. Front Cell Neurosci. (Mar. 8, 2019) 13:83. doi: 10.3389/fncel.2019.00083.
Main et al., Modulation of KCNQ2/3 potassium channels by the novel anticonvulsant retigabine. Mol Pharmacol. Aug. 2000;58(2):253-62. doi: 10.1124/mol.58.2.253.
Maki et al., The relationship between peripheral and early cortical activation induced by transcranial magnetic stimulation. Neurosci Lett. Jun. 30, 2010;478(1):24-8. doi: 10.1016/j.neulet.2010.04.059. Epub Apr. 29, 2010.
Mandal, Chapter 2 Preformulation and Product Development in: Manufacturing of Halal Pharmaceuticals. First Edition. Jan. 2015; pp. 2-1 to 2-21. IIUM Press, eds.
Marrion, Control of M-current. Annu Rev Physiol. 1997:59:483-504. doi: 10.1146/annurev.physiol.59.1.483.
Marvanova, M., Pharmacokinetic characteristics of antiepileptic drugs (AEDs). Ment Health Clin. (Mar. 8, 2016) 6(1):8-20. doi: 10.9740/mhc.2015.01.008.
Marzo et al., Pharmacokinetics and pharmacodynamics of safinamide, a neuroprotectant with antiparkinsonian and anticonvulsant activity. Pharmacol Res. (Jul. 2004) 50(1):77-85. doi: 10.1016/j.phrs.2003.12.004.
Massimini et al., Breakdown of cortical effective connectivity during sleep. Science. Sep. 30, 2005;309(5744):2228-32. doi: 10.1126/science.1117256.
Matysina et al., Surface Structure, Roughness, Energy and Texture of Crystals. J Phys Chem Solids. 1992; 53(1): 167-174.
Montgomery et al., A new depression scale designed to be sensitive to change. Br J Psychiatry. (Apr. 1979) 134:382-389. doi: 10.1192/bjp.134.4.382.
Nair et al., A simple practice guide for dose conversion between animals and human. J Basic Clin Pharm. (Mar. 2016) 7(2):27-31. doi: 10.4103/0976-0105.177703.
Nakonezny et al., Evaluation of anhedonia with the Snaith-Hamilton Pleasure Scale (SHAPS) in adult outpatients with major depressive disorder. J Psychiatr Res. (Jun. 2015) 65:124-130. doi: 10.1016/j.jpsychires.2015.03.010. Author Manuscript, 16 pages.
Nestler et al., The mesolimbic dopamine reward circuit in depression. Biol Psychiatry. (Jun. 15, 2006) 59(12):1151-1159. doi: 10.1016/j.biopsych.2005.09.018.
Nicholas et al., Trends in antiepileptic drug utilisation in UK primary care 1993-2008: cohort study using the General Practice Research Database. Seizure. Jul. 2012;21(6):466-70. doi: 10.1016/j.seizure.2012.04.014. Epub May 19, 2012.
Nielsen et al., Intracranial self-stimulation and sucrose intake differ as hedonic measures following chronic mild stress: interstrain and interindividual differences. Behav Brain Res. Jan. 2000;107(1-2):21-33. doi: 10.1016/s0166-4328(99)00110-2.
Nikouline et al., The role of the coil click in TMS assessed with simultaneous EEG. Clin Neurophysiol. Aug. 1999;110(8):1325-8. doi: 10.1016/s1388-2457(99)00070-x.
Ossemann et al., Effect of a single dose of retigabine in cortical excitability parameters: A cross-over, double-blind placebo-controlled TMS study. Epilepsy Res. (Oct. 2016) 126:78-82. doi: 10.1016/j.eplepsyres.2016.06.004.
Otto et al., Effects of the Anticonvulsant Retigabine on Cultured Cortical Neurons: Changes in Electroresponsive Properties and Synaptic Transmission. Mol Pharmacol. Apr. 2002;61(4):921-7. doi: 10.1124/mol.61.4.921.
Parcej et al., Structural characterisation of neuronal voltage-sensitive K+ channels heterologously expressed in Pichia pastoris. J Mol Biol. Oct. 10, 2003;333(1):103-16. doi: 10.1016/j.jmb.2003.07.009.
Passmore et al., KCNQ/M currents in sensory neurons: significance for pain therapy. J Neurosci. Aug. 6, 2003;23(18):7227-36. doi: 10.1523/JNEUROSCI.23-18-07227.2003.
Patani et al., Bioisosterism: A Rational Approach in Drug Design. Chem Rev. Dec. 19, 1996;96(8):3147-3176. doi: 10.1021/cr950066q.
Pavao-de-Souza et al., Acetic acid- and phenyl-p-benzoquinone-induced overt pain-like behavior depends on spinal activation of MAP kinases, PI(3)K and microglia in mice. Pharmacol Biochem Behav. (May 2012) 101(3):320-328. doi: 10.1016/j.pbb.2012.01.018.
Pelizza et al., Anhedonia in schizophrenia and major depression: state or trait? Ann Gen Psychiatry. Oct. 8, 2009;8:22. doi: 10.1186/1744-859X-8-22.
Pithavala et al., Evaluation of the effect of food on the pharmacokinetics of axitinib in healthy volunteers. Cancer Chemother Pharmacol. (Jul. 2012) 70(1):103-112. doi: 10.1007/s00280-012-1888-9.
Podczeck et al., The influence of particle size and shape on the angle of internal friction and the flow factor of unlubricated and lubricated powders. International Journal of Pharmaceutics. Nov. 29, 1996; 144(2): 187-194.
Porter et al., Retigabine. Neurotherapeutics. Jan. 2007;4(1):149-54. doi: 10.1016/j.nurt.2006.11.012.
Posner et al., The Columbia-Suicide Severity Rating Scale: initial validity and internal consistency findings from three multisite studies with adolescents and adults. Am J Psychiatry. Dec. 2011;168(12):1266-77. doi: 10.1176/appi.ajp.2011.10111704.
Premoli et al., Lamotrigine and levetiracetam exert a similar modulation of TMS-evoked EEG potentials. Epilepsia. (Jan. 2017) 58(1):42-50. doi: 10.1111/epi.13599.
Premoli et al., The impact of GABAergic drugs on TMS-induced brain oscillations in human motor cortex. Neuroimage. Dec. 2017:163:1-12. doi: 10.1016/j.neuroimage.2017.09.023. Epub Sep. 14, 2017.
Premoli et al., TMS-EEG signatures of GABAergic neurotransmission in the human cortex. J Neurosci. Apr. 16, 2014;34(16):5603-12. doi: 10.1523/JNEUROSCI.5089-13.2014.
Premoli, I., A First-in-Human Phase I Study to Assess the Pharmacodynamic Profile of a Novel Potassium Channel Opener (XEN1101) on Human Cortical Excitability with TMS-EEG and TMS-EMG. Presented at the 13th European Congress on Epileptology. King's College London Institute of Psychiatry, Psychology and Neuroscience. (Aug. 29, 2018) 15 pages.
Prescott et al., Pigmentary abnormalities (discoloration) associated with ezogabine/retigabine treatment: nonclinical aspects (Poster 2.324). Presented at the 68th Annual Meeting of the American Epilepsy Society (AES), Seattle, Washington, U.S.A., Dec. 5-9, 2014.
Reich et al., Design and synthesis of novel 6,7-imidazotetrahydroquinoline inhibitors of thymidylate synthase using iterative protein crystal structure analysis. J Med Chem. Mar. 6, 1992;35(5):847-58. doi: 10.1021/jm00083a007.
Reis et al., Contribution of transcranial magnetic stimulation to the understanding of cortical mechanisms involved in motor control. J Physiol. Jan. 15, 2008;586(2):325-51. doi: 10.1113/jphysiol.2007.144824. Epub Nov. 1, 2007.
Rizvi et al., Assessing anhedonia in depression: Potentials and pitfalls. Neurosci Biobehav Rev. (Jun. 2016) 65:21-35. doi: 10.1016/j.neubiorev.2016.03.004.
Rogasch et al., Assessing cortical network properties using TMS-EEG. Hum Brain Mapp. Jul. 2013;34(7):1652-69. doi: 10.1002/hbm.22016. Epub Feb. 29, 2012.
Rogawski et al., New molecular targets for antiepileptic drugs: alpha(2)delta, SV2A, and K(v)7/KCNQ/M potassium channels. Curr Neurol Neurosci Rep. Jul. 2008;8(4):345-52. doi: 10.1007/s11910-008-0053-7.
Rogawski et al., The neurobiology of antiepileptic drugs. Nat Rev Neurosci. Jul. 2004;5(7):553-64. doi: 10.1038/nrn1430.

(56) References Cited

OTHER PUBLICATIONS

Rogawski, KCNQ2/KCNQ3 K+ channels and the molecular pathogenesis of epilepsy: implications for therapy. Trends Neurosci. Sep. 2000;23(9):393-8. doi: 10.1016/s0166-2236(00)01629-5.

Rossi et al., The Safety of TMS Consensus Group. Safety, ethical considerations, and application guidelines for the use of transcranial magnetic stimulation in clinical practice and research. Clin Neurophysiol. Author manuscript; available in PMC Jan. 18, 2012. Published in final edited form as: Clin Neurophysiol. Dec. 2009; 120(12): 2008-2039. Published online Oct. 14, 2009. doi: 10.1016/j.clinph.2009.08.016.

Rostock et al., D-23129: a new anticonvulsant with a broad spectrum activity in animal models of epileptic seizures. Epilepsy Res. Apr. 1996;23(3):211-23. doi: 10.1016/0920-1211(95)00101-8.

Rundfeldt et al., Multiple actions of the new anticonvulsant D-23129 on voltagegated inward currents and GABA-induced currents in cultured neuronal cells (abstract). Naunyn-Schmiedeberg's Arch Pharmacol. 1995; 351 (Suppl):R160.

Rundfeldt, Characterization of the K+ channel opening effect of the anticonvulsant retigabine in PC12 cells. Epilepsy Res. Jun. 1999;35(2):99-107. doi: 10.1016/s0920-1211(98)00131-4.

Rundfeldt, The new anticonvulsant retigabine (D-23129) acts as an opener of K+ channels in neuronal cells. Eur J Pharmacol. Oct. 8, 1997;336(2-3):243-9. doi: 10.1016/s0014-2999(97)01249-1.

Rush et al., Acute and longer-term outcomes in depressed outpatients requiring one or several treatment steps: a STAR*D report. Am J Psychiatry. (Nov. 2006) 163(11):1905-1917. doi: 10.1176/ajp.2006.163.11.1905.

Rush et al., Sequenced treatment alternatives to relieve depression (STAR*D): rationale and design. Control Clin Trials. (Feb. 2004) 25(1):119-142. doi: 10.1016/s0197-2456(03)00112-0.

Sanguinetti et al., Coassembly of K(V)LQT1 and minK (IsK) proteins to form cardiac I(Ks) potassium channel. Nature. Nov. 7, 1996;384(6604):80-3. doi: 10.1038/384080a0.

Schroeder et al., KCNQ5, a novel potassium channel broadly expressed in brain, mediates M-type currents J Biol Chem. Aug. 4, 2000;275(31):24089-95. doi: 10.1074/jbc.M003245200.

Schroeder et al., Moderate loss of function of cyclic-AMP-modulated KCNQ2/KCNQ3 K+ channels causes epilepsy. Nature. Dec. 17, 1998;396(6712):687-90. doi: 10.1038/25367.

Scott et al., Anxiety and depressive disorders in people with epilepsy: A meta-analysis. Epilepsia. Jun. 2017;58(6):973-982. doi: 10.1111/epi.13769. Epub May 3, 2017.

Shah et al., A concise summary of powder processing methodologies for flow enhancement. Heliyon. May 24, 2023;9(6):e16498. doi: 10.1016/j.heliyon.2023.e16498. eCollection Jun. 2023.

Shah et al., Influence of particle properties on powder bulk behaviour and processability. Int J Pharm. Feb. 25, 2017;518(1-2):138-154. doi: 10.1016/j.ijpharm.2016.12.045. Epub Dec. 23, 2016.

Shankman et al., The different facets of anhedonia and their associations with different psychopathologies. Chapter 1 in: Anhedonia: A Comprehensive Handbook vol. I: Conceptual Issues and Neurobiological Advances. Published online. American Psychological Association. Springer Science+Business Media Dordrecht, eds. 2014:3-22. DOI 10.1007/978-94-017-8591-4_1.

Shieh et al., Potassium channels: molecular defects, diseases, and therapeutic opportunities. Pharmacol Rev. Dec. 2000;52(4):557-94.

Singh et al., A novel potassium channel gene, KCNQ2, is mutated in an inherited epilepsy of newborns. Nat Genet. Jan. 1998;18(1):25-9. doi: 10.1038/ng0198-25.

Snaith et al., A scale for the assessment of hedonic tone the Snaith-Hamilton Pleasure Scale. Br J Psychiatry. (Jul. 1995) 167(1):99-103. doi: 10.1192/bjp.167.1.99.

Soffin et al., The prescription opioid crisis: role of the anaesthesiologist in reducing opioid use and misuse. Br J Anaesth. Jun. 2019;122(6):e198-e208. doi: 10.1016/j.bja.2018.11.019. Epub Dec. 28, 2018.

Sotty et al., Antipsychotic-like effect of retigabine [N-(2-Amino-4-(fluorobenzylamino)- phenyl)carbamic acid ester], a KCNQ potassium channel opener, via modulation of mesolimbic dopaminergic neurotransmission. J Pharmacol Exp Ther. (Mar. 2009) 328(3):951-962. doi: 10.1124/jpet.108.146944.

Sourbron et al., Pharmacological Analysis of the Anti-epileptic Mechanisms of Fenfluramine in scn1a Mutant Zebrafish. Front Pharmacol. Apr. 6, 2017;8:191. doi: 10.3389/fphar.2017.00191. eCollection 2017.

Spitzer et al., A brief measure for assessing generalized anxiety disorder: the GAD-7. Arch Intern Med. May 22, 2006;166(10):1092-7. doi: 10.1001/archinte.166.10.1092.

Stewart et al., Development and testing of the Migraine Disability Assessment (MIDAS) Questionnaire to assess headache-related disability. Neurology. 2001;56(6 Suppl 1):S20-8. doi: 10.1212/wnl.56.suppl_1.s20.

Suhag et al., Factors Influencing Food Powder Flowability. Powders. 2024; 3: 65-76. https://doi.org/10.3390/powders3010006.

Suzuki et al., Neuropathic pain: nerves bursting with excitement. NeuroReport. Aug. 21, 2000;11(12):R17-21. doi: 10.1097/00001756-200008210-00001.

Tan et al., Effects of the KCNQ channel opener ezogabine on functional connectivity of the ventral striatum and clinical symptoms in patients with major depressive disorder. Mol Psychiatry. (Nov. 1, 2018) 25(6):1323-1333. doi: 10.1038/s41380-018-0283-2.

Taniguchi et al., A resource of Cre driver lines for genetic targeting of GABAergic neurons in cerebral cortex. Neuron. (Sep. 22, 2011) 71(6):995-1013. doi: 10.1016/j.neuron.2011.07.026.

Tatulian et al., Activation of expressed KCNQ potassium currents and native neuronal M-type potassium currents by the anti-convulsant drug retigabine. J Neurosci. Aug. 1, 2001;21(15):5535-45. doi: 10.1523/JNEUROSCI.21-15-05535.2001.

Tatulian et al., Effect of the KCNQ potassium channel opener retigabine on single KCNQ2/3 channels expressed in CHO cells. J Physiol. May 15, 2003;549(Pt 1):57-63. doi: 10.1113/jphysiol.2003.039842. Epub Apr. 17, 2003.

Tober et al., D-23129: a potent anticonvulsant in the amygdala kindling model of complex partial seizures. Eur J Pharmacol. May 15, 1996;303(3):163-9. doi: 10.1016/0014-2999(96)00073-8.

Touboul et al., A Comparative evaluation of the effects of Propafenone and lidocaine on early ventricular arrhythmias after acute myocardial infarction. Eur Heart J. Nov. 1988;9(11):1188-93. doi: 10.1093/oxfordjournals.eurheartj.a062428.

Treven et al., The anticonvulsant retigabine is a subtype selective modulator of GABAA receptors. Epilepsia. (2015) 56(4):647-657. doi: 10.1111/epi.12950.

Tung, Industrial Perspectives of Pharmaceutical Crystallization. Org Process Res Dev. 2013; 17(3): 445-454. https://doi.org/10.1021/op3002323.

Tung, The development of deuterium-containing drugs. Innovations in Pharmaceutical Technology. Mar. 2010; 32(32):24-28.

Tye et al., Dopamine neurons modulate neural encoding and expression of depression-related behaviour. Nature. (Jan. 24, 2013) 493(7433):537-541. doi: 10.1038/nature11740. Author Manuscript, 19 pages.

Verrotti et al., Photosensitivity: epidemiology, genetics, clinical manifestations, assessment, and management. Epileptic Disord. Dec. 2012;14(4):349-62. doi: 10.1684/epd.2012.0539.

Vippagunta et al., Crystalline solids. Adv Drug Deliv Rev. May 16, 2001;48(1):3-26. doi: 10.1016/s0169-409x(01)00097-7.

Virtanen et al., Instrumentation for the measurement of electric brain responses to transcranial magnetic stimulation. Med Biol Eng Comput. May 1999;37(3):322-6. doi: 10.1007/BF02513307.

Von Bebenburg et al., Substituierte Polyaminopyridine. Chemiker-Zeitung. 1979; 103:387-399. (German language article attached.).

Vrieze et al., Reduced reward learning predicts outcome in major depressive disorder. Biol Psychiatry. (Apr. 1, 2013) 73(7):639-645. doi: 10.1016/j.biopsych.2012.10.014. Author Manuscript, 17 pages.

Wang et al., KCNQ2 and KCNQ3 potassium channel subunits: molecular correlates of the M-channel. Science. Dec. 4, 1998;282(5395):1890-3. doi: 10.1126/science.282.5395.1890.

Wang et al., Positional cloning of a novel potassium channel gene: KVLQT1 mutations cause cardiac arrhythmias. Nat Genet. Jan. 1996;12(1):17-23. doi: 10.1038/ng0196-17.

(56) References Cited

OTHER PUBLICATIONS

Watanbe et al., Disruption of the epilepsy KCNQ2 gene results in neural hyperexcitability. J Neurochem. Jul. 2000;75(1):28-33. doi: 10.1046/j.1471-4159.2000.0750028.x.

Welling, P.G., Effects of food on drug absorption. Annu Rev Nutr. (1996) 16:383-415. doi: 10.1146/annurev.nu.16.070196.002123.

Werhahn et al. A randomized, double-blind comparison of antiepileptic drug treatment in the elderly with new-onset focal epilepsy. Epilepsia. (Mar. 2015) 56(3):450-459. doi: 10.1111/epi.12926.

West, Solid State Chemistry and Its Applications. John Wiley & Sons, New York, eds. 1988. pp. 358 and 365.

Wickenden et al., KCNQ potassium channels: drug targets for the treatment of epilepsy and pain. Exp Opin Thera Patents. 2004; 14(4): 457-469.

Wickenden et al., Retigabine, a novel anti-convulsant, enhances activation of KCNQ2/Q3 potassium channels. Mol Pharmacol. Sep. 2000;58(3):591-600. doi: 10.1124/mol.58.3.591.

Wolf (ed.), Burger's Medicinal Chemistry and Drug Discovery, 5th Edition vol. 1: Principles and Practice, John Wiley & Sons, New York, DD. 975-977 (1995).

Wood et al., Voltage-gated sodium channels and pain pathways. J Neurobiol. Oct. 2004;61(1):55-71. doi: 10.1002/neu.20094.

Wu et al., Discovery of (S,E)-3-(2-fluorophenyl)-N-(1-(3-(pyridin-3-yloxy)phenyl)ethyl)-acrylamide as a potent and efficacious KCNQ2 (Kv7.2) opener for the treatment of neuropathic pain. Bioorg Med Chem Lett. (Nov. 15, 2013) 23(22):6188-6191. doi: 10.1016/j.bmcl.2013.08.092.

Wu et al., Regulatory perspectives of Type II prod rug development and time-dependent toxicity management: nonclinical Pharm/Tox analysis and the role of comparative toxicology. Toxicology. Jul. 1, 2007;236(1-2):1-6. doi: 10.1016/j.tox.2007.04.005. Epub Apr. 21, 2007.

Wuttke, The new anticonvulsant retigabine favors voltage-dependent opening of the Kv7.2 (KCNQ2) channel by binding to its activation gate. Mol Pharmacol. Apr. 2005;67(4):1009-17. doi: 10.1124/mol.104.010793. Epub Jan. 20, 2005.

Yu et al., Prediction of Bulk Powder Flow Performance Using Comprehensive Particle Size and Particle Shape Distributions. J Pharm Sci. Jan. 2011;100(1):284-93. doi: 10.1002/jps.22254. Epub Jun. 22, 2010.

Yu et al., What is the "typical" particle shape of active pharmaceutical ingredients? Powder Technology. May 15, 2017; 313: 1-8. https://doi.org/10.1016/j.powtec.2017.02.043.

Zani et al., Sodium channels are required during in vivo sodium chloride hyperosmolarity to stimulate increase in intestinal endothelial nitric oxide production. Am J Physiol Heart Circ Physiol. Jan. 2005;288(1):H89-95. doi: 10.1152/ajpheart.00644.2004. Epub Aug. 26, 2004.

Ziemann et al., Effects of antiepileptic drugs on motor cortex excitability in humans: a transcranial magnetic stimulation study. Ann Neurol. Sep. 1996;40(3):367-78. doi: 10.1002/ana.410400306.

Ziemann et al., TMS and drugs revisited 2014. Clin Neurophysiol. (Oct. 2015) 126(10):1847-1868. doi: 10.1016/j.clinph.2014.08.028.

Ziemann, TMS and drugs. Clin Neurophysiol. Aug. 2004;115(8):1717-29. doi: 10.1016/j.clinph.2004.03.006.

\* cited by examiner

SOLID STATE CRYSTALLINE FORMS OF A SELECTIVE POTASSIUM CHANNEL MODULATOR

RELATED APPLICATIONS

This application is a continuation of and claims priority under 35 U.S.C. § 120 to U.S. patent application U.S. Ser. No. 18/540,582, filed Dec. 14, 2023, which is a continuation of and claims priority under 35 U.S.C. § 120 to U.S. patent application U.S. Ser. No. 17/368,766, filed Jul. 6, 2021, which is a continuation of and claims priority under 35 U.S.C. § 120 to U.S. patent application U.S. Ser. No. 17/069,386, filed Oct. 13, 2020, which claims priority under 35 U.S.C. § 119 (e) to U.S. Provisional Application, U.S. Ser. No. 62/913,574, filed on Oct. 10, 2019, each of which is incorporated herein by reference.

1. FIELD OF THE DISCLOSURE

The present disclosure is directed to solid state crystalline forms of a selective potassium channel modulator and pharmaceutical compositions comprising the solid state forms and pharmaceutically acceptable excipients, and processes for preparing the solid state forms and the pharmaceutical compositions. These solid state crystalline forms and their pharmaceutical compositions are useful in the treatment of seizure disorders in mammals, particularly humans.

2. BACKGROUND

Epilepsy is a common neurological disorder, with a worldwide estimated prevalence of 0.7% of the population (50 million people) (see Hirtz, D. et al., Neurology. (2007), 68:326-337). It is characterized by abnormal electrical activities in the brain leading to seizures. Patients with epilepsy have an increased mortality risk compared with the general population due primarily to the etiology of the disease. However, in patients with uncontrolled epilepsy, the greatest seizure-related risk of mortality is due to sudden unexpected death in epilepsy (SUDEP) (see, Hitiris, N. et al., Epilepsy and Behavior (2007), 10:363-376. Patients who participate in clinical trials of investigational antiepileptic drugs (AEDs) generally have had epilepsy for more than 10 years and have failed multiple AED therapies.

N-[4-(6-Fluoro-3,4-dihydro-1H-isoquinolin-2-yl)-2,6-dimethylphenyl]-3,3-dimethylbutanamide (herein referred to as "Compound A") is a small molecule currently being developed for the treatment of seizure disorders. Compound A and its use as a voltage-gated potassium channel modulator is disclosed in U.S. Pat. Nos. 8,293,911 and 8,993,593, the disclosures of which are hereby incorporated by reference in their entireties.

Polymorphism, the occurrence of different solid state crystalline forms, of the same molecule, is a property of some molecules and molecular complexes. A single molecule may give rise to a variety of polymorphs having distinct crystal structures and physical properties such as melting point, which can be measured using a range of techniques such as differential scanning calorimetry (DSC) or thermogravimetric analysis (TG), X-ray diffraction (XRPD or SCRXD), infrared absorption fingerprint (FT-IR), and solid state NMR spectrum (SS-NMR). One or more of these techniques may be used to distinguish between different polymorphic forms of a molecule.

Discovering new solid state crystalline forms of a pharmaceutical product may yield materials having desirable processing properties, such as ease of handling, ease of processing, storage stability, ease of purification or as desirable intermediate crystal forms that facilitate conversion to other polymorphic forms. New solid state crystalline forms of a pharmaceutically useful compound can also provide an opportunity to improve the performance characteristics of a pharmaceutical product. It enlarges the repertoire of materials that a formulation scientist has available for formulation optimization, for example by providing a product with different properties, e.g., a different crystal habit, higher crystallinity or polymorphic stability which may offer better processing or handling characteristics, improved dissolution profile, or improved shelf-life (chemical/physical stability).

Accordingly, there is a need to understand and develop the solid state crystalline forms of Compound A, particularly when used in therapy, such as in the treatment of seizure disorders.

3. SUMMARY

The present disclosure is generally directed to solid state forms of Compound A, particularly solid state crystalline forms, methods for their preparation, pharmaceutical compositions containing them and methods of using these solid state forms and their pharmaceutical compositions.

Accordingly, in one embodiment, the present disclosure is directed to a crystalline form of Compound A.

In another embodiment, the present disclosure is directed to a crystalline form of Compound A referred to herein as Compound A Form 1.

In another embodiment, the present disclosure is directed to a crystalline form of Compound A referred to herein as Compound A Form 2.

In another embodiment, the present disclosure is directed to a crystalline form of Compound A referred to herein as Compound A Form 3.

In another embodiment, the present disclosure is directed to a crystalline form of Compound A referred to herein as Compound A Form 4.

In another embodiment, the present disclosure is directed to a crystalline form of Compound A referred to herein as Compound A Form 5.

In another embodiment, the present disclosure is directed to a crystalline form of Compound A referred to herein as Compound A Form 6.

In another embodiment, the present disclosure is directed to a crystalline form of Compound A referred to herein as Compound A Form 7.

In another embodiment, the present disclosure is directed to a crystalline form of Compound A referred to herein as Compound A Form 8.

In another embodiment, the present disclosure is directed to a crystalline form of Compound A referred to herein as Compound A Form 9.

In another embodiment, the present disclosure is directed to a crystalline form of Compound A referred to herein as Compound A Form 10.

In another embodiment, the present disclosure is directed to a crystalline form of Compound A referred to herein as Compound A Form 11.

In another embodiment, the present disclosure is directed to a mixture of two or more of the crystalline forms of Compound A disclosed herein.

In another embodiment, the present disclosure is directed to a crystalline form of Compound A disclosed herein (e.g., Form 1, Form 2, Form 3, Form 4, Form 5, Form 6, Form 7, Form 8, Form 9, Form 10, or Form 11) substantially free of any other solid state form of Compound A disclosed herein.

In another embodiment, the present disclosure is directed to pharmaceutical compositions comprising a pharmaceutically acceptable excipient and a therapeutically effective amount of a crystalline form of Compound A.

In another embodiment, the present disclosure is directed to pharmaceutical compositions comprising a pharmaceutically acceptable excipient and a therapeutically effective amount of a crystalline form of Compound A referred to herein as Compound A Form 1, optionally substantially free of any other solid state form of Compound A disclosed herein.

In another embodiment, the present disclosure is directed to pharmaceutical compositions comprising a pharmaceutically acceptable excipient and a therapeutically effective amount of a crystalline form of Compound A referred to herein as Compound A Form 2, optionally substantially free of any other solid state form of Compound A disclosed herein.

In another embodiment, the present disclosure is directed to pharmaceutical compositions comprising a pharmaceutically acceptable excipient and a therapeutically effective amount of a crystalline form of Compound A referred to herein as Compound A Form 3, optionally substantially free of any other solid state form of Compound A disclosed herein.

In another embodiment, the present disclosure is directed to pharmaceutical compositions comprising a pharmaceutically acceptable excipient and a therapeutically effective amount of a crystalline form of Compound A referred to herein as Compound A Form 4, optionally substantially free of any other solid state form of Compound A disclosed herein.

In another embodiment, the present disclosure is directed to pharmaceutical compositions comprising a pharmaceutically acceptable excipient and a therapeutically effective amount of a crystalline form of Compound A referred to herein as Compound A Form 5, optionally substantially free of any other solid state form of Compound A disclosed herein.

In another embodiment, the present disclosure is directed to pharmaceutical compositions comprising a pharmaceutically acceptable excipient and a therapeutically effective amount of a crystalline form of Compound A referred to herein as Compound A Form 6, optionally substantially free of any other solid state form of Compound A disclosed herein.

In another embodiment, the present disclosure is directed to pharmaceutical compositions comprising a pharmaceutically acceptable excipient and a therapeutically effective amount of a solid state form of Compound A referred to herein as Compound A Form 7, optionally substantially free of any other solid state form of Compound A disclosed herein.

In another embodiment, the present disclosure is directed to pharmaceutical compositions comprising a pharmaceutically acceptable excipient and a therapeutically effective amount of a crystalline form of Compound A referred to herein as Compound A Form 8, optionally substantially free of any other solid state form of Compound A disclosed herein.

In another embodiment, the present disclosure is directed to pharmaceutical compositions comprising a pharmaceutically acceptable excipient and a therapeutically effective amount of a crystalline form of Compound A referred to herein as Compound A Form 9, optionally substantially free of any other solid state form of Compound A disclosed herein.

In another embodiment, the present disclosure is directed to pharmaceutical compositions comprising a pharmaceutically acceptable excipient and a therapeutically effective amount of a crystalline form of Compound A referred to herein as Compound A Form 10, optionally substantially free of any other solid state form of Compound A disclosed herein.

In another embodiment, the present disclosure is directed to pharmaceutical compositions comprising a pharmaceutically acceptable excipient and a therapeutically effective amount of a crystalline form of Compound A, referred to herein as Compound A Form 11, optionally substantially free of any other solid state form of Compound A disclosed herein.

In another embodiment, the present disclosure is directed pharmaceutical compositions comprising a pharmaceutically acceptable excipient and a therapeutically effective amount of a mixture of two or more crystalline forms of Compound A disclosed herein.

In another embodiment, the present disclosure is directed to a method of treating a seizure disorder in a human, wherein the method comprises administering a therapeutically effective amount of a crystalline form of Compound A disclosed herein to the human in need thereof.

In another embodiment, the present disclosure is directed to a method of treating a seizure disorder in a human, wherein the method comprises administering a therapeutically effective amount of Compound A Form 1, optionally substantially free of any other solid state form of Compound A disclosed herein, to the human in need thereof.

In another embodiment, the present disclosure is directed to a method of treating a seizure disorder in a human, wherein the method comprises administering a therapeutically effective amount of Compound A Form 2, optionally substantially free of any other solid state form of Compound A disclosed herein, to the human in need thereof.

In another embodiment, the present disclosure is directed to a method of treating a seizure disorder in a human, wherein the method comprises administering a therapeutically effective amount of Compound A Form 3, optionally substantially free of any other solid state form of Compound A disclosed herein, to the human in need thereof.

In another embodiment, the present disclosure is directed to a method of treating a seizure disorder in a human, wherein the method comprises administering a therapeutically effective amount of Compound A Form 4, optionally substantially free of any other solid state form of Compound A disclosed herein, to the human in need thereof.

In another embodiment, the present disclosure is directed to a method of treating a seizure disorder in a human, wherein the method comprises administering a therapeutically effective amount of Compound A Form 5, optionally substantially free of any other solid state form of Compound A disclosed herein, to the human in need thereof.

In another embodiment, the present disclosure is directed to a method of treating a seizure disorder in a human, wherein the method comprises administering a therapeutically effective amount of Compound A Form 6, optionally substantially free of any other solid state form of Compound A disclosed herein, to the human in need thereof.

In another embodiment, the present disclosure is directed to a method of treating a seizure disorder in a human, wherein the method comprises administering a therapeutically effective amount of Compound A Form 7, optionally substantially free of any other solid state form of Compound A disclosed herein, to the human in need thereof.

In another embodiment, the present disclosure is directed to a method of treating a seizure disorder in a human, wherein the method comprises administering a therapeutically effective amount of Compound A Form 8, optionally substantially free of any other solid state form of Compound A disclosed herein, to the human in need thereof.

In another embodiment, the present disclosure is directed to a method of treating a seizure disorder in a human, wherein the method comprises administering a therapeutically effective amount of Compound A Form 9, optionally substantially free of any other solid state form of Compound A disclosed herein, to the human in need thereof.

In another embodiment, the present disclosure is directed to a method of treating a seizure disorder in a human, wherein the method comprises administering a therapeutically effective amount of Compound A Form 10, optionally substantially free of any other solid state form of Compound A disclosed herein, to the human in need thereof.

In another embodiment, the present disclosure is directed to a method of treating a seizure disorder in a human, wherein the method comprises administering a therapeutically effective amount of Compound A Form 11, optionally substantially free of any other solid state form of Compound A disclosed herein, to the human in need thereof.

In another embodiment, the present disclosure is directed to a method of treating a seizure disorder in a human, wherein the method comprises administering a therapeutically effective amount of a mixture of two or more crystalline forms of Compound A disclosed herein to the human in need thereof.

In another embodiment, the present disclosure is directed to the use of any one of the crystalline forms of Compound A disclosed herein for the preparation of pharmaceutical compositions comprising the crystalline form of Compound A disclosed herein and a pharmaceutically acceptable excipient.

In another embodiment, the present disclosure is directed to methods of preparing the crystalline forms of Compound A disclosed herein.

In another embodiment, the present disclosure is directed to a method of preparing Compound A Form 1 as described herein, optionally substantially free of any other solid state form of Compound A disclosed herein.

In another embodiment, the present disclosure is directed to a method of preparing Compound A Form 2 as described herein, optionally substantially free of any other solid state form of Compound A disclosed herein.

In another embodiment, the present disclosure is directed to a method of preparing Compound A Form 3 as described herein, optionally substantially free of any other solid state form of Compound A disclosed herein.

In another embodiment, the present disclosure is directed to a method of preparing Compound A Form 4 as described herein, optionally substantially free of any other solid state form of Compound A disclosed herein.

In another embodiment, the present disclosure is directed to a method of preparing Compound A Form 5 as described herein, optionally substantially free of any other solid state form of Compound A disclosed herein.

In another embodiment, the present disclosure is directed to a method of preparing Compound A Form 6 as described herein, optionally substantially free of any other solid state form of Compound A disclosed herein.

In another embodiment, the present disclosure is directed to a method of preparing Compound A Form 7 as described herein, optionally substantially free of any other solid state form of Compound A disclosed herein.

In another embodiment, the present disclosure is directed to a method of preparing Compound A Form 8 as described herein, optionally substantially free of any other solid state form of Compound A disclosed herein.

In another embodiment, the present disclosure is directed to a method of preparing Compound A Form 9 as described herein, optionally substantially free of any other solid state form of Compound A disclosed herein.

In another embodiment, the present disclosure is directed to a method of preparing Compound A Form 10 as described herein, optionally substantially free of any other solid state form of Compound A disclosed herein.

In another embodiment, the present disclosure is directed to a method of preparing Compound A Form 11 as described herein, optionally substantially free of any other solid state form of Compound A disclosed herein.

In another embodiment, the present disclosure is directed to a method for preparing the above-mentioned pharmaceutical compositions comprising any one of the crystalline forms of Compound A disclosed herein and a pharmaceutically acceptable excipient. In one embodiment, the method comprises combining any one of the crystalline forms of Compound A disclosed herein with at least one pharmaceutically acceptable excipient.

In another embodiment, the present disclosure is directed to the use of any one of the crystalline forms of Compound A or a pharmaceutical composition comprising any one of the crystalline forms of Compound A and a pharmaceutically acceptable excipient as a medicament for the treatment of seizure disorders in a human.

In some embodiments of the present methods and uses, one or more of the crystalline forms of Compound A is orally administered to the human from between 30 minutes before to 2 hours after eating a meal, for example, the one or more crystalline forms of Compound A may be orally administered to the mammal during a meal or within 15 minutes after eating a meal.

In another embodiment, the present disclosure is directed to one or more of the crystalline forms of Compound A disclosed herein which have advantageous properties wherein the advantageous properties are selected from at least one or more of the following: chemical purity, flowability, solubility, dissolution rate, morphology or crystal habit, stability, such as chemical stability as well as thermal and mechanical stability with respect to polymorphic conversion, stability towards dehydration and/or storage stability, low content of residual solvent, a lower degree of hygroscopicity, and advantageous processing and handling characteristics, such as compressibility and bulk density.

In one embodiment, a crystalline form of Compound A exhibits better flowability (i.e., superior rheological properties) than amorphous Compound A or another solid state crystalline form of Compound A.

These embodiments are described in more detail below. To this end, various references are set forth herein which describe in more detail certain background information, procedures, compounds and/or compositions, and are each hereby incorporated by reference in their entirety.

4. BRIEF DESCRIPTION OF THE FIGURES

5. DETAILED DESCRIPTION

Figure 1:
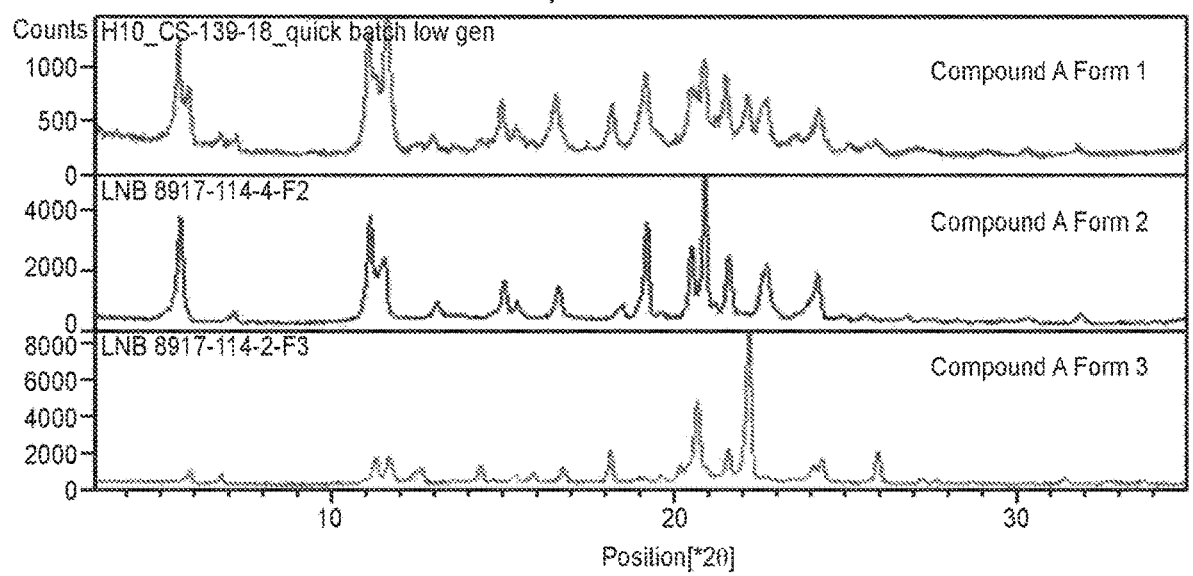
FIG. 1 depicts an X-ray powder diffraction (XRPD) pattern of Compound A Form 1, Compound A Form 2 and Compound A Form 3.

In the following description, certain specific details are set forth in order to provide a thorough understanding of various embodiments. However, one skilled in the art will understand that the disclosure may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed disclosure.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise. Further, the term "about" as used herein means±20% of the stated value and in more specific embodiments means±10%, ±5%, ±2% or ±1% of the stated value.

5.1. Definitions

As used in the specification and appended claims, unless specified to the contrary, the following terms and abbreviations have the meaning indicated:

As used herein, "Compound A" refers to the compound having the following chemical structure:

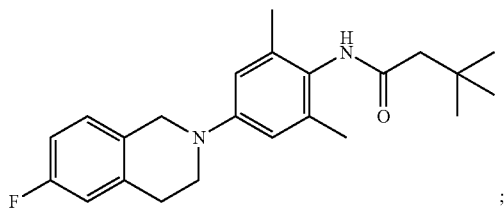 [SMILES: Cc1cc(N2CCc3cc(F)ccc3C2)cc(C)c1NC(=O)CC(C)(C)C]

and a chemical name of N-(4-(6-fluoro-3,4-dihydroisoquinolin-2(1H)-yl)-2,6-dimethylphenyl)-3,3-dimethylbutanamide. Preparation of Compound A and its use as a selective potassium channel modulator, particularly a Kv7.2/Kv7.3 (KCNQ2/3) opener is disclosed in U.S. Pat. Nos. 8,293,911 and 8,993,593. The mechanism of action of Compound A is different from most known AED's in that it involves potentiation or enhanced opening of the voltage-gated potassium channels Kv7.2 and Kv7.3 (Kv7.2/Kv7.3), which are important in controlling neuronal excitability. Compound A is used in the methods and uses described herein.

A solid state form of Compound A, such as a crystalline form, may be referred to herein as being characterized by graphical data "as depicted in" or "as substantially depicted in" a Figure. Such data include, for example, X-ray powder diffractograms, DSC thermograms, or NMR spectrums. As is well-known in the art, such graphical data potentially provides additional technical information to further define the respective solid state form (a so-called "fingerprint") which cannot necessarily be described by reference to numerical values or peak positions alone. In any event, the skilled person will understand that such graphical representations of data may be subject to small variations, e.g., in peak relative intensities and peak positions due to certain factors such as, but not limited to, variations in instrument response and variations in sample concentration and purity, which are well known to the skilled person. Nonetheless, the skilled person would readily be capable of comparing the graphical data in the Figures herein with graphical data generated for an unknown crystalline form and confirm whether the two sets of graphical data are characterizing the same crystal form or two different crystal forms. A solid state form of Compound A referred to herein as being characterized by graphical data "as depicted in" or "as substantially depicted in" a Figure will thus be understood to include any solid state forms of Compound A characterized with the graphical data having such small variations, as are well known to the skilled person, in comparison with the Figure.

As used herein, "solid state form of Compound A designated as Compound A Form 1", "solid state form of Compound A referred to herein as Compound A Form 1", "Compound A Form 1" or "Form 1" refers to the solid state form of Compound A which may be identified in a composition by detecting the peaks of the X-ray powder diffraction pattern as depicted in FIG. 1.

Figure 8:
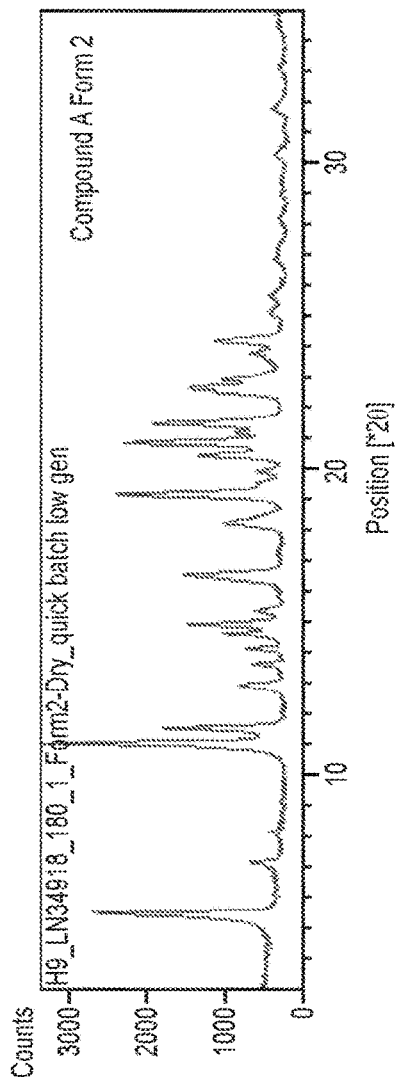
FIG. 8 depicts a XRPD diffractogram of Compound A Form 2.
Figure 9:
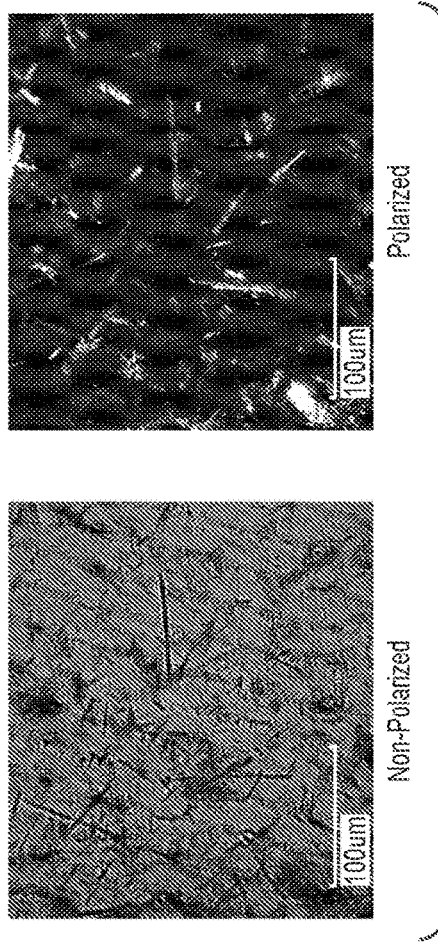
FIG. 9 depicts non-polarized and polarized light microscopy images of Compound A Form 2.

As used herein, "solid state form of Compound A designated as Compound A Form 2", "solid state form of Compound A referred to herein as Compound A Form 2", "Compound A Form 2" or "Form 2" refers to the solid state form of Compound A which may be identified in a composition by detecting the peaks of the X-ray powder diffraction pattern as depicted in FIG. 8.

Figure 16:
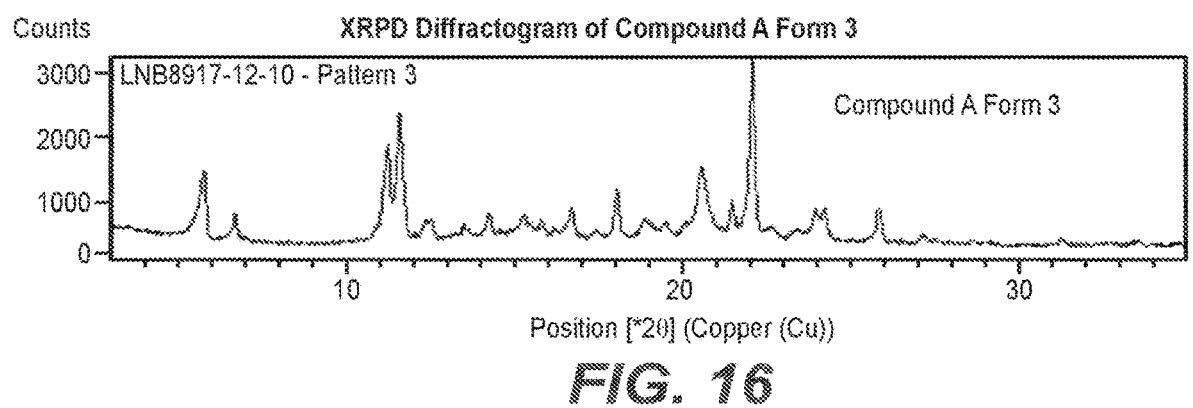
FIG. 16 depicts a XRPD diffractogram of Compound A Form 3.

As used herein, "solid state form of Compound A designated as Compound A Form 3", "solid state form of Compound A referred to herein as Compound A Form 3", "Compound A Form 3" or "Form 3" refers to the solid state form of Compound A which may be identified in a composition by detecting the peaks of the X-ray powder diffraction pattern as depicted in FIG. 16.

Figure 17:
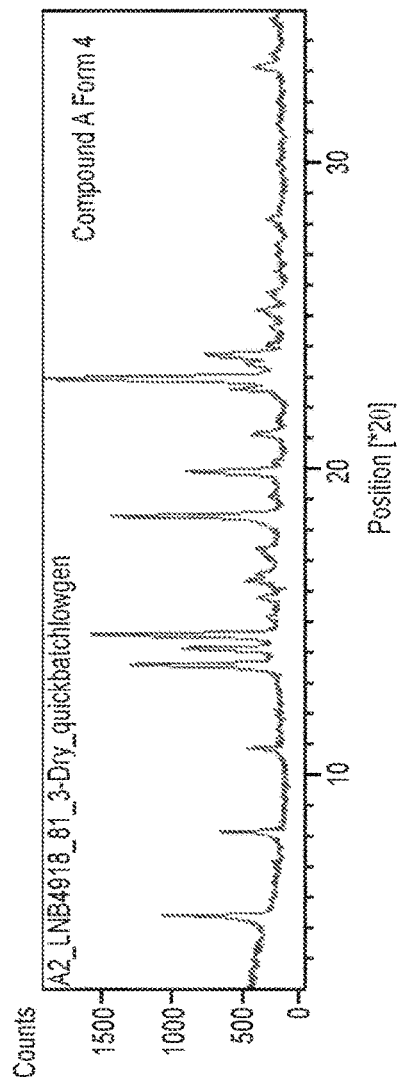
FIG. 17 depicts a XRPD diffractogram of Compound A Form 4.
Figure 18:
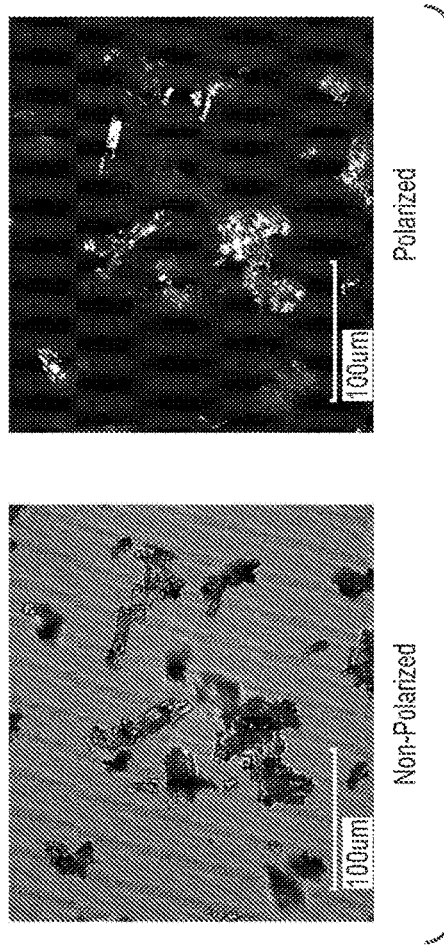
FIG. 18 depicts non-polarized and polarized light microscopy images of Compound A Form 4.

As used herein, "solid state form of Compound A designated herein as Compound A Form 4", "solid state form of Compound A referred to herein as Compound A Form 4", "Compound A Form 4" or "Form 4" refers to the solid state form of Compound A which may be identified in a composition by detecting the peaks of the X-ray powder diffraction pattern as depicted in FIG. 17.

Figure 25:
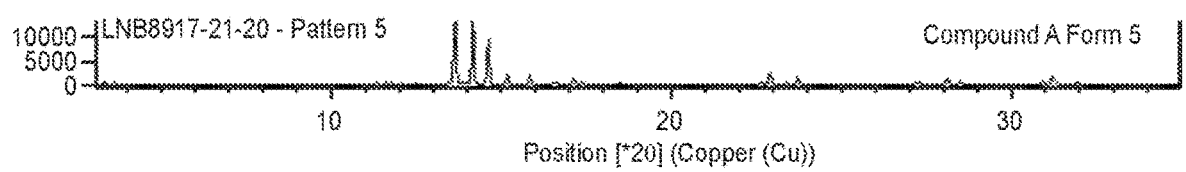
FIG. 25 depicts a XRPD diffractogram of Compound A Form 5.

As used herein, "solid state form of Compound A designated as Compound A Form 5", "solid state form of Compound A referred to herein as Compound A Form 5", "Compound A Form 5" or "Form 5" refers to the solid state form of Compound A which may be identified in a composition by detecting the peaks of the X-ray powder diffraction pattern as depicted in FIG. 25.

Figure 26:
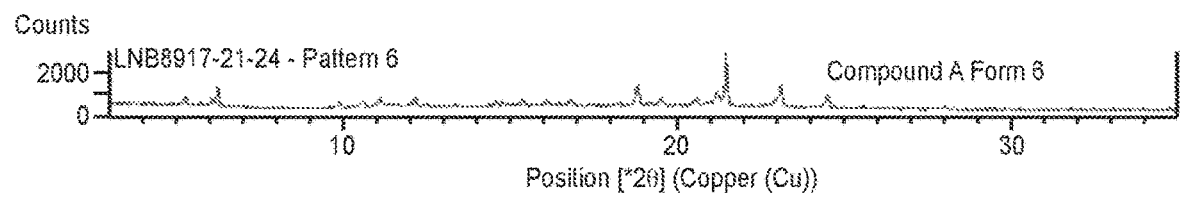
FIG. 26 depicts a XRPD diffractogram of Compound A Form 6.

As used herein, "solid state form of Compound A designated as Compound A Form 6, "solid state form of Compound A referred to herein as Compound A Form 6", "Compound A Form 6" or "Form 6" refers to the solid state form of Compound A which may be identified in a composition by detecting the peaks of the X-ray powder diffraction pattern as depicted in FIG. 26.

Figure 27:
FIG. 27 depicts a XRPD diffractogram of Compound A Form 7.

As used herein, "solid state form of Compound A designated as Compound A Form 7", "solid state form of Compound A referred to herein as Compound A Form 7", "Compound A Form 7" or "Form 7" refers to the solid state form of Compound A which may be identified in a composition by detecting the peaks of the X-ray powder diffraction pattern as depicted in FIG. 27.

Figure 28:
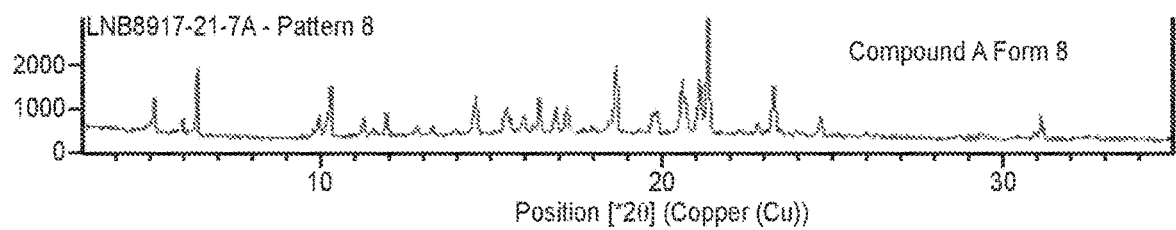
FIG. 28 depicts a XRPD diffractogram of Compound A Form 8.

As used herein, "solid state form of Compound A designated as Compound A Form 8", "solid state form of Compound A referred to herein as Compound A Form 8", "Compound A Form 8" or "Form 8" refers to the solid state form of Compound A which may be identified in a composition by detecting the peaks of the X-ray powder diffraction pattern as depicted in FIG. 28.

Figure 29:
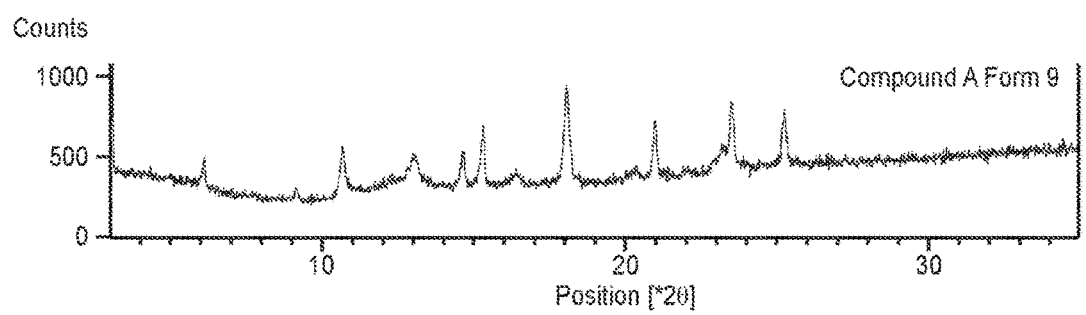
FIG. 29 depicts a XRPD diffractogram of Compound A Form 9.
Figure 30:
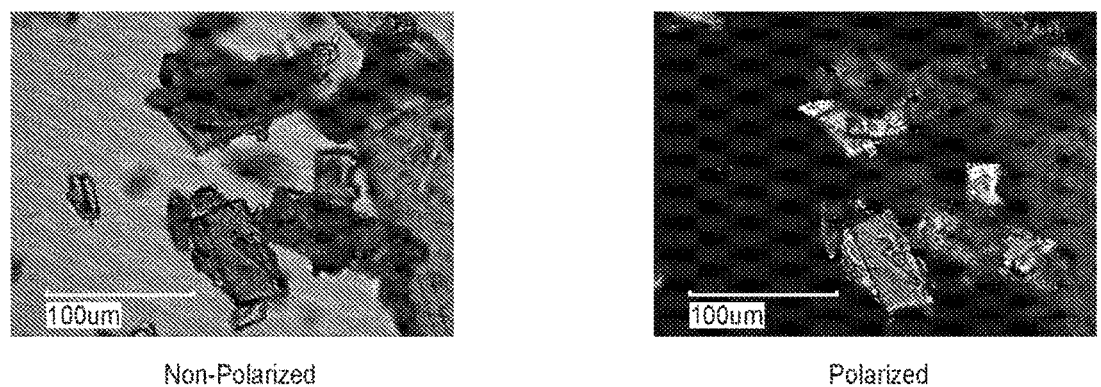
FIG. 30 depicts non-polarized and polarized light microscopy images of Compound A Form 9.

As used herein, "solid state form of Compound A designated herein as Compound A Form 9", "solid state form of Compound A referred to herein as Compound A Form 9", "Compound A Form 9" or "Form 9" refers to the solid state form of Compound A which may be identified in a composition by detecting the peaks of the X-ray powder diffraction pattern as depicted in FIG. 29.

Figure 37:
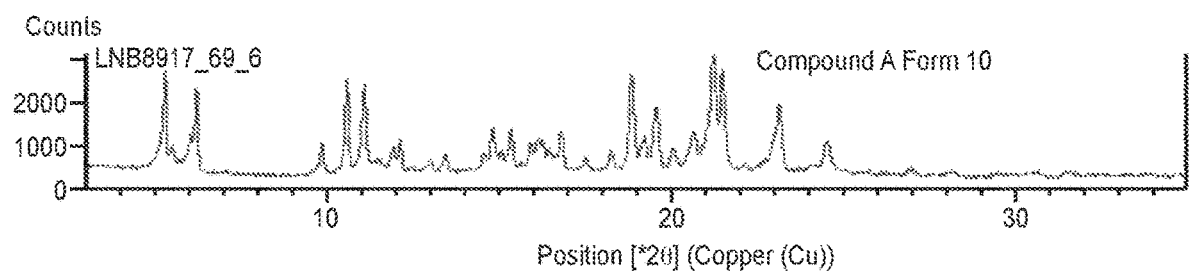
FIG. 37 depicts a XRPD diffractogram of Compound A Form 10.

As used herein, "solid state form of Compound A designated as Compound A Form 10", "solid state form of Compound A referred to herein as Compound A Form 10", "Compound A Form 10" or "Form 10" refers to the solid state form of Compound A which may be identified in a composition by detecting the peaks of the X-ray powder diffraction pattern as depicted in FIG. 37.

Figure 39:
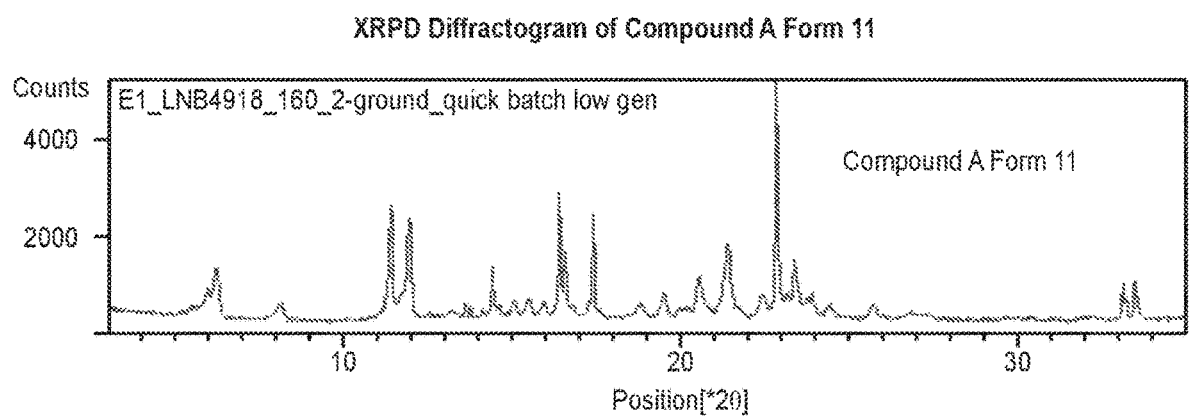
FIG. 39 depicts a XRPD diffractogram of Compound A Form 11.

As used herein, "solid state form of Compound A designated herein as Compound A Form 11", "solid state form of Compound A referred to herein as Compound A Form 11", "Compound A Form 11" or "Form 11" refers to the solid state form of Compound A which may be identified in a composition by detecting the peaks of the X-ray powder diffraction pattern as depicted in FIG. 39.

"AUC" refers to the area under the plasma concentration versus time curve. The AUC reflects the actual systemic exposure to a solid state form of Compound A after extravascular administration of a dose of the solid state form of Compound A and is expressed in the hours times the concentration of the solid state form of Compound A in the plasma. For purposes of the present disclosure, the AUC is expressed in hours times ng/mL.

"$AUC_{inf}$" refers to the AUC from time zero to infinity.

"$AUC_{infobs}$" refers to the AUC from time zero to infinity as observed.

"$AUC_{last}$" refers to the AUC from time zero to last detectable plasma concentration.

"% $AUC_{ext}$" refers to the AUC extrapolated from time zero to infinity as a percentage of total AUC.

"Bioavailability" refers to the rate and extent to which a solid state form of Compound A is absorbed and becomes available systemically for further distribution to the site of action.

"$C_{max}$" refers to the observed maximal plasma concentration.

"h" refers to hour or hours.

"High-fat meal" refers to any food product, solid or liquid, with approximately 50 percent of the total caloric content of the food product coming from fat.

"High-calorie meal" refers to any meal having approximately 800 to 1000 calories. A representative high-fat, high-calorie meal should derive approximately 150, 250, and 500-600 calories from protein, carbohydrate, and fat, respectively.

As used herein, the term "highly soluble" in reference to solid state forms of Compound A corresponds to a solid state form of Compound A having a solubility of above 100 mg/mL at room temperature. In an embodiment, the solid state forms of Compound A are highly soluble in solvents such as 1,4-dioxane, 1-butanol, 1-propanol, acetone, anisole, chloroform, cycohexanone, dichloromethane, dimethylsulfoxide, ethanol, ethyl acetate, 2-propanol, methylethyl ketone, N-methyl2-pyrrolidone, tetrahydrofuran and tetrahydrofuran/water (99:1 v/v).

A process or step may be referred to herein as being carried out "overnight." This refers to a time interval, e.g., for the process or step, that spans the time during the night, when that process or step may not be actively observed. This time interval is from about 8 to about 20 hours, or about 10-18 hours, or typically about 16 hours.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which is understood as being acceptable for use in humans or domestic animals.

When a mixture, such as a solid state form of Compound A and a solvent, is characterized herein as being at or allowed to come to "room temperature" or "ambient temperature" (often abbreviated as "RT"), it is intended to mean that the temperature of the object or mixture is close to, or the same as, that of the space, e.g., the room or fume hood, in which the object or mixture is located. Typically, room temperature is from about 20° C. to about 30° C., or about 22° C. to about 27° C., or about 25° C.

"SD" refers to standard deviation.

"Seizure disorders" refers to seizures and disorders associated with seizures such as partial onset (focal) seizures, photosensitive epilepsy, self-induced syncope, intractable epilepsy, Angelman syndrome, benign rolandic epilepsy, CDKL5 disorder, childhood and juvenile absence epilepsy, Dravet syndrome, frontal lobe epilepsy, Glut1 deficiency syndrome, hypothalamic hamartoma, infantile spasms/West's syndrome, juvenile myoclonic epilepsy, Landau-Kleffner syndrome, Lennox-Gastaut syndrome (LGS), epilepsy with myoclonic-absences, Ohtahara syndrome, Panayiotopoulos syndrome, PCDH19 epilepsy, progressive myoclonic epilepsies, Rasmussen's syndrome, ring chromosome 20 syndrome, reflex epilepsies, temporal lobe epilepsy, Lafora progressive myoclonus epilepsy, neurocutaneous syndromes, tuberous sclerosis complex, early infantile epileptic encephalopathy, early onset epileptic encephalopathy, generalized epilepsy with febrile seizures+, Rett syndrome, multiple sclerosis, Alzheimer's disease, autism, ataxia, hypotonia and paroxysmal dyskinesia. In certain embodiments, the term "seizure disorder" refers to focal onset epilepsy, also known as partial onset (focal) epilepsy.

As used herein, "substantially free" when referring to a solid state form of Compound A is intended to mean that the solid state form of the present disclosure contains 20% (w/w) or less of any other solid state forms of Compound A or of a specified solid state form of Compound A.

"$t1/2_{\lambda z}$" refers to the terminal elimination half-life of a solid state form of Compound A from plasma (i.e., the time required for the plasma concentration of the solid state form of Compound A to be reduced by one-half during the terminal elimination phase).

"$T_{max}$" refers to the time to reach maximum (peak) plasma concentration following extravascular administration of a solid state form of Compound A.

"Therapeutically effective amount" as used herein refers to an amount of a solid state form of Compound A that is sufficient to treat the indicated disease, disorder, or condition or have the desired stated effect, including ameliorating or preventing the disease, disorder, or condition or one or more mechanisms underlying the disease, disorder, or condition. In certain embodiments, when a solid state form of Compound A is administered for the treatment of a seizure disorder, therapeutically effective amount refers to a range of amounts of the solid state form of Compound A which, upon administration to a human, treats, ameliorates or prevents a seizure disorder in the human, or exhibits a detectable therapeutic or preventative effect in the human having a seizure disorder. The effect is detected by, for example, a reduction in seizures (frequency) or by the severity of seizures (quality). The precise therapeutically effective amount for a given human will depend upon the human's size and health, the nature and extent of the seizure disorder, the presence of any concomitant medications, and other variables known to those of skill in the art. The therapeutically effective amount for a given situation can be determined by routine experimentation and is within the capabilities of the clinician.

"Treatment" as used herein refers to therapeutic applications associated with administering a solid state form of Compound A that ameliorate or prevent the indicated disease, disorder, or condition or one or more underlying mechanisms of said disease, disorder, or condition, including slowing or stopping progression of the disease, disorder or condition or one or more of the underlying mechanisms. In certain embodiments, when a solid state form of Compound A is administered for the treatment of a seizure disorder, treatment refers to therapeutic applications to slow or stop progression of a seizure disorder, prophylactic application to prevent development of a seizure disorder, and/or reversal of a seizure disorder. Reversal of a seizure disorder differs from a therapeutic application which slows or stops a seizure disorder in that with a method of reversing, not only is progression of a seizure disorder completely stopped, cellular behavior is moved to some degree toward a normal state that would be observed in the absence of the seizure disorder.

"Under fed conditions" refers to the condition of having consumed food during the time period between from about 4 hours prior to the oral administration of an effective amount (e.g., within the therapeutically effective dose range) of a solid state form of Compound A to about 4 hours after the administration of the solid state form of Compound A. The food may be a solid, liquid, or mixture of solid and liquid food with sufficient bulk and fat content that it is not rapidly dissolved and absorbed in the stomach. In some instances, the food is a meal, such as breakfast, lunch, dinner or, alternatively, baby food (e.g., formula or breast milk). The therapeutically effective amount of a solid state form of Compound A may be orally administered to the subject, for example, between about 30 minutes prior to about 2 hours after eating a meal, most advantageously, the dosage unit of the solid state form of Compound A is orally administered during a meal or within 15 minutes after eating a meal. This "food effect" associated with the administration of Compound A in a human under fed conditions can be found in U.S. Published Patent Application No. 2019-0343823, the disclosure of which is hereby incorporated by reference in its entirety.

"Under fasted conditions" refers to the condition of not having consumed food during the time period between from at least 4 hours prior to the oral administration of a therapeutically effective amount of a solid state form of Compound A to about 4 hours after administration of the solid state form of Compound A.

As used herein, the term "under vacuum" or "in vacuo" refers to a pressure that is less than atmospheric pressure.

The amount of solvent employed in a chemical process, e.g., a reaction or a crystallization, may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending a 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding solvent X (1.5 v/v) to a 100 ml reaction mixture would indicate that 150 mL of solvent X was added.

5.2. Embodiments

In some embodiments, a solid state crystalline form of Compound A (e.g., Form 1, Form 2, Form 3, Form 4, Form 5, Form 6, Form 7, Form 8, Form 9, Form 10, or Form 11) contains 20% (w/w) or less, 19% (w/w) or less, 18% (w/w) or less, 17% (w/w) or less, 16% (w/w) or less, 15% (w/w) or less, 14% (w/w) or less, 13% (w/w) or less, 12% (w/w) or less, 11% (w/w) or less, 10% (w/w) or less, 9% (w/w) or less, 8% (w/w) or less, 7% (w/w) or less, 6% (w/w) or less, 5% (w/w) or less, 4% (w/w) or less, 3% (w/w) or less, 2% (w/w) or less, 1% (w/w) or less, 0.5% (w/w) or less, or 0.2% (w/w) or less of any other solid state crystalline forms of Compound A disclosed herein, or of a specified solid state crystalline form of Compound A disclosed herein.

In other embodiments, a solid state crystalline form of Compound A (e.g., Form 1, Form 2, Form 3, Form 4, Form 5, Form 6, Form 7, Form 8, Form 9, Form 10, or Form 11) contains from 0.1% to 20% (w/w), from 0.2% to 20% (w/w), from 0.5% to 20% (w/w), from 1% to 20% (w/w), from 2% to 20% (w/w), from 3% to 20% (w/w), from 4% to 20% (w/w), from 5% to 20% (w/w), from 6% to 20% (w/w), from 7% to 20% (w/w), from 8% to 20% (w/w), from 9% to 20% (w/w), from 10% to 20% (w/w), from 11% to 20% (w/w), from 12% to 20% (w/w), from 13% to 20% (w/w), from 14% to 20% (w/w), from 15% to 20% (w/w), from 16% to 20% (w/w), from 17% to 20% (w/w), from 18% to 20% (w/w), or from 19% to 20% (w/w) of any other solid state crystalline forms of Compound A disclosed herein, or of a specified solid state crystalline form of Compound A disclosed herein.

In other embodiments, a solid state crystalline form of Compound A (e.g., Form 1, Form 2, Form 3, Form 4, Form 5, Form 6, Form 7, Form 8, Form 9, Form 10, or Form 11) contains from 0.1% to 15% (w/w), from 0.2% to 15% (w/w), from 0.5% to 15% (w/w), from 1% to 15% (w/w), from 2% to 15% (w/w), from 3% to 15% (w/w), from 4% to 15% (w/w), from 5% to 15% (w/w), from 6% to 15% (w/w), from 7% to 15% (w/w), from 8% to 15% (w/w), from 9% to 15% (w/w), from 10% to 15% (w/w), from 11% to 15% (w/w), from 12% to 15% (w/w), from 13% to 15% (w/w), or from 14% to 15% (w/w) of any other solid state crystalline forms of Compound A disclosed herein, or of a specified solid state crystalline form of Compound A disclosed herein.

In other embodiments, a solid state crystalline form of Compound A (e.g., Form 1, Form 2, Form 3, Form 4, Form 5, Form 6, Form 7, Form 8, Form 9, Form 10, or Form 11) contains from 0.1% to 10% (w/w), from 0.2% to 10% (w/w), from 0.5% to 10% (w/w), from 1% to 10% (w/w), from 2% to 10% (w/w), from 3% to 10% (w/w), from 4% to 10% (w/w), from 5% to 10% (w/w), from 6% to 10% (w/w), from 7% to 10% (w/w), from 8% to 10% (w/w), or from 9% to 10% (w/w) of any other solid state crystalline forms of Compound A disclosed herein, or of a specified solid state crystalline form of Compound A disclosed herein.

In other embodiments, a solid state crystalline form of Compound A (e.g., Form 1, Form 2, Form 3, Form 4, Form 5, Form 6, Form 7, Form 8, Form 9, Form 10, or Form 11) contains from 0.1% to 5% (w/w), from 0.2% to 5% (w/w), from 0.3% to 5% (w/w), from 0.4% to 5% (w/w), from 0.5% to 5% (w/w), from 0.7% to 5% (w/w), from 0.8% to 5% (w/w), from 1% to 5% (w/w), from 1.5% to 5% (w/w), from 2% to 5% (w/w), from 2.5% to 5% (w/w), from 3% to 5% (w/w), or from 4% to 5% (w/w) of any other solid state crystalline forms of Compound A disclosed herein, or of a specified solid state crystalline form of Compound A disclosed herein.

5.2.1. Compound A Form 1 Mixtures

In some embodiments, a solid state crystalline form of Compound A contains Compound A Form 1 and 20% (w/w) or less, 19% (w/w) or less, 18% (w/w) or less, 17% (w/w) or less, 16% (w/w) or less, 15% (w/w) or less, 14% (w/w) or less, 13% (w/w) or less, 12% (w/w) or less, 11% (w/w) or less, 10% (w/w) or less, 9% (w/w) or less, 8% (w/w) or less, 7% (w/w) or less, 6% (w/w) or less, 5% (w/w) or less, 4% (w/w) or less, 3% (w/w) or less, 2% (w/w) or less, 1% (w/w) or less, 0.5% (w/w) or less, or 0.2% (w/w) or less of all other solid state crystalline forms of Compound A in total disclosed herein, or of a specified solid state crystalline form of Compound A disclosed herein, such as Compound A Form 2, Compound A Form 3, Compound A Form 4, Compound A Form 5, Compound A Form 6, Compound A Form 7, Compound A Form 8, Compound A Form 9, Compound A Form 10, or Compound A Form 11, or a combination of these.

In certain embodiments, a solid state crystalline form of Compound A contains Compound A Form 1 and from 0.1% to 20% (w/w), from 0.2% to 20% (w/w), from 0.5% to 20% (w/w), from 1% to 20% (w/w), from 2% to 20% (w/w), from 3% to 20% (w/w), from 4% to 20% (w/w), from 5% to 20% (w/w), from 6% to 20% (w/w), from 7% to 20% (w/w), from 8% to 20% (w/w), from 9% to 20% (w/w), from 10% to 20% (w/w), from 11% to 20% (w/w), from 12% to 20% (w/w), from 13% to 20% (w/w), from 14% to 20% (w/w), from 15% to 20% (w/w), from 16% to 20% (w/w), from 17% to 20% (w/w), from 18% to 20% (w/w), or from 19% to 20% (w/w) of all other solid state crystalline forms of Compound A in total disclosed herein, or of a specified solid state crystalline form of Compound A disclosed herein, such as Compound A Form 2, Compound A Form 3, Compound A Form 4, Compound A Form 5, Compound A Form 6, Compound A Form 7, Compound A Form 8, Compound A Form 9, Compound A Form 10, or Compound A Form 11, or a combination of these.

In some embodiments, a solid state crystalline form of Compound A contains Compound A Form 1 and from 0.1% to 15% (w/w), from 0.2% to 15% (w/w), from 0.5% to 15% (w/w), from 1% to 15% (w/w), from 2% to 15% (w/w), from 3% to 15% (w/w), from 4% to 15% (w/w), from 5% to 15% (w/w), from 6% to 15% (w/w), from 7% to 15% (w/w), from 8% to 15% (w/w), from 9% to 15% (w/w), from 10% to 15% (w/w), from 11% to 15% (w/w), from 12% to 15% (w/w), from 13% to 15% (w/w), or from 14% to 15% (w/w) of all other solid state crystalline forms of Compound A in total disclosed herein, or of a specified solid state crystalline form of Compound A disclosed herein, such as Compound A Form 2, Compound A Form 3, Compound A Form 4, Compound A Form 5, Compound A Form 6, Compound A Form 7, Compound A Form 8, Compound A Form 9, Compound A Form 10, or Compound A Form 11, or a combination of these.

In certain embodiments, a solid state crystalline form of Compound A contains Compound A Form 1 and from 0.1% to 10% (w/w), from 0.2% to 10% (w/w), from 0.5% to 10% (w/w), from 1% to 10% (w/w), from 2% to 10% (w/w), from 3% to 10% (w/w), from 4% to 10% (w/w), from 5% to 10% (w/w), from 6% to 10% (w/w), from 7% to 10% (w/w), from 8% to 10% (w/w), or from 9% to 10% (w/w) of all other solid state crystalline forms of Compound A in total disclosed herein, or of a specified solid state crystalline form of Compound A disclosed herein, such as Compound A Form 2, Compound A Form 3, Compound A Form 4, Compound A Form 5, Compound A Form 6, Compound A Form 7, Compound A Form 8, Compound A Form 9, Compound A Form 10, or Compound A Form 11, or a combination of these.

In some embodiments, a solid state crystalline form of Compound A contains Compound A Form 1 and from 0.2% to 5% (w/w), from 0.3% to 5% (w/w), from 0.4% to 5% (w/w), from 0.5% to 5% (w/w), from 0.7% to 5% (w/w), from 0.8% to 5% (w/w), from 1% to 5% (w/w), from 1.5% to 5% (w/w), from 2% to 5% (w/w), from 2.5% to 5% (w/w), from 3% to 5% (w/w), or from 4% to 5% (w/w) of all other solid state crystalline forms of Compound A in total disclosed herein, or of a specified solid state crystalline form of Compound A disclosed herein, such as Compound A Form 2, Compound A Form 3, Compound A Form 4, Compound A Form 5, Compound A Form 6, Compound A Form 7, Compound A Form 8, Compound A Form 9, Compound A Form 10, or Compound A Form 11, or a combination of these.

In other embodiments, a solid state form of Compound A comprises at least 25% (w/w), at least 50% (w/w), at least 75% (w/w), at least 80% (w/w), at least 85% (w/w), at least 90% (w/w), at least 95% (w/w), at least 98% (w/w), or at least 99% (w/w) of Compound A Form 1.

5.2.2. Compound A Form 2 Mixtures

In some embodiments, a solid state crystalline form of Compound A contains Compound A Form 2 and 20% (w/w) or less, 19% (w/w) or less, 18% (w/w) or less, 17% (w/w) or less, 16% (w/w) or less, 15% (w/w) or less, 14% (w/w) or less, 13% (w/w) or less, 12% (w/w) or less, 11% (w/w) or less, 10% (w/w) or less, 9% (w/w) or less, 8% (w/w) or less, 7% (w/w) or less, 6% (w/w) or less, 5% (w/w) or less, 4% (w/w) or less, 3% (w/w) or less, 2% (w/w) or less, 1% (w/w) or less, 0.5% (w/w) or less, or 0.2% (w/w) or less of all other solid state crystalline forms of Compound A in total disclosed herein, or of a specified solid state crystalline form of Compound A disclosed herein, such as Compound A Form 1, Compound A Form 3, Compound A Form 4, Compound A Form 5, Compound A Form 6, Compound A Form 7, Compound A Form 8, Compound A Form 9, Compound A Form 10, or Compound A Form 11, or a combination of these.

In certain embodiments, a solid state crystalline form of Compound A contains Compound A Form 2 and from 0.1% to 20% (w/w), from 0.2% to 20% (w/w), from 0.5% to 20% (w/w), from 1% to 20% (w/w), from 2% to 20% (w/w), from 3% to 20% (w/w), from 4% to 20% (w/w), from 5% to 20% (w/w), from 6% to 20% (w/w), from 7% to 20% (w/w), from 8% to 20% (w/w), from 9% to 20% (w/w), from 10% to 20% (w/w), from 11% to 20% (w/w), from 12% to 20% (w/w), from 13% to 20% (w/w), from 14% to 20% (w/w), from 15% to 20% (w/w), from 16% to 20% (w/w), from 17% to 20% (w/w), from 18% to 20% (w/w), or from 19% to 20% (w/w) of all other solid state crystalline forms of Compound A in total disclosed herein, or of a specified solid state crystalline form of Compound A disclosed herein, such as Compound A Form 1, Compound A Form 3, Compound A Form 4, Compound A Form 5, Compound A Form 6, Compound A Form 7, Compound A Form 8, Compound A Form 9, Compound A Form 10, or Compound A Form 11, or a combination of these.

In some embodiments, a solid state crystalline form of Compound A contains Compound A Form 2 and from 0.1% to 15% (w/w), from 0.2% to 15% (w/w), from 0.5% to 15% (w/w), from 1% to 15% (w/w), from 2% to 15% (w/w), from 3% to 15% (w/w), from 4% to 15% (w/w), from 5% to 15% (w/w), from 6% to 15% (w/w), from 7% to 15% (w/w), from 8% to 15% (w/w), from 9% to 15% (w/w), from 10% to 15% (w/w), from 11% to 15% (w/w), from 12% to 15% (w/w), from 13% to 15% (w/w), or from 14% to 15% (w/w) of all other solid state crystalline forms of Compound A in total disclosed herein, or of a specified solid state crystalline form of Compound A disclosed herein, such as Compound A Form 1, Compound A Form 3, Compound A Form 4, Compound A Form 5, Compound A Form 6, Compound A Form 7, Compound A Form 8, Compound A Form 9, Compound A Form 10, or Compound A Form 11, or a combination of these.

In certain embodiments, a solid state crystalline form of Compound A contains Compound A Form 2 and from 0.1% to 10% (w/w), from 0.2% to 10% (w/w), from 0.5% to 10% (w/w), from 1% to 10% (w/w), from 2% to 10% (w/w), from 3% to 10% (w/w), from 4% to 10% (w/w), from 5% to 10% (w/w), from 6% to 10% (w/w), from 7% to 10% (w/w), from 8% to 10% (w/w), or from 9% to 10% (w/w) of all other solid state crystalline forms of Compound A in total disclosed herein, or of a specified solid state crystalline form of Compound A disclosed herein, such as Compound A Form 1, Compound A Form 3, Compound A Form 4, Compound A Form 5, Compound A Form 6, Compound A Form 7, Compound A Form 8, Compound A Form 9, Compound A Form 10, or Compound A Form 11, or a combination of these.

In some embodiments, a solid state crystalline form of Compound A contains Compound A Form 2 and from 0.2% to 5% (w/w), from 0.3% to 5% (w/w), from 0.4% to 5% (w/w), from 0.5% to 5% (w/w), from 0.7% to 5% (w/w), from 0.8% to 5% (w/w), from 1% to 5% (w/w), from 1.5% to 5% (w/w), from 2% to 5% (w/w), from 2.5% to 5% (w/w), from 3% to 5% (w/w), or from 4% to 5% (w/w) of all other solid state crystalline forms of Compound A in total disclosed herein, or of a specified solid state crystalline form of Compound A disclosed herein, such as Compound A Form 1, Compound A Form 3, Compound A Form 4, Compound A Form 5, Compound A Form 6, Compound A Form 7, Compound A Form 8, Compound A Form 9, Compound A Form 10, or Compound A Form 11, or a combination of these.

In other embodiments, a solid state crystalline form of Compound A comprises at least 25% (w/w), at least 50% (w/w), at least 75% (w/w), at least 80% (w/w), at least 85% (w/w), at least 90% (w/w), at least 95% (w/w), at least 98% (w/w), or at least 99% (w/w) of Compound A Form 2.

5.2.3. Compound A Form 3 Mixtures

In some embodiments, a solid state crystalline form of Compound A contains Compound A Form 3 and 20% (w/w) or less, 19% (w/w) or less, 18% (w/w) or less, 17% (w/w) or less, 16% (w/w) or less, 15% (w/w) or less, 14% (w/w) or less, 13% (w/w) or less, 12% (w/w) or less, 11% (w/w) or less, 10% (w/w) or less, 9% (w/w) or less, 8% (w/w) or less, 7% (w/w) or less, 6% (w/w) or less, 5% (w/w) or less, 4% (w/w) or less, 3% (w/w) or less, 2% (w/w) or less, 1% (w/w) or less, 0.5% (w/w) or less, or 0.2% (w/w) or less of all other solid state crystalline forms of Compound A in total disclosed herein, or of a specified solid state crystalline form of Compound A disclosed herein, such as Compound A Form 1, Compound A Form 2, Compound A Form 4, Compound A Form 5, Compound A Form 6, Compound A Form 7, Compound A Form 8, Compound A Form 9, Compound A Form 10, or Compound A Form 11, or a combination of these.

In certain embodiments, a solid state crystalline form of Compound A contains Compound A Form 3 and from 0.1% to 20% (w/w), from 0.2% to 20% (w/w), from 0.5% to 20% (w/w), from 1% to 20% (w/w), from 2% to 20% (w/w), from 3% to 20% (w/w), from 4% to 20% (w/w), from 5% to 20% (w/w), from 6% to 20% (w/w), from 7% to 20% (w/w), from 8% to 20% (w/w), from 9% to 20% (w/w), from 10% to 20% (w/w), from 11% to 20% (w/w), from 12% to 20% (w/w), from 13% to 20% (w/w), from 14% to 20% (w/w), from 15% to 20% (w/w), from 16% to 20% (w/w), from 17% to 20% (w/w), from 18% to 20% (w/w), or from 19% to 20% (w/w) of all other solid state crystalline forms of Compound A in total disclosed herein, or of a specified solid state crystalline form of Compound A disclosed herein, such as Compound A Form 1, Compound A Form 2, Compound A Form 4, Compound A Form 5, Compound A Form 6, Compound A Form 7, Compound A Form 8, Compound A Form 9, Compound A Form 10, or Compound A Form 11, or a combination of these.

In some embodiments, a solid state crystalline form of Compound A contains Compound A Form 3 and from 0.1% to 15% (w/w), from 0.2% to 15% (w/w), from 0.5% to 15% (w/w), from 1% to 15% (w/w), from 2% to 15% (w/w), from 3% to 15% (w/w), from 4% to 15% (w/w), from 5% to 15% (w/w), from 6% to 15% (w/w), from 7% to 15% (w/w), from 8% to 15% (w/w), from 9% to 15% (w/w), from 10% to 15% (w/w), from 11% to 15% (w/w), from 12% to 15% (w/w), from 13% to 15% (w/w), or from 14% to 15% (w/w) of all other solid state crystalline forms of Compound A in total disclosed herein, or of a specified solid state crystalline form of Compound A disclosed herein, such as Compound A Form 1, Compound A Form 2, Compound A Form 4, Compound A Form 5, Compound A Form 6, Compound A Form 7, Compound A Form 8, Compound A Form 9, Compound A Form 10, or Compound A Form 11, or a combination of these.

In certain embodiments, a solid state crystalline form of Compound A contains Compound A Form 3 and from 0.1% to 10% (w/w), from 0.2% to 10% (w/w), from 0.5% to 10% (w/w), from 1% to 10% (w/w), from 2% to 10% (w/w), from 3% to 10% (w/w), from 4% to 10% (w/w), from 5% to 10% (w/w), from 6% to 10% (w/w), from 7% to 10% (w/w), from 8% to 10% (w/w), or from 9% to 10% (w/w) of all other solid state crystalline forms of Compound A in total disclosed herein, or of a specified solid state crystalline form of Compound A disclosed herein, such as Compound A Form 1, Compound A Form 2, Compound A Form 4, Compound A Form 5, Compound A Form 6, Compound A Form 7, Compound A Form 8, Compound A Form 9, Compound A Form 10, or Compound A Form 11, or a combination of these.

In some embodiments, a solid state crystalline form of Compound A contains Compound A Form 3 and from 0.2% to 5% (w/w), from 0.3% to 5% (w/w), from 0.4% to 5% (w/w), from 0.5% to 5% (w/w), from 0.7% to 5% (w/w), from 0.8% to 5% (w/w), from 1% to 5% (w/w), from 1.5% to 5% (w/w), from 2% to 5% (w/w), from 2.5% to 5% (w/w), from 3% to 5% (w/w), or from 4% to 5% (w/w) of all other solid state crystalline forms of Compound A in total disclosed herein, or of a specified solid state crystalline form of Compound A disclosed herein, such as Compound A Form 1, Compound A Form 2, Compound A Form 4, Compound A Form 5, Compound A Form 6, Compound A Form 7, Compound A Form 8, Compound A Form 9, Compound A Form 10, or Compound A Form 11, or a combination of these.

In other embodiments, a solid state form of Compound A comprises at least 25% (w/w), at least 50% (w/w), at least 75% (w/w), at least 80% (w/w), at least 85% (w/w), at least 90% (w/w), at least 95% (w/w), at least 98% (w/w), or at least 99% (w/w) of Compound A Form 3.

5.2.4. Compound A Form 4 Mixtures

In some embodiments, a solid state crystalline form of Compound A contains Compound A Form 4 and 20% (w/w) or less, 19% (w/w) or less, 18% (w/w) or less, 17% (w/w) or less, 16% (w/w) or less, 15% (w/w) or less, 14% (w/w) or less, 13% (w/w) or less, 12% (w/w) or less, 11% (w/w) or less, 10% (w/w) or less, 9% (w/w) or less, 8% (w/w) or less, 7% (w/w) or less, 6% (w/w) or less, 5% (w/w) or less, 4% (w/w) or less, 3% (w/w) or less, 2% (w/w) or less, 1% (w/w) or less, 0.5% (w/w) or less, or 0.2% (w/w) or less of all other solid state crystalline forms of Compound A in total disclosed herein, or of a specified solid state crystalline form of Compound A disclosed herein, such as Compound A Form 1, Compound A Form 2, Compound A Form 3, Compound A Form 5, Compound A Form 6, Compound A Form 7, Compound A Form 8, Compound A Form 9, Compound A Form 10, or Compound A Form 11, or a combination of these.

In certain embodiments, a solid state crystalline form of Compound A contains Compound A Form 4 and from 0.1% to 20% (w/w), from 0.2% to 20% (w/w), from 0.5% to 20% (w/w), from 1% to 20% (w/w), from 2% to 20% (w/w), from 3% to 20% (w/w), from 4% to 20% (w/w), from 5% to 20% (w/w), from 6% to 20% (w/w), from 7% to 20% (w/w), from 8% to 20% (w/w), from 9% to 20% (w/w), from 10% to 20% (w/w), from 11% to 20% (w/w), from 12% to 20% (w/w), from 13% to 20% (w/w), from 14% to 20% (w/w), from 15% to 20% (w/w), from 16% to 20% (w/w), from 17% to 20% (w/w), from 18% to 20% (w/w), or from 19% to 20% (w/w) of all other solid state crystalline forms of Compound A in total disclosed herein, or of a specified solid state crystalline form of Compound A disclosed herein, such as Compound A Form 1, Compound A Form 2, Compound A Form 3, Compound A Form 5, Compound A Form 6, Compound A Form 7, Compound A Form 8, Compound A Form 9, Compound A Form 10, or Compound A Form 11, or a combination of these.

In some embodiments, a solid state crystalline form of Compound A contains Compound A Form 4 and from 0.1% to 15% (w/w), from 0.2% to 15% (w/w), from 0.5% to 15% (w/w), from 1% to 15% (w/w), from 2% to 15% (w/w), from 3% to 15% (w/w), from 4% to 15% (w/w), from 5% to 15% (w/w), from 6% to 15% (w/w), from 7% to 15% (w/w), from 8% to 15% (w/w), from 9% to 15% (w/w), from 10% to 15% (w/w), from 11% to 15% (w/w), from 12% to 15% (w/w), from 13% to 15% (w/w), or from 14% to 15% (w/w) of all other solid state crystalline forms of Compound A in total disclosed herein, or of a specified solid state crystalline form of Compound A disclosed herein, such as Compound A Form 1, Compound A Form 2, Compound A Form 3, Compound A Form 5, Compound A Form 6, Compound A Form 7, Compound A Form 8, Compound A Form 9, Compound A Form 10, or Compound A Form 11, or a combination of these.

In certain embodiments, a solid state crystalline form of Compound A contains Compound A Form 4 and from 0.1% to 10% (w/w), from 0.2% to 10% (w/w), from 0.5% to 10% (w/w), from 1% to 10% (w/w), from 2% to 10% (w/w), from 3% to 10% (w/w), from 4% to 10% (w/w), from 5% to 10% (w/w), from 6% to 10% (w/w), from 7% to 10% (w/w), from 8% to 10% (w/w), or from 9% to 10% (w/w) of all other solid state crystalline forms of Compound A in total disclosed herein, or of a specified solid state crystalline form of Compound A disclosed herein, such as Compound A Form 1, Compound A Form 2, Compound A Form 3, Compound A Form 5, Compound A Form 6, Compound A Form 7, Compound A Form 8, Compound A Form 9, Compound A Form 10, or Compound A Form 11, or a combination of these.

In some embodiments, a solid state crystalline form of Compound A contains Compound A Form 4 and from 0.2% to 5% (w/w), from 0.3% to 5% (w/w), from 0.4% to 5% (w/w), from 0.5% to 5% (w/w), from 0.7% to 5% (w/w), from 0.8% to 5% (w/w), from 1% to 5% (w/w), from 1.5% to 5% (w/w), from 2% to 5% (w/w), from 2.5% to 5% (w/w), from 3% to 5% (w/w), or from 4% to 5% (w/w) of all other solid state crystalline forms of Compound A in total disclosed herein, or of a specified solid state crystalline form of Compound A disclosed herein, such as Compound A Form 1, Compound A Form 2, Compound A Form 3, Compound A Form 5, Compound A Form 6, Compound A Form 7, Compound A Form 8, Compound A Form 9, Compound A Form 10, or Compound A Form 11, or a combination of these.

In other embodiments, a solid state crystalline form of Compound A comprises at least 25% (w/w), at least 50% (w/w), at least 75% (w/w), at least 80% (w/w), at least 85% (w/w), at least 90% (w/w), at least 95% (w/w), at least 98% (w/w), or at least 99% (w/w) of Compound A Form 4.

5.2.5. Compound A Form 5 Mixtures

In some embodiments, a solid state crystalline form of Compound A contains Compound A Form 5 and 20% (w/w) or less, 19% (w/w) or less, 18% (w/w) or less, 17% (w/w) or less, 16% (w/w) or less, 15% (w/w) or less, 14% (w/w) or less, 13% (w/w) or less, 12% (w/w) or less, 11% (w/w) or less, 10% (w/w) or less, 9% (w/w) or less, 8% (w/w) or less, 7% (w/w) or less, 6% (w/w) or less, 5% (w/w) or less, 4% (w/w) or less, 3% (w/w) or less, 2% (w/w) or less, 1% (w/w) or less, 0.5% (w/w) or less, or 0.2% (w/w) or less of all other solid state crystalline forms of Compound A in total disclosed herein, or of a specified solid state crystalline form of Compound A disclosed herein, such as Compound A Form 1, Compound A Form 2, Compound A Form 3, Compound A Form 4, Compound A Form 6, Compound A Form 7, Compound A Form 8, Compound A Form 9, Compound A Form 10, or Compound A Form 11, or a combination of these.

In certain embodiments, a solid state crystalline form of Compound A contains Compound A Form 5 and from 0.1% to 20% (w/w), from 0.2% to 20% (w/w), from 0.5% to 20% (w/w), from 1% to 20% (w/w), from 2% to 20% (w/w), from 3% to 20% (w/w), from 4% to 20% (w/w), from 5% to 20% (w/w), from 6% to 20% (w/w), from 7% to 20% (w/w), from 8% to 20% (w/w), from 9% to 20% (w/w), from 10% to 20% (w/w), from 11% to 20% (w/w), from 12% to 20% (w/w), from 13% to 20% (w/w), from 14% to 20% (w/w), from 15% to 20% (w/w), from 16% to 20% (w/w), from 17% to 20% (w/w), from 18% to 20% (w/w), or from 19% to 20% (w/w) of all other solid state crystalline forms of Compound A in total disclosed herein, or of a specified solid state crystalline form of Compound A disclosed herein, such as Compound A Form 1, Compound A Form 2, Compound A Form 3, Compound A Form 4, Compound A Form 6, Compound A Form 7, Compound A Form 8, Compound A Form 9, Compound A Form 10, or Compound A Form 11, or a combination of these.

In some embodiments, a solid state crystalline form of Compound A contains Compound A Form 5 and from 0.1% to 15% (w/w), from 0.2% to 15% (w/w), from 0.5% to 15% (w/w), from 1% to 15% (w/w), from 2% to 15% (w/w), from 3% to 15% (w/w), from 4% to 15% (w/w), from 5% to 15% (w/w), from 6% to 15% (w/w), from 7% to 15% (w/w), from 8% to 15% (w/w), from 9% to 15% (w/w), from 10% to 15% (w/w), from 11% to 15% (w/w), from 12% to 15% (w/w), from 13% to 15% (w/w), or from 14% to 15% (w/w) of all other solid state crystalline forms of Compound A in total disclosed herein, or of a specified solid state crystalline form of Compound A disclosed herein, such as Compound A Form 1, Compound A Form 2, Compound A Form 3, Compound A Form 4, Compound A Form 6, Compound A Form 7, Compound A Form 8, Compound A Form 9, Compound A Form 10, or Compound A Form 11, or a combination of these.

In certain embodiments, a solid state crystalline form of Compound A contains Compound A Form 5 and from 0.1% to 10% (w/w), from 0.2% to 10% (w/w), from 0.5% to 10% (w/w), from 1% to 10% (w/w), from 2% to 10% (w/w), from 3% to 10% (w/w), from 4% to 10% (w/w), from 5% to 10% (w/w), from 6% to 10% (w/w), from 7% to 10% (w/w), from 8% to 10% (w/w), or from 9% to 10% (w/w) of all other solid state crystalline forms of Compound A in total disclosed herein, or of a specified solid state crystalline form of Compound A disclosed herein, such as Compound A Form 1, Compound A Form 2, Compound A Form 3, Compound A Form 4, Compound A Form 6, Compound A Form 7, Compound A Form 8, Compound A Form 9, Compound A Form 10, or Compound A Form 11, or a combination of these.

In some embodiments, a solid state crystalline form of Compound A contains Compound A Form 5 and from 0.2% to 5% (w/w), from 0.3% to 5% (w/w), from 0.4% to 5% (w/w), from 0.5% to 5% (w/w), from 0.7% to 5% (w/w), from 0.8% to 5% (w/w), from 1% to 5% (w/w), from 1.5% to 5% (w/w), from 2% to 5% (w/w), from 2.5% to 5% (w/w), from 3% to 5% (w/w), or from 4% to 5% (w/w) of all other solid state crystalline forms of Compound A in total disclosed herein, or of a specified solid state crystalline form of Compound A disclosed herein, such as Compound A Form 1, Compound A Form 2, Compound A Form 3, Compound A Form 4, Compound A Form 6, Compound A Form 7, Compound A Form 8, Compound A Form 9, Compound A Form 10, or Compound A Form 11, or a combination of these.

In other embodiments, a solid state crystalline form of Compound A comprises at least 25% (w/w), at least 50% (w/w), at least 75% (w/w), at least 80% (w/w), at least 85% (w/w), at least 90% (w/w), at least 95% (w/w), at least 98% (w/w), or at least 99% (w/w) of Compound A Form 5.

5.2.6. Compound A Form 6 Mixtures

In some embodiments, a solid state crystalline form of Compound A contains Compound A Form 6 and 20% (w/w) or less, 19% (w/w) or less, 18% (w/w) or less, 17% (w/w) or less, 16% (w/w) or less, 15% (w/w) or less, 14% (w/w) or less, 13% (w/w) or less, 12% (w/w) or less, 11% (w/w) or less, 10% (w/w) or less, 9% (w/w) or less, 8% (w/w) or less, 7% (w/w) or less, 6% (w/w) or less, 5% (w/w) or less, 4% (w/w) or less, 3% (w/w) or less, 2% (w/w) or less, 1% (w/w) or less, 0.5% (w/w) or less, or 0.2% (w/w) or less of all other solid state crystalline forms of Compound A in total disclosed herein, or of a specified solid state crystalline form of Compound A disclosed herein, such as Compound A Form 1, Compound A Form 2, Compound A Form 3, Compound A Form 4, Compound A Form 5, Compound A Form 7, Compound A Form 8, Compound A Form 9, Compound A Form 10, or Compound A Form 11, or a combination of these.

In certain embodiments, a solid state crystalline form of Compound A contains Compound A Form 6 and from 0.1% to 20% (w/w), from 0.2% to 20% (w/w), from 0.5% to 20% (w/w), from 1% to 20% (w/w), from 2% to 20% (w/w), from 3% to 20% (w/w), from 4% to 20% (w/w), from 5% to 20% (w/w), from 6% to 20% (w/w), from 7% to 20% (w/w), from 8% to 20% (w/w), from 9% to 20% (w/w), from 10% to 20% (w/w), from 11% to 20% (w/w), from 12% to 20% (w/w), from 13% to 20% (w/w), from 14% to 20% (w/w), from 15% to 20% (w/w), from 16% to 20% (w/w), from 17% to 20% (w/w), from 18% to 20% (w/w), or from 19% to 20% (w/w) of all other solid state crystalline forms of Compound A in total disclosed herein, or of a specified solid state crystalline form of Compound A disclosed herein, such as Compound A Form 1, Compound A Form 2, Compound A Form 3, Compound A Form 4, Compound A Form 5, Compound A Form 7, Compound A Form 8, Compound A Form 9, Compound A Form 10, or Compound A Form 11, or a combination of these.

In some embodiments, a solid state crystalline form of Compound A contains Compound A Form 6 and from 0.1% to 15% (w/w), from 0.2% to 15% (w/w), from 0.5% to 15% (w/w), from 1% to 15% (w/w), from 2% to 15% (w/w), from 3% to 15% (w/w), from 4% to 15% (w/w), from 5% to 15% (w/w), from 6% to 15% (w/w), from 7% to 15% (w/w), from 8% to 15% (w/w), from 9% to 15% (w/w), from 10% to 15% (w/w), from 11% to 15% (w/w), from 12% to 15% (w/w), from 13% to 15% (w/w), or from 14% to 15% (w/w) of all other solid state crystalline forms of Compound A in total disclosed herein, or of a specified solid state crystalline form of Compound A disclosed herein, such as Compound A Form 1, Compound A Form 2, Compound A Form 3, Compound A Form 4, Compound A Form 5, Compound A Form 7, Compound A Form 8, Compound A Form 9, Compound A Form 10, or Compound A Form 11, or a combination of these.

In certain embodiments, a solid state crystalline form of Compound A contains Compound A Form 6 and from 0.1% to 10% (w/w), from 0.2% to 10% (w/w), from 0.5% to 10% (w/w), from 1% to 10% (w/w), from 2% to 10% (w/w), from 3% to 10% (w/w), from 4% to 10% (w/w), from 5% to 10% (w/w), from 6% to 10% (w/w), from 7% to 10% (w/w), from 8% to 10% (w/w), or from 9% to 10% (w/w) of all other solid state crystalline forms of Compound A in total disclosed herein, or of a specified solid state crystalline form of Compound A disclosed herein, such as Compound A Form 1, Compound A Form 2, Compound A Form 3, Compound A Form 4, Compound A Form 5, Compound A Form 7, Compound A Form 8, Compound A Form 9, Compound A Form 10, or Compound A Form 11, or a combination of these.

In some embodiments, a solid state crystalline form of Compound A contains Compound A Form 6 and from 0.2% to 5% (w/w), from 0.3% to 5% (w/w), from 0.4% to 5% (w/w), from 0.5% to 5% (w/w), from 0.7% to 5% (w/w), from 0.8% to 5% (w/w), from 1% to 5% (w/w), from 1.5% to 5% (w/w), from 2% to 5% (w/w), from 2.5% to 5% (w/w), from 3% to 5% (w/w), or from 4% to 5% (w/w) of all other solid state crystalline forms of Compound A in total disclosed herein, or of a specified solid state crystalline form of Compound A disclosed herein, such as Compound A Form 1, Compound A Form 2, Compound A Form 3, Compound A Form 4, Compound A Form 5, Compound A Form 7, Compound A Form 8, Compound A Form 9, Compound A Form 10, or Compound A Form 11, or a combination of these.

In other embodiments, a solid state form of Compound A comprises at least 25% (w/w), at least 50% (w/w), at least 75% (w/w), at least 80% (w/w), at least 85% (w/w), at least 90% (w/w), at least 95% (w/w), at least 98% (w/w), or at least 99% (w/w) of Compound A Form 6.

5.2.7. Compound A Form 7 Mixtures

In some embodiments, a solid state crystalline form of Compound A contains Compound A Form 1 and 20% (w/w)

or less, 19% (w/w) or less, 18% (w/w) or less, 17% (w/w) or less, 16% (w/w) or less, 15% (w/w) or less, 14% (w/w) or less, 13% (w/w) or less, 12% (w/w) or less, 11% (w/w) or less, 10% (w/w) or less, 9% (w/w) or less, 8% (w/w) or less, 7% (w/w) or less, 6% (w/w) or less, 5% (w/w) or less, 4% (w/w) or less, 3% (w/w) or less, 2% (w/w) or less, 1% (w/w) or less, 0.5% (w/w) or less, or 0.2% (w/w) or less of all other solid state crystalline forms of Compound A in total disclosed herein, or of a specified solid state crystalline form of Compound A disclosed herein, such as Compound A Form 1, Compound A Form 2, Compound A Form 3, Compound A Form 4, Compound A Form 5, Compound A Form 6, Compound A Form 8, Compound A Form 9, Compound A Form 10, or Compound A Form 11, or a combination of these.

In certain embodiments, a solid state crystalline form of Compound A contains Compound A Form 7 and from 0.1% to 20% (w/w), from 0.2% to 20% (w/w), from 0.5% to 20% (w/w), from 1% to 20% (w/w), from 2% to 20% (w/w), from 3% to 20% (w/w), from 4% to 20% (w/w), from 5% to 20% (w/w), from 6% to 20% (w/w), from 7% to 20% (w/w), from 8% to 20% (w/w), from 9% to 20% (w/w), from 10% to 20% (w/w), from 11% to 20% (w/w), from 12% to 20% (w/w), from 13% to 20% (w/w), from 14% to 20% (w/w), from 15% to 20% (w/w), from 16% to 20% (w/w), from 17% to 20% (w/w), from 18% to 20% (w/w), or from 19% to 20% (w/w) of all other solid state crystalline forms of Compound A in total disclosed herein, or of a specified solid state crystalline form of Compound A disclosed herein, such as Compound A Form 1, Compound A Form 2, Compound A Form 3, Compound A Form 4, Compound A Form 5, Compound A Form 6, Compound A Form 8, Compound A Form 9, Compound A Form 10, or Compound A Form 11, or a combination of these.

In some embodiments, a solid state crystalline form of Compound A contains Compound A Form 7 and from 0.1% to 15% (w/w), from 0.2% to 15% (w/w), from 0.5% to 15% (w/w), from 1% to 15% (w/w), from 2% to 15% (w/w), from 3% to 15% (w/w), from 4% to 15% (w/w), from 5% to 15% (w/w), from 6% to 15% (w/w), from 7% to 15% (w/w), from 8% to 15% (w/w), from 9% to 15% (w/w), from 10% to 15% (w/w), from 11% to 15% (w/w), from 12% to 15% (w/w), from 13% to 15% (w/w), or from 14% to 15% (w/w) of all other solid state crystalline forms of Compound A in total disclosed herein, or of a specified solid state crystalline form of Compound A disclosed herein, such as Compound A Form 1, Compound A Form 2, Compound A Form 3, Compound A Form 4, Compound A Form 5, Compound A Form 6, Compound A Form 8, Compound A Form 9, Compound A Form 10, or Compound A Form 11, or a combination of these.

In certain embodiments, a solid state crystalline form of Compound A contains Compound A Form 7 and from 0.1% to 10% (w/w), from 0.2% to 10% (w/w), from 0.5% to 10% (w/w), from 1% to 10% (w/w), from 2% to 10% (w/w), from 3% to 10% (w/w), from 4% to 10% (w/w), from 5% to 10% (w/w), from 6% to 10% (w/w), from 7% to 10% (w/w), from 8% to 10% (w/w), or from 9% to 10% (w/w) of all other solid state crystalline forms of Compound A in total disclosed herein, or of a specified solid state crystalline form of Compound A disclosed herein, such as Compound A Form 1, Compound A Form 2, Compound A Form 3, Compound A Form 4, Compound A Form 5, Compound A Form 6, Compound A Form 8, Compound A Form 9, Compound A Form 10, or Compound A Form 11, or a combination of these.

In some embodiments, a solid state crystalline form of Compound A contains Compound A Form 7 and from 0.2% to 5% (w/w), from 0.3% to 5% (w/w), from 0.4% to 5% (w/w), from 0.5% to 5% (w/w), from 0.7% to 5% (w/w), from 0.8% to 5% (w/w), from 1% to 5% (w/w), from 1.5% to 5% (w/w), from 2% to 5% (w/w), from 2.5% to 5% (w/w), from 3% to 5% (w/w), or from 4% to 5% (w/w) of all other solid state crystalline forms of Compound A in total disclosed herein, or of a specified solid state crystalline form of Compound A disclosed herein, such as Compound A Form 1, Compound A Form 2, Compound A Form 3, Compound A Form 4, Compound A Form 5, Compound A Form 6, Compound A Form 8, Compound A Form 9, Compound A Form 10, or Compound A Form 11, or a combination of these.

In other embodiments, a solid state crystalline form of Compound A comprises at least 25% (w/w), at least 50% (w/w), at least 75% (w/w), at least 80% (w/w), at least 85% (w/w), at least 90% (w/w), at least 95% (w/w), at least 98% (w/w), or at least 99% (w/w) of Compound A Form 7.

5.2.8. Compound A Form 8 Mixtures

In some embodiments, a solid state crystalline form of Compound A contains Compound A Form 8 and 20% (w/w) or less, 19% (w/w) or less, 18% (w/w) or less, 17% (w/w) or less, 16% (w/w) or less, 15% (w/w) or less, 14% (w/w) or less, 13% (w/w) or less, 12% (w/w) or less, 11% (w/w) or less, 10% (w/w) or less, 9% (w/w) or less, 8% (w/w) or less, 7% (w/w) or less, 6% (w/w) or less, 5% (w/w) or less, 4% (w/w) or less, 3% (w/w) or less, 2% (w/w) or less, 1% (w/w) or less, 0.5% (w/w) or less, or 0.2% (w/w) or less of all other solid state crystalline forms of Compound A in total disclosed herein, or of a specified solid state crystalline form of Compound A disclosed herein, such as Compound A Form 1, Compound A Form 2, Compound A Form 3, Compound A Form 4, Compound A Form 5, Compound A Form 6, Compound A Form 7, Compound A Form 9, Compound A Form 10, or Compound A Form 11, or a combination of these.

In certain embodiments, a solid state crystalline form of Compound A contains Compound A Form 8 and from 0.1% to 20% (w/w), from 0.2% to 20% (w/w), from 0.5% to 20% (w/w), from 1% to 20% (w/w), from 2% to 20% (w/w), from 3% to 20% (w/w), from 4% to 20% (w/w), from 5% to 20% (w/w), from 6% to 20% (w/w), from 7% to 20% (w/w), from 8% to 20% (w/w), from 9% to 20% (w/w), from 10% to 20% (w/w), from 11% to 20% (w/w), from 12% to 20% (w/w), from 13% to 20% (w/w), from 14% to 20% (w/w), from 15% to 20% (w/w), from 16% to 20% (w/w), from 17% to 20% (w/w), from 18% to 20% (w/w), or from 19% to 20% (w/w) of all other solid state crystalline forms of Compound A in total disclosed herein, or of a specified solid state crystalline form of Compound A disclosed herein, such as Compound A Form 1, Compound A Form 2, Compound A Form 3, Compound A Form 4, Compound A Form 5, Compound A Form 6, Compound A Form 7, Compound A Form 9, Compound A Form 10, or Compound A Form 11, or a combination of these.

In some embodiments, a solid state crystalline form of Compound A contains Compound A Form 8 and from 0.1% to 15% (w/w), from 0.2% to 15% (w/w), from 0.5% to 15% (w/w), from 1% to 15% (w/w), from 2% to 15% (w/w), from 3% to 15% (w/w), from 4% to 15% (w/w), from 5% to 15% (w/w), from 6% to 15% (w/w), from 7% to 15% (w/w), from 8% to 15% (w/w), from 9% to 15% (w/w), from 10% to 15% (w/w), from 11% to 15% (w/w), from 12% to 15% (w/w), from 13% to 15% (w/w), or from 14% to 15% (w/w) of all other solid state crystalline forms of Compound A in total disclosed herein, or of a specified solid state crystalline form of Compound A disclosed herein, such as Compound A Form 1, Compound A Form 2, Compound A Form 3, Compound A Form 4, Compound A Form 5, Compound A Form 6, Compound A Form 7, Compound A Form 9, Compound A Form 10, or Compound A Form 11, or a combination of these.

In certain embodiments, a solid state crystalline form of Compound A contains Compound A Form 8 and from 0.1% to 10% (w/w), from 0.2% to 10% (w/w), from 0.5% to 10% (w/w), from 1% to 10% (w/w), from 2% to 10% (w/w), from 3% to 10% (w/w), from 4% to 10% (w/w), from 5% to 10% (w/w), from 6% to 10% (w/w), from 7% to 10% (w/w), from 8% to 10% (w/w), or from 9% to 10% (w/w) of all other solid state crystalline forms of Compound A in total disclosed herein, or of a specified solid state crystalline form of Compound A disclosed herein, such as Compound A Form 1, Compound A Form 2, Compound A Form 3, Compound A Form 4, Compound A Form 5, Compound A Form 6, Compound A Form 7, Compound A Form 9, Compound A Form 10, or Compound A Form 11, or a combination of these.

In some embodiments, a solid state crystalline form of Compound A contains Compound A Form 8 and from 0.2% to 5% (w/w), from 0.3% to 5% (w/w), from 0.4% to 5% (w/w), from 0.5% to 5% (w/w), from 0.7% to 5% (w/w), from 0.8% to 5% (w/w), from 1% to 5% (w/w), from 1.5% to 5% (w/w), from 2% to 5% (w/w), from 2.5% to 5% (w/w), from 3% to 5% (w/w), or from 4% to 5% (w/w) of all other solid state crystalline forms of Compound A in total disclosed herein, or of a specified solid state crystalline form of Compound A disclosed herein, such as Compound A Form 1, Compound A Form 2, Compound A Form 3, Compound A Form 4, Compound A Form 5, Compound A Form 6, Compound A Form 7, Compound A Form 9, Compound A Form 10, or Compound A Form 11, or a combination of these.

In other embodiments, a solid state crystalline form of Compound A comprises at least 25% (w/w), at least 50% (w/w), at least 75% (w/w), at least 80% (w/w), at least 85% (w/w), at least 90% (w/w), at least 95% (w/w), at least 98% (w/w), or at least 99% (w/w) of Compound A Form 8.

5.2.9. Compound A Form 9 Mixtures

In some embodiments, a solid state crystalline form of Compound A contains Compound A Form 9 and 20% (w/w) or less, 19% (w/w) or less, 18% (w/w) or less, 17% (w/w) or less, 16% (w/w) or less, 15% (w/w) or less, 14% (w/w) or less, 13% (w/w) or less, 12% (w/w) or less, 11% (w/w) or less, 10% (w/w) or less, 9% (w/w) or less, 8% (w/w) or less, 7% (w/w) or less, 6% (w/w) or less, 5% (w/w) or less, 4% (w/w) or less, 3% (w/w) or less, 2% (w/w) or less, 1% (w/w) or less, 0.5% (w/w) or less, or 0.2% (w/w) or less of all other solid state crystalline forms of Compound A in total disclosed herein, or of a specified solid state crystalline form of Compound A disclosed herein, such as Compound A Form 1, Compound A Form 2, Compound A Form 3, Compound A Form 4, Compound A Form 5, Compound A Form 6, Compound A Form 7, Compound A Form 8, Compound A Form 10, or Compound A Form 11, or a combination of these.

In certain embodiments, a solid state crystalline form of Compound A contains Compound A Form 9 and from 0.1% to 20% (w/w), from 0.2% to 20% (w/w), from 0.5% to 20% (w/w), from 1% to 20% (w/w), from 2% to 20% (w/w), from 3% to 20% (w/w), from 4% to 20% (w/w), from 5% to 20% (w/w), from 6% to 20% (w/w), from 7% to 20% (w/w), from 8% to 20% (w/w), from 9% to 20% (w/w), from 10% to 20% (w/w), from 11% to 20% (w/w), from 12% to 20% (w/w), from 13% to 20% (w/w), from 14% to 20% (w/w), from 15% to 20% (w/w), from 16% to 20% (w/w), from 17% to 20% (w/w), from 18% to 20% (w/w), or from 19% to 20% (w/w) of all other solid state crystalline forms of Compound A in total disclosed herein, or of a specified solid state crystalline form of Compound A disclosed herein, such as Compound A Form 1, Compound A Form 2, Compound A Form 3, Compound A Form 4, Compound A Form 5, Compound A Form 6, Compound A Form 7, Compound A Form 8, Compound A Form 10, or Compound A Form 11, or a combination of these.

In some embodiments, a solid state crystalline form of Compound A contains Compound A Form 9 and from 0.1% to 15% (w/w), from 0.2% to 15% (w/w), from 0.5% to 15% (w/w), from 1% to 15% (w/w), from 2% to 15% (w/w), from 3% to 15% (w/w), from 4% to 15% (w/w), from 5% to 15% (w/w), from 6% to 15% (w/w), from 7% to 15% (w/w), from 8% to 15% (w/w), from 9% to 15% (w/w), from 10% to 15% (w/w), from 11% to 15% (w/w), from 12% to 15% (w/w), from 13% to 15% (w/w), or from 14% to 15% (w/w) of all other solid state crystalline forms of Compound A in total disclosed herein, or of a specified solid state crystalline form of Compound A disclosed herein, such as Compound A Form 1, Compound A Form 2, Compound A Form 3, Compound A Form 4, Compound A Form 5, Compound A Form 6, Compound A Form 7, Compound A Form 8, Compound A Form 10, or Compound A Form 11, or a combination of these.

In certain embodiments, a solid state crystalline form of Compound A contains Compound A Form 9 and from 0.1% to 10% (w/w), from 0.2% to 10% (w/w), from 0.5% to 10% (w/w), from 1% to 10% (w/w), from 2% to 10% (w/w), from 3% to 10% (w/w), from 4% to 10% (w/w), from 5% to 10% (w/w), from 6% to 10% (w/w), from 7% to 10% (w/w), from 8% to 10% (w/w), or from 9% to 10% (w/w) of all other solid state crystalline forms of Compound A in total disclosed herein, or of a specified solid state crystalline form of Compound A disclosed herein, such as Compound A Form 1, Compound A Form 2, Compound A Form 3, Compound A Form 4, Compound A Form 5, Compound A Form 6, Compound A Form 7, Compound A Form 8, Compound A Form 10, or Compound A Form 11, or a combination of these.

In some embodiments, a solid state crystalline form of Compound A contains Compound A Form 9 and from 0.2% to 5% (w/w), from 0.3% to 5% (w/w), from 0.4% to 5% (w/w), from 0.5% to 5% (w/w), from 0.7% to 5% (w/w), from 0.8% to 5% (w/w), from 1% to 5% (w/w), from 1.5% to 5% (w/w), from 2% to 5% (w/w), from 2.5% to 5% (w/w), from 3% to 5% (w/w), or from 4% to 5% (w/w) of all other solid state crystalline forms of Compound A in total disclosed herein, or of a specified solid state crystalline form of Compound A disclosed herein, such as Compound A Form 1, Compound A Form 2, Compound A Form 3, Compound A Form 4, Compound A Form 5, Compound A Form 6, Compound A Form 7, Compound A Form 8, Compound A Form 10, or Compound A Form 11, or a combination of these.

In other embodiments, a solid state crystalline form of Compound A comprises at least 25% (w/w), at least 50% (w/w), at least 75% (w/w), at least 80% (w/w), at least 85%

(w/w), at least 90% (w/w), at least 95% (w/w), at least 98% (w/w), or at least 99% (w/w) of Compound A Form 9.

5.2.10. Compound A Form 10 Mixtures

In some embodiments, a solid state crystalline form of Compound A contains Compound A Form 10 and 20% (w/w) or less, 19% (w/w) or less, 18% (w/w) or less, 17% (w/w) or less, 16% (w/w) or less, 15% (w/w) or less, 14% (w/w) or less, 13% (w/w) or less, 12% (w/w) or less, 11% (w/w) or less, 10% (w/w) or less, 9% (w/w) or less, 8% (w/w) or less, 7% (w/w) or less, 6% (w/w) or less, 5% (w/w) or less, 4% (w/w) or less, 3% (w/w) or less, 2% (w/w) or less, 1% (w/w) or less, 0.5% (w/w) or less, or 0.2% (w/w) or less of all other solid state crystalline forms of Compound A in total disclosed herein, or of a specified solid state crystalline form of Compound A disclosed herein, such as Compound A Form 1, Compound A Form 2, Compound A Form 3, Compound A Form 4, Compound A Form 5, Compound A Form 6, Compound A Form 7, Compound A Form 6, Compound A Form 9, or Compound A Form 11, or a combination of these.

In certain embodiments, a solid state crystalline form of Compound A contains Compound A Form 10 and from 0.1% to 20% (w/w), from 0.2% to 20% (w/w), from 0.5% to 20% (w/w), from 1% to 20% (w/w), from 2% to 20% (w/w), from 3% to 20% (w/w), from 4% to 20% (w/w), from 5% to 20% (w/w), from 6% to 20% (w/w), from 7% to 20% (w/w), from 8% to 20% (w/w), from 9% to 20% (w/w), from 10% to 20% (w/w), from 11% to 20% (w/w), from 12% to 20% (w/w), from 13% to 20% (w/w), from 14% to 20% (w/w), from 15% to 20% (w/w), from 16% to 20% (w/w), from 17% to 20% (w/w), from 18% to 20% (w/w), or from 19% to 20% (w/w) of all other solid state crystalline forms of Compound A in total disclosed herein, or of a specified solid state crystalline form of Compound A disclosed herein, such as Compound A Form 1, Compound A Form 2, Compound A Form 3, Compound A Form 4, Compound A Form 5, Compound A Form 6, Compound A Form 7, Compound A Form 8, Compound A Form 9, or Compound A Form 11, or a combination of these.

In some embodiments, a solid state crystalline form of Compound A contains Compound A Form 10 and from 0.1% to 15% (w/w), from 0.2% to 15% (w/w), from 0.5% to 15% (w/w), from 1% to 15% (w/w), from 2% to 15% (w/w), from 3% to 15% (w/w), from 4% to 15% (w/w), from 5% to 15% (w/w), from 6% to 15% (w/w), from 7% to 15% (w/w), from 8% to 15% (w/w), from 9% to 15% (w/w), from 10% to 15% (w/w), from 11% to 15% (w/w), from 12% to 15% (w/w), from 13% to 15% (w/w), or from 14% to 15% (w/w) of all other solid state crystalline forms of Compound A in total disclosed herein, or of a specified solid state crystalline form of Compound A disclosed herein, such as Compound A Form 1, Compound A Form 2, Compound A Form 3, Compound A Form 4, Compound A Form 5, Compound A Form 6, Compound A Form 7, Compound A Form 8, Compound A Form 9, or Compound A Form 11, or a combination of these.

In certain embodiments, a solid state crystalline form of Compound A contains Compound A Form 10 and from 0.1% to 10% (w/w), from 0.2% to 10% (w/w), from 0.5% to 10% (w/w), from 1% to 10% (w/w), from 2% to 10% (w/w), from 3% to 10% (w/w), from 4% to 10% (w/w), from 5% to 10% (w/w), from 6% to 10% (w/w), from 7% to 10% (w/w), from 8% to 10% (w/w), or from 9% to 10% (w/w) of all other solid state crystalline forms of Compound A in total disclosed herein, or of a specified solid state crystalline form of Compound A disclosed herein, such as Compound A Form 1, Compound A Form 2, Compound A Form 3, Compound A Form 4, Compound A Form 5, Compound A Form 6, Compound A Form 7, Compound A Form 8, Compound A Form 9, or Compound A Form 11, or a combination of these.

In some embodiments, a solid state crystalline form of Compound A contains Compound A Form 10 and from 0.2% to 5% (w/w), from 0.3% to 5% (w/w), from 0.4% to 5% (w/w), from 0.5% to 5% (w/w), from 0.7% to 5% (w/w), from 0.8% to 5% (w/w), from 1% to 5% (w/w), from 1.5% to 5% (w/w), from 2% to 5% (w/w), from 2.5% to 5% (w/w), from 3% to 5% (w/w), or from 4% to 5% (w/w) of all other solid state crystalline forms of Compound A in total disclosed herein, or of a specified solid state crystalline form of Compound A disclosed herein, such as Compound A Form 1, Compound A Form 2, Compound A Form 3, Compound A Form 4, Compound A Form 5, Compound A Form 6, Compound A Form 7, Compound A Form 8, Compound A Form 9, or Compound A Form 11, or a combination of these.

In other embodiments, a solid state crystalline form of Compound A comprises at least 25% (w/w), at least 50% (w/w), at least 75% (w/w), at least 80% (w/w), at least 85% (w/w), at least 90% (w/w), at least 95% (w/w), at least 98% (w/w), or at least 99% (w/w) of Compound A Form 10.

5.2.11. Compound A Form 11 Mixtures

In some embodiments, a solid state crystalline form of Compound A contains Compound A Form 11 and 20% (w/w) or less, 19% (w/w) or less, 18% (w/w) or less, 17% (w/w) or less, 16% (w/w) or less, 15% (w/w) or less, 14% (w/w) or less, 13% (w/w) or less, 12% (w/w) or less, 11% (w/w) or less, 10% (w/w) or less, 9% (w/w) or less, 8% (w/w) or less, 7% (w/w) or less, 6% (w/w) or less, 5% (w/w) or less, 4% (w/w) or less, 3% (w/w) or less, 2% (w/w) or less, 1% (w/w) or less, 0.5% (w/w) or less, or 0.2% (w/w) or less of all other solid state crystalline forms of Compound A in total disclosed herein, or of a specified solid state crystalline form of Compound A disclosed herein, such as Compound A Form 1, Compound A Form 2, Compound A Form 3, Compound A Form 4, Compound A Form 5, Compound A Form 6, Compound A Form 7, Compound A Form 8, Compound A Form 9, or Compound A Form 10, or a combination of these.

In certain embodiments, a solid state crystalline form of Compound A contains Compound A Form 11 and from 0.1% to 20% (w/w), from 0.2% to 20% (w/w), from 0.5% to 20% (w/w), from 1% to 20% (w/w), from 2% to 20% (w/w), from 3% to 20% (w/w), from 4% to 20% (w/w), from 5% to 20% (w/w), from 6% to 20% (w/w), from 7% to 20% (w/w), from 8% to 20% (w/w), from 9% to 20% (w/w), from 10% to 20% (w/w), from 11% to 20% (w/w), from 12% to 20% (w/w), from 13% to 20% (w/w), from 14% to 20% (w/w), from 15% to 20% (w/w), from 16% to 20% (w/w), from 17% to 20% (w/w), from 18% to 20% (w/w), or from 19% to 20% (w/w) of all other solid state crystalline forms of Compound A in total disclosed herein, or of a specified solid state crystalline form of Compound A disclosed herein, such as Compound A Form 1, Compound A Form 2, Compound A Form 3, Compound A Form 4, Compound A Form 5, Compound A Form 6, Compound A Form 7, Compound A Form 8, Compound A Form 9, or Compound A Form 10, or a combination of these.

In some embodiments, a solid state crystalline form of Compound A contains Compound A Form 11 and from 0.1% to 15% (w/w), from 0.2% to 15% (w/w), from 0.5% to 15% (w/w), from 1% to 15% (w/w), from 2% to 15% (w/w), from 3% to 15% (w/w), from 4% to 15% (w/w), from 5% to 15% (w/w), from 6% to 15% (w/w), from 7% to 15% (w/w), from 8% to 15% (w/w), from 9% to 15% (w/w), from 10% to 15% (w/w), from 11% to 15% (w/w), from 12% to 15% (w/w), from 13% to 15% (w/w), or from 14% to 15% (w/w) of all other solid state crystalline forms of Compound A in total disclosed herein, or of a specified solid state crystalline form of Compound A disclosed herein, such as Compound A Form 1, Compound A Form 2, Compound A Form 3, Compound A Form 4, Compound A Form 5, Compound A Form 6, Compound A Form 7, Compound A Form 8, Compound A Form 9, Compound A Form 10, or a combination of these.

In certain embodiments, a solid state crystalline form of Compound A contains Compound A Form 11 and from 0.1% to 10% (w/w), from 0.2% to 10% (w/w), from 0.5% to 10% (w/w), from 1% to 10% (w/w), from 2% to 10% (w/w), from 3% to 10% (w/w), from 4% to 10% (w/w), from 5% to 10% (w/w), from 6% to 10% (w/w), from 7% to 10% (w/w), from 8% to 10% (w/w), or from 9% to 10% (w/w) of all other solid state crystalline forms of Compound A in total disclosed herein, or of a specified solid state crystalline form of Compound A disclosed herein, such as Compound A Form 1, Compound A Form 2, Compound A Form 3, Compound A Form 4, Compound A Form 5, Compound A Form 6, Compound A Form 7, Compound A Form 8, Compound A Form 9, Compound A Form 10, or a combination of these.

In some embodiments, a solid state crystalline form of Compound A contains Compound A Form 11 and from 0.2% to 5% (w/w), from 0.3% to 5% (w/w), from 0.4% to 5% (w/w), from 0.5% to 5% (w/w), from 0.7% to 5% (w/w), from 0.8% to 5% (w/w), from 1% to 5% (w/w), from 1.5% to 5% (w/w), from 2% to 5% (w/w), from 2.5% to 5% (w/w), from 3% to 5% (w/w), or from 4% to 5% (w/w) of all other solid state f crystalline forms of Compound A in total disclosed herein, or of a specified solid state crystalline form of Compound A disclosed herein, such as Compound A Form 1, Compound A Form 2, Compound A Form 3, Compound A Form 4, Compound A Form 5, Compound A Form 6, Compound A Form 7, Compound A Form 8, Compound A Form 9, Compound A Form 10, or a combination of these.

In other embodiments, a solid state crystalline form of Compound A comprises at least 25% (w/w), at least 50% (w/w), at least 75% (w/w), at least 80% (w/w), at least 85% (w/w), at least 90% (w/w), at least 95% (w/w), at least 98% (w/w), or at least 99% (w/w) of Compound A Form 11.

5.2.12. Methods of Treating Using Solid Forms of Compound A

In some embodiments, the present disclosure is directed to a method of treating a disease, disorder, or condition associated with Kv7 potassium channel dysfunction in a human in need thereof, comprising orally administering a therapeutically effective amount of a solid state form, such as a crystalline form, of Compound A to the human. In certain instances, the disease, disorder, or condition associated with Kv7 potassium channel dysfunction is a seizure disorder, such as focal onset epilepsy. In certain embodiments, the solid state form of Compound A is Form 1, Form 2, Form 3, Form 4, Form 5, Form 6, Form 7, Form 8, Form 9, Form 10, or Form 11.

In some embodiments, the present disclosure is directed to a compound for use in treating a disease, disorder, or condition associated with Kv7 potassium channel dysfunction in a human in need thereof, wherein the compound is a solid state form of Compound A and a therapeutically effective amount of the compound is orally administered to the human. In certain instances, the disease, disorder, or condition associated with Kv7 potassium channel dysfunction is a seizure disorder, such as focal onset epilepsy. In certain embodiments, the solid state form of Compound A is Form 1, Form 2, Form 3, Form 4, Form 5, Form 6, Form 7, Form 8, Form 9, Form 10, or Form 11.

In embodiments directed to a disease, disorder, or condition associated with Kv7 potassium channel dysfunction, in some instances, the method enhances opening of a Kv7 potassium channel, such as one or more of Kv7.2, Kv7.3, Kv7.4, and Kv7.5. In certain instances, the method or use is selective for enhancing the opening of a Kv7 potassium channel selected from one or more of Kv7.2, Kv7.3, Kv7.4, and Kv7.5 over Kv7.1. In some embodiments, the method or use is selective for Kv7.2, optionally over Kv7.1. In other embodiments, the method or use is selective for Kv7.3, optionally over Kv7.1. In yet other embodiments, the method or use is selective for Kv7.4, optionally over Kv7.1. In yet further other embodiments, the method or use is selective for Kv7.5, optionally over Kv7.1. In certain embodiments, the method or use is selective for Kv7.2 and Kv7.3, optionally over Kv7.1.

In one embodiment, the present disclosure provides a method of treating a seizure disorder in a human in need thereof, comprising orally administering an amount of a solid state form of Compound A to the human, wherein the amount of the solid state form of Compound A is sufficient to treat the seizure disorder in the human. In certain embodiments, the amount is sufficient to reduce the severity of seizures, the frequency of seizures, or both. In certain embodiments, the solid state form of Compound A is Form 1, Form 2, Form 3, Form 4, Form 5, Form 6, Form 7, Form 8, Form 9, Form 10, or Form 11.

In one embodiment, the present disclosure provides a compound for use in treating a seizure disorder in a human in need thereof, wherein the compound is a solid state form of Compound A and the compound is orally administered to the human. In certain embodiments, the amount is sufficient to reduce the severity of seizures, the frequency of seizures, or both. In certain embodiments, the solid state form of Compound A is Form 1, Form 2, Form 3, Form 4, Form 5, Form 6, Form 7, Form 8, Form 9, Form 10, or Form 11.

In one embodiment, the present disclosure provides a method of treating a seizure disorder in a human in need thereof, comprising orally administering an amount of a solid state form of Compound A to the human, wherein the amount of the solid state form of Compound A is from 2 to 200 mg. In certain embodiments, 2 to 200 mg of Compound A Form 1, Form 2, Form 3, Form 4, Form 5, Form 6, Form 7, Form 8, Form 9, Form 10, or Form 11, is orally administered.

In some embodiments, the present disclosure is directed to a method of treating a disease, disorder, or condition associated with Kv7 potassium channel dysfunction in a human in need thereof, comprising orally administering a therapeutically effective amount of a solid state form of Compound A to the human under fed conditions. In certain instances, the disease, disorder, or condition associated with Kv7 potassium channel dysfunction is a seizure disorder, such as focal onset epilepsy. In certain embodiments, the solid state form of Compound A is Form 1, Form 2, Form 3, Form 4, Form 5, Form 6, Form 7, Form 8, Form 9, Form 10, or Form 11.

In certain embodiments, the present disclosure is directed to a method of treating a disease, disorder, or condition associated with Kv7 potassium channel dysfunction in a human in need thereof, comprising orally administering a therapeutically effective amount of a solid state form of Compound A to the human from between 30 minutes prior to consuming food until 2 hours after consuming food. In certain instances, the disease, disorder, or condition associated with Kv7 potassium channel dysfunction is a seizure disorder, such as focal onset epilepsy. In certain embodiments, the solid state form of Compound A is Form 1, Form 2, Form 3, Form 4, Form 5, Form 6, Form 7, Form 8, Form 9, Form 10, or Form 11.

In some embodiments, the present disclosure is directed to a compound for use in treating a disease, disorder, or condition associated with Kv7 potassium channel dysfunction in a human in need thereof, wherein the compound is a solid state form of Compound A and a therapeutically effective amount of the compound is orally administered to the human under fed conditions. In certain instances, the disease, disorder, or condition associated with Kv7 potassium channel dysfunction is a seizure disorder, such as focal onset epilepsy. In certain embodiments, the solid state form of Compound A is Form 1, Form 2, Form 3, Form 4, Form 5, Form 6, Form 7, Form 8, Form 9, Form 10, or Form 11.

In certain embodiments, the present disclosure is directed to a compound for use in treating a disease, disorder, or condition associated with Kv7 potassium channel dysfunction in a human in need thereof, wherein the compound is a solid state form of Compound A and a therapeutically effective amount of the compound is orally administered to the human from between 30 minutes prior to consuming food until 2 hours after consuming food. In certain instances, the disease, disorder, or condition associated with Kv7 potassium channel dysfunction is a seizure disorder, such as focal onset epilepsy. In certain embodiments, the solid state form of Compound A is Form 1, Form 2, Form 3, Form 4, Form 5, Form 6, Form 7, Form 8, Form 9, Form 10, or Form 11.

In one embodiment, the present disclosure provides a method of treating a seizure disorder in a human in need thereof, comprising orally administering an amount of a solid state form of Compound A to the human under fed conditions, wherein the amount of Compound A is sufficient to treat the seizure disorder in the human. In certain embodiments, the amount is sufficient to reduce the severity of seizures, the frequency of seizures, or both. In certain embodiments, the solid state form of Compound A is Form 1, Form 2, Form 3, Form 4, Form 5, Form 6, Form 7, Form 8, Form 9, Form 10, or Form 11.

In one embodiment, the present disclosure provides a compound for use in treating a seizure disorder in a human in need thereof, wherein the compound is a solid state form of Compound A and the compound is orally administered to the human under fed conditions. In certain embodiments, the amount is sufficient to reduce the severity of seizures, the frequency of seizures, or both. In certain embodiments, the solid state form of Compound A is Form 1, Form 2, Form 3, Form 4, Form 5, Form 6, Form 7, Form 8, Form 9, Form 10, or Form 11.

In one embodiment, the present disclosure provides a method of treating a seizure disorder in a human in need thereof, comprising orally administering an amount of a solid state form of Compound A to the human from between 30 minutes prior to consuming food until 2 hours after consuming food, wherein the amount of a solid state form of Compound A is sufficient to treat the seizure disorder in the human. In certain embodiments, the amount is sufficient to reduce the severity of seizures, the frequency of seizures, or both. In certain embodiments, the solid state form of Compound A is Form 1, Form 2, Form 3, Form 4, Form 5, Form 6, Form 7, Form 8, Form 9, Form 10, or Form 11.

In one embodiment, the present disclosure provides a compound for use in treating a seizure disorder in a human in need thereof, wherein the compound is a solid state form of Compound A and the compound is orally administered to the human from between 30 minutes prior to consuming food until 2 hours after consuming food. In certain embodiments, the amount is sufficient to reduce the severity of seizures, the frequency of seizures, or both. In certain embodiments, the solid state form of Compound A is Form 1, Form 2, Form 3, Form 4, Form 5, Form 6, Form 7, Form 8, Form 9, Form 10, or Form 11.

In one embodiment, the present disclosure provides a method of treating a seizure disorder in a human in need thereof, comprising orally administering an amount of a solid state form of Compound A to the human under fed conditions, wherein the amount of the solid state form of Compound A is from 2 to 200 mg. In certain embodiments, 2 to 200 mg of Compound A Form 1, Form 2, Form 3, Form 4, Form 5, Form 6, Form 7, Form 8, Form 9, Form 10, or Form 11, is orally administered.

In one embodiment, the present disclosure provides a method of treating a seizure disorder in a human in need thereof, comprising orally administering an amount of a solid state form of Compound A to the human from between 30 minutes prior to consuming food until 2 hours after consuming food, wherein the amount of the solid state form of Compound A is from 2 to 200 mg. In certain embodiments, 2 to 200 mg of Compound A Form 1, Form 2, Form 3, Form 4, Form 5, Form 6, Form 7, Form 8, Form 9, Form 10, or Form 11, is orally administered.

In one embodiment, the present disclosure provides a method of increasing one or more of the $C_{max}$, $AUC_{inf}$, $T_{max}$, or $t1/2_{\lambda z}$ of a solid state form of Compound A (e.g., Form 1, Form 2, Form 3, Form 4, Form 5, Form 6, Form 7, Form 8, Form 9, Form 10, or Form 11) in a human receiving an oral administration of the solid state form of Compound A, comprising orally administering an amount of the solid state form of Compound A to the human under fed conditions. In certain embodiments, the method increases one or more of $C_{max}$, $AUC_{inf}$, $T_{max}$, or $t1/2_{\lambda z}$ as compared to when the same amount of the solid state form of Compound A is orally administered to the human under fasted conditions.

In one embodiment, the present disclosure provides a method of increasing one or more of the $C_{max}$, $AUC_{inf}$, $T_{max}$, or $t1/2_{\lambda z}$ of a solid state form of Compound A (e.g., Form 1, Form 2, Form 3, Form 4, Form 5, Form 6, Form 7, Form 8, Form 9, Form 10, or Form 11) in a human receiving an oral administration of the solid state form of Compound A, comprising orally administering an amount of the solid state form of Compound A to the human from between 30 minutes prior to consuming food until 2 hours after consuming food. In certain embodiments, the method increases one or more of $C_{max}$, $AUC_{inf}$, $T_{max}$, or $t1/2_{\lambda z}$ as compared to when the same amount of the solid state form of Compound A is orally administered to the human under fasted conditions.

In one embodiment, the present disclosure provides a method of orally administering a solid state form of Compound A (e.g., Form 1, Form 2, Form 3, Form 4, Form 5, Form 6, Form 7, Form 8, Form 9, Form 10, or Form 11) to a human in need thereof, comprising orally administering the solid state form of Compound A to the human under fed conditions. In certain embodiments, the method increases one or more of $C_{max}$, $AUC_{inf}$, $T_{max}$, or $t1/2_{\lambda z}$ of a solid state form of Compound A as compared to when the same amount of the solid state form of Compound A is orally administered to the human under fasted conditions.

In one embodiment, the present disclosure provides a method of orally administering a solid state form of Compound A (e.g., Form 1, Form 2, Form 3, Form 4, Form 5, Form 6, Form 7, Form 8, Form 9, Form 10, or Form 11) to a human in need thereof, comprising orally administering the solid state form of Compound A to the human from between 30 minutes prior to consuming food until 2 hours after consuming food. In certain embodiments, the method increases one or more of $C_{max}$, $AUC_{inf}$, $T_{max}$, or $t1/2_{\lambda z}$ of a solid state form of Compound A as compared to when the same amount of the solid state form of Compound A is orally administered to the human under fasted conditions.

In one embodiment, a solid state form of Compound A (e.g., Form 1, Form 2, Form 3, Form 4, Form 5, Form 6, Form 7, Form 8, Form 9, Form 10, or Form 11) is provided in a dosage unit form suitable for oral administration. Compound A is present in the dosage unit form at a level ranging from about of 0.05 mg/kg to about 2.0 mg/kg. More specific representative levels include 0.05 mg/kg, 0.10 mg/kg, 0.20 mg/kg, 0.30 mg/kg, 0.40 mg/kg, 0.5 mg/kg, 0.6 mg/kg, 0.7 mg/kg, 0.80 mg/kg, 0.90 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg and 2.0 mg/kg. In some aspects, the method includes orally administering 0.1-1.0 mg/kg of a solid state form of Compound A. In some aspects, the method includes orally administering 0.2-0.5 mg/kg of a solid state form of Compound A.

In some embodiments, the methods and uses described herein, such as the method of or use in treating a seizure disorder in a human in need thereof according to the methods and uses described herein, is achieved by orally administering 2 to 200 mg of a solid state form of Compound A (e.g., Form 1, Form 2, Form 3, Form 4, Form 5, Form 6, Form 7, Form 8, Form 9, Form 10, or Form 11). For example, the method can include orally administering about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 51 mg, about 52 mg, about 53 mg, about 54 mg, about 55 mg, about 56 mg, about 57 mg, about 58 mg, about 59 mg, about 60 mg, about 61 mg, about 62 mg, about 63 mg, about 64 mg, about 65 mg, about 66 mg, about 67 mg, about 68 mg, about 69 mg, about 70 mg, about 71 mg, about 72 mg, about 73 mg, about 74 mg, about 75 mg, about 76 mg, about 77 mg, about 78 mg, about 79 mg, about 80 mg, about 81 mg, about 82 mg, about 83 mg, about 84 mg, about 85 mg, about 86 mg, about 87 mg, about 88 mg, about 89 mg, about 90 mg, about 91 mg, about 92 mg, about 93 mg, about 94 mg, about 95 mg, about 96 mg, about 97 mg, about 98 mg, about 99 mg, about 100 mg, about 101 mg, about 102 mg, about 103 mg, about 104 mg, about 105 mg, about 106 mg, about 107 mg, about 108 mg, about 109 mg, about 110 mg, about 111 mg, about 112 mg, about 113 mg, about 114 mg, about 115 mg, about 116 mg, about 117 mg, about 118 mg, about 119 mg, about 120 mg, about 121 mg, about 122 mg, about 123 mg, about 124 mg, about 125 mg, about 126 mg, about 127 mg, about 129 mg, about 130 mg, about 131 mg, about 132 mg, about 133 mg, about 134 mg, about 135 mg, about 136 mg, about 137 mg, about 138 mg, about 139 mg, about 140 mg, about 141 mg, about 142 mg, about 143 mg, about 144 mg, about 145 mg, about 146 mg, about 147 mg, about 148 mg, about 149 mg, about 150 mg, about 151 mg, about 152 mg, about 153 mg, about 154 mg, about 155 mg, about 156 mg, about 157 mg, about 158 mg, about 159 mg, about 160 mg, about 161 mg, about 162 mg, about 163 mg, about 164 mg, about 165 mg, about 166 mg, about 167 mg, about 168 mg, about 169 mg, about 170 mg, about 171 mg, about 172 mg, about 173 mg, about 174 mg, about 175 mg, about 176 mg, about 177 mg, about 178 mg, about 179 mg, about 180 mg, about 181 mg, about 182 mg, about 183 mg, about 184 mg, about 185 mg, about 186 mg, about 187 mg, about 188 mg, about 189 mg, about 190 mg, about 191 mg, about 192 mg, about 193 mg, about 194 mg, about 195 mg, about 196 mg, about 197 mg, about 198 mg, about 199 mg, or about 200 mg. In some aspects, the oral administration includes 5 to 50 mg of Compound A. In some aspects, the oral administration includes 10, 20, or 25 mg of Compound A. In some aspects, the oral administration includes 20 mg of Compound A. In some aspects, the oral administration includes at least 20 mg of Compound A.

In some embodiments, the methods and uses described herein, such as the method of or use in treating a seizure disorder in a human in need thereof according to the methods and uses described herein, is achieved by orally administering 5 to 1000 mg of a solid state form of Compound A (e.g., Form 1, Form 2, Form 3, Form 4, Form 5, Form 6, Form 7, Form 8, Form 9, Form 10, or Form 11) per day, such as 5 to 500 mg or 5 to 250 mg of the solid state form of Compound A per day. For example, the method can include orally administering about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 105 mg, about 110 mg, about 115 mg, about 120 mg, about 125 mg, about 130 mg, about 135 mg, about 140 mg, about 145 mg, about 150 mg, about 155 mg, about 160 mg, about 165 mg, about 170 mg, about 175 mg, about 180 mg, about 185 mg, about 190 mg, about 195 mg, about 200 mg, about 205 mg, about 210 mg, about 215 mg, about 220 mg, about 225 mg, about 230 mg, about 235 mg, about 240 mg, about 245 mg, about 250 mg, about 255 mg, about 260 mg, about 265 mg, about 270 mg, about 275 mg, about 280 mg, about 285 mg, about 290 mg, about 295 mg, about 300 mg, about 305 mg, about 310 mg, about 315 mg, about 320 mg, about 325 mg, about 330 mg, about 335 mg, about 340 mg, about 345 mg, about 350 mg, about 355 mg, about 360 mg, about 365 mg, about 370 mg, about 375 mg, about 380 mg, about 385 mg, about 390 mg, about 395 mg, about 400 mg, about 405 mg, about 410 mg, about 415 mg, about 420 mg, about 425 mg, about 430 mg, about 435 mg, about 440 mg, about 445 mg, about 450 mg, about 455 mg, about 460 mg, about 465 mg, about 470 mg, about 475 mg, about 480 mg, about 485 mg, about 490 mg, about 495 mg, about 500 mg, or about 1000 mg per day. In some aspects, the oral administration includes orally administering 10-200 mg of a solid state form of Compound A per day, such as 10, 15, 20, 25, 30, 35, or 40 mg to 75, 100, 125, 150, 175, or 200 mg of the solid state form of Compound A per day, including 20 to 150 mg per day. In some aspects, the oral administration includes 50, 75, 100, or 125 mg of a solid state form of Compound A per day, such as 100 mg per day.

In certain instances, the above daily doses of a solid state form of Compound A are orally administered as multiple doses per day, such as in two, three, four, or five doses per day. For Example, a daily dose of 100 mg, maybe administered in four 25 mg doses throughout the day.

In some embodiments, the above daily doses of a solid state form of Compound A are orally administered as a single dose. For example, about 5, 10, 15, 20, 25, or 30 mg to about 50, 65, 75, 100, 125, or 150 mg of a solid state form of Compound A per day can be orally administered as a single dose, including 10-25 mg, 10-30 mg, and 10-40 mg per day as a single dose, such as 10-25 mg per day as a single dose.

In one embodiment of the present disclosure, administration of a solid state form of Compound A, such as for treating a seizure disorder, would benefit from the opening of the Kv7.2/Kv7.3 (KCNQ2/3) potassium channel. Compound A is a Kv7.2/Kv7.3 (KCNQ2/3) opener. In certain embodiments, the present disclosure provides a method of opening of the Kv7.2/Kv7.3 (KCNQ2/3) potassium channel in a human in need thereof comprising administering an amount of a solid state form of Compound A (e.g., Form 1, Form 2, Form 3, Form 4, Form 5, Form 6, Form 7, Form 8, Form 9, Form 10, or Form 11). In similar embodiments, the present disclosure provides a solid state form of Compound A for use in opening of the Kv7.2/Kv7.3 (KCNQ2/3) potassium channel in a human in need thereof.

In certain embodiments, the methods and uses described herein administer a solid state form of Compound A in the form of a pharmaceutically acceptable oral composition that comprises the solid state form of Compound A (e.g., Form 1, Form 2, Form 3, Form 4, Form 5, Form 6, Form 7, Form 8, Form 9, Form 10, or Form 11) and one or more pharmaceutically acceptable carriers or excipients. The amount of a solid state form of Compound A included in these compositions correspond to one or more of the amounts described herein. In some embodiments, the compositions are a unit dose.

Examples of pharmaceutically acceptable oral compositions that comprise a solid state form of Compound A include solid formulations (such as tablets, capsules, lozenges, dragées, granules, powders, multi-particulates, and films) and liquid formulations (such as aqueous solutions, elixirs, tinctures, suspensions, and dispersions). In one embodiment, a pharmaceutically acceptable oral composition of a solid state form of Compound A includes a pediatric suspension or granulate. All above-noted amounts of a solid state form of Compound A may be included in such formulations, e.g., a capsule comprising 5, 10, 15, 10, 25, 30, or 35 mg of the solid state form of Compound A.

In one embodiment of the present disclosure, the therapeutically effective amount of a solid state form of Compound A is from about 0.05 mg/kg to about 2.0 mg/kg.

In certain embodiments herein, wherein a comparison is made involving a human orally administered a solid state form of Compound A under fasted conditions, an analogous comparison can be made involving a human who has not consumed food during a time period between about 4 hours prior to the oral administration of the solid state form of Compound A to about 4 hours after the oral administration of the solid state form of Compound A, such as between about 4, 3, 2, 1.5, 1, or 0.5 hours prior to the oral administration of the solid state form of Compound A to about 0.5, 1, 1.5, 2, 3, or 4 hours after the oral administration of the solid state form of Compound A.

In certain embodiments when a seizure disorder is treated herein, the seizure disorder is selected from partial onset (focal) seizures, photosensitive epilepsy, self-induced syncope, intractable epilepsy, Angelman syndrome, benign rolandic epilepsy, CDKL5 disorder, childhood and juvenile absence epilepsy, Dravet syndrome, frontal lobe epilepsy, Glut1 deficiency syndrome, hypothalamic hamartoma, infantile spasms/West's syndrome, juvenile myoclonic epilepsy, Landau-Kleffner syndrome, Lennox-Gastaut syndrome (LGS), epilepsy with myoclonic-absences, Ohtahara syndrome, Panayiotopoulos syndrome, PCDH19 epilepsy, progressive myoclonic epilepsies, Rasmussen's syndrome, ring chromosome 20 syndrome, reflex epilepsies, temporal lobe epilepsy, Lafora progressive myoclonus epilepsy, neurocutaneous syndromes, tuberous sclerosis complex, early infantile epileptic encephalopathy, early onset epileptic encephalopathy, generalized epilepsy with febrile seizures+, Rett syndrome, multiple sclerosis, Alzheimer's disease, autism, ataxia, hypotonia and paroxysmal dyskinesia. In certain embodiments, the seizure disorder is focal onset epilepsy, also known as partial onset (focal) epilepsy.

Additional embodiments and examples of the present disclosure are described herein. These embodiments and examples are illustrative and should not be construed as limiting the scope of the claimed disclosure.

5.3. Pharmaceutical Compositions and Administration

In some embodiments, the present disclosure is directed to pharmaceutical compositions comprising the solid state forms of Compound A described herein (e.g., Form 1, Form 2, Form 3, Form 4, Form 5, Form 6, Form 7, Form 8, Form 9, Form 10, or Form 11) and a pharmaceutically acceptable excipient. In one embodiment, the present disclosure is directed to compositions comprising a solid state form of Compound A and a pharmaceutically acceptable excipient in an amount effective to treat a seizure disorder when administered to an animal, preferably a mammal, most preferably a human.

Administration of a solid state form of Compound A (e.g., Form 1, Form 2, Form 3, Form 4, Form 5, Form 6, Form 7, Form 8, Form 9, Form 10, or Form 11), in pure form or in an appropriate pharmaceutical composition, can be carried out via any of the accepted modes of administration of agents for serving similar utilities. In one embodiment, the pharmaceutical compositions disclosed herein can be prepared by combining a solid state form of Compound A disclosed herein with an appropriate pharmaceutically acceptable excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, rectal, vaginal, and intranasal. The term parenteral as used herein includes subcutaneous injections, intravenous, intramuscular, intrasternal injection or infusion techniques. Pharmaceutical compositions disclosed herein are formulated so as to allow the active ingredients contained therein to be bioavailable upon administration of the composition to a patient. Pharmaceutical compositions that will be administered to a mammal, preferably a human, take the form of one or more dosage units, where for example, a tablet may be a single dosage unit, and a container of a compound of the disclosure in aerosol form may hold a plurality of dosage units. Actual methods of preparing such dosage forms are known, or will be apparent, to those skilled in this art; for example, see The Science and Practice of Pharmacy, latest edition (Philadelphia College of Pharmacy and Science, 2000). The composition to be administered will, in any event, contain a therapeutically effective amount of a solid state form of Compound A disclosed herein, such as a crystalline form, for treatment of a disease or condition of interest in accordance with this disclosure.

In one embodiment, the pharmaceutical compositions disclosed herein also contain a pharmaceutically acceptable excipient, which includes any pharmaceutical agent that does not itself induce the production of antibodies harmful to the individual receiving the composition, and which may be administered without undue toxicity. In one embodiment, pharmaceutically acceptable excipients include, but are not limited to, liquids, such as water, saline, glycerol, and ethanol, and the like. A thorough discussion of pharmaceutically acceptable excipients is presented in Remington's Pharmaceutical Sciences (Mack Pub. Co., N.J., current edition).

In one embodiment, a pharmaceutical composition disclosed herein may be in the form of a solid or liquid. In one aspect, the excipient(s) are particulate, so that the compositions are, for example, in tablet or powder form. The excipient(s) may be liquid, with the compositions being, for example, an oral syrup, injectable liquid or an aerosol, which is useful in, for example, inhalation administration.

In one embodiment, when intended for oral administration, a pharmaceutical composition disclosed herein is preferably in either solid or liquid form, where semi-solid, semi-liquid, suspension and gel forms are included within the forms considered herein as either solid or liquid.

In one embodiment, as a solid composition for oral administration, the pharmaceutical composition disclosed herein may be formulated into a powder, granule, compressed tablet, pill, capsule, chewing gum, wafer, or the like form. Such a solid composition will typically contain one or more inert or edible excipients. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

In one embodiment, when the pharmaceutical composition disclosed herein is in the form of a capsule, for example, a gelatin capsule, it may contain, in addition to materials of the above type, a liquid excipient such as polyethylene glycol or oil.

In one embodiment, the pharmaceutical composition disclosed herein may be in the form of a liquid, for example, an elixir, syrup, solution, emulsion, or suspension. The liquid may be for oral administration or for delivery by injection, as two examples. When intended for oral administration, preferred compositions contain, in addition to the solid state form of Compound A, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

In one embodiment, the liquid pharmaceutical compositions disclosed herein, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

In one embodiment, a liquid pharmaceutical composition disclosed herein intended for either parenteral or oral administration should contain an amount of a solid state form of Compound A such that a suitable dosage will be obtained. In one embodiment, this amount is at least 0.01% of the solid state form of Compound A in the formulation. When intended for oral administration, this amount in one embodiment may be varied to be between 0.1 and about 70% of the weight of the composition. In one embodiment, oral pharmaceutical compositions disclosed herein contain between about 4% and about 50% of a solid state form of Compound A. In another embodiment, pharmaceutical compositions disclosed herein are prepared so that a parenteral dosage unit contains between 0.01 to 10% by weight of a solid state form of Compound A prior to dilution.

In one embodiment, the pharmaceutical composition disclosed herein may be intended for topical administration, in which case the excipient may suitably comprise a solution, emulsion, ointment, or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of a solid state form of Compound A from about 0.1 to about 10% w/v (weight per unit volume).

In one embodiment, the pharmaceutical composition disclosed herein may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter, and polyethylene glycol.

In one embodiment, a pharmaceutical composition disclosed herein for intramuscular or intrathecal administration will consist of a suspension or solution of active in an oil or solution of active ingredient in an oil, for example *arachis* oil or sesame oil. In one embodiment, a pharmaceutical composition disclosed herein for intravenous or intrathecal administration will consist of sterile isotonic aqueous solution containing, for example active ingredient and dextrose or sodium chloride or a mixture of dextrose and sodium chloride.

In one embodiment, the pharmaceutical compositions disclosed herein can be formulated so as to provide quick, sustained, or delayed release of the active ingredient, i.e, a solid state form of Compound A, after administration to the patient by employing procedures known in the art. Controlled release drug delivery systems include osmotic pump systems and dissolutional systems containing polymer-coated reservoirs or drug-polymer matrix formulations. Examples of controlled release systems are given in U.S.

Pat. Nos. 3,845,770 and 4,326,525 and in P. J. Kuzma et al., Regional Anesthesia 22 (6): 543-551 (1997), all of which are incorporated herein by reference.

In one embodiment, the pharmaceutical compositions disclosed herein can also be delivered through intra-nasal drug delivery systems for local, systemic, and nose-to-brain medical therapies. Controlled Particle Dispersion (CPD)™ technology, traditional nasal spray bottles, inhalers or nebulizers are known by those skilled in the art to provide effective local and systemic delivery of drugs by targeting the olfactory region and paranasal sinuses.

In one embodiment, the pharmaceutical compositions disclosed herein are directed to an intravaginal shell or core drug delivery device suitable for administration to the human or animal female. The device may be comprised of the active pharmaceutical ingredient in a polymer matrix, surrounded by a sheath, and capable of releasing the solid state form of Compound A in a substantially zero order pattern on a daily basis.

In one embodiment, the most suitable route of administration of a solid state form of Compound A or a pharmaceutical composition disclosed herein will depend on the nature and severity of the condition being treated. Those skilled in the art are also familiar with determining administration methods (e.g., oral, intravenous, inhalation, subcutaneous, rectal etc.), dosage forms, suitable pharmaceutical excipients and other matters relevant to the delivery of a solid state form of Compound A to a subject in need thereof.

In some embodiments, the pharmaceutical compositions disclosed herein may include various materials, which modify the physical form of a solid or liquid dosage unit. For example, the pharmaceutical composition may include materials that form a coating shell around the active ingredients. The materials that form the coating shell are typically inert, and may be selected from, for example, sugar, shellac, and other enteric coating agents. Alternatively, the active ingredients may be encased in a polymer capsule.

In one embodiment, the pharmaceutical composition disclosed herein in solid or liquid form may include an agent that binds to a solid state form of Compound A and thereby assists in the delivery of the solid state form. Suitable agents that may act in this capacity include a monoclonal or polyclonal antibody, a protein, or a liposome.

In one embodiment, the pharmaceutical compositions disclosed herein may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of a solid state form of Compound A may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

In one embodiment, the pharmaceutical compositions disclosed herein may be prepared by methodology well known in the pharmaceutical art. For example, a pharmaceutical composition intended to be administered by injection can be prepared by combining a solid state form of Compound A with sterile, distilled water so as to form a solution. A surfactant may be added to facilitate the formation of a homogeneous solution or suspension. Surfactants are compounds that non-covalently interact with a solid state form of Compound A so as to facilitate dissolution or homogeneous suspension of the compound in the aqueous delivery system.

In one embodiment, a solid state form of Compound A or a pharmaceutical composition comprising a solid state form of Compound A disclosed herein, such as a crystalline form (e.g., Form 1, Form 2, Form 3, Form 4, Form 5, Form 6, Form 7, Form 8, Form 9, Form 10, or Form 11) is to be administered in a therapeutically effective amount. Generally, a therapeutically effective daily dose of a solid state form of Compound A is (for a 70 Kg mammal) from about 0.001 mg/Kg (i.e., 0.07 mg) to about 100 mg/Kg (i.e., 7.0 g); preferably a therapeutically effective dose is (for a 70 Kg mammal) from about 0.01 mg/Kg (i.e., 0.70 mg) to about 50 mg/Kg (i.e., 3.5 g); and more preferably a therapeutically effective dose is (for a 70 Kg mammal) from about 1 mg/Kg (i.e., 70 mg) to about 25 mg/Kg (i.e., 1.75 g).

The ranges of effective doses provided herein are not intended to be limiting and represent preferred dose ranges. However, an effective dose can be determined by one skilled in the relevant arts by well-known methods. (see, e.g., Berkow et al., eds., *The Merck Manual*, $19^{th}$ edition, Merck and Co., Rahway, N.J., 2011; Brunton et al. eds., *Goodman and Cilman's The Pharmacological Basis of Therapeutics*, $12^{th}$ edition, McGraw-Hill 2011; Avery's Drug Treatment: Principles and Practice of Clinical Pharmacology and Therapeutics, 3rd edition, ADIS Press, LTD., Williams and Wilkins, Baltimore, MD. (1987), Ebadi, *Pharmacology*, Little, Brown and Co., Boston, (1985); Osolci al., eds., *Remington's Pharmaceutical Sciences*, current edition, Mack Publishing Co., Easton, PA; Katzung, *Basic and Clinical Pharmacology*, Appleton and Lange, Norwalk, CT (1992)).

The total dose required for each treatment can be administered by multiple doses or in a single dose over the course of the day, if desired. Generally, treatment is initiated with smaller dosages, which are less than the optimum dose of the compound. Thereafter, the dosage is increased by small increments until the optimum effect under the circumstances is reached. The diagnostic pharmaceutical compound or composition can be administered alone or in conjunction with other diagnostics and/or pharmaceuticals directed to the pathology, or directed to other symptoms of the pathology. Effective amounts of the solid state form of Compound A are from about 0.1 g to about 100 mg/Kg body weight, administered at intervals of 4-72 hours, for a period of 2 hours to 1 year, and/or any range or value therein, such as 0.0001-0.001, 0.001-0.01, 0.01-0.1, 0.1-1.0, 1.0-10, 5-10, 10-20, 20-50 and 50-100 mg/Kg, at intervals of 1-4, 4-10, 10-16, 16-24, 24-36, 24-36, 36-48, 48-72 hours, for a period of 1-14, 14-28, or 30-44 days, or 1-24 weeks, or any range or value therein.

In one embodiment, the recipients of administration of a solid state form of Compound A or a pharmaceutical composition comprising a solid state form of Compound A as described herein can be any animal, such as mammals. Among mammals, the preferred recipients are mammals of the Orders Primate (including humans, apes and monkeys), Arteriodactyla (including horses, goats, cows, sheep, pigs), Rodenta (including mice, rats, and hamsters), Lagamorpha (including rabbits) and Carnivora (including cats and dogs). Among birds, the preferred recipients are turkeys, chickens and other members of the same order. The most preferred recipients are humans.

5.4. Methods of Preparing Solid State Crystalline Forms of Compound A

In certain embodiments, the present disclosure provides a method for preparing a solid-state crystalline form of Compound A as described herein (e.g., Form 1, Form 2, Form 3, Form 4, Form 5, Form 6, Form 7, Form 8, Form 9, Form 10, or Form 11), for example, by recrystallizing from another form of Compound A.

In one embodiment, the present disclosure provides a method for preparing Compound A Form 2 from Compound A Form 1, for example, by forming a slurry of Compound A Form 1 in an alcohol-water solution (e.g., ethanol-water), optionally shaking the slurry (e.g., at ambient temperature), cooling the slurry, and separating the slurry (e.g., by centrifugation) to prepare Compound A Form 2.

In one embodiment, the present disclosure provides a method for preparing Compound A Form 3 from Compound A Form 2 and Compound A Form 4, for example, by forming a slurry of Compound A Form 2 and Compound A Form 4 in a halocarbon solvent (e.g., dichloromethane), optionally shaking the slurry (e.g., at ambient temperature), cooling the slurry, and separating the slurry (e.g., by centrifugation) to prepare Compound A Form 3.

In one embodiment, the present disclosure provides a method for preparing Compound A Form 4 from Compound A Form 1, for example, by dissolving Compound A Form 1 in a warm alcohol solvent (e.g., ethanol at 40° C.), cooling the slurry, adding an antisovent (e.g., water), and separating the precipitate (e.g., by centrifugation) to prepare Compound A Form 4.

In one embodiment, the present disclosure provides a method for preparing Compound A Form 5 from Compound A Form 1, for example, by forming a slurry of Compound A Form 1 in an acyclic ketone solvent (e.g., methyl isobutyl ketone), optionally adding additional Compound A Form 1, treating the slurry with one or more heating and cooling cycles (e.g., between 40° C. and ambient temperature), and separating the slurry (e.g., by filtration) to prepare Compound A Form 5.

In one embodiment, the present disclosure provides a method for preparing Compound A Form 6 from Compound A Form 1, for example, by forming a slurry of Compound A Form 1 in an etheral-water solution (e.g., tetrahydrofuran-water), optionally adding additional Compound A Form 1, treating the slurry with one or more heating and cooling cycles (e.g., between 40° C. and ambient temperature), and separating the slurry (e.g., by filtration) to prepare Compound A Form 6.

In one embodiment, the present disclosure provides a method for preparing Compound A Form 7 from Compound A Form 1, for example, by forming a slurry of Compound A Form 1 in an etheral solvent (e.g., tetrahydrofuran) or ketone-water solution (e.g., acetone-water), optionally adding additional Compound A Form 1, treating the slurry with one or more heating and cooling cycles (e.g., between 40° C. and ambient temperature), and separating the slurry (e.g., by filtration) to prepare Compound A Form 7.

In one embodiment, the present disclosure provides a method for preparing Compound A Form 8 from Compound A Form 1, for example, by forming a slurry of Compound A Form 1 in a cyclic ketone solvent (e.g., cyclohexanone), optionally adding additional Compound A Form 1, treating the slurry with one or more heating and cooling cycles (e.g., between 40° C. and ambient temperature), separating the slurry (e.g., by filtration), and allowing slow evaporation of the supernatant to prepare Compound A Form 8.

In one embodiment, the present disclosure provides a method for preparing Compound A Form 9 from Compound A Form 4, for example, by placing Compound A Form 4 in a VT-XRPD sample holder, optionally pressing Compound A Form 4 flat before adding to the VT-XPRD sample holder, and treating with one or more scanning and heating cycles (e.g., between 25° C. and 140° C.), to prepare Compound A Form 9.

In one embodiment, the present disclosure provides a method for preparing Compound A Form 9 from Compound A Form 1, for example, by dissolving in an alcohol solvent (e.g., methanol), adding aqueous acid (e.g., 1M sulfuric acid), adding an antisolvent (e.g., water), and separating the precipitate (e.g., by filtration) to prepare Compound A Form 9.

In one embodiment, the present disclosure provides a method for preparing Compound A Form 10 from Compound A Form 1, for example, by slurrying Compound A Form 1 in an etheral solvent (e.g., tetrahydrofuran), diluting the slurry in further etheral solvent (e.g., tetrahydrofuran), treating the slurry with one or more heating and cooling cycles (e.g., between 40° C. and ambient temperature), separating the slurry (e.g., by centrifugation) to prepare Compound A Form 10

In one embodiment, the present disclosure provides a method for preparing Compound A Form 11 from Compound A Form 1, for example, by forming a slurry of Compound A Form 1 in an alcohol solvent (e.g., ethanol), shaking and cooling the slurry (e.g., at 5° C.), heating the slurry until dissolution and cooling the solution (e.g., at 5° C.), and treating the with one or more heating and cooling cycles (e.g., between 40° C. and ambient temperature), separating the slurry (e.g., by centrifugation) to prepare Compound A Form 11.

In another embodiment, the present disclosure provides a method of preparing a pharmaceutical composition comprising a pharmaceutical excipient and a solid state crystalline form of Compound A described herein (e.g., Form 1, Form 2, Form 3, Form 4, Form 5, Form 6, Form 7, Form 8, Form 9, Form 10, or Form 11), such as by combining the solid state crystalline form of Compound A with the pharmaceutical excipient to form the pharmaceutical composition.

6. EXAMPLES

6.1. Methods of Analysis

The solid state crystalline forms of Compound A were characterized by one or more of the following analytical methods. It is understood that similar instruments can be used to generate equivalent data.

6.1.1. A. X-ray Powder Diffraction (XRPD)

XRPD analysis was carried out on a PANalytical X'pert pro with PIXcel detector (128 channels), scanning the samples between 3 and 35θ 2θ. The material was gently ground to release any agglomerates and loaded onto a multi-well plate with Kapton or Mylar polymer film to support the sample. The multi-well plate was then placed into the diffractometer and analyzed using Cu K radiation ($\alpha_1$ λ=1.54060 Å; $\alpha_2$=1.54443 Å; β=1.39225 Å; $\alpha_1$:$\alpha_2$ ratio=0.5) running in transmission mode (step size 0.0130° 2θ, step time 18.87s) using 40 kV/40 mA generator settings. Data were visualized and images generated using the HighScore Plus 4.7 desktop application (PANalytical, 2017).

6.1.2. B. Polarised Light Microscopy (PLM)

The presence of crystallinity (birefringence) was determined using an Olympus BX50 microscope, equipped with cross-polarising lenses and a Motic camera. Images were captured using Motic Images Plus 2.0. All images were recorded using the 20× objective, unless otherwise stated. All images were collected with crossed and non-crossed polarizers to highlight areas of birefringence.

6.1.3. C. Hot Stage Light Microscopy

Thermal events were monitored visually using a calibrated Linkam THM600 hotstage with connected controller unit coupled to an Olympus BX50 polarising microscope equipped with a Motic camera and image capture software (Motic Images Plus 2.0). A sufficient amount of material was placed onto a microscope coverslip and heated at a rate of 10° C./min with images taken at routine intervals to document any thermal transitions. All images were recorded using the 10× objective, unless otherwise stated. The following heating program was used for all samples:
1. Initial heating from ambient temperature to 100° C. was carried out at 10° C./min, with images were taken at every 10° C. increment.
2. Heating between 100° C. and 160° C. was carried out at 1° C./min, with images taken at every 1° C. increment.
3. The final heating between 160° C. and 200° C. was carried out at 10° C./min, with images taken every 10° C.

6.1.4. D. Thermogravimetric/Differential Thermal Analysis (TG/DTA)

Approximately, 5 mg of material was weighed into an open aluminum pan and loaded into a simultaneous thermogravimetric/differential thermal analyzer (TG/DTA) and held at room temperature. The sample was then heated at a rate of 10° C./min from 20° C. to 400° C. during which time the change in sample weight was recorded along with any differential thermal events (DTA). Nitrogen was used as the purge gas, at a flow rate of 300 cm³/min.

6.1.5. E. Differential Scanning Calorimetry (DSC)

Approximately, 5 mg of material was weighed into an aluminum DSC pan and sealed non-hermetically with a pierced aluminum lid. The sample pan was then loaded into a Seiko DSC6200 (equipped with a cooler) cooled and held at 20° C. Once a stable heat-flow response was obtained, the sample and reference were heated to 220° C. at scan rate of 10° C./min and the resulting heat flow response monitored. Nitrogen was used as the purge gas, at a flow rate of 50 cm³/min. Analogous data were then obtained in a cooling cycle, where the sample (initially at 220° C.) was cooled at a scan rate of 10° C./min until a final temperature of 20° C. was reached. After holding the sample at 20° C. for 3 min, a second heating cycle was performed. This second heating cycle was conducted at a scan rate of 10° C./min up to a final temperature of 220° C. and was followed by a 5 min hold at 220° C.

6.1.6. F. Karl Fischer Coulometric Titration (KF)

Approximately 10-15 mg of solid material was accurately weighed into a vial. The solid was then manually introduced into the titration cell of a Mettler Toledo C30 Compact Titrator. The vial was back-weighed after the addition of the solid and the weight of the added solid entered on the instrument. Titration was initiated once the sample had fully dissolved in the cell. The water content was calculated automatically by the instrument as a percentage and the data printed.

6.1.7. G. Fourier-Transform Infrared Spectroscopy (FTIR)

Infrared spectroscopy was carried out on a Bruker ALPHA P spectrometer. Sufficient material was placed onto the center of the plate of the spectrometer and the spectra were obtained using the following parameters:
Resolution: 4 cm$^{-1}$
Background Scan Time: 16 scans
Sample Scan Time: 16 scans
Data Collection: 4000 to 400 cm$^{-1}$
Result Spectrum: Transmittance
Software: OPUS version 6

6.1.8. H. $^1$H Nuclear Magnetic Resonance ($^1$H NMR)

$^1$H NMR experiments were performed on a Bruker AVIIIHD spectrometer equipped with a DCH cryoprobe operating at 500.12 MHz for protons. Experiments were performed in deuterated DMSO-d$_6$ and each sample was prepared to approximately 10 mM concentration.

6.1.9. I. Gravimetric Vapour Sorption (GVS)

Approximately 10-20 mg of sample was placed into a mesh vapor sorption balance pan and loaded into an IGASorp Moisture Sorption Analyser balance by Hiden Analytical. The sample was subjected to a ramping profile from 40-90% relative humidity (RH) at 10% increments, maintaining the sample at each step until a stable weight had been achieved (98% step completion, minimum step length 30 minutes, maximum step length 60 minutes) at 25° C. After completion of the sorption cycle, the sample was dried using the same procedure to 0% RH, and finally taken back to the starting point of 40% RH, using the same parameters outlined above. Two complete cycles were performed. The weight change during the sorption/desorption cycles were plotted, allowing for the hygroscopic nature of the sample to be determined.

6.1.10. J. Variable Temperature X-ray Powder Diffraction (VT-XRPD)

VT-XRPD analysis was carried out on a Philips X'Pert Pro Multipurpose diffractometer equipped with a temperature chamber. The samples were loaded onto the VT stage and scanned between 4 and 35.99° 2θ using Cu K radiation ($\alpha_1$ λ=1.54060 Å; $\alpha_2$=1.54443 Å; β=1.39225 Å; $\alpha_1$:$\alpha_2$ ratio=0.5) running in Bragg-Brentano geometry (step size 0.008 020) using 40 kV/40 mA generator settings. Measurements were performed at various temperature profiles. Any holds at specific temperatures are described in the temperature profiles for individual samples.

6.1.11. K. High Performance Liquid Chromatography-Ultraviolet Detection (HPLC-UV)

HPLC-UV was performed on Compound A with the following parameters:
Column: LC 201/216 Waters Acquity C18 2.1×50 mm, 1.7 μm
Column Temperature: 50° C.

Autosampler Temperature: Ambient
UV wavelength: 265 nm
Injection Volume: 2.00 μL
Flow Rate: 0.75 mL/min
Mobile Phase A: 0.1% TFA in 90:10 v/v % Water:Acetonitrile
Mobile Phase B: 0.1% TFA in Acetonitrile
Diluent: 75:25 v/v % Acetonitrile:Water
Gradient Program:

| Time (minutes) | Mobile Phase A [%] | Mobile Phase B [%] |
|---|---|---|
| 0.0 | 100 | 0 |
| 8.0 | 20 | 80 |
| 10.0 | 20 | 80 |
| 10.1 | 100 | 0 |
| 12.0 | 100 | 0 |

Note: Any peaks not integrated in the results were present in the blank.

6.1.12. L. Gas Chromatography (GC)

GC was performed on Compound A with the following parameters:
Column: Agilent J&W DB-624 30 m×0.32 mm 1.8 μm d.f. or equivalent
Oven Temperature: 35° C. (hold 0.5 min) to 45° C. @16.5° C./min to 70° C. @5.0° C./min to 220° C. @30.0° C./min
Flow Rate: 2.2 mL/min (constant flow)
Carrier gas: Hydrogen
Injection Mode: Split
Injection Temperature: 225° C.
Injection Split ratio: 5:1
Detector Temperature: 270° C.
Detector Hydrogen: 40.0 mL/min
Detector Air: 400 mL/min
Make-up Flow: 30.0 mL/min
Make-up Gas: Air
Headspace Parameters:
  Oven temperature: 100° C.
  Loop temperature: 110° C.
  Transfer line temperature: 150° C.
  Vial equilibration time: 10.0 min
  Pressurization time: 0.2 min
  Loop fill time: 0.2 min
  Loop equilibration time:0.05 min
  Loop volume: 1 mL
  Inject time: 1.0 min
  Vial Shaking: High
  GC cycle time: 15 min

6.1.13. M. Particle Size Distribution (PSD)

Approximately 60 mg of sample was weighed into a 20 mL scintillation vial. 10 mL of dispersant was added and mixed. The sample was sonicated for 30 seconds, then thoroughly agitated with a pipette and added to the dispersion unit to achieve an obscuration of 8-20%. Measurements were taken according to the following parameters:
Absorption 1.0
Particle RI 1.56
Dispersant RI 1.39
Dispersant 0.05% w/v span-85 in heptane
Stir Speed 2000 rpm
Obscuration Limits 8-20%
Sonication time 30 seconds
Measurements 3×10s
Background 10s
Analysis model General purpose
Sensitivity Normal
Particle Shape Irregular

6.2. Preparation of Compound A and Solid State Forms of Compound A

6.2.1. A. Preparation of Compound A Form 1

In one embodiment, Compound A Form 1 was prepared as set forth in the following Reaction Scheme wherein compounds (1), (2), (3) and (4) are commercially available or can be prepared according to methods known to one skilled in the art:

Reaction Scheme

REACTION SCHEME

Step 1: An acetonitrile solution of 4-bromo-2,6-dimethylaniline (Compound 1) was treated with N,N-diisopropylethylamine (DIPEA) and the mixture cooled to 0° C. To the solution of Compound 1 was added tert-butylacetyl chloride (Compound 2) over a period of 90 minutes, while maintaining a temperature below 10° C. The mixture was then diluted with acetonitrile and the solution warmed to 20-25° C. and stirred for 2 hours. Once complete, the mixture was diluted with process water and the resulting slurry stirred for 30 minutes. The solids were then collected by vacuum filtration, washed twice with process water and dried under nitrogen for a minimum of 2 hours. The filter cake was then allowed to further dry under $N_2$ at 50° C. in a vacuum oven to afford N-(4-bromo-2,6-dimethylphenyl)-3,3-dimethylbutanamide (Compound 2).

Step 2A: N-(4-bromo-2,6-dimethylphenyl)-3,3-dimethylbutanamide (Compound 3) was reacted with 6-fluoro-1,2,3,4-tetrahydroisoquinoline (Compound 4) and potassium tert-butoxide in 2-methyltetrahydrofuran (2-MeTHF). The mixture was sparged with nitrogen ($N_2$) gas for 1 hour, then bis(dibenzylideneacetone) palladium (Pd(dba)$_2$) and 2-dicyclohexylphosphino-2'-(N,N-dimethylamine)biphenyl (DavePhos) was added and the mixture heated to 77° C. under a $N_2$ atmosphere and stirred for 12 hours. The mixture was then cooled to 40° C. and diluted with 2-MeTHF. The solution was further diluted with Water for Injection (WFI), the mixture cooled to 25° C. and agitated for 30 minutes. The resulting biphasic mixture was allowed to settle for a minimum of 1 hour prior to separation. The aqueous and organic phases were then removed and the reactor rinsed with additional 2-MeTHF.

Step 2B: The combined organics were added to a separate reactor, charged with SiliaMetS-DMT® and diluted with additional 2-MeTHF. The mixture was purged with nitrogen five times and stirred at 45° C. for a minimum of 4 hours. The mixture was then filtered and the solids rinsed with 2-MeTHF at 50° C. and then cooled to approximately 20-30° C. The SiliaMetS-DMT® treatment was then repeated an additional time in a manner identical to that previously described.

A solution of 10% n-heptane in 2-MeTHF is then added to the solution of Compound A Form 1 in 2-MeTHF isolated following treatment with SiliaMetS-DMT®. The mixture was heated to 50° C. for 15 minutes until all solids had appeared to dissolve. The solution was then cooled, further diluted with 2-MeTHF and concentrated in vacuo. The concentrated solution was then diluted an additional time with 2-MeTHF and heated to 50° C. for 15 minutes. The solution was then cooled, diluted with additional 2-MeTHF and concentrated in vacuo until solids were evident. The solution was then heated to reflux to dissolve all solids present, then diluted with n-heptane, cooled and concentrated in vacuo. The concentrated solution was then diluted with n-heptane, concentrated in vacuo and the solids filtered, rinsed with the filtrate and twice with a 10% solution of n-heptane in 2-MeTHF. The filtered solids were dried under vacuum, then transferred to a vacuum oven and dried further.

The solids were then recrystallized a second time in 2-methyltetrahydrofuran (2-MeTHF) that had previously been sparged with $N_2$ for a minimum of 15 minutes. Upon addition of the solids, the mixture was sparged for an additional 15 minutes with $N_2$ and then heated to 76° C. The solution was then cooled to 20-25° C. and stirred for a minimum of 1 hour. The suspension was then filtered and the solids maintained under a steady flow of $N_2$. The filter cake was rinsed with heptane and then allowed to dry under a $N_2$ blanket before transferring to a vacuum oven and heated to 50° C. under an atmosphere of $N_2$ to afford Compound A Form 1 (see FIG. 1).

6.2.2. B. Preparation of Compound A Form 2

In one embodiment, Compound A Form 2 was prepared by first slurrying approximately 500 mg of Compound A Form 1 in about 3 mL ethanol:water (10:90 v/v %) solution. The slurry was then shaken for approximately 2 hours at ambient temperature before being stored at 5° C. for approximately 72 hours. The slurry was then separated by centrifugation and the damp solids were dried under vacuum at 40° C. for about 24 hours. The resulting dry material was found to be Compound A Form 2 having the XRPD pattern depicted in FIG. 8.

6.2.3. C. Preparation of Compound A Form 3

In one embodiment, Compound A Form 3 was prepared by weighing about 15 mg of Compound A Form 2 and Compound A Form 4 into a 2 mL glass vial. An aliquot of dichloromethane was added to the vial at ambient temperature until a mobile slurry was formed. The resulting slurry was agitated under ambient temperature for about 24 hours. The observed solids were isolated and characterized by XRPD and found to be Compound A Form 3 having the XRPD pattern depicted in FIG. 16.

6.2.4. D. Preparation of Compound A Form 4

In one embodiment, Compound A Form 4 was prepared by dissolving about 250 mg Compound A Form 1 in about 3.5 mL of ethanol at 40° C. After 1 hour at 40° C., the solution was cooled to 20° C. at a rate of 0.2° C./min. The solution was held at 20° C. for 1 hour before being cooled to 5° C. at 0.1° C./min. After 18 hours at 5° C., 15 mL of water as an anti-solvent was added and then held at 5° C. for 2 hours prior to separation using centrifugation. The mother liquor was then analyzed for concentration by HPLC. The damp solid was dried under vacuum at 40° C. for about 2 hours before being analyzed. The resulting dry material was found to be Compound Form 4 having the XRPD pattern depicted in FIG. 17.

6.2.5. E. Preparation of Compound A Form 5

In one embodiment, approximately 40 mg of Compound A Form 1 was added to 500 µL of methyl isobutyl ketone to prepare a slurry. If dissolution occurred during the preparation, an additional amount of Compound A Form 1 was added. The resulting slurry was subjected to successive 4-hour heat-cool cycles between 40° C. and ambient temperature for 72 hours. The resulting mixture was filtered and the isolated wet solids were analyzed by XRPD and found to be Compound Form 5 having the XRPD pattern depicted in FIG. 25.

6.2.6. F. Preparation of Compound A Form 6

In one embodiment, approximately 40 mg of Compound A Form 1 was added to 300 µL of tetrahydrofuran/water (99:1) to prepare a slurry. If dissolution occurred during the preparation, an additional amount of Compound A Form 1 was added. The resulting slurry was subjected to successive 4-hour heat-cool cycles between 40° C. and ambient temperature for 72 hours. The resulting mixture was filtered and the isolated wet solids were analyzed by XRPD and found to be Compound Form 6 having the XRPD pattern depicted in FIG. 26.

6.2.7. G. Preparation of Compound A Form 7

In one embodiment, approximately 40 mg of Compound A Form 1 was added to 300 µL of tetrahydrofuran to prepare a slurry. If dissolution occurred during the preparation, an additional amount of Compound A Form 1 was added. The resulting slurry was subjected to successive 4-hour heat-cool cycles between 40° C. and ambient temperature for 72 hours. The resulting mixture was filtered and the isolated wet solids were analyzed by XRPD and found to be Compound Form 7 having the XRPD pattern depicted in FIG. 27.

In another embodiment, approximately 40 mg of Compound A Form 1 was added to 1500 µL of acetone/water (75:25) to prepare a slurry. If dissolution occurred during the preparation, an additional amount of Compound A Form 1 was added. The resulting slurry was subjected to successive 4-hour heat-cool cycles between 40° C. and ambient temperature for 72 hours. The resulting mixture was filtered and the isolated wet solids were analyzed by XRPD and found to be Compound Form 7 having the XRPD pattern depicted in FIG. 27.

6.2.8. H. Preparation of Compound A Form 8

In one embodiment, approximately 40 mg of Compound A Form 1 was added to 300 µL of cyclohexanone to prepare a slurry. If dissolution occurred during the preparation, an additional amount of Compound A Form 1 was added. The resulting slurry was subjected to successive 4-hour heat-cool cycles between 40° C. and ambient temperature for 72 hours. The resulting mixture was filtered and the supernatant was transferred into a vail and left uncapped to evaporate at ambient temperature. When enough material was obtained, the material was analyzed by XRPD and found to be Compound Form 8 having the XRPD pattern depicted in FIG. 28.

6.2.9. I. Preparation of Compound A Form 9

In one embodiment, a sample of Compound A Form 4 was placed in a VT-XRPD sample holder and pressed flat before being loaded into the VT-XRPD and heated to above approximately 140° C. and then cooled using the method below in Table 13.

TABLE 13

| VT-XRPD Procedure for Production of Form 9 | |
|---|---|
| Temperature | Procedure |
| 25° C. | Scan then heat in 10 minutes to next temperature |
| 50° C. | Scan then heat in 10 minutes to next temperature |
| 60° C. | Scan then heat in 10 minutes to next temperature |
| 70° C. | Scan then heat in 10 minutes to next temperature |
| 80° C. | Scan then heat in 10 minutes to next temperature |
| 90° C. | Scan then heat in 10 minutes to next temperature |
| 100° C. | Scan and wait 5 minutes, then heat in 10 minutes to next temperature |
| 110° C. | Scan and wait 5 minutes, then heat in 10 minutes to next temperature |
| 120° C. | Scan and wait 5 minutes, then heat in 10 minutes to next temperature |
| 130° C. | Scan and wait 5 minutes, then heat in 10 minutes to next temperature |
| 140° C. | Scan then cool start temperature |
| 25° C. | Scan at temperature |

The resulting dry material was found to be Compound A Form 9 having the XRPD pattern depicted in FIG. 29.

In another embodiment, Compound A Form 9 was prepared by adding methanol (3 mL) to approximately 500 mg of Compound A Form 1 followed by the addition of aqueous sulfuric acid (1M, 1425 µl, 1.05 eq.). After about 2 minutes, water (5 mL) was added as an antisolvent, causing precipitation to make a thick slurry. The solid was filtered and analyzed by XRPD and found to be Compound A Form 9 having the XRPD pattern depicted in FIG. 29.

6.2.10. J. Preparation of Compound A Form 10

In one embodiment, about 500 mg of Compound A Form 1 was weighed into a 20 mL scintillation vial. 500 µL aliquots of tetrahydrofuran was added until a mobile slurry was formed. 2 mL of tetrahydrofuran was added. The sample was temperature cycled between ambient and 40° C. in 1-hour cycles for about 4 hours. The observed solid was isolated by centrifugation and characterized by XRPD and found to be Compound A Form 10 as depicted in FIG. 37.

6.2.11. K. Preparation of Compound A Form 11

In one embodiment, Compound A Form 11 was prepared by dissolving about 500 mg of Compound A Form 1 in about 3 mL ethanol. The resulting slurry was shaken for about 2 hours at ambient temperature before being stored at 5° C. for about 90 hours. A sample, analyzed by XRPD, indicated the material was Compound A Form 4. The slurry was then heated to 40° C. for about 2 hours until the solid fully dissolved. The material was then stored at 5° C. for 72 hours. The slurry was then temperature-cycled between ambient temperature and 40° C. for about 72 hours. The slurry was then separated by centrifugation and the damp solids dried at ambient temperature for 18 hours before drying under vacuum at 40° C. for about 6 hours. The resulting dry material was analyzed by XRPD to be Compound A Form 11 having the XRPD pattern depicted in FIG. 39.

6.3. Characterization of the Solid State Forms of Compound A

6.3.1. A. Characterization of Compound A Form 1

In one embodiment, the present disclosure provides a solid form of Compound A referred to herein as Compound A Form 2. In some embodiments, the present disclosure provides Compound A Form 2 having a XRPD pattern substantially similar to that depicted in FIG. 1. In other embodiments, the present disclosure provides a mixture of Compound A Form 2 and Compound A Form 3, in which Compound A Form 2 predominates. These forms can be distinguished by XRPD (see FIG. 1).

Figure 2:
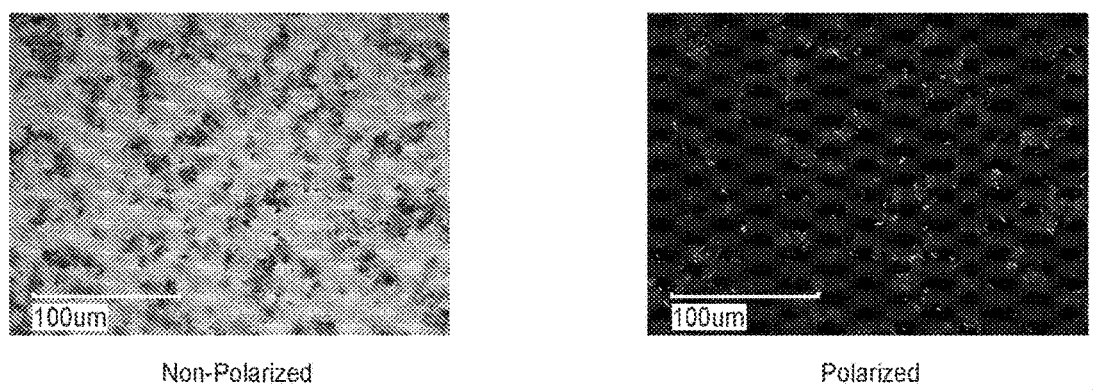
FIG. 2 depicts non-polarized and polarized light microscopy images of Compound A Form 1.

In one embodiment, PGM analysis of Compound A Form 1 showed small particles with no clear morphology, some agglomeration and birefringence (see FIG. 2).

Figure 3:
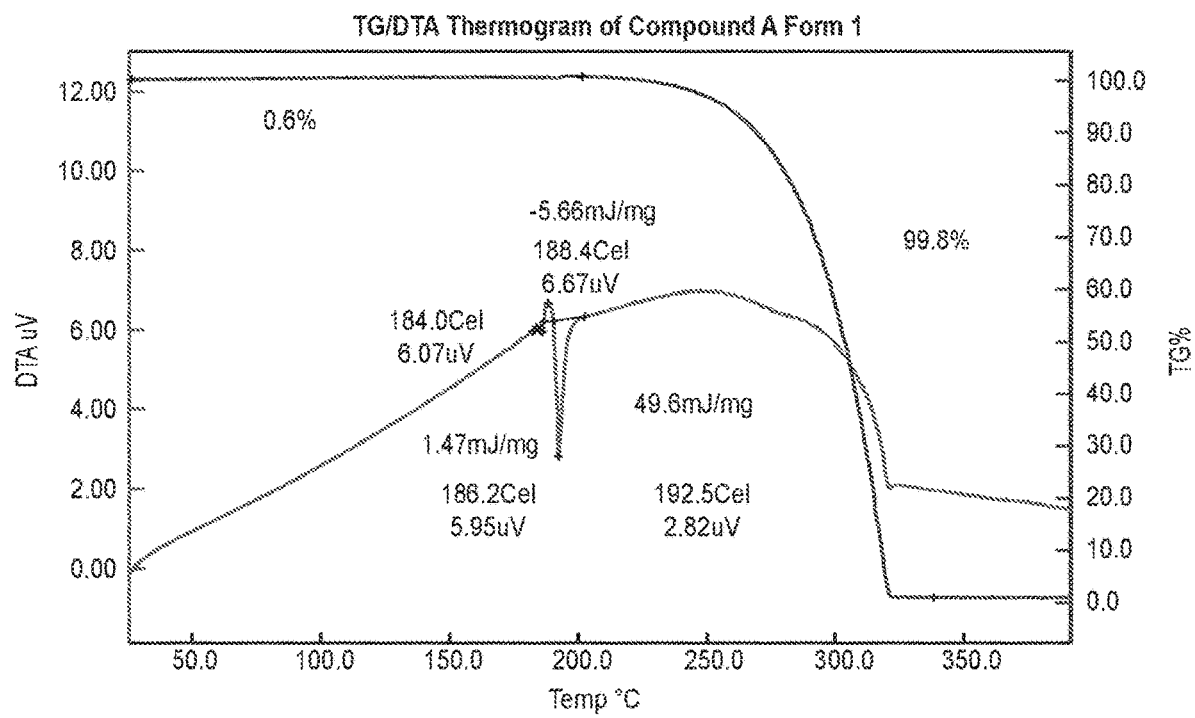
FIG. 3 depicts a thermogravimetric/differential thermal analysis (TG/DTA) thermogram of Compound A Form 1.

In another embodiment, TG analysis of Compound A Form 1 showed a 0.6% weight loss up to 200° C., followed decomposition. A complex thermal event is noted in the DTA at onset 184° C., with an endothermic peak at 186° C., an exothermic peak at 188° C. and a larger endothermic peak at 193° C. (see FIG. 3).

Figure 4:
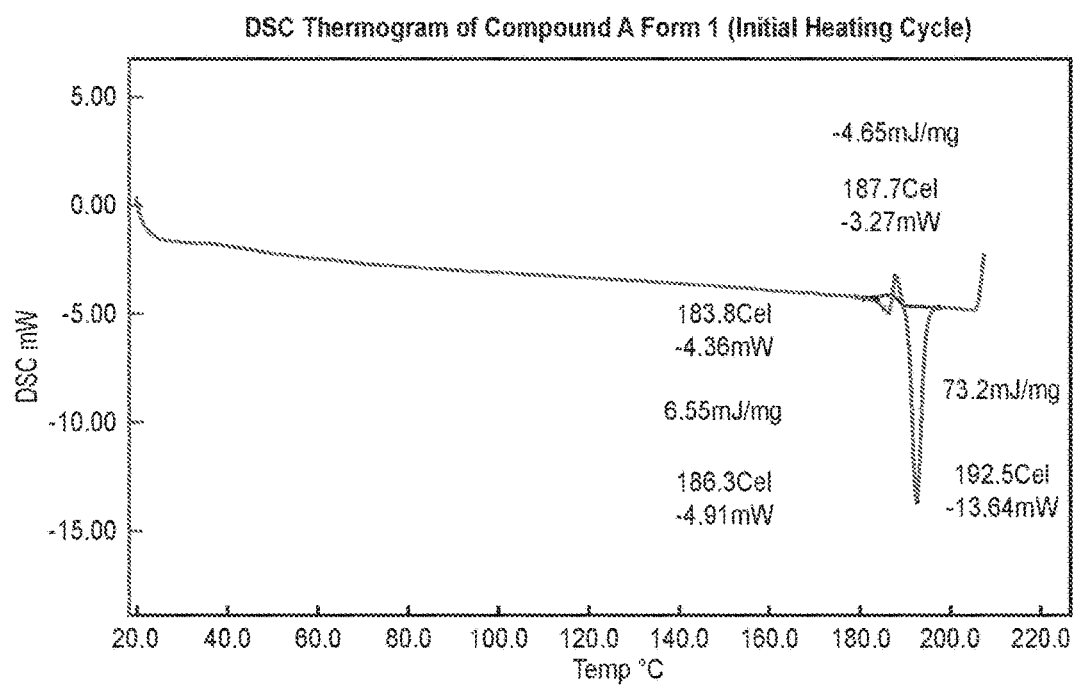
FIG. 4 depicts a differential scanning calorimetry (DSC) thermogram of Compound A Form 1 (Initial Heating Cycle).
Figure 5:
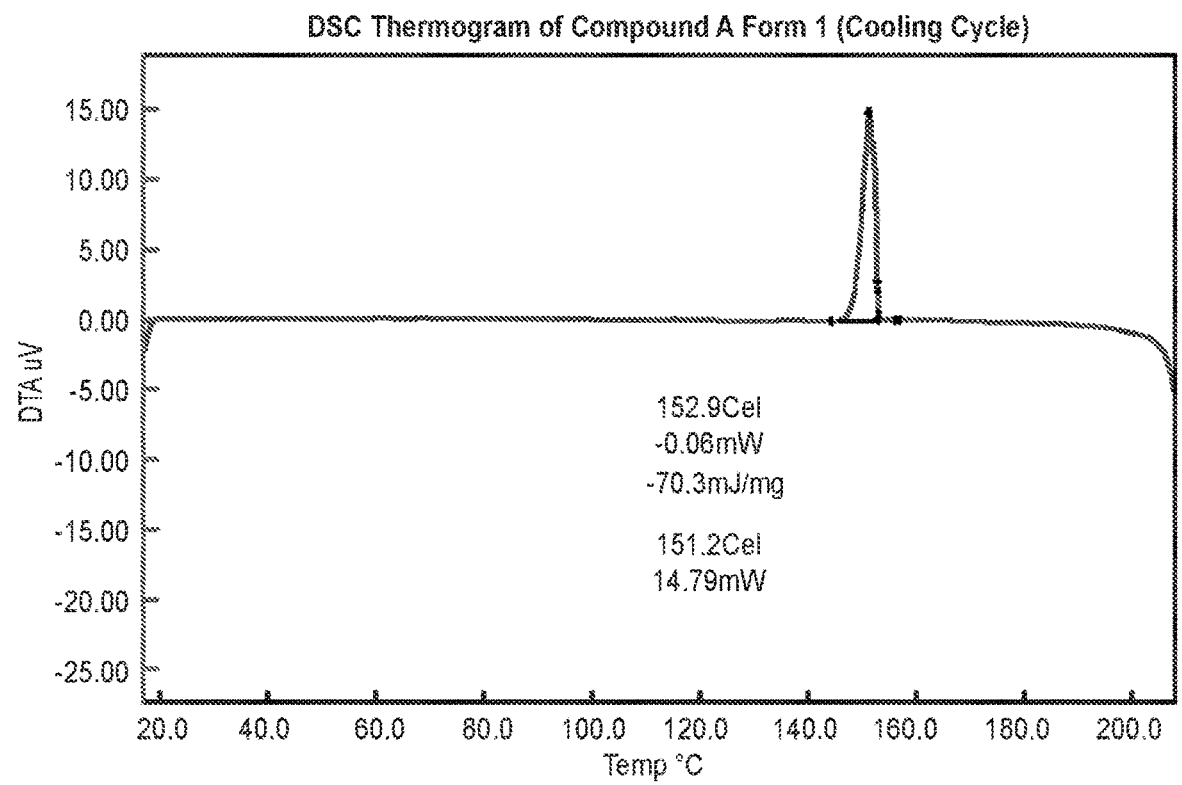
FIG. 5 depicts a DSC thermogram of Compound A Form 1 (Cooling Cycle).
Figure 6:
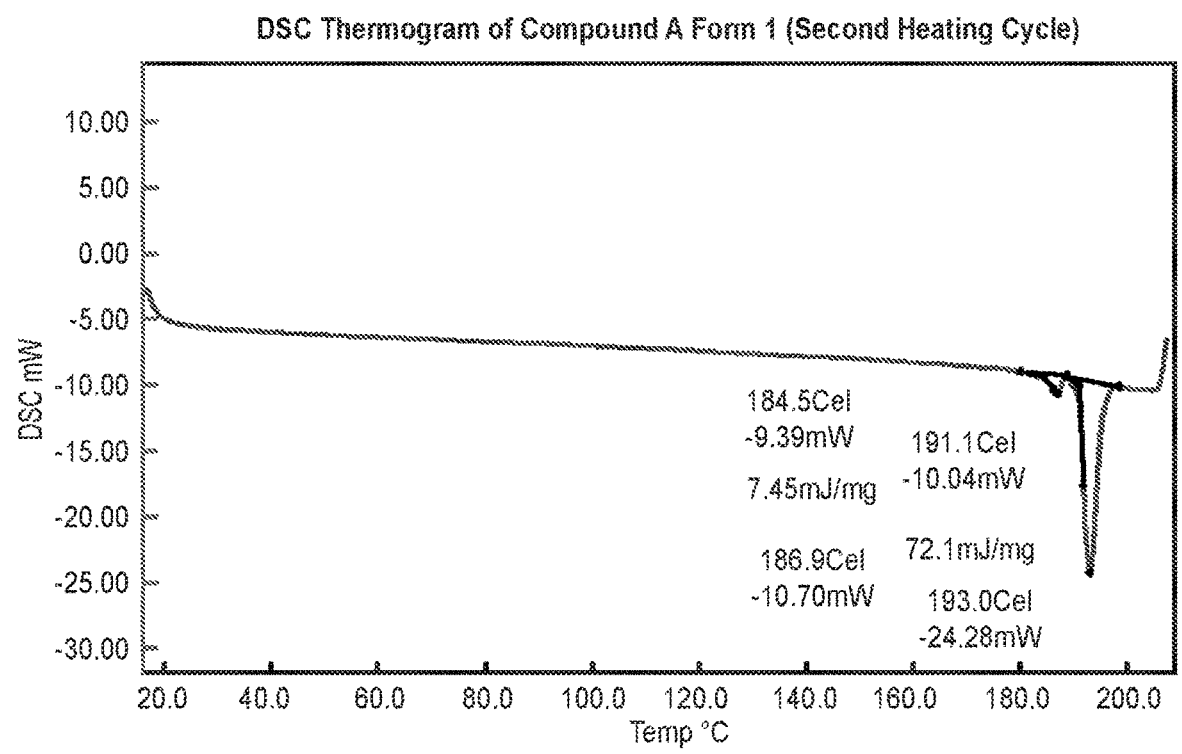
FIG. 6 depicts a DSC thermogram of Compound A Form 1 (Second Heating Cycle).

In another embodiment, DSC analysis of Compound A Form 1 with initial heat showed a complex thermal event at onset 184° C., with an endothermic peak at 186° C., an exothermic peak at 188° C. and a larger endothermic peak at 193° C. (see FIG. 4). The cooling cycle showed an exothermic peak at onset 153° C., with a peak at 151° C. (see FIG. 5). The second heat showed two endothermic events; a small one at onset 185° C., with a peak at 187° C., and a second larger peak at onset 191° C., with a peak at 193° C. (see FIG. 6).

Figure 7:
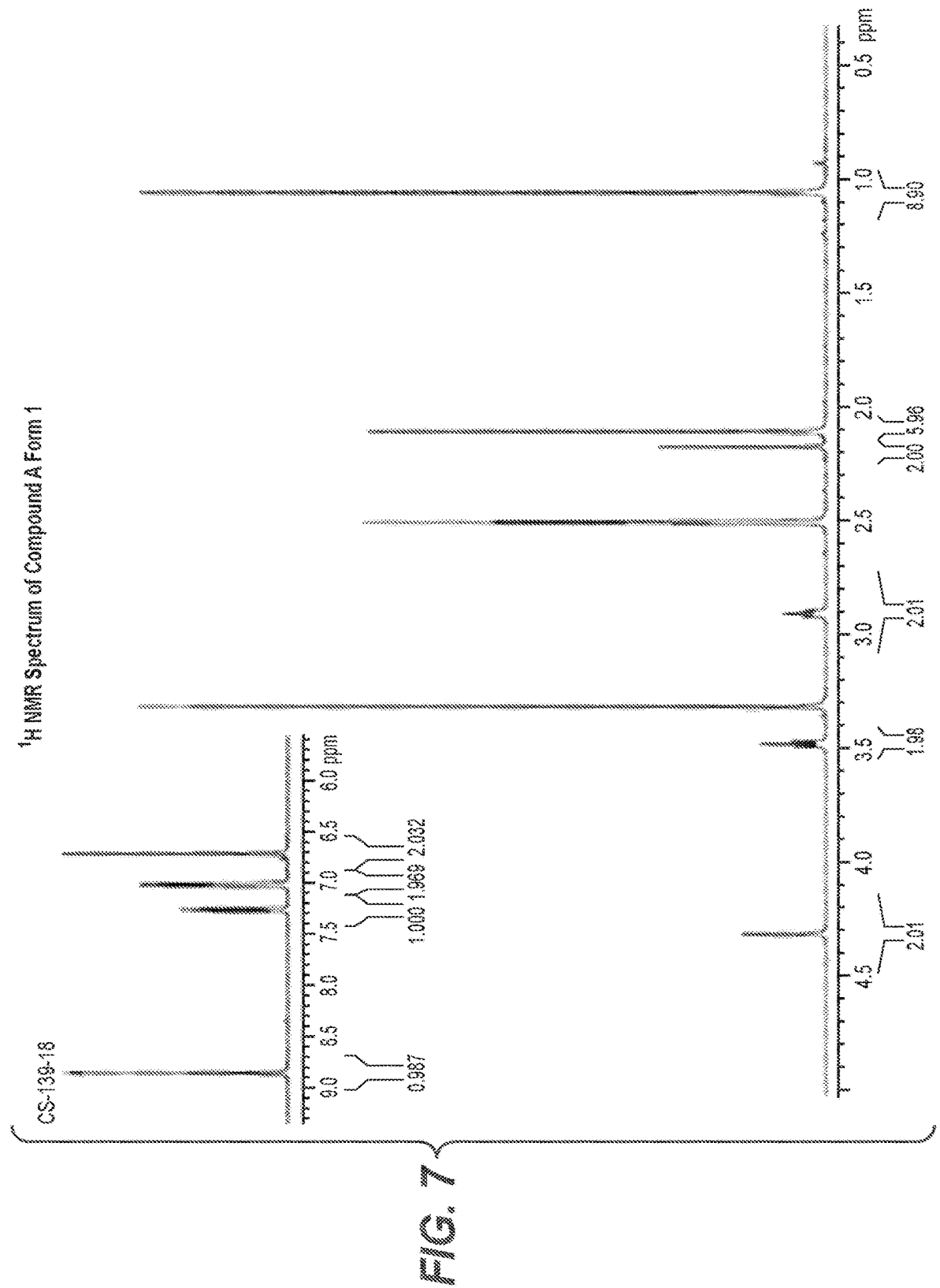
FIG. 7 depicts a $^1$H NMR spectrum of Compound A Form 1.

Compound A Form 1 was analyzed by $^1$H NMR after dissolution in DMSO-$d_6$. In one embodiment, the resulting $^1$H NMR spectrograph (see FIG. 7) showed consistency with the structure of Compound A Form 1.

6.3.2. B. Characterization of Compound A Form 2

In one embodiment, the present disclosure is directed to a solid state form of Compound A referred to herein as Compound A Form 2. In some embodiments, the present disclosure provides Compound A Form 2 having a XRPD pattern substantially similar to that depicted in FIG. 8.

In some embodiments, Compound A Form 2 is identified in a composition by detecting one or more peaks in the composition's XRPD pattern selected from those listed in Table 1 below.

TABLE 1

Compound A Form 2 XRPD Peaks

| Peak No. | Pos. [°2 θ] | d-spacing [Å] | Height [counts] | Rel. Int. [%] |
|---|---|---|---|---|
| 1 | 5.5139 | 16.02804 | 2184.86 | 69.89 |
| 2 | 7.1405 | 12.38014 | 368.19 | 11.78 |
| 3 | 8.1338 | 10.87038 | 149.51 | 4.78 |
| 4 | 11.0081 | 8.03759 | 3125.97 | 100 |
| 5 | 11.5343 | 7.67211 | 1545.01 | 49.42 |
| 6 | 12.9135 | 6.85563 | 582.53 | 18.64 |
| 7 | 13.6473 | 6.48861 | 353.43 | 11.31 |
| 8 | 14.1422 | 6.26266 | 456.89 | 14.62 |
| 9 | 14.6119 | 6.06237 | 776.04 | 24.83 |
| 10 | 14.9124 | 5.94089 | 1246.87 | 39.89 |
| 11 | 15.3496 | 5.77263 | 385.8 | 12.34 |
| 12 | 16.5426 | 5.35893 | 1285.32 | 41.12 |
| 13 | 17.291 | 5.12861 | 78.64 | 2.52 |
| 14 | 18.1679 | 4.88302 | 710.37 | 22.72 |
| 15 | 19.1749 | 4.62879 | 2077.87 | 66.47 |
| 16 | 19.8994 | 4.46188 | 336.46 | 10.76 |
| 17 | 20.4374 | 4.34561 | 1087.39 | 34.79 |
| 18 | 20.8344 | 4.26369 | 2041.58 | 65.31 |
| 19 | 21.169 | 4.19705 | 594.79 | 19.03 |
| 20 | 21.4806 | 4.13686 | 1694.01 | 54.19 |
| 21 | 22.4725 | 3.95647 | 744.1 | 23.8 |
| 22 | 22.681 | 3.92057 | 1199.9 | 38.38 |
| 23 | 22.9286 | 3.87879 | 777.68 | 24.88 |
| 24 | 23.7574 | 3.74532 | 423.21 | 13.54 |
| 25 | 24.1837 | 3.68025 | 908.84 | 29.07 |
| 26 | 25.1025 | 3.54759 | 187.88 | 6.01 |
| 27 | 25.6658 | 3.47099 | 166.65 | 5.33 |
| 28 | 26.8125 | 3.3251 | 121.59 | 3.89 |
| 29 | 28.1745 | 3.16738 | 61.53 | 1.97 |
| 30 | 28.937 | 3.08563 | 61.98 | 1.98 |
| 31 | 30.2008 | 2.95933 | 110.63 | 3.54 |
| 32 | 31.7616 | 2.81737 | 150.45 | 4.81 |
| 33 | 33.116 | 2.70518 | 61.87 | 1.98 |

In some embodiments, Compound A Form 2 is identified in a composition by detecting two or more peaks in the composition's XRPD pattern selected from those in Table 1. In some embodiments, Compound A Form 2 is identified in a composition by detecting three or more peaks in the composition's XRPD pattern selected from those in Table 1. In some embodiments, Compound A Form 2 is identified in a composition by detecting four or more peaks in the composition's XRPD pattern selected from those in Table 1. In some embodiments, Compound A Form 2 is identified in a composition by detecting five or more peaks in the composition's XRPD pattern selected from those in Table 1. In some embodiments, Compound A Form 2 is identified in a composition by detecting six or more peaks in the composition's XRPD pattern selected from those in Table 1. In some embodiments, Compound A Form 2 is identified in a composition by detecting seven or more peaks in the composition's XRPD pattern selected from those in Table 1. In some embodiments, Compound A Form 2 is identified in a composition by detecting eight or more peaks in the composition's XRPD pattern selected from those in Table 1. In some embodiments, Compound A Form 2 is identified in a composition by detecting all of the peaks in Table 1 in the composition's XRPD pattern.

In some embodiments, Compound A Form 2 is identified in a composition by detecting at least eight peaks in the composition's XRPD pattern corresponding to the eight most intense peaks (based on relative percent intensity) in Table 1±0.3 degrees 2θ, more preferably ±0.2 degrees 2θ, even more preferably ±0.1 degrees 2θ, most preferably ±0.05 degrees 2θ.

In some embodiments, Compound A Form 2 is identified in a composition by detecting at least seven peaks in the composition's XRPD pattern corresponding to the seven most intense peaks (based on relative percent intensity) in Table 1±0.3 degrees 2θ, more preferably ±0.2 degrees 2θ, even more preferably ±0.1 degrees 2θ, most preferably ±0.05 degrees 2θ.

In some embodiments, Compound A Form 2 is identified in a composition by detecting at least six peaks in the composition's XRPD pattern corresponding to the six most intense peaks (based on relative percent intensity) in Table 1±0.3 degrees 2θ, more preferably ±0.2 degrees 2θ, even more preferably ±0.1 degrees 2θ, most preferably ±0.05 degrees 2θ.

In some embodiments, Compound A Form 2 is identified in a composition by detecting at least five peaks in the composition's XRPD pattern corresponding to the five most intense peaks (based on relative percent intensity) in Table 1±0.3 degrees 2θ, more preferably ±0.2 degrees 2θ, even more preferably ±0.1 degrees 2θ, most preferably ±0.05 degrees 2θ. For example, in certain embodiments, Compound A Form 2 is identified in a composition by detecting at least the following five peaks in the composition's XRPD pattern: about 5.51, about 11.01, about 19.17, about 20.83, and about 21.48 degrees 2θ±0.3 degrees 2θ, more preferably ±0.2 degrees 2θ, even more preferably ±0.1 degrees 2θ, most preferably ±0.05 degrees 2θ.

In some embodiments, Compound A Form 2 is identified in a composition by detecting at least four peaks in the composition's XRPD pattern corresponding to the four most intense peaks (based on relative percent intensity) in Table 1±0.3 degrees 2θ, more preferably ±0.2 degrees 2θ, even more preferably ±0.1 degrees 2θ, most preferably ±0.05 degrees 2θ. For example, in certain embodiments, Compound A Form 2 is identified in a composition by detecting at least the following four peaks in the composition's XRPD pattern: about 5.51, about 11.01, about 19.17, and about 20.83 degrees 2θ±0.3 degrees 2θ, more preferably ±0.2 degrees 2θ, even more preferably ±0.1 degrees 2θ, most preferably ±0.05 degrees 2θ.

In some embodiments, Compound A Form 2 is identified in a composition by detecting at least three peaks in the composition's XRPD pattern corresponding to the three most intense peaks (based on relative percent intensity) in Table 1±0.3 degrees 2θ, more preferably ±0.2 degrees 2θ, even more preferably ±0.1 degrees 2θ, most preferably ±0.05 degrees 2θ. For example, in certain embodiments, Compound A Form 2 is identified in a composition by detecting at least the following three peaks in the composition's XRPD pattern: about 5.51, about 11.01, and about 19.17 degrees 2θ±0.3 degrees 2θ, more preferably ±0.2 degrees 2θ, even more preferably ±0.1 degrees 2θ, most preferably ±0.05 degrees 2θ.

In some embodiments, Compound A Form 2 is identified in a composition by detecting at least two peaks in the composition's XRPD pattern corresponding to the two most intense peaks (based on relative percent intensity) in Table 1±0.3 degrees 2θ, more preferably ±0.2 degrees 2θ, even more preferably ±0.1 degrees 2θ, most preferably ±0.05 degrees 2θ.

In some embodiments, Compound A Form 2 is identified in a composition by detecting at least one peak in the composition's XRPD pattern corresponding to the most intense peak (based on relative percent intensity) in Table 1±0.3 degrees 2θ, more preferably ±0.2 degrees 2θ, even more preferably ±0.1 degrees 2θ, most preferably ±0.05 degrees 2θ. In some embodiments, Compound A Form 2 is identified in a composition by detecting one or more peaks in the composition's XRPD pattern selected from those at about 5.51, about 11.01, about 11.53, about 14.91, about 16.54, about 19.17, about 20.83, about 21.48, about 22.68, about 24.18 degrees 2θ±0.3 degrees 2θ, more preferably ±0.2 degrees 2θ, even more preferably ±0.1 degrees 2θ, most preferably ±0.05 degrees 2θ.

In some embodiments, Compound A Form 2 is identified in a composition by detecting two or more peaks, such as at least the two most intense peaks, in the composition's XRPD pattern selected from those at about 5.51, about 11.01, about 11.53, about 14.91, about 16.54, about 19.17, about 20.83, about 21.48, about 22.68, about 24.18 degrees 2θ±0.3 degrees 2θ, more preferably ±0.2 degrees 2θ, even more preferably ±0.1 degrees 2θ, most preferably ±0.05 degrees 2θ.

In some embodiments, Compound A Form 2 is identified in a composition by detecting three or more peaks in the composition's XRPD pattern selected from those at about 5.51, about 11.01, about 11.53, about 14.91, about 16.54, about 19.17, about 20.83, about 21.48, about 22.68, about 24.18 degrees 2θ±0.3 degrees 2θ, more preferably ±0.2 degrees 2θ, even more preferably ±0.1 degrees 2θ, most preferably ±0.05 degrees 2θ.

In some embodiments, Compound A Form 2 is identified in a composition by detecting four or more peaks in the composition's XRPD pattern selected from those at about 5.51, about 11.01, about 11.53, about 14.91, about 16.54, about 19.17, about 20.83, about 21.48, about 22.68, about 24.18 degrees 2θ±0.3 degrees 2θ, more preferably ±0.2 degrees 2θ, even more preferably ±0.1 degrees 2θ, most preferably ±0.05 degrees 2θ.

In some embodiments, Compound A Form 2 is identified in a composition by detecting five or more peaks in the composition's XRPD pattern selected from those at about 5.51, about 11.01, about 11.53, about 14.91, about 16.54, about 19.17, about 20.83, about 21.48, about 22.68, about 24.18 degrees 2θ±0.3 degrees 2θ, more preferably ±0.2 degrees 2θ, even more preferably ±0.1 degrees 2θ, most preferably ±0.05 degrees 2θ.

In some embodiments, Compound A Form 2 is identified in a composition by detecting six or more peaks in the composition's XRPD pattern selected from those at about 5.51, about 11.01, about 11.53, about 14.91, about 16.54, about 19.17, about 20.83, about 21.48, about 22.68, about 24.18 degrees 2θ±0.3 degrees 2θ, more preferably ±0.2 degrees 2θ, even more preferably ±0.1 degrees 2θ, most preferably ±0.05 degrees 2θ.

In some embodiments, Compound A Form 2 is identified in a composition by detecting seven or more peaks in the composition's XRPD pattern selected from those at about 5.51, about 11.01, about 11.53, about 14.91, about 16.54, about 19.17, about 20.83, about 21.48, about 22.68, about 24.18 degrees 2θ±0.3 degrees 2θ, more preferably ±0.2 degrees 2θ, even more preferably ±0.1 degrees 2θ, most preferably ±0.05 degrees 2θ.

In some embodiments, Compound A Form 2 is identified in a composition by detecting eight or more peaks in the composition's XRPD pattern selected from those at about 5.51, about 11.01, about 11.53, about 14.91, about 16.54, about 19.17, about 20.83, about 21.48, about 22.68, about 24.18 degrees 2θ±0.3 degrees 2θ, more preferably ±0.2 degrees 2θ, even more preferably ±0.1 degrees 2θ, most preferably ±0.05 degrees 2θ.

In some embodiments, Compound A Form 2 is identified in a composition by detecting peaks in the composition's XRPD pattern at about 5.51, about 11.01, about 11.53, about 14.91, about 16.54, about 19.17, about 20.83, about 21.48, about 22.68, about 24.18 degrees 2θ±0.3 degrees 2θ, more preferably ±0.2 degrees 2θ, even more preferably ±0.1 degrees 2θ, most preferably ±0.05 degrees 2θ.

In another embodiment, PLM analysis of Compound A Form 2 showed the solid to have a needle-like morphology with agglomeration and birefringence.

In another embodiment, TG analysis of Compound A Form 2 showed a 0.9% weight loss up to 200° C. and decomposition. In another embodiment, in the DTA, multiple thermal events are noted at an onset of approximately 183° C., with an endothermic peak at 186° C., an exothermic peak at 188° C. and a second endothermic peak at 192° C. (see FIG. 10).

Figure 10:
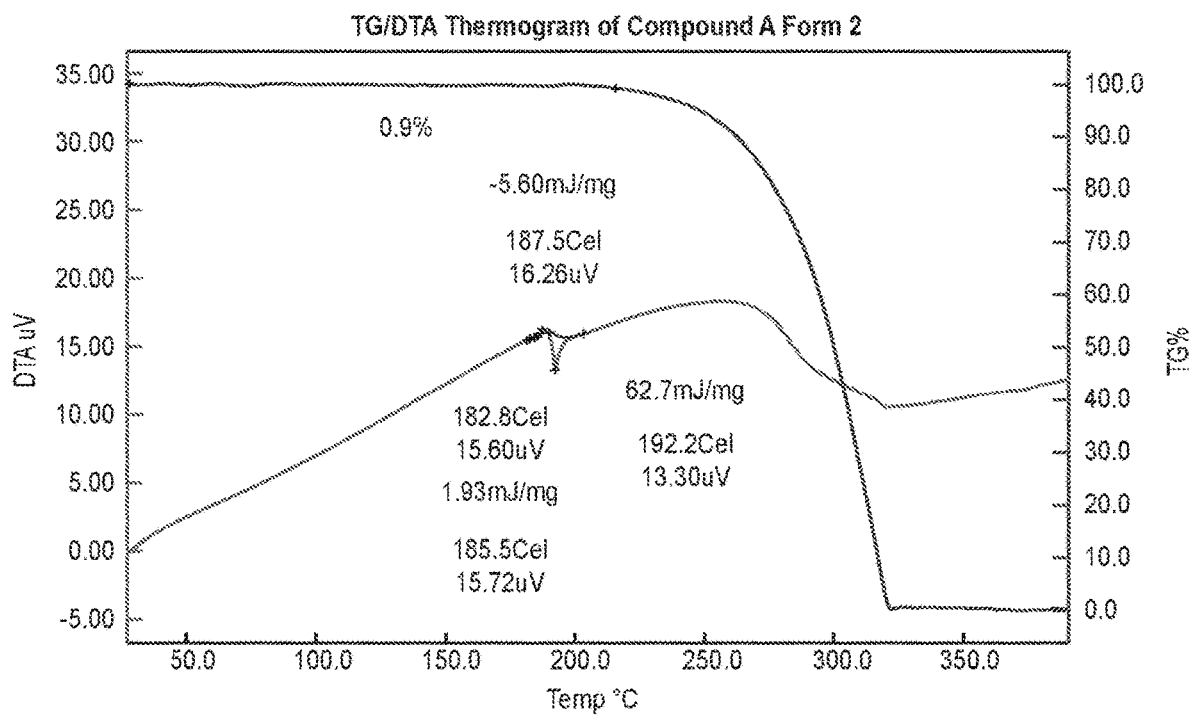
FIG. 10 depicts a TG/DTA thermogram of Compound A Form 2.

Accordingly, in some embodiments, the present disclosure provides Compound A Form 2 having a TG/DTA thermogram substantially similar to FIG. 10. In some embodiments, Compound A Form 2 is identified in a composition by detecting a DTA thermogram with an onset of approximately 183° C., with an endothermic peak at 186° C., an exothermic peak at 188° C. and a second endothermic peak at 192° C.

In another embodiment, DSC analysis of Compound A Form 2 showed a shallow endothermic event in the initial heat at onset 122° C., with a peak at 132° C. This is followed by multiple thermal events at an onset of 183° C., with a small endothermic peak at 186° C., an exothermic peak at 187° C. and a large endothermic peak at 192° C. (see FIG. 11). In the cooling cycle, a single exothermic event is noted at onset 151° C., with a peak at 149° C. (see FIG. 12). During the second heating cycle, a small exothermic event at onset 172° C. and a peak at 180° C. is noted. This is followed by a large endothermic event at onset 191° C., with a peak at 192° C. (see FIG. 13).

Figure 11:
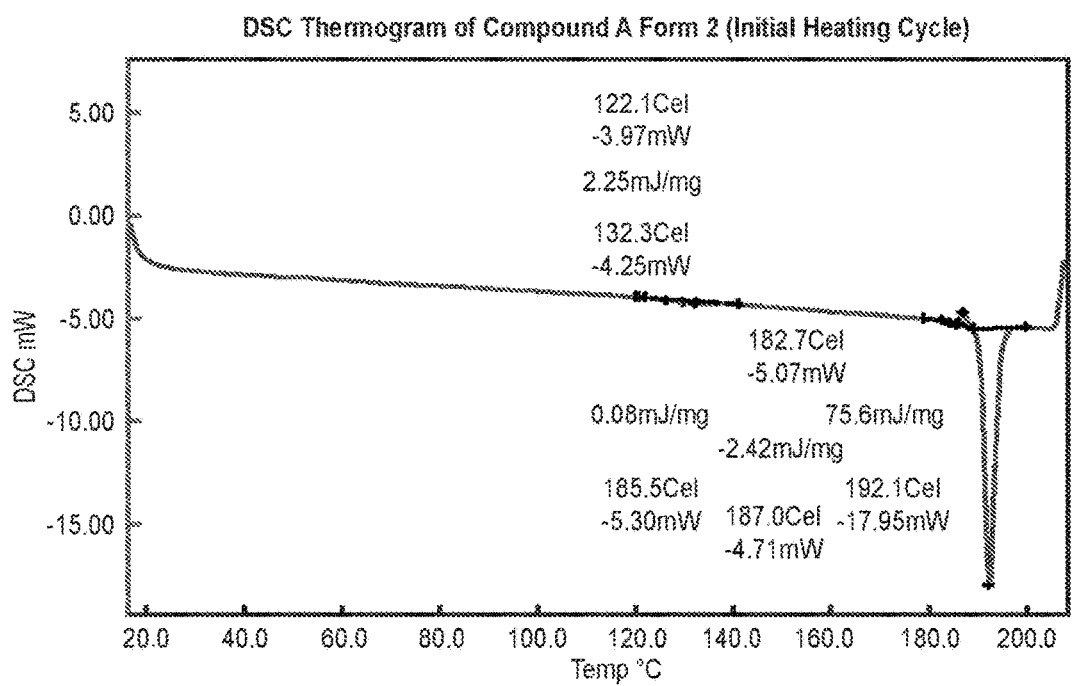
FIG. 11 depicts a DSC thermogram of Compound A Form 2 (Initial Heating Cycle).
Figure 12:
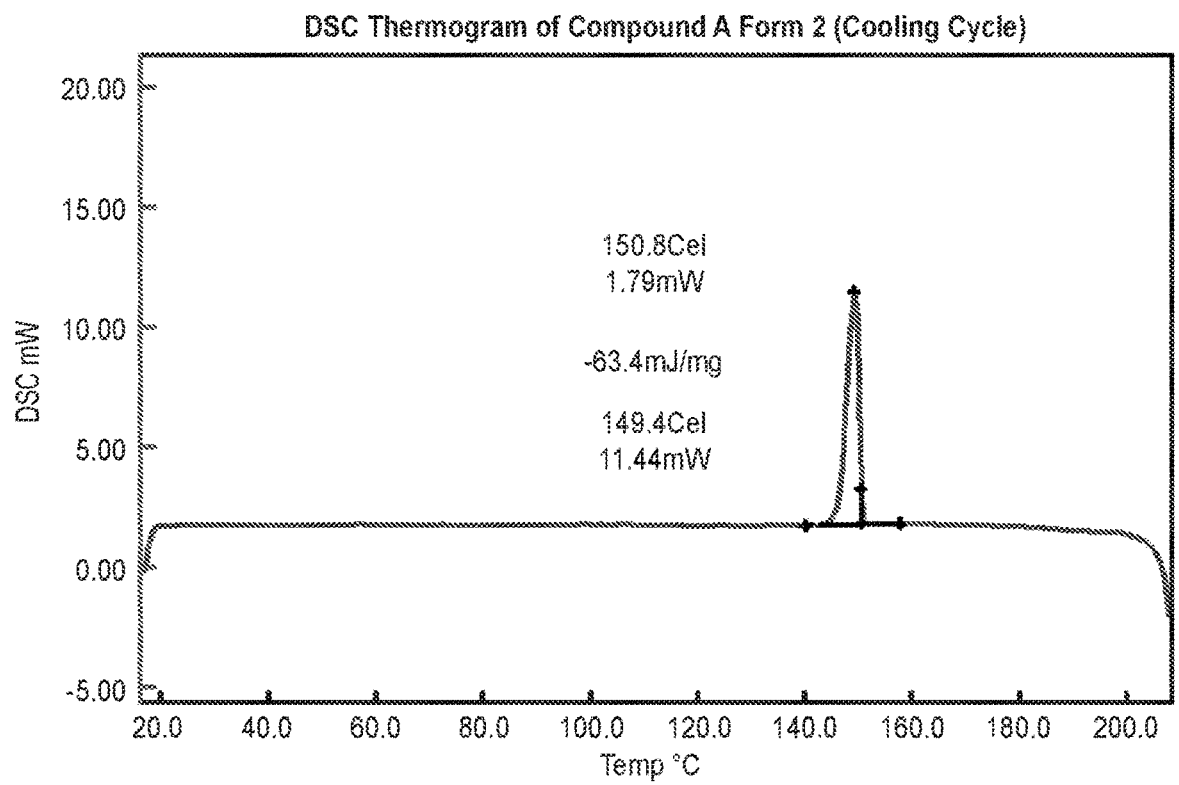
FIG. 12 depicts a DSC thermogram of Compound A Form 2 (Cooling Cycle).
Figure 13:
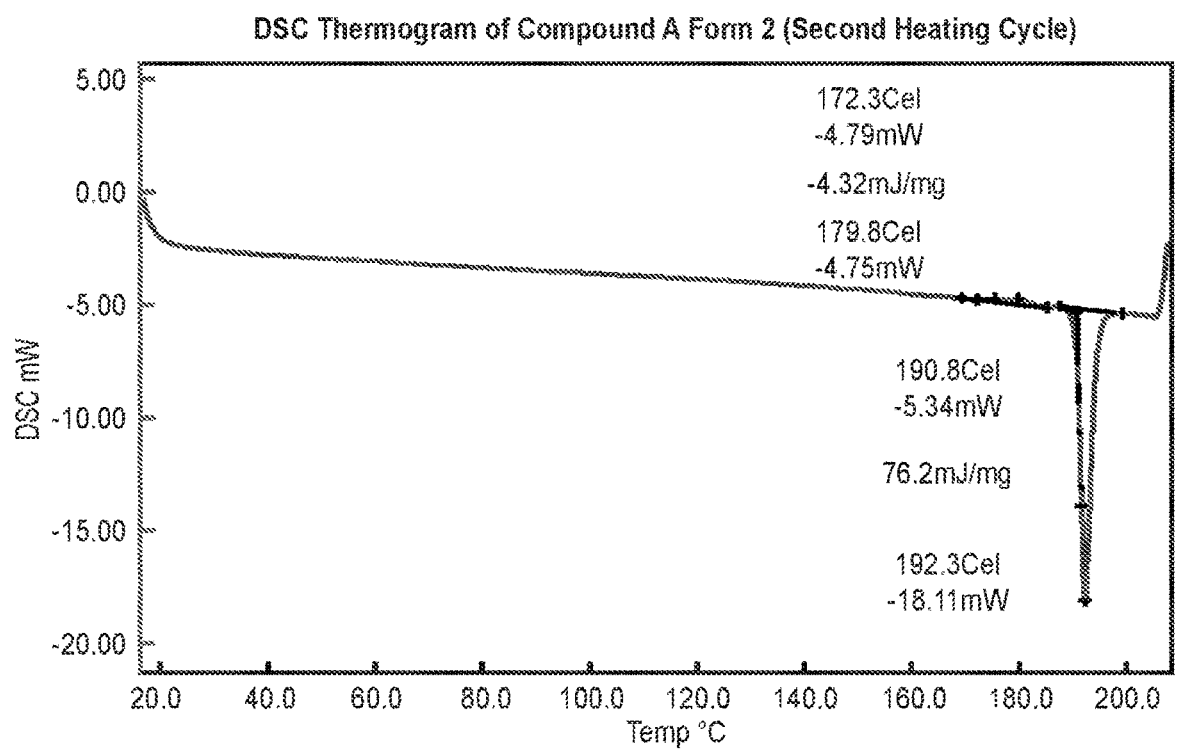
FIG. 13 depicts a DSC thermogram of Compound A Form 2 (Second Heating Cycle).

Accordingly, in some embodiments, the present disclosure provides Compound A Form 2 having a DSC thermogram substantially similar to FIG. 11, FIG. 12 and FIG. 13. In some embodiments, Compound A Form 2 is identified in a composition by detecting a DSC thermogram having, in the first heating cycle, a shallow endothermic event at onset 122° C., with a characterizing peak at 132° C., followed by, at onset 183° C., a second characterizing small endothermic peak at 186° C., a third characterizing exothermic peak at 187° C. and a large characterizing endothermic peak at 192° C.; in the cooling cycle, a single characterizing exothermic event at onset 151° C. with a peak at 149° C.; and, in the second heating cycle, a characterizing small exothermic event at onset 172° C. with a characterizing peak at 180° C., followed by, at onset 191° C., a characterizing peak at 192° C.

Figure 14:
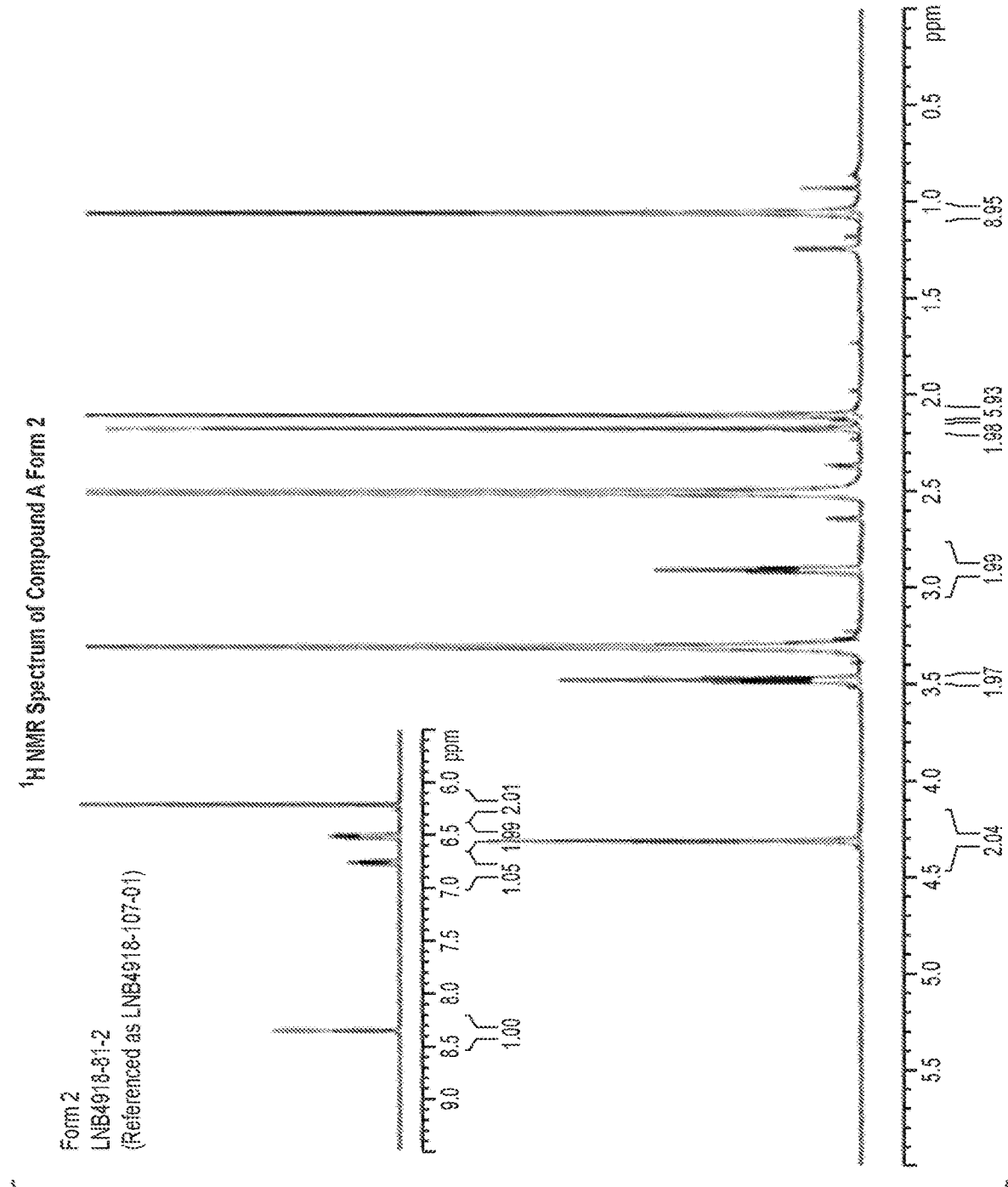
FIG. 14 depicts a $^1$H NMR spectrum of Compound A Form 2.

Compound A Form 2 was analyzed by $^1$H NMR after dissolution in DMSO-$d_6$. In another embodiment, the resulting $^1$H NMR spectrograph (see FIG. 14) showed consistency with the structure of Compound A Form 2.

Figure 15:
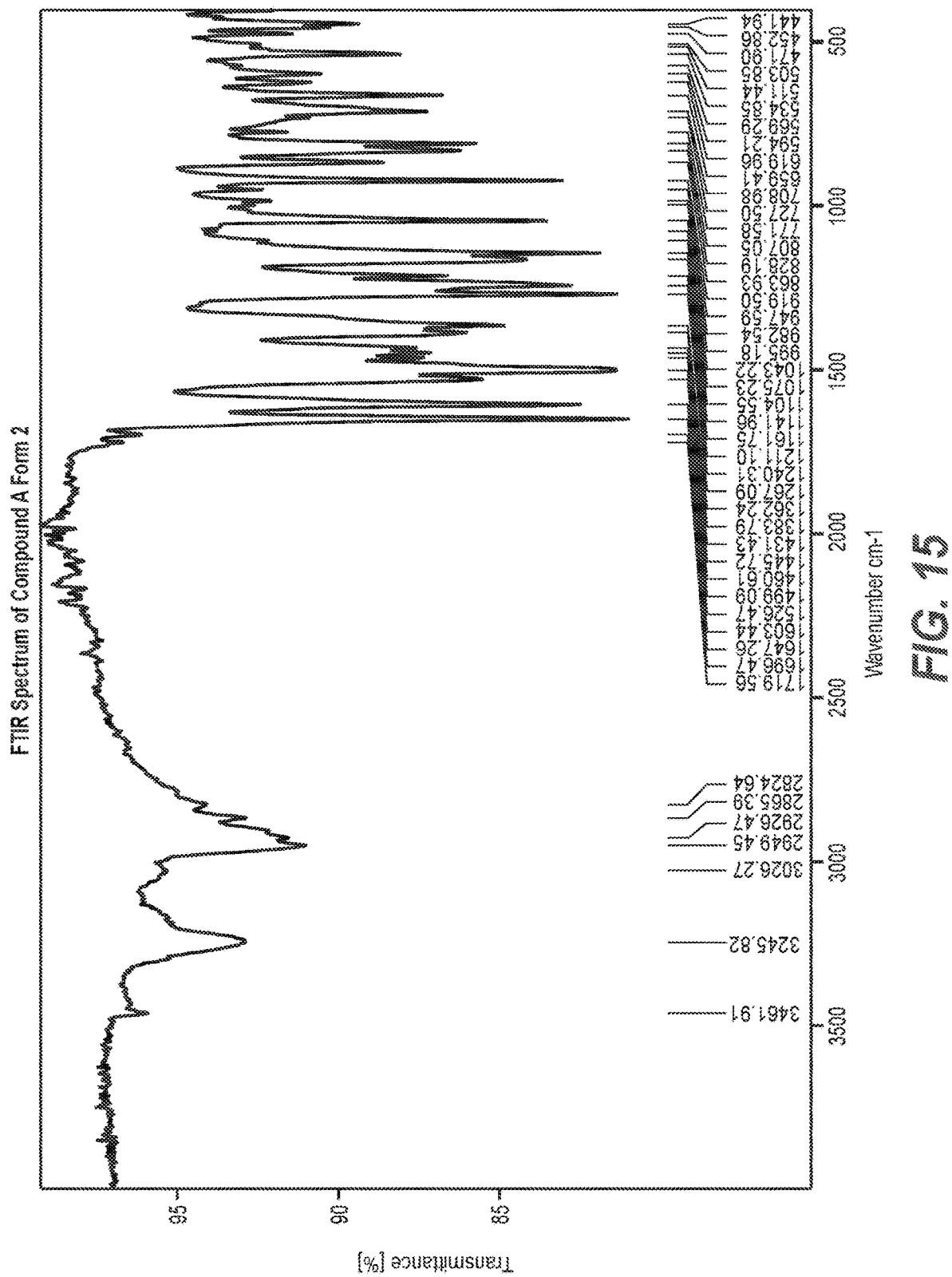
FIG. 15 depicts a FTIR spectrogram of Compound A Form 2.

In another embodiment, Compound A Form 2 was analyzed by FTIR for reference (see FIG. 15).

In another embodiment, HPLC purity analysis of Compound A Form 2 showed a purity value of 99.3%.

In another embodiment, GVS analysis of Compound A Form 2 found it to be slightly hygroscopic with an uptake of 0.37% at between 0-90% RH. The material tested was analyzed post-GVS by XRPD and was found to be Compound A Form 2.

In another embodiment, aqueous solubility of Compound A Form 2 returned a solubility value of <0.1 mg/mL and the pH of the sample post-solubility was 6.4. Post analysis, the excess solid was analyzed by XRPD and found to be Compound A Form 2.

In another embodiment, VT-XRPD analysis of Compound A Form 2 was carried out using the heating program below in Table 2:

TABLE 2

VT-XRPD Heating Program for Compound A Form 2

| Temperature | Procedure |
|---|---|
| 25° C. | Scan then heat at 2° C./min to next temperature |
| 50° C. | Scan then heat at 2° C./min to next temperature |
| 100° C. | Scan then heat at 2° C./min to next temperature |
| 150° C. | Scan then wait 5 minutes, then heat at 1° C./min to next temperature |
| 160° C. | Scan then wait 5 minutes, then heat at 0.5° C./min to next temperature |
| 165° C. | Scan then wait 5 minutes, then heat at 0.5° C./min to next temperature |
| 170° C. | Scan then wait 5 minutes, then heat at 1° C./min to next temperature |
| 180° C. | Scan then hold for 10 minutes before scanning again |
| 25° C. | Cool to temperature and scan |

In another embodiment, the solid state form of Compound A Form 2 at each temperature was analyzed by XRPD and the results are shown below in Table 3.

TABLE 3

VT-XRPD Results for Compound A Form 2

| Temperature | Polymorphic Form |
|---|---|
| 25° C. | Form 2 |
| 50° C. | Form 2 |
| 100° C. | Form 2 |
| 150° C. | Similar to Form 2 |
| 160° C. | Partially crystalline |
| 165° C. | Partially crystalline |
| 170° C. | Amorphous |
| 180° C. | Amorphous |
| 180° C. (post 10 minute hold) | Amorphous |
| 25° C. | Amorphous |

In another embodiment, hot stage microscopy of Compound A Form 2 was carried out using the method described herein. Compound A Form 2 was noted to begin melting at approximately 143° C., with the material fully melted after heating to 148° C.

6.3.3. C. Characterization of Compound A Form 3

In one embodiment, the present disclosure is directed to a solid state form of Compound A referred to herein as Compound A Form 3. In some embodiments, the present disclosure provides Compound A Form 3 having a XRPD pattern substantially similar to that depicted in FIG. 16.

6.3.4. D. Characterization of Compound A Form 4

In one embodiment, the present disclosure is directed to a solid state form of Compound A referred to herein as Compound A Form 4. In some embodiments, the present disclosure provides Compound A Form 4 having a XRPD pattern substantially similar to that depicted in FIG. 17.

In some embodiments, Compound A Form 4 is identified in a composition by detecting one or more peaks in the composition's XRPD pattern selected from those listed in Table 4 below.

TABLE 4

Compound A Form 4 XRPD Peaks

| No. | Pos. [°2 θ] | d-spacing [Å] | Height [counts] | Rel. Int. [%] |
|---|---|---|---|---|
| 1 | 5.4342 | 16.26283 | 693.72 | 40.75 |
| 2 | 8.147 | 10.85271 | 443.67 | 26.06 |
| 3 | 10.887 | 8.12677 | 214.39 | 12.59 |
| 4 | 13.6239 | 6.49969 | 1067.48 | 62.71 |
| 5 | 14.1617 | 6.25406 | 707.43 | 41.56 |
| 6 | 14.611 | 6.06274 | 1349.19 | 79.26 |
| 7 | 15.1464 | 5.84962 | 123.53 | 7.26 |
| 8 | 15.8296 | 5.59865 | 181.47 | 10.66 |
| 9 | 16.3411 | 5.42453 | 261.59 | 15.37 |
| 10 | 17.3936 | 5.0986 | 187.21 | 11 |
| 11 | 18.4431 | 4.81076 | 1192.5 | 70.05 |
| 12 | 19.1097 | 4.64443 | 94.4 | 5.55 |
| 13 | 19.9272 | 4.45571 | 634.39 | 37.27 |
| 14 | 21.1474 | 4.20129 | 209.02 | 12.28 |
| 15 | 22.6233 | 3.93043 | 385.21 | 22.63 |
| 16 | 22.9665 | 3.87248 | 1702.33 | 100.0 |
| 17 | 23.4359 | 3.79596 | 263.58 | 15.48 |
| 18 | 23.7277 | 3.74994 | 543.89 | 31.95 |
| 19 | 24.6717 | 3.60856 | 92.73 | 5.45 |
| 20 | 25.1909 | 3.53535 | 193.25 | 11.35 |
| 21 | 25.7845 | 3.45529 | 99.32 | 5.83 |
| 22 | 27.2593 | 3.2716 | 39.23 | 2.3 |
| 23 | 28.1532 | 3.16973 | 118.26 | 6.95 |
| 24 | 31.242 | 2.86303 | 30.28 | 1.78 |
| 25 | 33.1495 | 2.70252 | 167.4 | 9.83 |

In some embodiments, Compound A Form 4 is identified in a composition by detecting two or more peaks in the composition's XRPD pattern selected from those in Table 4. In some embodiments, Compound A Form 4 is identified in a composition by detecting three or more peaks in the composition's XRPD pattern selected from those in Table 4. In some embodiments, Compound A Form 4 is identified in a composition by detecting four or more peaks in the composition's XRPD pattern selected from those in Table 4. In some embodiments, Compound A Form 4 is identified in a composition by detecting five or more peaks in the composition's XRPD pattern selected from those in Table 4. In some embodiments, Compound A Form 4 is identified in a composition by detecting six or more peaks in the composition's XRPD pattern selected from those in Table 4. In some embodiments, Compound A Form 4 is identified in a composition by detecting seven or more peaks in the composition's XRPD pattern selected from those in Table 4. In some embodiments, Compound A Form 4 is identified in a composition by detecting all of the peaks in Table 4 in the composition's XRPD pattern.

In some embodiments, Compound A Form 4 is identified in a composition by detecting at least eight peaks in the composition's XRPD pattern corresponding to the eight most intense peaks (based on relative percent intensity) in Table 4±0.3 degrees 2θ, more preferably ±0.2 degrees 2θ, even more preferably ±0.1 degrees 2θ, most preferably ±0.05 degrees 2θ.

In some embodiments, Compound A Form 4 is identified in a composition by detecting at least seven peaks in the composition's XRPD pattern corresponding to the seven most intense peaks (based on relative percent intensity) in Table 4±0.3 degrees 2θ, more preferably ±0.2 degrees 2θ, even more preferably ±0.1 degrees 2θ, most preferably ±0.05 degrees 2θ.

In some embodiments, Compound A Form 4 is identified in a composition by detecting at least six peaks in the composition's XRPD pattern corresponding to the six most intense peaks (based on relative percent intensity) in Table 4±0.3 degrees 2θ, more preferably ±0.2 degrees 2θ, even more preferably ±0.1 degrees 2θ, most preferably ±0.05 degrees 2θ.

In some embodiments, Compound A Form 4 is identified in a composition by detecting at least five peaks in the composition's XRPD pattern corresponding to the five most intense peaks (based on relative percent intensity) in Table 4±0.3 degrees 2θ, more preferably ±0.2 degrees 2θ, even more preferably ±0.1 degrees 2θ, most preferably ±0.05 degrees 2θ. For example, in certain embodiments, Compound A Form 4 is identified in a composition by detecting at least the following five peaks in the composition's XRPD pattern: about 13.62, about 14.16, about 14.61, about 18.44, and about 22.97 degrees 2θ±0.3 degrees 2θ, more preferably ±0.2 degrees 2θ, even more preferably ±0.1 degrees 2θ, most preferably ±0.05 degrees 2θ.

In some embodiments, Compound A Form 4 is identified in a composition by detecting at least four peaks in the composition's XRPD pattern corresponding to the four most intense peaks (based on relative percent intensity) in Table 4±0.3 degrees 2θ, more preferably ±0.2 degrees 2θ, even more preferably ±0.1 degrees 2θ, most preferably ±0.05 degrees 2θ. For example, in certain embodiments, Compound A Form 4 is identified in a composition by detecting at least the following four peaks in the composition's XRPD pattern: about 13.62, about 14.61, about 18.44, and about 22.97 degrees 2θ±0.3 degrees 2θ, more preferably ±0.2 degrees 2θ, even more preferably ±0.1 degrees 2θ, most preferably ±0.05 degrees 2θ.

In some embodiments, Compound A Form 4 is identified in a composition by detecting at least three peaks in the composition's XRPD pattern corresponding to the three most intense peaks (based on relative percent intensity) in Table 4±0.3 degrees 2θ, more preferably ±0.2 degrees 2θ, even more preferably ±0.1 degrees 2θ, most preferably ±0.05 degrees 2θ. For example, in certain embodiments, Compound A Form 4 is identified in a composition by detecting at least the following three peaks in the composition's XRPD pattern: about 14.61, about 18.44, and about 22.97 degrees 2θ±0.3 degrees 2θ, more preferably ±0.2 degrees 2θ, even more preferably ±0.1 degrees 2θ, most preferably ±0.05 degrees 2θ.

In some embodiments, Compound A Form 4 is identified in a composition by detecting at least two peaks in the composition's XRPD pattern corresponding to the two most intense peaks (based on relative percent intensity) in Table 4±0.3 degrees 2θ, more preferably ±0.2 degrees 2θ, even more preferably ±0.1 degrees 2θ, most preferably ±0.05 degrees 2θ.

In some embodiments, Compound A Form 4 is identified in a composition by detecting at least one peak in the composition's XRPD pattern corresponding to the most intense peak (based on relative percent intensity) in Table 4±0.3 degrees 2θ, more preferably ±0.2 degrees 2θ, even more preferably ±0.1 degrees 2θ, most preferably ±0.05 degrees 2θ.

In some embodiments, Compound A Form 4 is identified in a composition by detecting one or more peaks in the composition's XRPD pattern selected from those at about 13.62, about 14.16, about 14.61, about 18.44, about 19.92, about 22.97, about 23.73 degrees 2θ±0.3 degrees 2θ, more preferably ±0.2 degrees 2θ, even more preferably ±0.1 degrees 2θ, most preferably ±0.05 degrees 2θ.

In some embodiments, Compound A Form 4 is identified in a composition by detecting two or more peaks, such as at least the two most intense peaks, in the composition's XRPD pattern selected from those at about 13.62, about 14.16, about 14.61, about 18.44, about 19.92, about 22.97, about 23.73 degrees 2θ±0.3 degrees 2θ, more preferably ±0.2 degrees 2θ, even more preferably ±0.1 degrees 2θ, most preferably ±0.05 degrees 2θ.

In some embodiments, Compound A Form 4 is identified in a composition by detecting three or more peaks in the composition's XRPD pattern selected from those at about 13.62, about 14.16, about 14.61, about 18.44, about 19.92, about 22.97, about 23.73 degrees 2θ±0.3 degrees 2θ, more preferably ±0.2 degrees 2θ, even more preferably ±0.1 degrees 2θ, most preferably ±0.05 degrees 2θ.

In some embodiments, Compound A Form 4 is identified in a composition by detecting four or more peaks in the composition's XRPD pattern selected from those at about 13.62, about 14.16, about 14.61, about 18.44, about 19.92, about 22.97, about 23.73 degrees 2θ±0.3 degrees 2θ, more preferably ±0.2 degrees 2θ, even more preferably ±0.1 degrees 2θ, most preferably ±0.05 degrees 2θ.

In some embodiments, Compound A Form 4 is identified in a composition by detecting five or more peaks in the composition's XRPD pattern selected from those at about 13.62, about 14.16, about 14.61, about 18.44, about 19.92, about 22.97, about 23.73 degrees 2θ±0.3 degrees 2θ, more preferably ±0.2 degrees 2θ, even more preferably ±0.1 degrees 2θ, most preferably ±0.05 degrees 2θ.

In some embodiments, Compound A Form 4 is identified in a composition by detecting six or more peaks in the composition's XRPD pattern selected from those at about 13.62, about 14.16, about 14.61, about 18.44, about 19.92, about 22.97, about 23.73 degrees 2θ±0.3 degrees 2θ, more preferably ±0.2 degrees 2θ, even more preferably ±0.1 degrees 2θ, most preferably ±0.05 degrees 2θ.

In some embodiments, Compound A Form 4 is identified in a composition by detecting peaks in the composition's XRPD pattern at about 13.62, about 14.16, about 14.61, about 18.44, about 19.92, about 22.97, about 23.73 degrees 2θ±0.3 degrees 2θ, more preferably ±0.2 degrees 2θ, even more preferably ±0.1 degrees 2θ, most preferably ±0.05 degrees 2θ.

In another embodiment, PLM analysis of Compound A Form 4 showed the solid to be lath-like in morphology with agglomeration and birefringence.

In another embodiment, TG analysis of Compound A Form 4 showed a 1.0% weight loss up to 200° C. and decomposition. In another embodiment, In the DTA, a shallow endothermic event at onset 127° C. with a peak at 135° C. was noted, followed by a large endothermic event at onset 191° C., with a peak at 193° C. (see FIG. 19).

Figure 19:
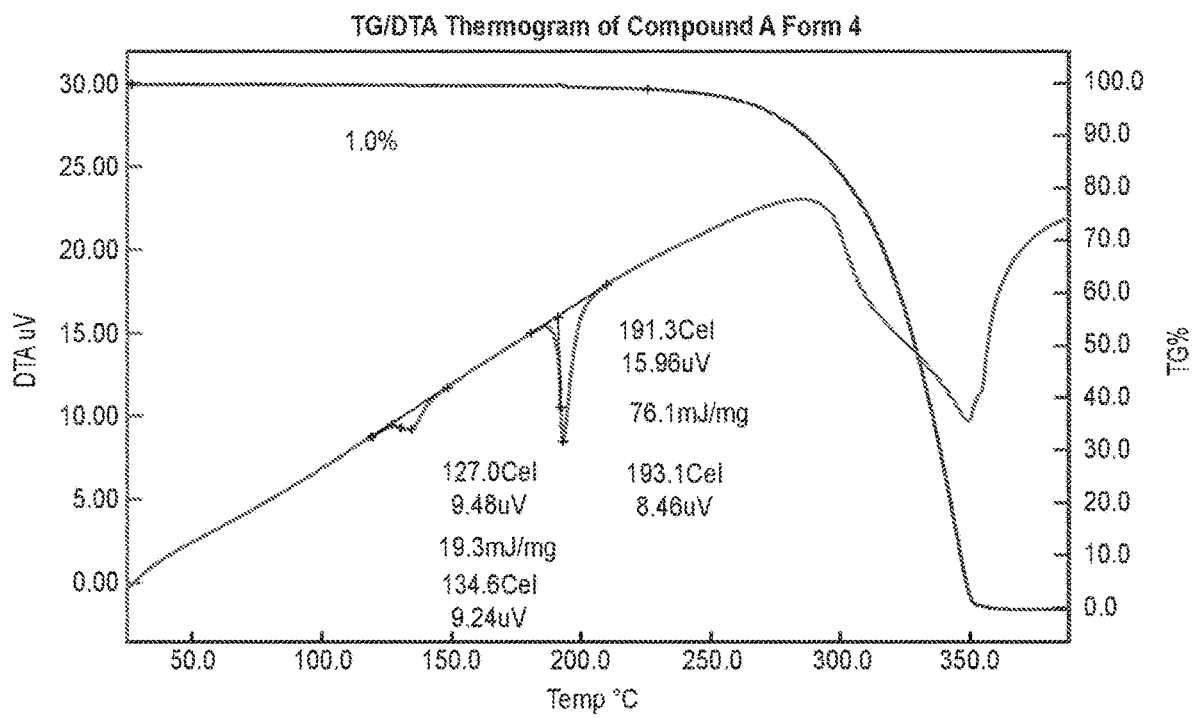
FIG. 19 depicts a TG/DTA thermogram of Compound A Form 4.

Accordingly, in some embodiments, the present disclosure provides Compound A Form 4 having a TG/DTA thermogram substantially similar to FIG. 19. In some embodiments, Compound A Form 4 is identified in a composition by detecting a DTA thermogram with a shallow endothermic event at onset 127° C. with a peak at 135° C., and a large endothermic event at onset 191° C., with a peak at 193° C.

In another embodiment, DSC analysis of Compound A Form 4 showed a shallow endothermic event in the initial heat at onset 122° C., with a peak at 130° C. This is followed by a large endothermic event at onset 190° C. with a peak at 192° C. (see FIG. 20). In the cooling cycle, a single exothermic event was noted at onset 151° C., with a peak at 150° C. (see FIG. 21). During the second heating cycle, a small endothermic event was noted at onset 183° C. with a peak at 180° C. This was connected to a larger endothermic peak at 193° C. (see FIG. 22).

Figure 20:
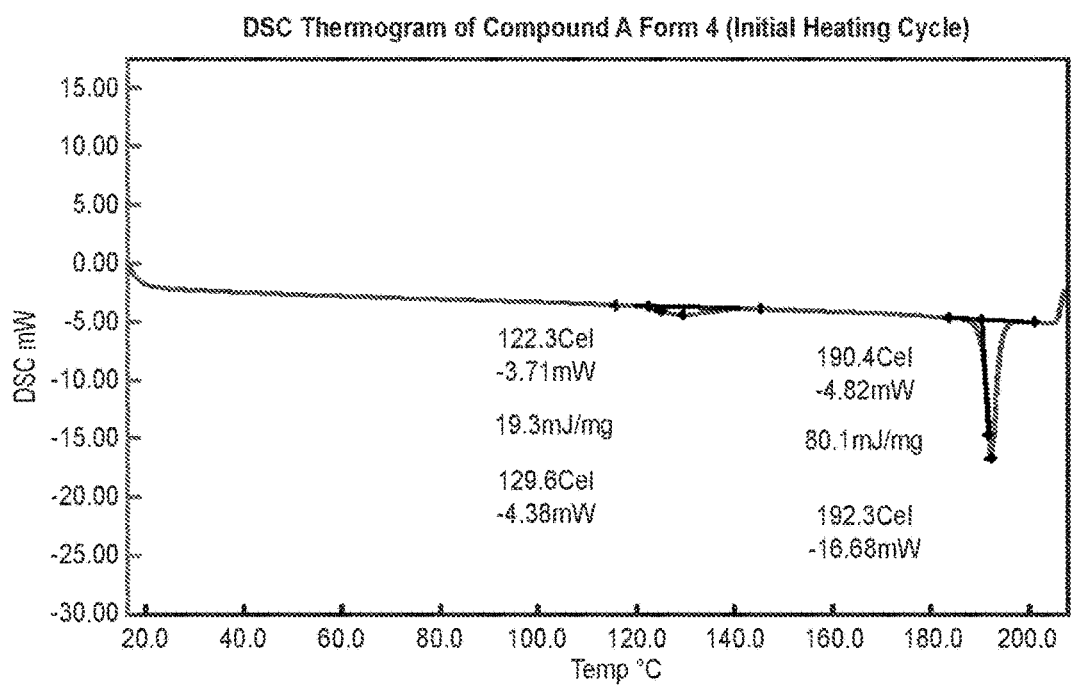
FIG. 20 depicts a DSC thermogram of Compound A Form 4 (Initial Heating Cycle).
Figure 21:
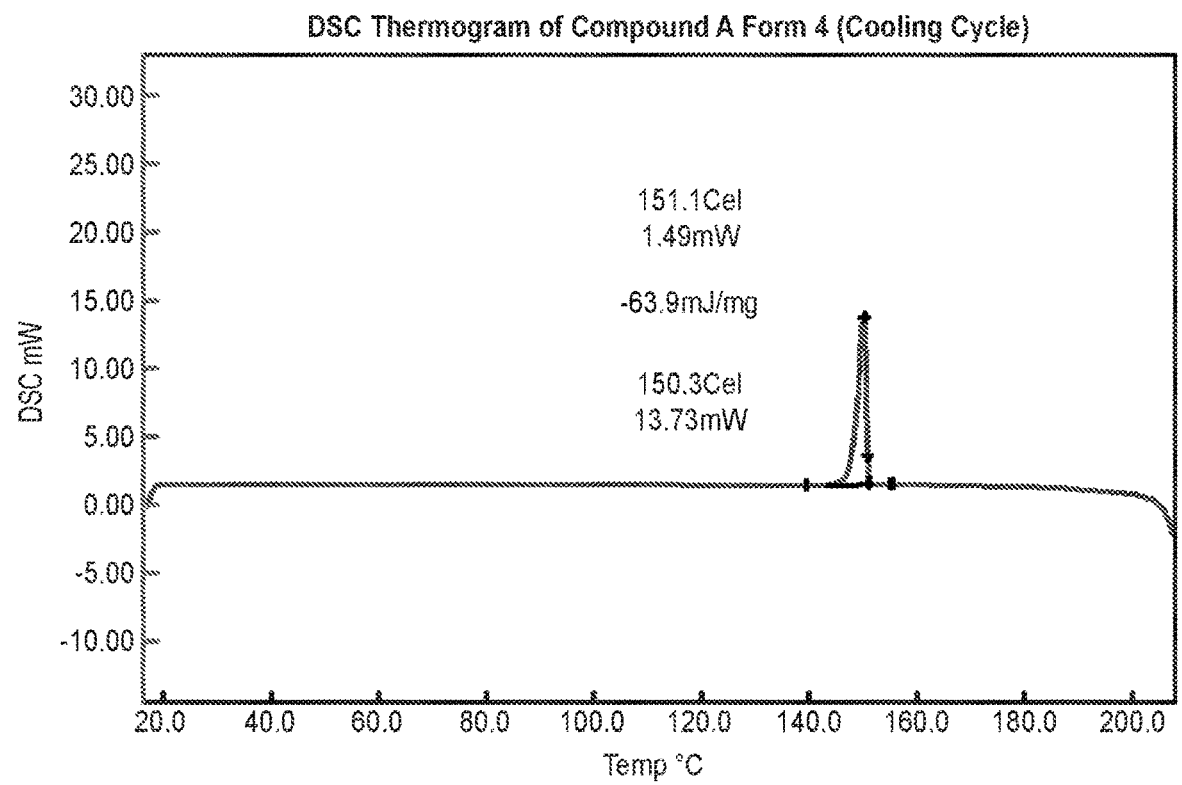
FIG. 21 depicts a DSC thermogram of Compound A Form 4 (Cooling Cycle).
Figure 22:
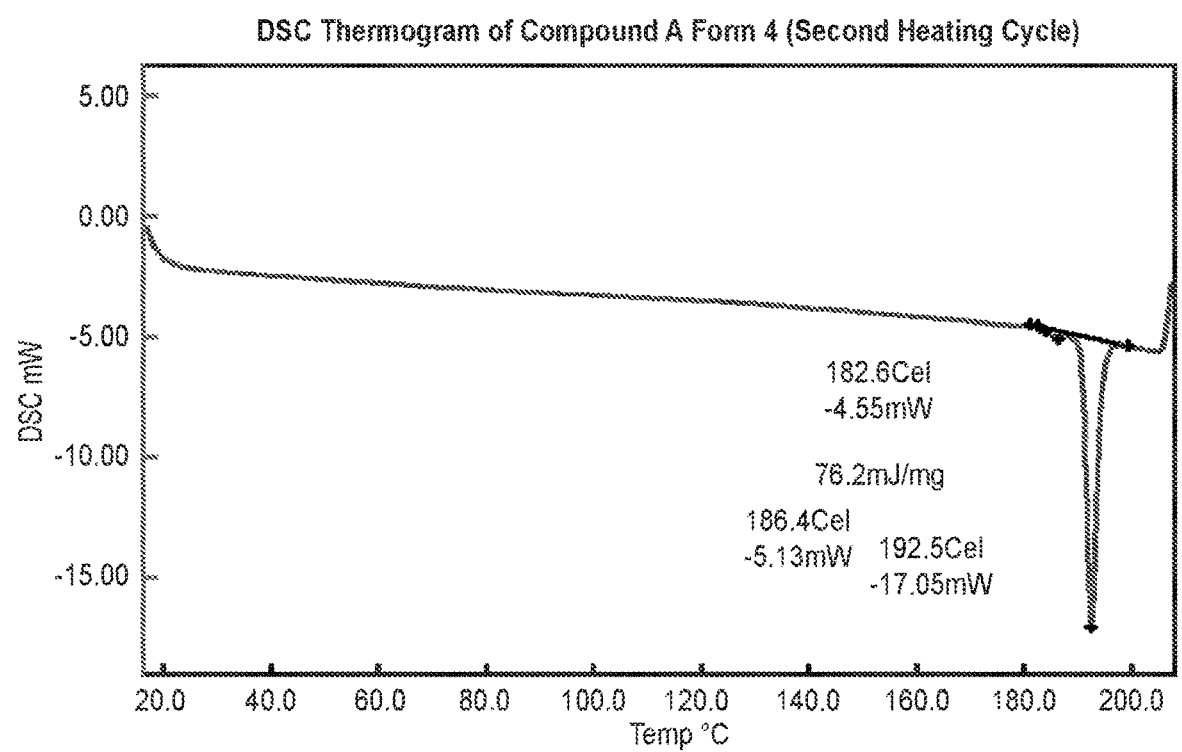
FIG. 22 depicts a DSC thermogram of Compound A Form 4 (Second Heating Cycle).

Accordingly, in some embodiments, the present disclosure provides Compound A Form 4 having a DSC thermogram substantially similar to FIG. 20, FIG. 21, and FIG. 22. In some embodiments, Compound A Form 4 is identified in a composition by detecting a DSC thermogram having, in the first heating cycle, a shallow endothermic event at onset 122° C., with a characterizing peak at 130° C., followed by, at onset 190° C., a large endothermic event with a characterizing peak at 192° C.; in the cooling cycle, an exothermic event at onset 151° C. with a characterizing peak at 150° C.; and, in the second heating cycle, a small exothermic event at onset 183° C. with a characterizing peak at 180° C. connected to a larger characterizing endothermic peak at 193° C.

Figure 23:
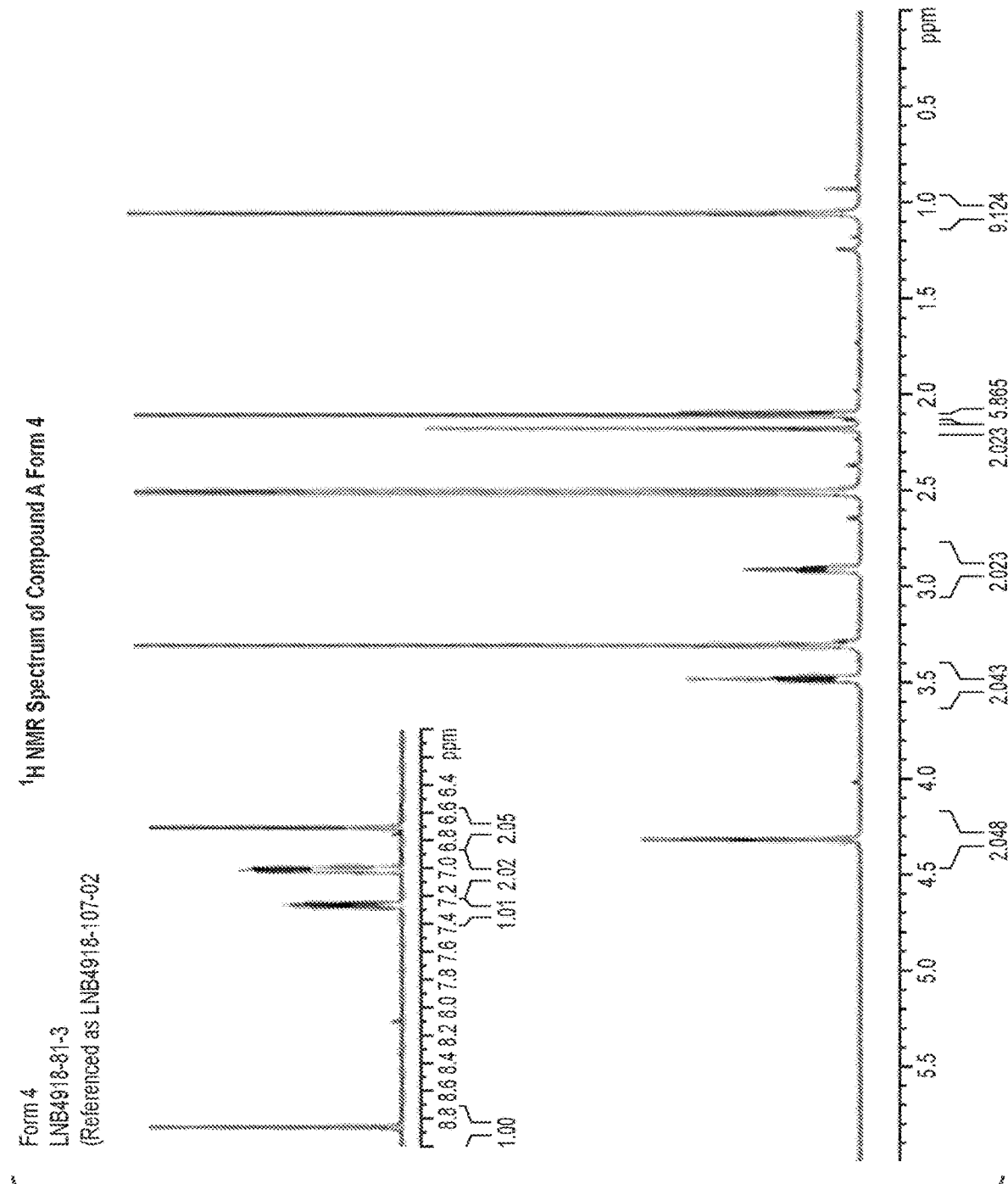
FIG. 23 depicts a $^1$H NMR spectrum of Compound A Form 4.

Compound A Form 4 was analyzed by $^1$H NMR after dissolution in DMSO-$d_6$. In another embodiment, the resulting $^1$H NMR spectrograph (see FIG. 23) showed consistency with the structure of Compound A Form 4.

Figure 24:
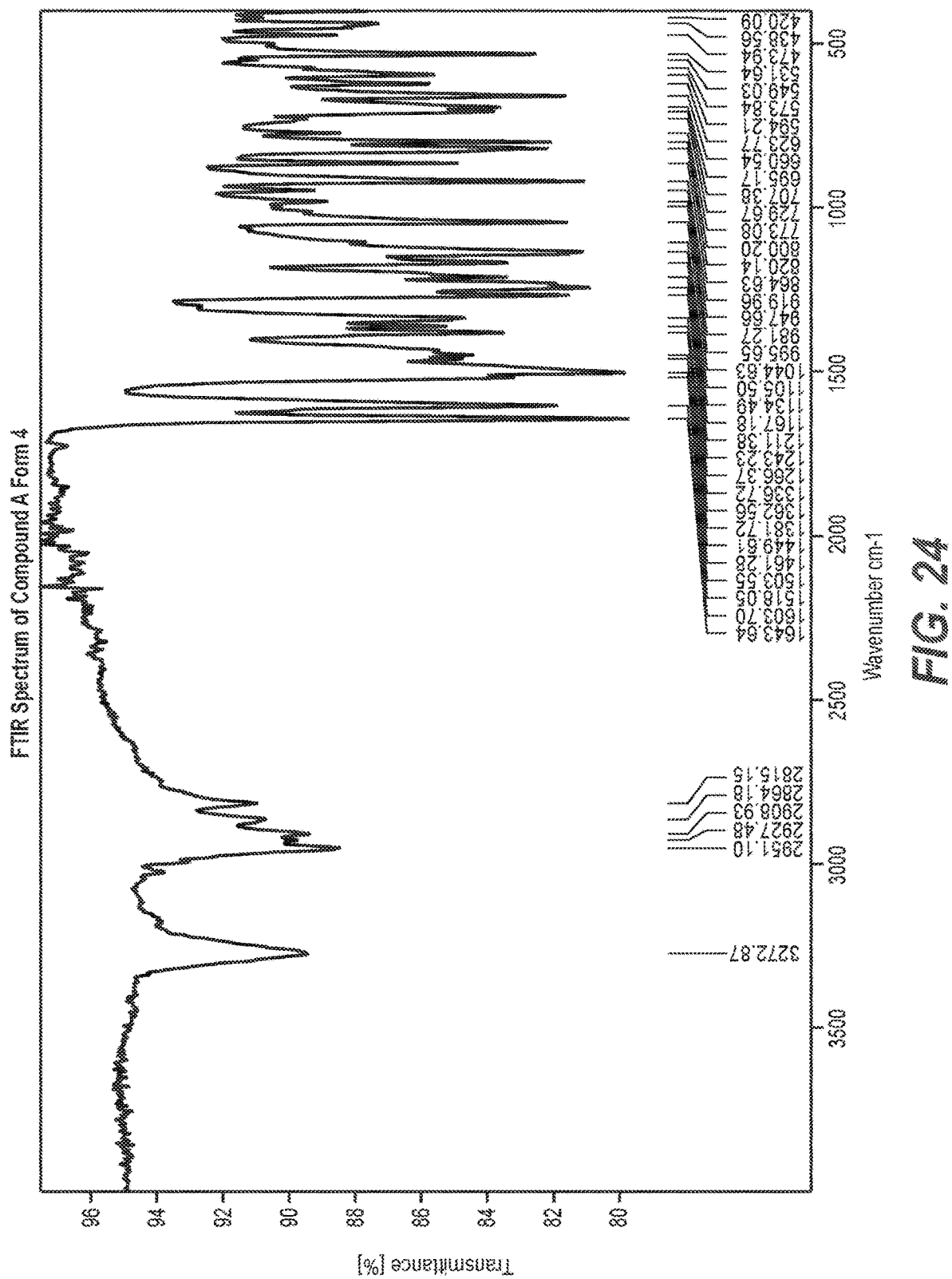
FIG. 24 depicts a FTIR spectrogram of Compound A Form 4.

In another embodiment, Compound A Form 4 was analyzed by FTIR for reference (see FIG. 24).

In another embodiment, HPLC purity analysis of Compound A Form 4 showed a purity value of 99.5%.

In another embodiment, GVS analysis of Compound A Form 4 found it to be slightly hygroscopic with an uptake of 0.4% at 90% RH. The material tested was analyzed post-GVS by XRPD and was found to be Compound A Form 4.

In another embodiment, aqueous solubility of Compound A Form 4 returned a solubility value of <0.1 mg/mL and the pH of the sample post-solubility was 6.3. Post analysis, the excess solid was analyzed by XRPD and found to be Compound A Form 4.

In another embodiment, VT-XRPD analysis of Compound A Form 4 was carried out using the heating program below in Table 5.

TABLE 5

VT-XRPD Heating Program for Compound A Form 4

| Temperature | Procedure |
| --- | --- |
| 25° C. | Scan then heat in 10 minutes to next temperature |
| 50° C. | Scan then heat in 10 minutes to next temperature |

TABLE 5-continued

VT-XRPD Heating Program for Compound A Form 4

| Temperature | Procedure |
| --- | --- |
| 60° C. | Scan then heat in 10 minutes to next temperature |
| 70° C. | Scan then heat in 10 minutes to next temperature |
| 80° C. | Scan then heat in 10 minutes to next temperature |
| 90° C. | Scan then heat in 10 minutes to next temperature |
| 100° C. | Scan and wait 5 minutes, then heat in 10 minutes to next temperature |
| 110° C. | Scan and wait 5 minutes, then heat in 10 minutes to next temperature |
| 120° C. | Scan and wait 5 minutes, then heat in 10 minutes to next temperature |
| 130° C. | Scan and wait 5 minutes, then heat in 10 minutes to next temperature |
| 140° C. | Scan then cool start temperature |
| 25° C. | Scan at temperature |

In another embodiment, the solid state form of Compound A Form 4 at each temperature was analyzed by XRPD and the results are shown below in Table 6:

TABLE 6

VT-XRPD Results for Compound A Form 4

| Temperature | Polymorphic Form |
| --- | --- |
| 25° C. | Form 4 |
| 50° C. | Form 4 |
| 60° C. | Form 4 |
| 70° C. | Form 4 |
| 80° C. | Form 4 |
| 95° C. | Form 4 |
| 100° C. | Form 4 |
| 110° C. (5 minute hold) | Form 4 + additional peaks |
| 120° C. (5 minute hold) | Form 4 + additional peaks |
| 130° C. (5 minute hold) | Form 4 + Form 9 |
| 140° C. (5 minute hold) | Form 9 |
| 25° C. | Form 9 |

In another embodiment, hot stage microscopy of Compound A Form 4 was carried out using the method described herein. Compound A Form 4 was noted to begin melting at approximately 138° C., with the material fully melted after heating to 160° C.

6.3.5. E. Characterization of Compound A Form 5

In one embodiment, the present disclosure is directed to a solid state form of Compound A referred to herein as Compound A Form 5. In some embodiments, the present disclosure provides Compound A Form 5 having a XRPD pattern substantially similar to that depicted in FIG. 25.

6.3.6. F. Characterization of Compound A Form 6

In one embodiment, the present disclosure is directed to a solid state form of Compound A referred to herein as Compound A Form 6. In some embodiments, the present disclosure provides Compound A Form 6 having a XRPD pattern substantially similar to that depicted in FIG. 26.

6.3.7. G. Characterization of Compound A Form 7

In one embodiment, the present disclosure is directed to a solid state form of Compound A referred to herein as Compound A Form 7. In some embodiments, the present disclosure provides Compound A Form 7 having a XRPD pattern substantially similar to that depicted in FIG. 27.

6.3.8. H. Characterization of Compound A Form 8

In one embodiment, the present disclosure is directed to a solid state form of Compound A referred to herein as Compound A Form 8. In some embodiments, the present disclosure provides Compound A Form 8 having a XRPD pattern substantially similar to that depicted in FIG. 28.

6.3.9. I. Characterization of Compound A Form 9

In one embodiment, the present disclosure is directed to a solid state form of Compound A referred to herein as Compound A Form 9. In some embodiments, the present disclosure provides Compound A Form 9 having a XRPD pattern substantially similar to that depicted in FIG. 29.

In some embodiments, Compound A Form 9 is identified in a composition by detecting one or more peaks in the composition's XRPD pattern selected from those listed in Table 7 below.

TABLE 7

Compound A Form 9 XRPD Peaks

| No. | Pos. [°2 θ] | d-spacing [A] | Height [counts] | Rel. Int. [%] |
|---|---|---|---|---|
| 1 | 3.0544 | 28.92663 | 1035.69 | 100.00 |
| 2 | 6.1066 | 14.47375 | 186.78 | 18.03 |
| 3 | 9.1718 | 9.64232 | 61.31 | 5.92 |
| 4 | 10.6856 | 8.27949 | 319.44 | 30.84 |
| 5 | 13.0577 | 6.78022 | 231.16 | 22.32 |
| 6 | 14.6683 | 6.03917 | 237.30 | 22.91 |
| 7 | 15.3322 | 5.77914 | 392.46 | 37.89 |
| 8 | 16.4080 | 5.40257 | 83.49 | 8.06 |
| 9 | 18.0795 | 4.90670 | 604.36 | 58.35 |
| 10 | 20.3496 | 4.36056 | 53.27 | 5.14 |
| 11 | 20.9827 | 4.23389 | 358.34 | 34.60 |
| 12 | 23.1871 | 3.83294 | 129.61 | 12.51 |
| 13 | 23.4925 | 3.78694 | 445.22 | 42.99 |
| 14 | 25.2458 | 3.52778 | 318.18 | 30.72 |

In some embodiments, Compound A Form 9 is identified in a composition by detecting two or more peaks in the composition's XRPD pattern selected from those in Table 7. In some embodiments, Compound A Form 9 is identified in a composition by detecting three or more peaks in the composition's XRPD pattern selected from those in Table 7. In some embodiments, Compound A Form 9 is identified in a composition by detecting four or more peaks in the composition's XRPD pattern selected from those in Table 7. In some embodiments, Compound A Form 9 is identified in a composition by detecting five or more peaks in the composition's XRPD pattern selected from those in Table 7. In some embodiments, Compound A Form 9 is identified in a composition by detecting six or more peaks in the composition's XRPD pattern selected from those in Table 7. In some embodiments, Compound A Form 9 is identified in a composition by detecting seven or more peaks in the composition's XRPD pattern selected from those in Table 7. In some embodiments, Compound A Form 9 is identified in a composition by detecting all of the peaks in Table 7 in the composition's XRPD pattern.

In some embodiments, Compound A Form 9 is identified in a composition by detecting at least eight peaks in the composition's XRPD pattern corresponding to the eight most intense peaks (based on relative percent intensity) in Table 7±0.3 degrees 2θ, more preferably ±0.2 degrees 2θ, even more preferably ±0.1 degrees 2θ, most preferably ±0.05 degrees 2θ.

In some embodiments, Compound A Form 9 is identified in a composition by detecting at least seven peaks in the composition's XRPD pattern corresponding to the seven most intense peaks (based on relative percent intensity) in Table 7±0.3 degrees 2θ, more preferably ±0.2 degrees 2θ, even more preferably ±0.1 degrees 2θ, most preferably ±0.05 degrees 2θ.

In some embodiments, Compound A Form 9 is identified in a composition by detecting at least six peaks in the composition's XRPD pattern corresponding to the six most intense peaks (based on relative percent intensity) in Table 7±0.3 degrees 2θ, more preferably ±0.2 degrees 2θ, even more preferably ±0.1 degrees 2θ, most preferably ±0.05 degrees 2θ.

In some embodiments, Compound A Form 9 is identified in a composition by detecting at least five peaks in the composition's XRPD pattern corresponding to the five most intense peaks (based on relative percent intensity) in Table 7±0.3 degrees 2θ, more preferably ±0.2 degrees 2θ, even more preferably ±0.1 degrees 2θ, most preferably ±0.05 degrees 2θ. For example, in certain embodiments, Compound A Form 9 is identified in a composition by detecting at least the following five peaks in the composition's XRPD pattern: about 3.05, about 15.33, about 18.08, about 20.98, and about 23.49 degrees 2θ±0.3 degrees 2θ, more preferably ±0.2 degrees 2θ, even more preferably ±0.1 degrees 2θ, most preferably ±0.05 degrees 2θ.

In some embodiments, Compound A Form 9 is identified in a composition by detecting at least four peaks in the composition's XRPD pattern corresponding to the four most intense peaks (based on relative percent intensity) in Table 7±0.3 degrees 2θ, more preferably ±0.2 degrees 2θ, even more preferably ±0.1 degrees 2θ, most preferably ±0.05 degrees 2θ. For example, in certain embodiments, Compound A Form 9 is identified in a composition by detecting at least the following four peaks in the composition's XRPD pattern: about 3.05, about 15.33, about 18.08, and about 23.49 degrees 2θ±0.3 degrees 2θ, more preferably ±0.2 degrees 2θ, even more preferably ±0.1 degrees 2θ, most preferably ±0.05 degrees 2θ.

In some embodiments, Compound A Form 9 is identified in a composition by detecting at least three peaks in the composition's XRPD pattern corresponding to the three most intense peaks (based on relative percent intensity) in Table 7±0.3 degrees 2θ, more preferably ±0.2 degrees 2θ, even more preferably ±0.1 degrees 2θ, most preferably ±0.05 degrees 2θ. For example, in certain embodiments, Compound A Form 9 is identified in a composition by detecting at least the following three peaks in the composition's XRPD pattern: about 3.05, about 18.08, and about 23.49 degrees 2θ±0.3 degrees 2θ, more preferably ±0.2 degrees 2θ, even more preferably ±0.1 degrees 2θ, most preferably ±0.05 degrees 2θ.

In some embodiments, Compound A Form 9 is identified in a composition by detecting at least two peaks in the composition's XRPD pattern corresponding to the two most intense peaks (based on relative percent intensity) in Table 7±0.3 degrees 2θ, more preferably ±0.2 degrees 2θ, even more preferably ±0.1 degrees 2θ, most preferably ±0.05 degrees 2θ.

In some embodiments, Compound A Form 9 is identified in a composition by detecting at least one peak in the composition's XRPD pattern corresponding to the most intense peak (based on relative percent intensity) in Table 7±0.3 degrees 2θ, more preferably ±0.2 degrees 2θ, even more preferably ±0.1 degrees 2θ, most preferably ±0.05 degrees 2θ.

In some embodiments, Compound A Form 9 is identified in a composition by detecting one or more peaks in the composition's XRPD pattern selected from those at about 3.05, about 6.107, about 10.69, about 15.33, about 18.08, about 20.98, about 23.49, about 25.25 degrees 2θ±0.3 degrees 2θ, more preferably ±0.2 degrees 2θ, even more preferably ±0.1 degrees 2θ, most preferably ±0.05 degrees 2θ.

In some embodiments, Compound A Form 9 is identified in a composition by detecting two or more peaks, such as at least the two most intense peaks, in the composition's XRPD pattern selected from those at about 3.05, about 6.107, about 10.69, about 15.33, about 18.08, about 20.98, about 23.49, about 25.25 degrees 2θ±0.3 degrees 2θ, more preferably ±0.2 degrees 2θ, even more preferably ±0.1 degrees 2θ, most preferably ±0.05 degrees 2θ.

In some embodiments, Compound A Form 9 is identified in a composition by detecting three or more peaks in the composition's XRPD pattern selected from those at about 3.05, about 6.107, about 10.69, about 15.33, about 18.08, about 20.98, about 23.49, about 25.25 degrees 2θ±0.3 degrees 2θ, more preferably ±0.2 degrees 2θ, even more preferably ±0.1 degrees 2θ, most preferably ±0.05 degrees 2θ.

In some embodiments, Compound A Form 9 is identified in a composition by detecting four or more peaks in the composition's XRPD pattern selected from those at about 3.05, about 6.107, about 10.69, about 15.33, about 18.08, about 20.98, about 23.49, about 25.25 degrees 2θ±0.3 degrees 2θ, more preferably ±0.2 degrees 2θ, even more preferably ±0.1 degrees 2θ, most preferably ±0.05 degrees 2θ.

In some embodiments, Compound A Form 9 is identified in a composition by detecting five or more peaks in the composition's XRPD pattern selected from those at about 3.05, about 6.107, about 10.69, about 15.33, about 18.08, about 20.98, about 23.49, about 25.25 degrees 2θ±0.3 degrees 2θ, more preferably ±0.2 degrees 2θ, even more preferably ±0.1 degrees 2θ, most preferably ±0.05 degrees 2θ.

In some embodiments, Compound A Form 9 is identified in a composition by detecting six or more peaks in the composition's XRPD pattern selected from those at about 3.05, about 6.107, about 10.69, about 15.33, about 18.08, about 20.98, about 23.49, about 25.25 degrees 2θ±0.3 degrees 2θ, more preferably ±0.2 degrees 2θ, even more preferably ±0.1 degrees 2θ, most preferably ±0.05 degrees 2θ.

In some embodiments, Compound A Form 9 is identified in a composition by detecting peaks in the composition's XRPD pattern at about 6.107, about 10.69, about 15.33, about 18.08, about 20.98, about 23.49, about 25.25 degrees 2θ±0.3 degrees 2θ, more preferably ±0.2 degrees 2θ, even more preferably ±0.1 degrees 2θ, most preferably ±0.05 degrees 2θ.

In another embodiment, PLM analysis of Compound A Form 9 showed the solid to be plate-like in morphology with agglomeration and birefringence.

In another embodiment, TG analysis of Compound A Form 9 showed a 0.4% weight loss up to 200° C. and decomposition. In the DTA, an endothermic event at onset 191° C. with a peak at 192° C. was noted (see FIG. 31).

Figure 31:
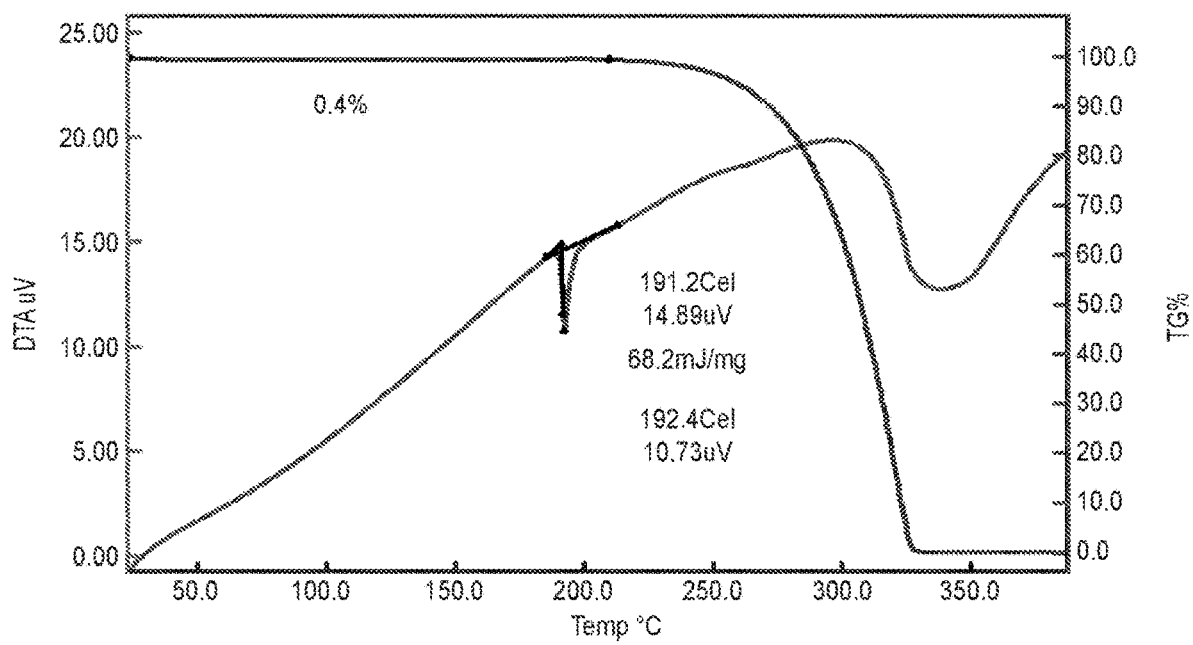
FIG. 31 depicts a TG/DTA thermogram of Compound A Form 9.

Accordingly, in some embodiments, the present disclosure provides Compound A Form 9 having a TG/DTA thermogram substantially similar to FIG. 31. In some embodiments, Compound A Form 4 is identified in a composition by detecting a DTA thermogram with an endothermic event at onset 191° C. with a peak at 192° C.

In another embodiment, DSC analysis of Compound A Form 9 showed a shallow exothermic event at the initial heat onset 42° C., with a peak at 55° C., followed by a shallow endothermic event at onset 127° C., with a peak at 133° C. This was followed by a large endothermic event at onset 189° C., with a peak at 192° C. (see FIG. 32). In the cooling cycle, a single exothermic event was noted at onset 157° C., with a peak at 155° C. (see FIG. 33). During the second heating cycle, a small exothermic event at onset 140° C., with a peak at 142° C. was noted, which was followed by a complex endothermic event with an onset 181° C., with a peak at 187° C. and a second onset at 190° C. and a peak at 192° C. (see FIG. 34).

Figure 32:
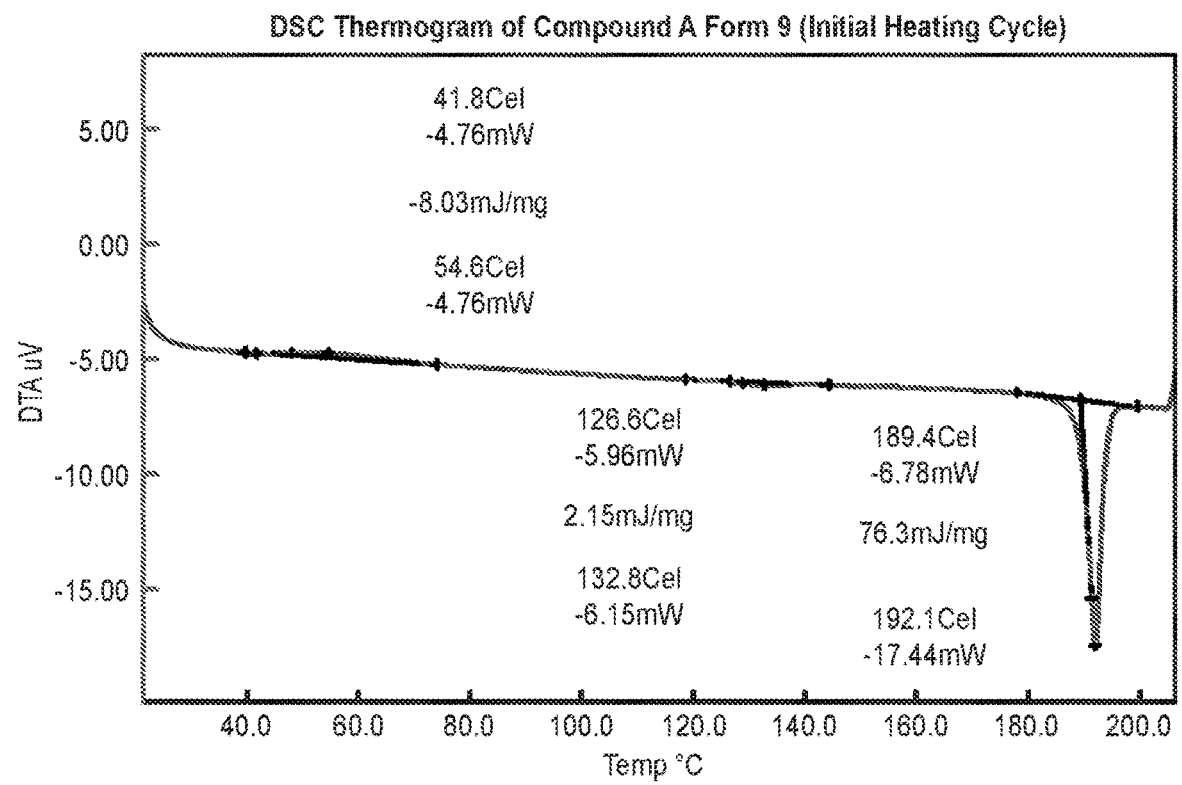
FIG. 32 depicts a DSC thermogram of Compound A Form 9 (Initial Heating Cycle).
Figure 33:
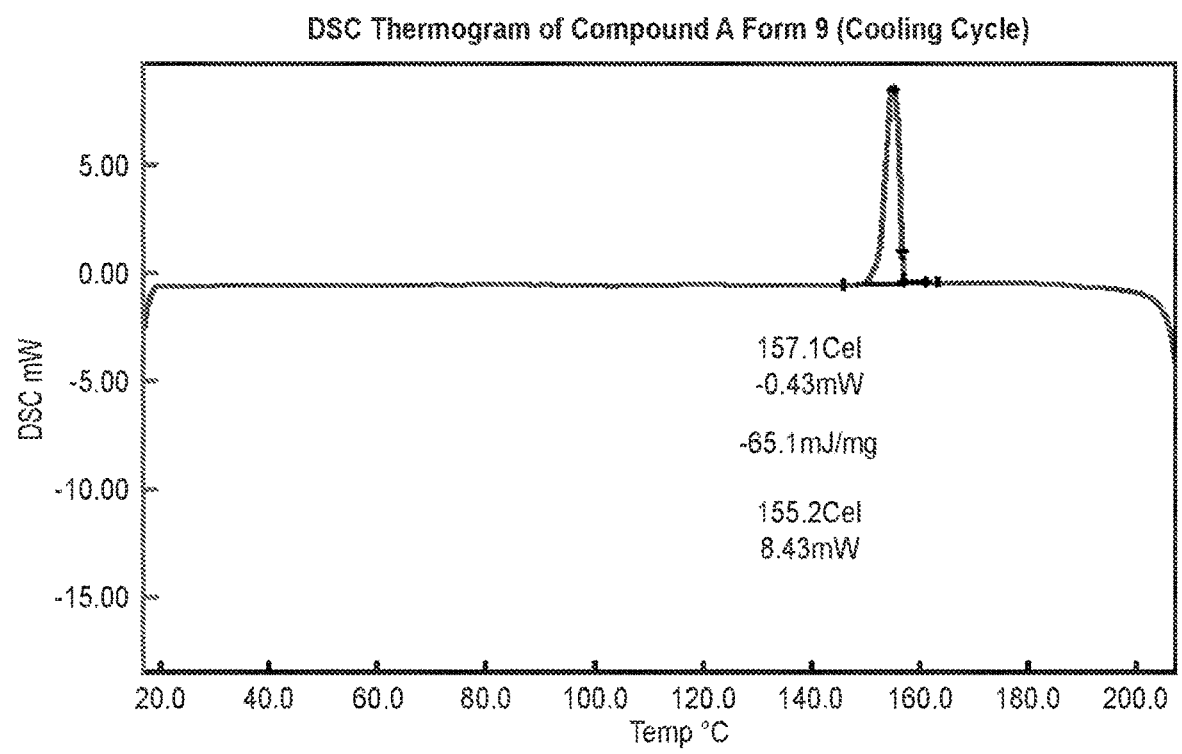
FIG. 33 depicts a DSC thermogram of Compound A Form 9 (Cooling Cycle).
Figure 34:
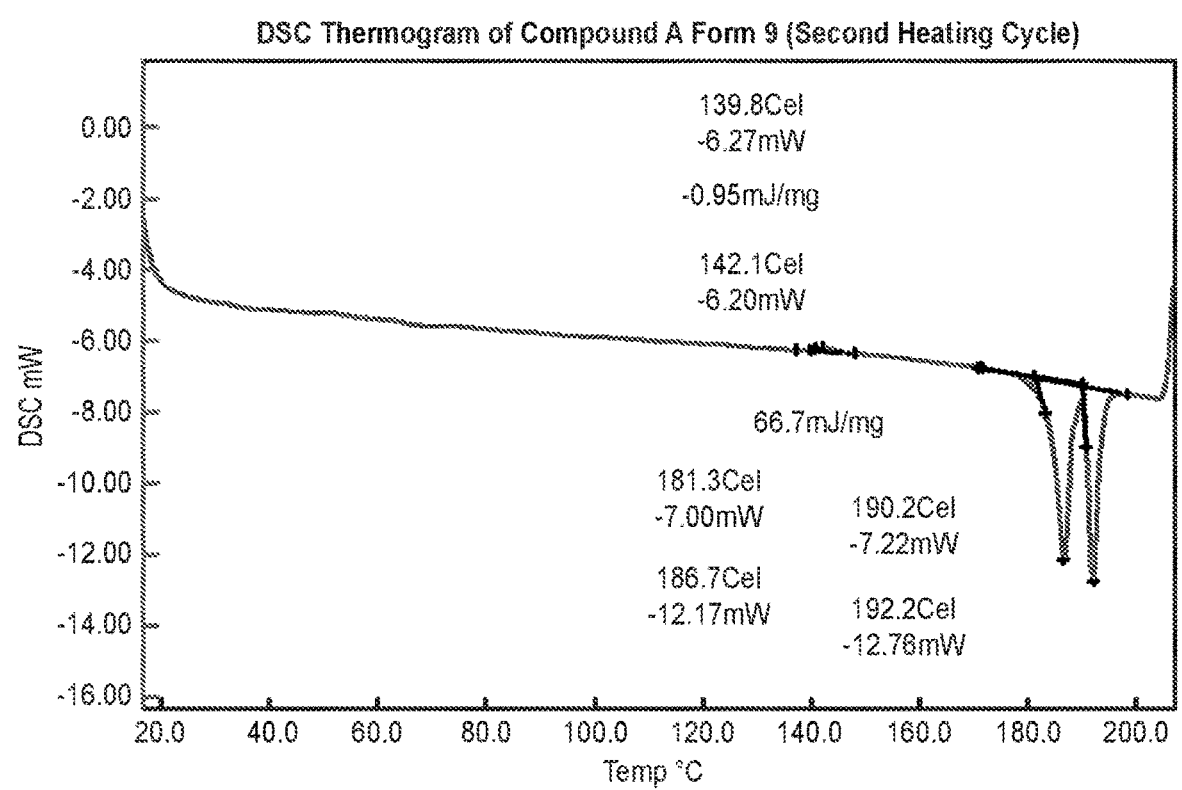
FIG. 34 depicts a DSC thermogram of Compound A Form 9 (Second Heating Cycle).

Accordingly, in some embodiments, the present disclosure provides Compound A Form 9 having a DSC thermogram substantially similar to FIG. 32, FIG. 33, and FIG. 34. In some embodiments, Compound A Form 9 is identified in a composition by detecting a DSC thermogram having, in the first heating cycle, by a large endothermic event at onset 189° C., with a characterizing peak at 192° C.; in the cooling cycle, a single exothermic event at onset 157° C., with a characterizing peak at 155° C.; and, in the second heating cycle, a complex endothermic event with an onset 181° C., with a characterizing peak at 187° C. and a second onset at 190° C. with a characterizing peak at 192° C.

Figure 35:
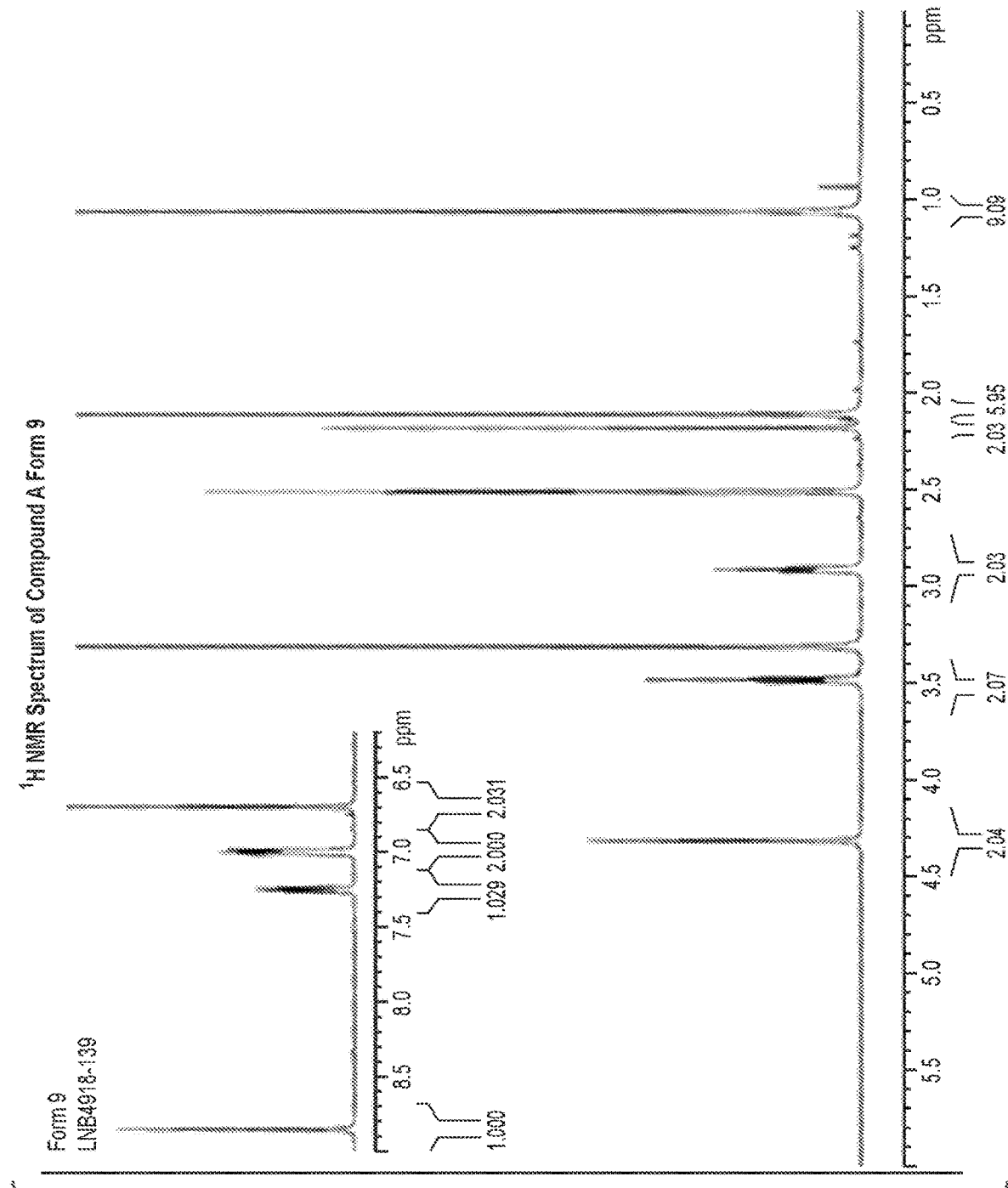
FIG. 35 depicts a $^1$H NMR spectrum of Compound A Form 9.

Compound A Form 9 was analyzed by $^1$H NMR after dissolution in DMSO-$d_6$. In another embodiment, the resulting $^1$H NMR spectrograph (see FIG. 35) showed consistency with the structure of Compound A Form 9.

Figure 36:
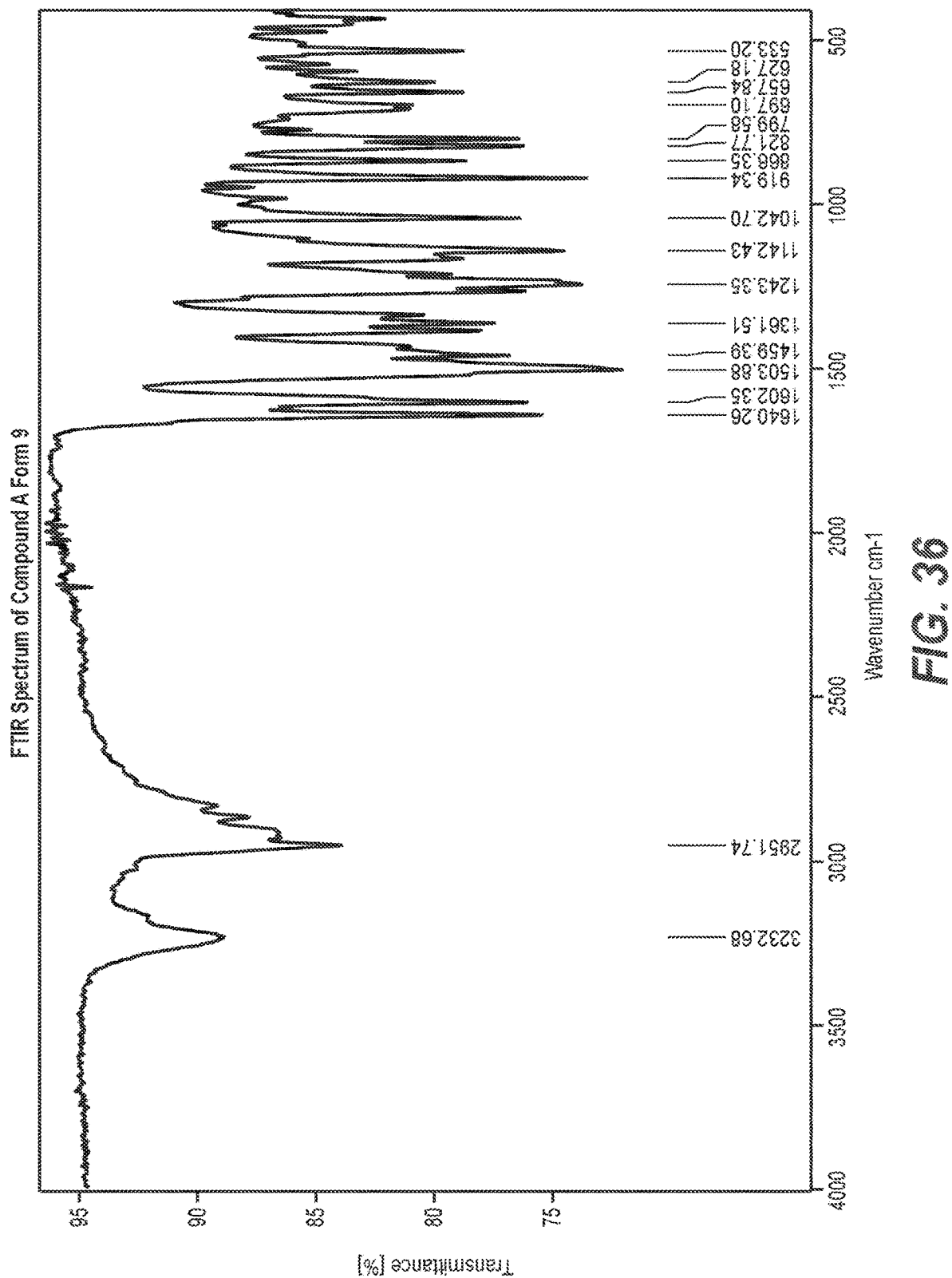
FIG. 36 depicts a FTIR spectrogram of Compound A Form 9.

In another embodiment, Compound A Form 9 was analyzed by FTIR for reference (see FIG. 36).

In another embodiment, HPLC purity analysis of Compound A Form 9 showed a purity value of 97.6%.

In another embodiment, GVS analysis of Compound A Form 9 found it to be slightly hygroscopic with an uptake of 0.8% at 90% RH. The material tested was analyzed post-GVS by XRPD and was found to be Compound A Form 9.

In another embodiment, aqueous solubility of Compound A Form 9 returned a solubility value of <0.1 mg/mL and the pH of the sample post-solubility was 7.3. Post analysis, the excess solid was analyzed by XRPD and found to have converted to Compound A Form 4.

In another embodiment, VT-XRPD analysis of Compound A Form 9 was carried out using the heating program below in Table 8:

TABLE 8

VT-XRPD Heating Program for Compound A Form 9

| Temperature | Procedure |
| --- | --- |
| 25° C. | Scan then heat at 5° C./min to next temperature |
| 50° C. | Scan then heat at 5° C./min to next temperature |
| 100° C. | Scan then heat at 3.3° C./min to next temperature |
| 150° C. | Scan then heat at 0.5° C./min to next temperature |
| 155° C. | Scan then heat at 0.5° C./min to next temperature |
| 160° C. | Scan then heat at 0.5° C./min to next temperature |
| 165° C. | Scan then heat at 0.5° C./min to next temperature |
| 170° C. | Scan then heat at 1° C./min to next temperature |
| 180° C. | Scan and then cool to 25° C. |
| 25° C. | Scan at temperature |

In another embodiment, The solid state form of Compound A Form 9 at each temperature was analyzed by XRPD and the results are shown below in Table 9.

TABLE 9

VT-XRPD Results for Compound A Form 9

| Temperature | Polymorphic Form |
|---|---|
| 25° C. | Form 9 |
| 50° C. | Form 9 |
| 100° C. | Form 9 |
| 150° C. | Form 9 |
| 155° C. | Form change noted - Similar to Form 9 |
| 160° C. | Similar to Form 9 |
| 165° C. | Partially crystalline |
| 170° C. | Partially crystalline |
| 180° C. | Amorphous |
| 25° C. | Amorphous |

In another embodiment, hot stage microscopy of Compound A Form 9 was carried out using the method described herein. Compound A Form 9 was noted to begin melting at approximately 156° C., with the material fully melted after heating to 172° C.

6.3.10. J. Characterization of Compound A Form 10

In one embodiment, the present disclosure is directed to a solid state form of Compound A referred to herein as Compound A Form 10. In some embodiments, the present disclosure provides Compound A Form 10 having a XRPD pattern substantially similar to that depicted in FIG. 37.

Figure 38:
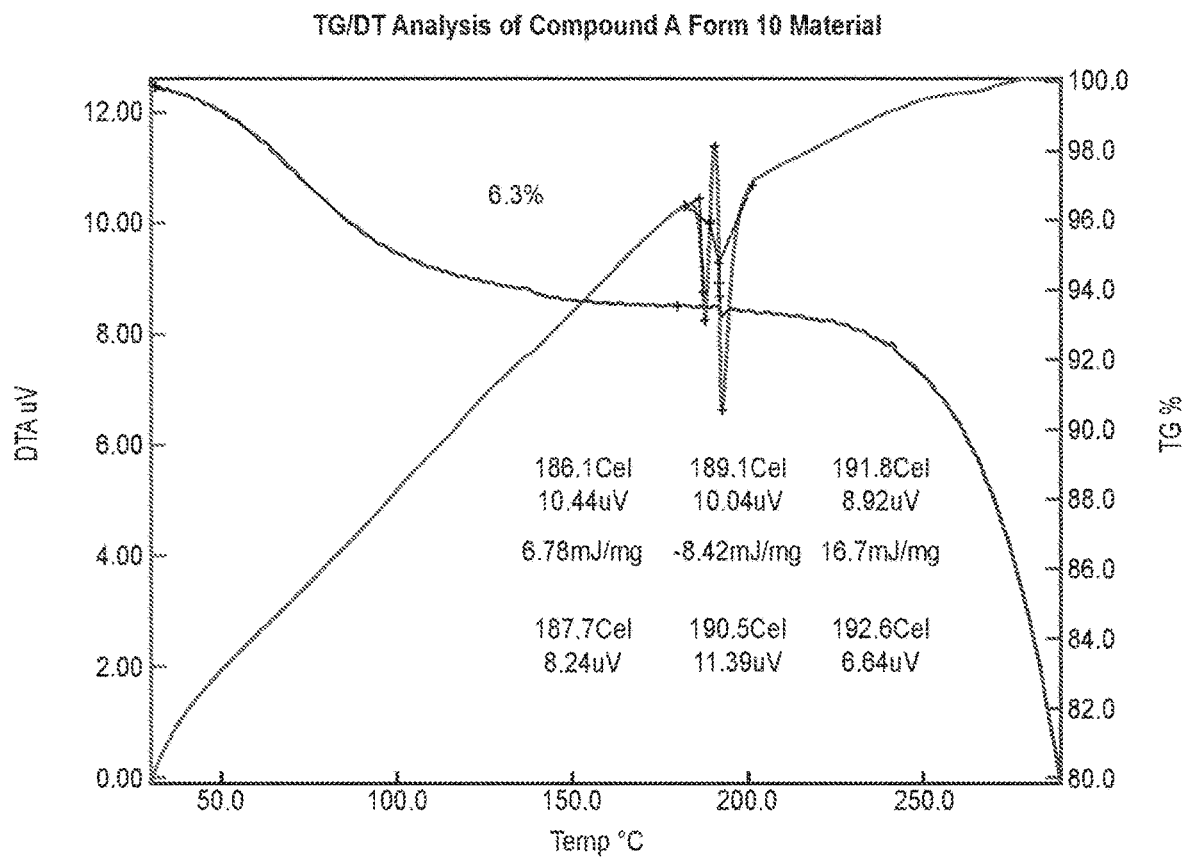
FIG. 38 depicts a TG/DTA thermogram of Compound A Form 10.

In another embodiment, TG analysis of Compound A Form 10 showed a weight loss of about 6.3% from the onset of heating (see FIG. 38). The observed mass loss corresponds to 0.34 equivalents of tetrahydrofuran.

In another embodiment, DTA analysis of Compound A Form 10 showed a small endotherm event at about 186° C. followed by an exotherm event at about 189° C., relating to the recrystallization observed in Compound A Form 1 and Compound A Form 2. A large melting endotherm was observed at about 192° C. (see FIG. 38).

The thermal analysis indicated that Compound A Form 10 is a tetrahydrofuran solvate which desolvates upon heating and converts to Compound A Form 1 and Compound Form 2.

6.3.11. K. Characterization of Compound A Form 11

In one embodiment, the present disclosure is directed to a solid state form of Compound A referred to herein as Compound A Form 11. In some embodiments, the present disclosure provides Compound A Form 11 having a XRPD pattern substantially similar to that depicted in FIG. 39.

In some embodiments, Compound A Form 11 identified in a composition by detecting one or more peaks in the composition's XRPD pattern selected from those listed in Table 10 below.

TABLE 10

Compound A Form 11 XRPD Peaks

| No. | Pos. [°2 θ] | d-spacing [A] | Height [counts] | Rel. Int. [%] |
|---|---|---|---|---|
| 1 | 6.2346 | 14.17671 | 1028.93 | 35.41 |
| 2 | 8.1142 | 10.89653 | 167.21 | 5.75 |
| 3 | 11.3991 | 7.76281 | 2541.18 | 87.45 |
| 4 | 11.6865 | 7.57253 | 644.88 | 22.19 |
| 5 | 11.9401 | 7.41226 | 439.99 | 15.14 |
| 6 | 13.2296 | 6.69252 | 100.33 | 3.45 |
| 7 | 14.4446 | 6.13221 | 217.69 | 7.49 |
| 8 | 15.0763 | 5.87665 | 614.9 | 21.16 |
| 9 | 15.5059 | 5.71479 | 293.84 | 10.11 |
| 10 | 15.9629 | 5.55221 | 497.52 | 17.12 |
| 11 | 16.4898 | 5.37596 | 373.32 | 12.85 |
| 12 | 16.8026 | 5.27658 | 335.7 | 11.55 |
| 13 | 17.3217 | 5.11959 | 303.52 | 10.45 |
| 14 | 17.6002 | 5.03921 | 223.53 | 7.69 |
| 15 | 18.8108 | 4.71754 | 221.11 | 7.61 |
| 16 | 19.4817 | 4.55659 | 879.13 | 30.25 |
| 17 | 19.9804 | 4.44397 | 439.72 | 15.13 |
| 18 | 20.1868 | 4.39899 | 320.34 | 11.02 |
| 19 | 20.5167 | 4.329 | 1724.71 | 59.35 |
| 20 | 21.3968 | 4.15287 | 2905.87 | 100 |
| 21 | 21.7353 | 4.08896 | 359.16 | 12.36 |
| 22 | 22.4708 | 3.95676 | 677.18 | 23.3 |
| 23 | 22.8636 | 3.88967 | 805.6 | 27.72 |
| 24 | 23.1521 | 3.84184 | 483.38 | 16.63 |
| 25 | 23.4425 | 3.7949 | 969.09 | 33.35 |
| 26 | 23.6149 | 3.76759 | 1174.92 | 40.43 |
| 27 | 23.8389 | 3.73269 | 381.29 | 13.12 |
| 28 | 24.3967 | 3.64861 | 440.48 | 15.16 |
| 29 | 24.9391 | 3.57046 | 95.4 | 3.28 |
| 30 | 25.6838 | 3.46861 | 382.7 | 13.17 |
| 31 | 26.7804 | 3.32901 | 96.5 | 3.32 |
| 32 | 27.3368 | 3.2625 | 114.63 | 3.94 |
| 33 | 29.6248 | 3.01554 | 95.05 | 3.27 |
| 34 | 30.0408 | 2.97472 | 70.19 | 2.42 |
| 35 | 30.4322 | 2.93734 | 118.33 | 4.07 |
| 36 | 30.9364 | 2.89061 | 49.28 | 1.7 |
| 37 | 31.9063 | 2.80492 | 81.43 | 2.8 |
| 38 | 33.4981 | 2.67519 | 66.06 | 2.27 |

In some embodiments, Compound A Form 11 is identified in a composition by detecting two or more peaks in the composition's XRPD pattern selected from those in Table 10. In some embodiments, Compound A Form 11 is identified in a composition by detecting three or more peaks in the composition's XRPD pattern selected from those in Table 10. In some embodiments, Compound A Form 11 is identified in a composition by detecting four or more peaks in the composition's XRPD pattern selected from those in Table 10. In some embodiments, Compound A Form 11 is identified in a composition by detecting five or more peaks in the composition's XRPD pattern selected from those in Table 10. In some embodiments, Compound A Form 11 is identified in a composition by detecting six or more peaks in the composition's XRPD pattern selected from those in Table 10. In some embodiments, Compound A Form 11 is identified in a composition by detecting seven or more peaks in the composition's XRPD pattern selected from those in Table 10. In some embodiments, Compound A Form 11 is identified in a composition by detecting eight or more peaks in the composition's XRPD pattern selected from those in Table 10. In some embodiments, Compound A Form 11 is identified in a composition by detecting nine or more peaks in the composition's XRPD pattern selected from those in Table 10. In some embodiments, Compound A Form 11 is identified in a composition by detecting all of the peaks in Table 10 in the composition's XRPD pattern.

In some embodiments, Compound A Form 11 is identified in a composition by detecting at least eight peaks in the composition's XRPD pattern corresponding to the eight most intense peaks (based on relative percent intensity) in Table 10±0.3 degrees 2θ, more preferably ±0.2 degrees 2θ, even more preferably ±0.1 degrees 2θ, most preferably ±0.05 degrees 2θ.

In some embodiments, Compound A Form 11 is identified in a composition by detecting at least seven peaks in the composition's XRPD pattern corresponding to the seven most intense peaks (based on relative percent intensity) in Table 10±0.3 degrees 2θ, more preferably ±0.2 degrees 2θ, even more preferably ±0.1 degrees 2θ, most preferably ±0.05 degrees 2θ.

In some embodiments, Compound A Form 11 is identified in a composition by detecting at least six peaks in the composition's XRPD pattern corresponding to the six most intense peaks (based on relative percent intensity) in Table 10±0.3 degrees 2θ, more preferably ±0.2 degrees 2θ, even more preferably ±0.1 degrees 2θ, most preferably ±0.05 degrees 2θ.

In some embodiments, Compound A Form 11 is identified in a composition by detecting at least five peaks in the composition's XRPD pattern corresponding to the five most intense peaks (based on relative percent intensity) in Table 10±0.3 degrees 2θ, more preferably ±0.2 degrees 2θ, even more preferably ±0.1 degrees 2θ, most preferably ±0.05 degrees 2θ. For example, in certain embodiments, Compound A Form 11 is identified in a composition by detecting at least the following five peaks in the composition's XRPD pattern: about 3.05, about 15.33, about 18.08, about 20.98, and about 23.49 degrees 2θ±0.3 degrees 2θ, more preferably ±0.2 degrees 2θ, even more preferably ±0.1 degrees 2θ, most preferably ±0.05 degrees 2θ.

In some embodiments, Compound A Form 11 is identified in a composition by detecting at least four peaks in the composition's XRPD pattern corresponding to the four most intense peaks (based on relative percent intensity) in Table 10±0.3 degrees 2θ, more preferably ±0.2 degrees 2θ, even more preferably ±0.1 degrees 2θ, most preferably ±0.05 degrees 2θ. For example, in certain embodiments, Compound A Form 11 is identified in a composition by detecting at least the following four peaks in the composition's XRPD pattern: about 3.05, about 15.33, about 18.08, and about 23.49 degrees 2θ±0.3 degrees 2θ, more preferably ±0.2 degrees 2θ, even more preferably ±0.1 degrees 2θ, most preferably ±0.05 degrees 2θ.

In some embodiments, Compound A Form 11 is identified in a composition by detecting at least three peaks in the composition's XRPD pattern corresponding to the three most intense peaks (based on relative percent intensity) in Table 10±0.3 degrees 2θ, more preferably ±0.2 degrees 2θ, even more preferably ±0.1 degrees 2θ, most preferably ±0.05 degrees 2θ. For example, in certain embodiments, Compound A Form 11 is identified in a composition by detecting at least the following three peaks in the composition's XRPD pattern: about 3.05, about 18.08, and about 23.49 degrees 2θ±0.3 degrees 2θ, more preferably ±0.2 degrees 2θ, even more preferably ±0.1 degrees 2θ, most preferably ±0.05 degrees 2θ.

In some embodiments, Compound A Form 11 is identified in a composition by detecting at least two peaks in the composition's XRPD pattern corresponding to the two most intense peaks (based on relative percent intensity) in Table 10±0.3 degrees 2θ, more preferably ±0.2 degrees 2θ, even more preferably ±0.1 degrees 2θ, most preferably ±0.05 degrees 2θ.

In some embodiments, Compound A Form 11 is identified in a composition by detecting at least one peak in the composition's XRPD pattern corresponding to the most intense peak (based on relative percent intensity) in Table 10±0.3 degrees 2θ, more preferably ±0.2 degrees 2θ, even more preferably ±0.1 degrees 2θ, most preferably ±0.05 degrees 2θ.

In some embodiments, Compound A Form 11 is identified in a composition by detecting one or more peaks in the composition's XRPD pattern selected from those at about 11.40, about 11.69, about 15.08, about 19.48, about 20.52, about 21.40, about 22.47, about 23.44, about 23.61 degrees 2θ±0.3 degrees 2θ, more preferably ±0.2 degrees 2θ, even more preferably ±0.1 degrees 2θ, most preferably ±0.05 degrees 2θ.

In some embodiments, Compound A Form 11 is identified in a composition by detecting two or more peaks, such as at least the two most intense peaks, in the composition's XRPD pattern selected from those at about 11.40, about 11.69, about 15.08, about 19.48, about 20.52, about 21.40, about 22.47, about 23.44, about 23.61 degrees 2θ±0.3 degrees 2θ, more preferably ±0.2 degrees 2θ, even more preferably ±0.1 degrees 2θ, most preferably ±0.05 degrees 2θ.

In some embodiments, Compound A Form 11 is identified in a composition by detecting three or more peaks in the composition's XRPD pattern selected from those at about 11.40, about 11.69, about 15.08, about 19.48, about 20.52, about 21.40, about 22.47, about 23.44, about 23.61 degrees 2θ±0.3 degrees 2θ, more preferably ±0.2 degrees 2θ, even more preferably ±0.1 degrees 2θ, most preferably ±0.05 degrees 2θ.

In some embodiments, Compound A Form 11 is identified in a composition by detecting four or more peaks in the composition's XRPD pattern selected from those at about 11.40, about 11.69, about 15.08, about 19.48, about 20.52, about 21.40, about 22.47, about 23.44, about 23.61 degrees 2θ±0.3 degrees 2θ, more preferably ±0.2 degrees 2θ, even more preferably ±0.1 degrees 2θ, most preferably ±0.05 degrees 2θ.

In some embodiments, Compound A Form 11 is identified in a composition by detecting five or more peaks in the composition's XRPD pattern selected from those at about 11.40, about 11.69, about 15.08, about 19.48, about 20.52, about 21.40, about 22.47, about 23.44, about 23.61 degrees 2θ±0.3 degrees 2θ, more preferably ±0.2 degrees 2θ, even more preferably ±0.1 degrees 2θ, most preferably ±0.05 degrees 2θ.

In some embodiments, Compound A Form 11 is identified in a composition by detecting six or more peaks in the composition's XRPD pattern selected from those at about 11.40, about 11.69, about 15.08, about 19.48, about 20.52, about 21.40, about 22.47, about 23.44, about 23.61 degrees 2θ±0.3 degrees 2θ, more preferably ±0.2 degrees 2θ, even more preferably ±0.1 degrees 2θ, most preferably ±0.05 degrees 2θ.

In some embodiments, Compound A Form 11 is identified in a composition by detecting seven or more peaks in the composition's XRPD pattern selected from those at about 11.40, about 11.69, about 15.08, about 19.48, about 20.52, about 21.40, about 22.47, about 23.44, about 23.61 degrees 2θ±0.3 degrees 2θ, more preferably ±0.2 degrees 2θ, even more preferably ±0.1 degrees 2θ, most preferably ±0.05 degrees 2θ.

In some embodiments, Compound A Form 11 is identified in a composition by detecting eight or more peaks in the composition's XRPD pattern selected from those at about 11.40, about 11.69, about 15.08, about 19.48, about 20.52, about 21.40, about 22.47, about 23.44, about 23.61

2θ±0.3 degrees 2θ, more preferably ±0.2 degrees 2θ, even more preferably ±0.1 degrees 2θ, most preferably ±0.05 degrees 2θ.

In some embodiments, Compound A Form 11 is identified in a composition by detecting peaks in the composition's XRPD pattern at about 11.40, about 11.69, about 15.08, about 19.48, about 20.52, about 21.40, about 22.47, about 23.44, about 23.61 degrees 2θ±0.3 degrees 2θ, more preferably ±0.2 degrees 2θ, even more preferably ±0.1 degrees 2θ, most preferably ±0.05 degrees 2θ.

Figure 40:
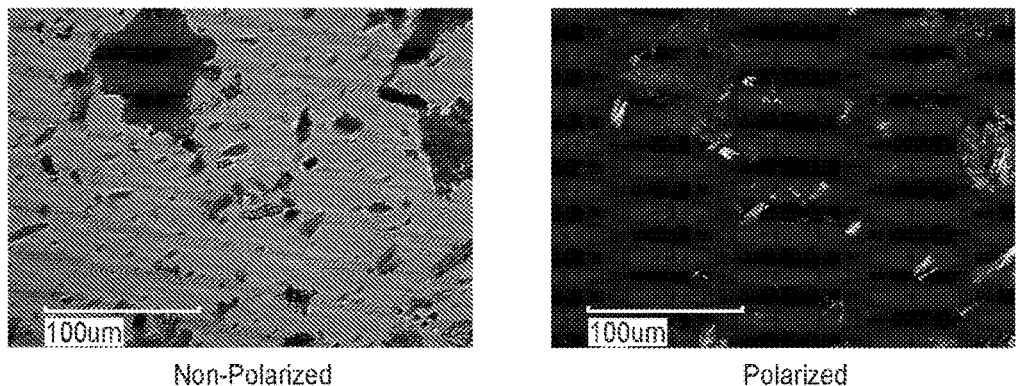
FIG. 40 depicts non-polarized and polarized light microscopy images of Compound A Form 11.

In another embodiment, PLM analysis of Compound A Form 11 showed the solid to be small particles with a rod-like morphology with agglomeration and birefringence (see FIG. 40).

In another embodiment, TG analysis of Compound A Form 11 showed a 1.1% weight loss up to 200° C. and decomposition. In the DTA, an endothermic event at onset 191° C., with a peak at 192° C. (see FIG. 41).

Figure 41:
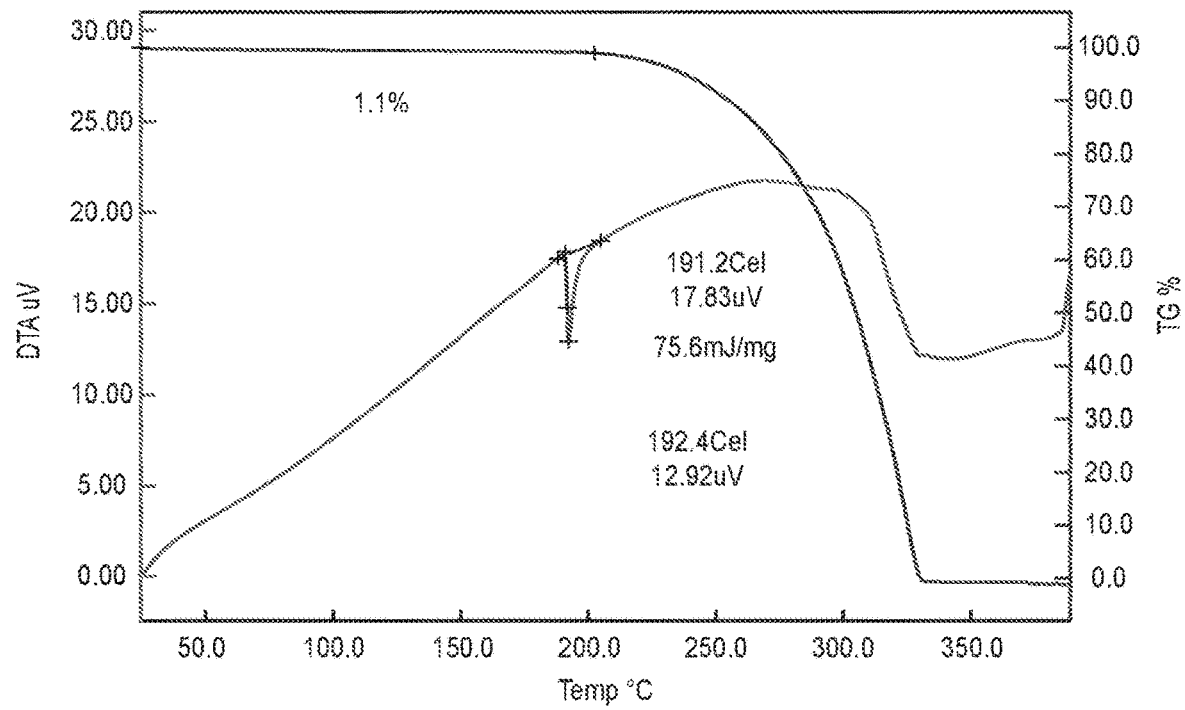
FIG. 41 depicts a TG/DTA thermogram of Compound A Form 11.

Accordingly, in some embodiments, the present disclosure provides Compound A Form 11 having a TG/DTA thermogram substantially similar to FIG. 41. In some embodiments, Compound A Form 4 is identified in a composition by detecting a DTA thermogram with an endothermic event at onset 191° C., with a peak at 192° C.

In another embodiment, DSC analysis of Compound A Form 11 showed in the initial heat a shallow exothermic event at onset 41° C., with a peak at 50° C., followed by a shallow endothermic event at onset 116° C., with a peak at 122° C. This is followed by a small exothermic event at onset 176° C., with a peak at 180° C. connected to a large endothermic event at onset 188° C., with a peak at 192° C. (see FIG. 42). In the cooling cycle, a single exothermic event was noted at onset 148° C., with a peak at 147° C. (see FIG. 43). During the second heating cycle, two endothermic events were noted, the first at onset 184° C., with a peak at 187° C., and the second at onset 191° C. with a peak at 192° C. (see FIG. 44).

Figure 42:
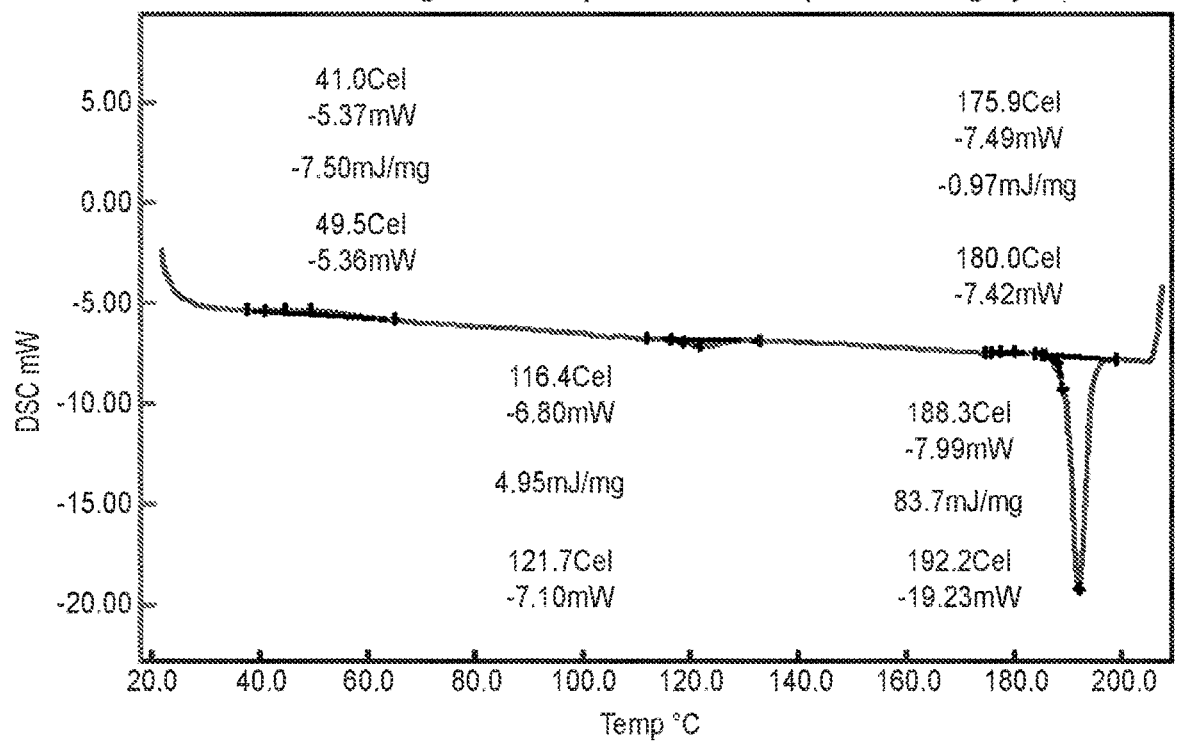
FIG. 42 depicts a DSC thermogram of Compound A Form 11 (Initial Heating Cycle).
Figure 43:
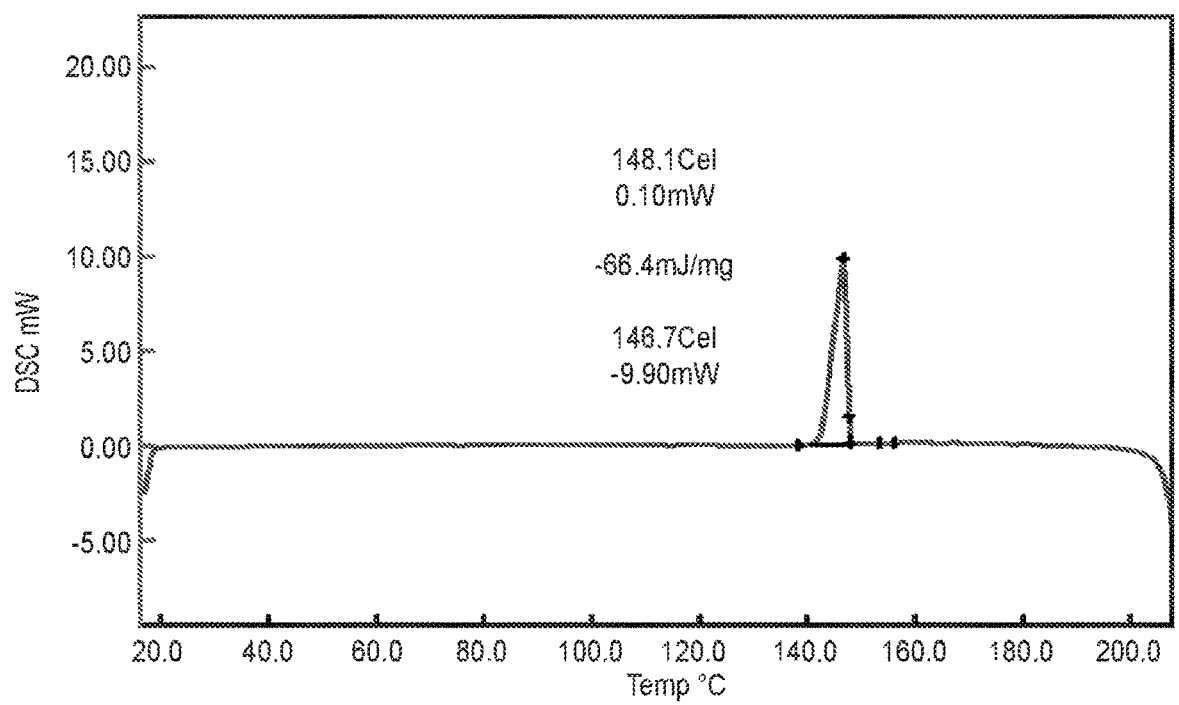
FIG. 43 depicts a DSC thermogram of Compound A Form 11 (Cooling Cycle).
Figure 44:
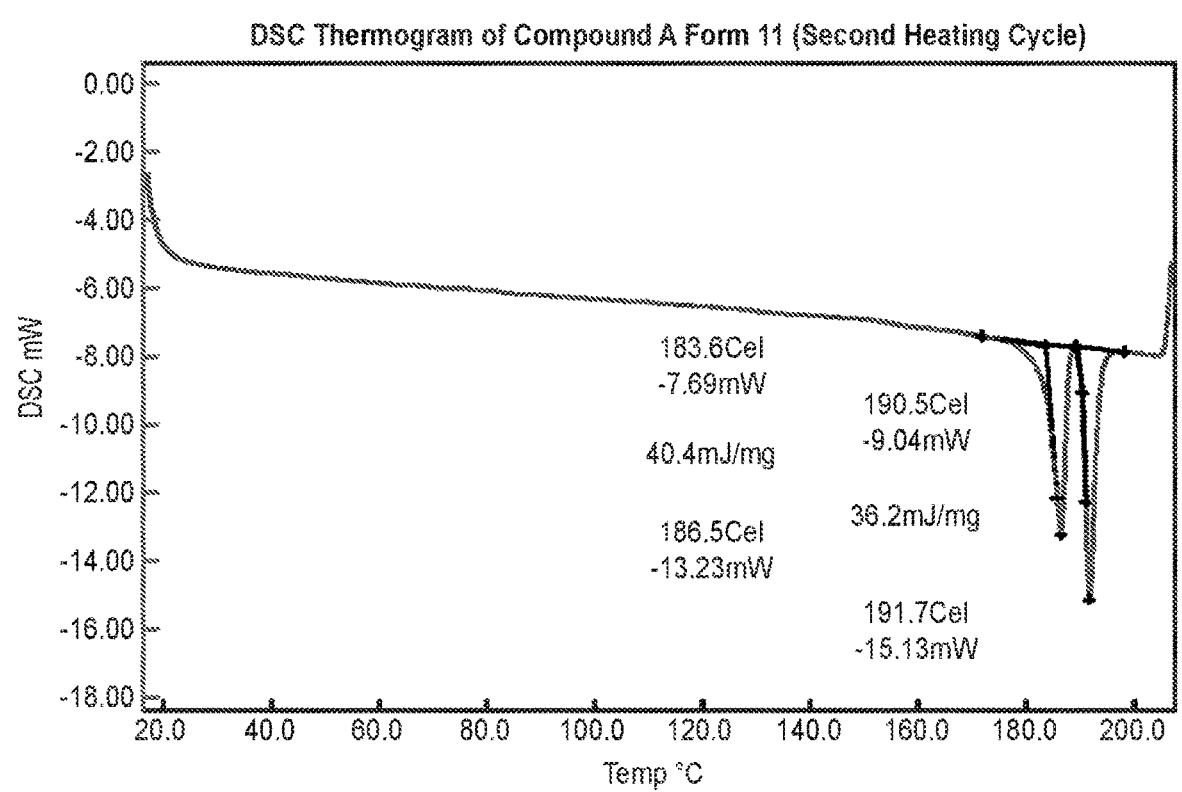
FIG. 44 depicts a DSC thermogram of Compound A Form 11 (Second Heating Cycle).

Accordingly, in some embodiments, the present disclosure provides Compound A Form 11 having a DSC thermogram substantially similar to FIG. 42, FIG. 43 and FIG. 44. In some embodiments, Compound A Form 11 is identified in a composition by detecting a DSC thermogram having, in the first heating cycle, a shallow exothermic event at onset 41° C., with a characterizing peak at 50° C., followed by a shallow endothermic event at onset 116° C., with a characterizing peak at 122° C., followed by a small exothermic event at onset 176° C., with a characterizing peak at 180° C. connected to a large endothermic event at onset 188° C., with a characterizing peak at 192°; a single exothermic event at onset 148° C., with a peak at 147° C.; and, in the second heating cycle, a first endothermic event at onset 184° C., with a characterizing peak at 187° C., and a second endothermic event at onset 191° C. with a characterizing peak at 192° C.

Figure 45:
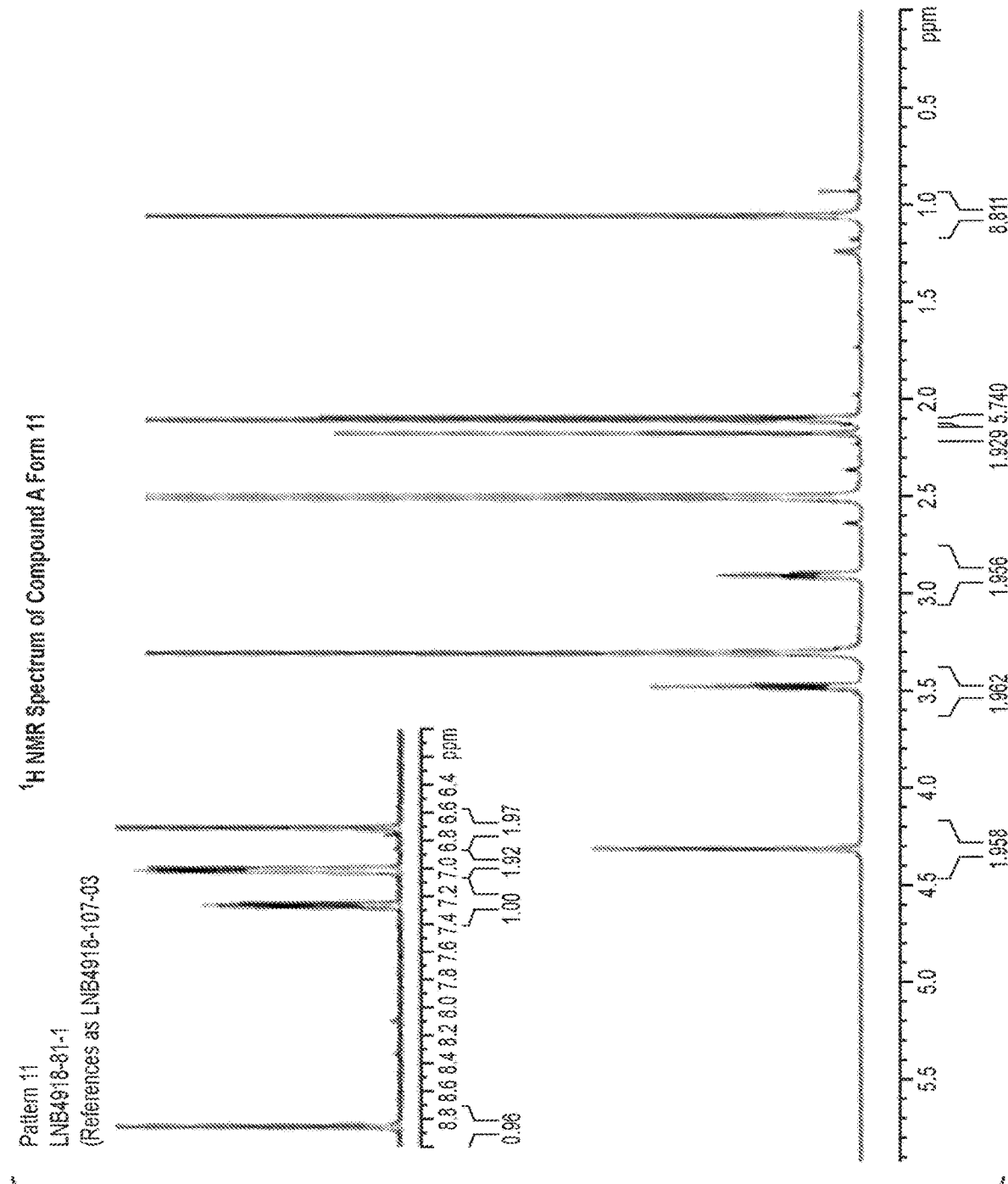
FIG. 45 depicts a $^1$H NMR spectrum of Compound A Form 11.

Compound A Form 11 was analyzed by $^1$H NMR after dissolution in DMSO-$d_6$. In another embodiment, the resulting $^1$H NMR spectrograph (see FIG. 45) showed consistency with the structure of Compound A Form 11.

Figure 46:
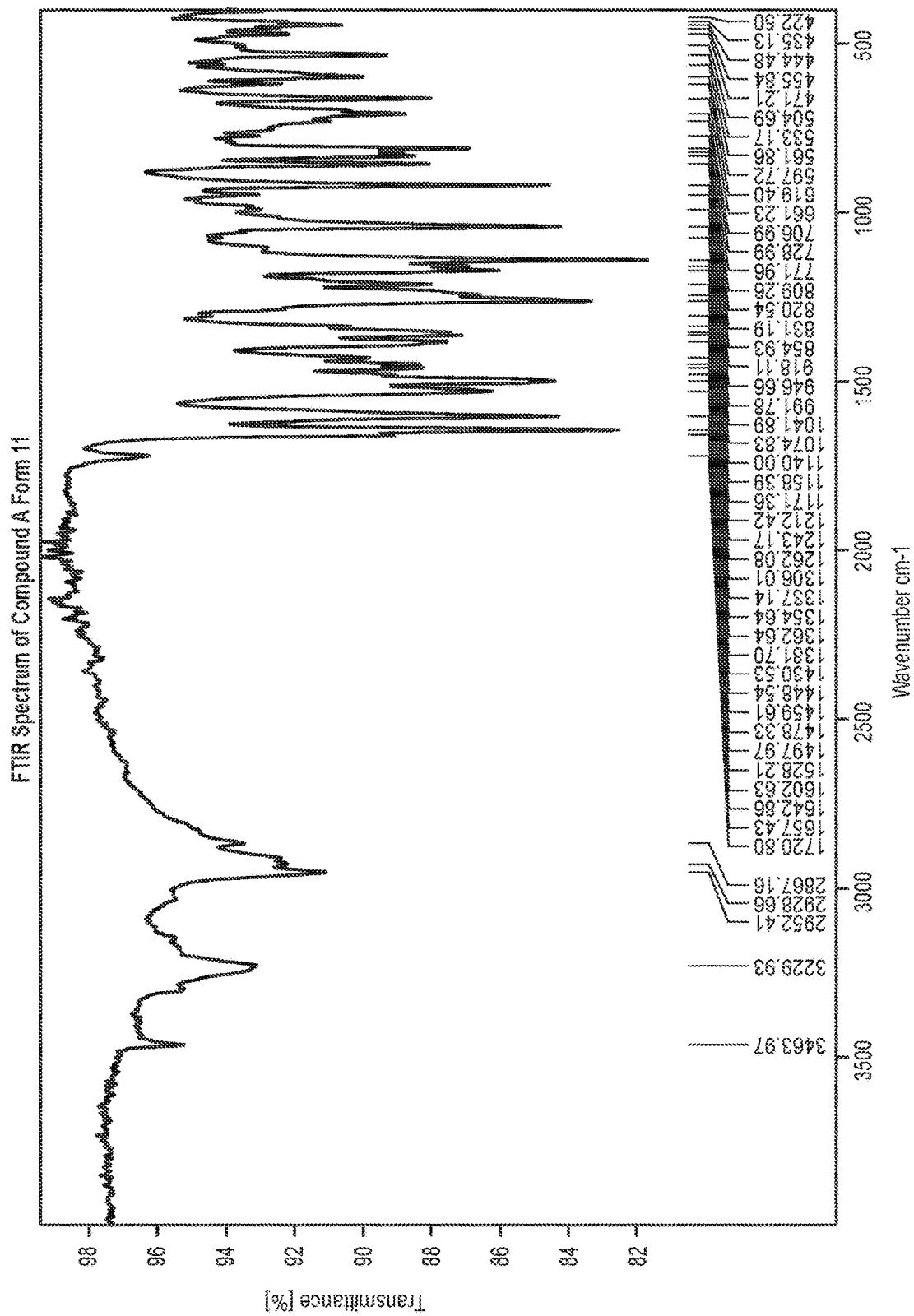
FIG. 46 depicts a FTIR spectrogram of Compound A Form 11.

In another embodiment, Compound A Form 11 was analyzed by FTIR for reference (see FIG. 46).

In another embodiment, HPLC purity analysis of Compound A Form 11 showed a purity value of 99.6%.

In another embodiment, GVS analysis of Compound A Form 11 found it to be slightly hygroscopic with an uptake of 0.5% at 90% RH. The material tested was analyzed post-GVS by XRPD and was found to be a mixture of Compound A Form 4 and Compound A Form 11.

In another embodiment, aqueous solubility of Compound A Form 4 returned a solubility value of <0.1 mg/mL and the pH of the sample post-solubility was 4.9. Post analysis, the excess solid was analyzed by XRPD and found to be a mixture of Compound A Form 4 and Compound A Form 11.

In another embodiment, VT-XRPD analysis of Compound A Form 11 was carried out using the heating program below in Table 11.

TABLE 11

VT-XRPD Heating Program for Compound A Form 11

| Temperature | Procedure |
| --- | --- |
| 25° C. | Scan then heat at 2° C./min to next temperature |
| 50° C. | Scan then heat at 2° C./min to next temperature |
| 100° C. | Scan then heat at 1° C./min to next temperature |
| 150° C. | Scan then heat at 0.5° C./min to next temperature |
| 155° C. | Wait 5 minutes then scan and heat at 1° C./min to next temperature |
| 160° C. | Wait 5 minutes then scan and heat at 0.5° C./min to next temperature |
| 165° C. | Wait 5 minutes then scan and heat at 0.5° C./min to next temperature |
| 170° C. | Scan then heat at 1° C./min to next temperature |
| 180° C. | Scan then heat at 1° C./min to next temperature |
| 190° C. | Scan and then cool to 25° C. |
| 25° C. | Scan at temperature |

In another embodiment, The solid state form of Compound A Form 11 at each temperature was analyzed by XRPD and the results are shown below in Table 12.

TABLE 12

VT-XRPD Results for Compound A Form 11

| Temperature | Polymorphic Form |
| --- | --- |
| 25° C. | Form 11 |
| 50° C. | Form 11 |
| 100° C. | Form 11 |
| 150° C. | Form change |
| 155° C. | Partially crystalline |
| 160° C. | Partially crystalline |
| 165° C. | Partially crystalline |
| 170° C. | Partially crystalline |
| 180° C. | Partially crystalline |
| 190° C. | Amorphous |
| 25° C. | Amorphous |

In another embodiment, hot stage microscopy of Compound A Form 11 was carried out using the method described herein. Compound A Form 11 was noted to begin melting at approximately 150° C., with the material fully melted after heating to 185° C.

6.4. Determination of Carr's Index

For therapeutic use, Compound A and solid state crystalline forms of Compound A are advantageously administered in an acceptable dosage form (such as capsules, tablets, sterile injectables, topical preparations, etc.). In order to successfully manufacture these dosage forms (particularly at commercial scale) while meeting all of the relevant quality requirements, one generally requires that the active pharmaceutical ingredient in question exhibit acceptable rheological (flow) properties. Active pharmaceutical ingredients with poor rheological properties are often incompatible with manufacturing equipment such as automated high-speed capsule fillers, which rely on gravity- and/or vibrational-fed hoppers. Active pharmaceutical ingredients with poor rheological properties do not flow evenly through these process trains, leading to significant and unacceptable variability in the resultant dosage form. As such, it is well recognized in the art that when selecting a form of an active pharmaceutical ingredient for development, the rheological properties of that form are an important consideration.

A widely-used metric for how well a powder flows is Carr's index (see, for example, Wang, Y. B. and Williams, R. O. III, "Powders" in Remington: Essentials of Pharmaceutics, Felton, L., ed., London: Pharmaceutical Press, 2013 at pp. 422-423). The bulk density of a powder is measured, along with its corresponding tapped density (after allowing the powder to be compressed in a standard tap density tester, such as the Gardco JV1000, Paul N. Gardner Company, Pompano Beach, FL, according to a standard method such as that described in Chapter 616 of the United States Pharmacopeia). Once the bulk and tapped densities of a powder have been determined experimentally, Carr's index can be calculated from the following equation:

Carr's index=(tapped density—bulk density)/tapped density×100.

The relationship between Carr's index and powder flowability is summarized in the table below:

| Carr's Index | Flowability |
| --- | --- |
| >38 | Extremely poor |
| 35-38 | Very poor |
| 23-35 | Poor |
| 18-23 | Fair |
| 12-18 | Good |
| 5-12 | Excellent |

Both Compound A and Compound A Form 4 were each micronized to a Specification of $d_{50} \leq 3$ μm and $d_{90} \leq 5$ m and their respective Carr's indices determined. Compound A exhibited a Carr's index of 36 (i.e., very poor flowability) while Compound A Form 4 was found to have a Carr's index of 8 (i.e., excellent flowability).

6.5. Stability Studies

To determine the thermodynamic relationship between Compound A Form 4 and Compound A Form 11, slurry trials using Compound A Form 4 and Compound Form 11 as seeds and ethanol and 1-propanol as solvents were carried out. Samples of the Compound A Form slurries and the Compound A Form 11 slurries were taken for XRPD analysis after 24 hours at 40° C., after 2 hours at 5° C. and after 24 hours at 5° C. The results for all four experiments are shown in the following Table 13, with the solid isolated from all four experiments after 2 hours at 5° C. and after 24 hours at 5° C. identified as Compound A Form 4.

The ethanol experiment seeded with Compound A Form 4 returned Compound A Form 4 material at all sample points tested, while the 1-propanol experiment was noted to be a mixture of Compound A Form 2 and Compound A Form 4 after 24 hours at 40° C. This material converted back to Form 4 after cooling to 5° C.

Despite two of the experiments being seeded with Compound A Form 11, no Compound A Form 11 material was noted in any of the slurry samples. The slurry with ethanol and Compound A Form 11 seed was noted to be Compound A Form 2 after 24 hours at 40° C., which converts to Compound A Form 4 after cooling to 5° C. There was insufficient solid for XRPD analysis in the 1-propanol experiment seeded with Compound A Form 11 after 24 hours at 40° C., however, after 2 hours at 5° C., the amount of solid increased and was identified as Compound A Form 4 by XRPD.

TABLE 13

XRPD Results for Slurry Samples

| | Solvent | Seed material | Solid after 24 hours at 40° C. | Solid after 2 hours at 5° C. | Solid after 24 hours at 5° C. |
| --- | --- | --- | --- | --- | --- |
| 1 | Ethanol | Form 4 | Form 4 | Form 4 | Form 4 |
| 2 | Ethanol | Form 11 | Form 2 | Form 4 | Form 4 |
| 3 | 1-Propanol | Form 4 | Form 2 + 4 | Form 4 | Form 4 |
| 4 | 1-Propanol | Form 11 | Insufficient solid | Form 4 | Form 4 |

6.6. Crystallization Studies

The following crystallization studies were performed for Compound A Form 4:

6.6.1. A. Crystallization Study 1

In one embodiment, a crystallization study of Compound A Form 4 was completed at a concentration of 60 mg/mL, using degassed ethanol and water. After complete dissolution at 45° C., the system was cooled to 30° C. and a clear solution was noted prior to seeding. The seed persisted over about 1 hour before anti-solvent was added at 30° C. The following results were obtained for the samples and final products of the dried solid:
1. The sample taken post anti-solvent addition was separated by centrifugation and the solid was analyzed by XRPD. The material was confirmed to be Form 4.
2. The final recovered solids were analyzed by XRPD, as both damp and dry solids, with both samples confirmed to be Form 4.
3. The recovered material had an isolated yield of 90%, with a solid purity of 99.6% by HPLC.
4. The recovered mother liquor had a concentration of 0.7 mg/mL, which corresponds to a theoretical recovered yield of 98%. The mother liquor purity was determined to be 88%. The wash liquor had a concentration of <0.1 mg/mL.
5. PLM analysis of the dry solid showed the material to be plate-like crystals, with agglomeration and birefringence.
6. TG analysis of the solid showed a 0.3% weight loss up to ca. 220° C., followed by decomposition. An endothermic event is noted in the DTA at onset 118° C., with a peak at 127° C. This is followed by a second, larger endothermic event at onset 191° C., with a peak at 192° C., likely associated with material melt.
7. KF analysis was carried out using a direct addition method on three samples of the solid. An average moisture content of 0.53 wt. % was determined.
8. GC analysis of the dried solid returned a residual ethanol value of 188 ppm.
9. Particle size analysis of the material was carried out and the following PSD values were obtained:
   D10=8.0 μm
   D50=22.1 μm
   D90=52.1 μm

6.6.2. B. Crystallization Study 2

In another embodiment, a crystallization study of Compound A Form 4 was completed at a concentration of 60 mg/mL, using degassed 1-propanol and water. After complete dissolution at 45° C., the system was cooled to 30° C. and a clear solution was noted prior to seeding. The seed persisted over about 1 hour before anti-solvent was added at 30° C. The following results were obtained for the samples and final products of the dried solid:

1. The sample taken post anti-solvent addition was separated by centrifugation and the solid was analyzed by XRPD. The material was confirmed to be Form 4.
2. The recovered solids were analyzed by XRPD, as both damp and dry solids, with both samples confirmed to be Form 4.
3. The final recovered material had an isolated yield of 80%, with a solid purity of 99.6% by HPLC. The recovered yield was lower due to some handling losses.
4. The recovered mother liquor had a concentration of 2.6 mg/mL, which corresponds to a theoretical recovered yield of 93%. The mother liquor purity was determined to be 84%. The wash liquor had a concentration of <0.1 mg/mL.
5. PLM analysis of the dry solid showed the material to be plate-like crystals, with agglomeration and birefringence. Due to the large particle size, images were taken with both 20× and 10× magnification.
6. TG analysis of the solid showed a 0.1% weight loss up to about 200° C., followed by decomposition. An endothermic event is noted in the DTA at onset 108° C., with a peak at 116° C. This is followed by a second, larger endothermic event at onset 192° C., with a peak at 193° C., likely associated with material melt.
7. KF analysis was carried out using a direct addition method on two samples of the solid. An average moisture content of 0.08 wt. % was determined.
8. GC analysis of the dried solid returned a residual 1-propanol value of 391 ppm.
9. Particle size analysis of the material was carried out and the following PSD values were obtained:
    $D_{10}$=18.1 μm
    $D_{50}$=65.1 μm
    $D_{90}$=152.9 μm

6.6.3. C. Crystallization Study 3

In another embodiment, a crystallization study of Compound A Form 4 was carried out using the 1-propanol:water system, with anti-solvent addition at a lower temperature. The concentration was kept at the same value as the Crystallization Study 2. After complete dissolution at 45° C., the system was cooled to 30° C. and a clear solution was noted prior to seeding. The seed persisted over about 1 hour before vessel temperature was increased to 35° C., which led to some dissolution of the seed. The system was then cooled to 30° C., before holding for a further 30 minutes and then cooling to 5° C. Anti-solvent was then added at 5° C. The following results were obtained for the samples and final products of the dried solid:

1. The sample taken after holding at 5° C. was separated by centrifugation and the solid was analyzed by XRPD. The material was confirmed to be Form 4. The concentration of the sample mother liquor was determined to be 52.8 mg/mL.
2. The recovered solids were analyzed by XRPD, as both damp and dry materials, with both samples confirmed to be Form 4.
3. The recovered material had an isolated yield of 80%, with a solid purity of 99.6% by HPLC.
4. The recovered mother liquor had a concentration of 3.7 mg/mL, which corresponds to a theoretical recovered yield of 90%. The mother liquor purity was determined to be 92%. The wash liquor had a concentration of 0.2 mg/mL.
5. PLM analysis of the dry solid showed the material to be plate-like crystals, with agglomeration and birefringence.
6. TG analysis of the solid showed a 0.1% weight loss up to about 220° C., followed by decomposition. An endothermic event is noted in the DTA at onset 113° C., with a peak at 119° C. This is followed by a second, larger endothermic event at onset 191° C., with a peak at 192° C., likely associated with material melt.
7. KF analysis was carried out using the direct addition method on two samples of the solid. An average moisture content of 0.08 wt. % was determined.
8. GC analysis of the dried solid returned a residual 1-propanol value of 477 ppm.
9. Particle size analysis of the material was carried out and the following PSD values were obtained:
    $D_{10}$=16.4 μm
    $D_{50}$=54.4 μm
    $D_{90}$=146.7 μm

6.6.4. D. Crystallization Study 4

In another embodiment, a crystallization study of Compound A Form 4 was carried out at a higher concentration of 65 mg/mL. The solvent system used was again 1-propanol:water, with a final solvent ratio of 65:35 v/v %. After complete dissolution at 45° C., the system was cooled to 30° C. and a clear solution was noted prior to seeding. The seed persisted over about 1 hour, before cooling to 5° C. and a sample was taken at 5° C. Anti-solvent was then added, and the following results were obtained for the samples and final products of the dried solid:

1. The sample taken after holding at 5° C. was separated by centrifugation and the solid was analyzed by XRPD. The material was confirmed to be Form 4. The concentration of the sample mother liquor was determined to be 37.7 mg/mL. PLM images of the slurry sample showed the material to be plate-like in morphology with agglomeration and birefringence noted.
2. The recovered solids were analyzed by XRPD, as both damp and dry solids, with both samples confirmed to be Form 4.
3. The recovered material had an isolated yield of 87%, with a solid purity of 99.6% by HPLC.
4. The recovered mother liquor had a concentration of 3.1 mg/mL, which corresponds to a theoretical recovered yield of 90%. The mother liquor purity was determined to be 93%. The wash liquor had a concentration of <0.1 mg/mL.
5. PLM analysis of the damp solid showed the material to be plate-like in morphology, with the solids also showing agglomeration and birefringence.
6. PLM analysis of the dry solid showed the material to be plate-like crystals, with the presence of some rod-like particles. The particle size visually appeared smaller than the previous crystallizations. The recovered solids also showed agglomeration and birefringence.
7. TG analysis of the dry solid showed a 0.1% weight loss up to about 200° C., followed by decomposition. An endothermic event is noted in the DTA at onset 120° C., with a peak at 127° C. This is followed by a second, larger endothermic event at onset 191° C., with a peak at 192° C., likely associated with material melt.
8. KF analysis was carried out using a direct addition method on two samples of the solid. An average moisture content of 0.06 wt. % was determined.
9. GC analysis of the dried solid returned a residual 1-propanol value of 477 ppm.
10. Particle size analysis of the material was carried out and the following PSD values were obtained:
$D_{10}$=6.0 µm
$D_{50}$=18.0 µm
$D_{90}$=45.8 µm

6.6.5. E. Crystallization Study 5

In another embodiment, a crystallization study of Compound A Form 4 was carried out at the lower concentration of 60 mg/mL in 1-propanol:water. After complete dissolution at 45° C., the system was cooled to 30° C. and a clear solution was noted prior to seeding. The seed persisted over about 1 hour, before cooling to 25° C. where anti-solvent was added at a slower rate. Post addition a sample was taken at 25° C. and the system was then cooled to 5° C., prior to separation. The following results were obtained for the samples and final products of the dried solid:
1. The sample taken after anti-solvent addition was separated by centrifugation and the solid was analyzed by XRPD. The material was confirmed to be Form 4. The concentration of the sample mother liquor was determined to be 4.2 mg/mL.
2. The recovered solids were analyzed by XRPD, as both damp and dry solids, with both samples confirmed to be Form 4. Due to the noted preferred orientation of the dry sample, the material was lightly ground and re-analyzed by XRPD, this material was also identified as Form 4.
3. The recovered material had an isolated yield of 85%, with a solid purity of 99.5% by HPLC.
4. The recovered mother liquor had a concentration of 2.3 mg/mL, which corresponds to a theoretical recovered yield of 94%. The mother liquor purity was determined to be 87%. The wash liquor had a concentration of 0.2 mg/mL.
5. PLM analysis of the damp solid showed the material to be plate-like in morphology, with the solids also showing agglomeration and birefringence. Due to particle size, images were taken with both 20× and 10× magnification.
6. PLM analysis of the dry solid showed the material to be plate-like crystals, with agglomeration and birefringence.
7. TG analysis of the dry solid showed no weight loss prior to decomposition. An endothermic event is noted in the DTA at onset 112° C., with a peak at 117° C. This is followed by a second, larger endothermic event at onset 191° C., with a peak at 192° C., likely associated with material melt.
8. KF analysis was carried out using a direct addition method on two samples of the solid. An average moisture content of 0.09 wt. % was determined.
9. GC analysis of the dried solid returned a residual 1-propanol value of 380 ppm.
10. Particle size analysis of the material was carried out and the following PSD values were obtained:
$D_{10}$=13.1 µm
$D_{50}$=54.5 µm
$D_{90}$=162.1 µm

6.6.6. F. Crystallization Study 6

In another embodiment, a crystallization study of Compound A Form 4 was carried out at the higher concentration of 65 mg/mL in the 1-propanol:water system. After complete dissolution at 45° C., the system was cooled to 35° C. and a clear solution was noted prior to seeding. The seed persisted over about 1 hour, before cooling to 5° C. and anti-solvent was then added at a slower rate.
The following results were obtained for the samples and final products of the dried solid:
1. The recovered solids were analyzed by XRPD, as both damp and dry solids, with both samples confirmed to be Form 4. Due to the noted preferred orientation of the dry sample, the material was lightly ground and re-analyzed by XRPD, this material was also identified as Form 4.
2. The recovered material had an isolated yield of 88%, with a solid purity of 99.5% by HPLC.
3. The recovered mother liquor had a concentration of 1.9 mg/mL, which corresponds to a theoretical recovered yield of 96%. The mother liquor purity was determined to be 84%. The wash liquor had a concentration of 0.1 mg/mL.
4. PLM analysis of the damp solid showed the material to be plate-like in morphology, with the solids also showing agglomeration and birefringence.
5. PLM analysis of the dry solid showed the material to be plate-like crystals, with agglomeration and birefringence. Due to particle size, images were taken with both 20× and 10× magnification.
6. TG analysis of the dry solid showed a 0.2% weight loss up to 200° C., followed by decomposition. An endothermic event is noted in the DTA at onset 117° C., with a peak at 123° C. This is followed by a second, larger endothermic event at onset 191° C., with a peak at 192° C., likely associated with material melt.
7. KF analysis was carried out using a direct addition method on two samples of the solid. An average moisture content of 0.03 wt. % was determined.
8. GC analysis of the dried solid returned a residual 1-propanol value of 331 ppm.
9. Particle size analysis of the material was carried out and the following PSD values were obtained:
$D_{10}$=14.6 µm
$D_{50}$=45.0 µm
$D_{90}$=119.1 µm

6.6.7. G. Crystallization Study 7

In another embodiment, a crystallization study of Compound A Form 4 was carried out using de-gassed solvents at the higher concentration of 65 mg/ml in the 1-propanol:water system. After complete dissolution at 45° C., the system was cooled to 32° C. and a clear solution was noted prior to seeding. The seed persisted over about 1 hour, before cooling to 5° C. where anti-solvent was then added. The following results were obtained for the samples and final products of the dried solid.
1. The recovered solids were analyzed by XRPD, as both damp and dry solids, with both samples confirmed to be Form 4. Due to the noted preferred orientation of the dry sample, the material was lightly ground and re-analyzed by XRPD, this material was also identified as Form 4.

2. The recovered material had an isolated yield of 84%, with a solid purity of 99.5% by HPLC. 3. The recovered mother liquor had a concentration of 4.5 mg/mL, which corresponds to a theoretical recovered yield of 89%. The mother liquor purity was determined to be 92%. The wash liquor had a concentration of 0.2 mg/mL.
4. PLM analysis of the damp solid showed the material to be plate-like in morphology, with the solids also showing agglomeration and birefringence.
5. PLM analysis of the dry solid showed the material to be plate-like crystals, with agglomeration and birefringence.
6. TG analysis of the dry solid showed a 0.2% weight loss up to 200° C., followed by decomposition. An endothermic event is noted in the DTA at onset 111° C., with a peak at 120° C. This is followed by a second, larger endothermic event at onset 191° C., with a peak at 192° C., likely associated with material melt.
7. KF analysis was carried out using a direct addition method on two samples of the solid. An average moisture content of 0.07 wt. % was determined.
8. GC analysis of the dried solid returned a residual 1-propanol value of 349 ppm.
9. Particle size analysis of the material was carried out and the following PSD values were obtained:
   $D_{10}$=13.4 µm
   $D_{50}$=48.6 µm
   $D_{90}$=132.5 µm

6.6.8. H. Crystallization Study 8

In another embodiment, a crystallization study of Compound A Form 4 was carried out using degassed solvents at the higher concentration of 65 mg/mL in 1-propanol:water. After complete dissolution at 45° C., the system was cooled to 32° C. and a clear solution was noted prior to seeding. The seed persisted over about 1 hour, before cooling to 30° C. where anti-solvent was then added. Following anti-solvent addition, the system was cooled to 5° C. The following results were obtained for the samples and final products of the dried solid:
1. The recovered solids were analyzed by XRPD, as both damp and dry solids, with both samples confirmed to be Form 4. Due to the noted preferred orientation of the dry sample, the material was lightly ground and re-analyzed by XRPD, this material was also identified as Form 4.
2. The recovered material had an isolated yield of 88%, with a solid purity of 99.6% by HPLC.
3. The recovered mother liquor had a concentration of 1.8 mg/mL, which corresponds to a theoretical recovered yield of 96%. The mother liquor purity was determined to be 91%. The wash liquor had a concentration of 0.6 mg/mL.
4. PLM analysis of the damp solid showed the material to be plate-like in morphology, with the solids also showing agglomeration and birefringence. Due to particle size, images were taken with both 20× and 10× magnification.
5. PLM analysis of the dry solid showed the material to be plate-like crystals, with agglomeration and birefringence. Due to particle size, images were taken with both 20× and 10× magnification.
6. TG analysis of the dry solid showed a 0.3% weight loss up to 200° C., followed by decomposition. An endothermic event is noted in the DTA at onset 113° C., with a peak at 115° C. This is followed by a second, larger endothermic event at onset 191° C., with a peak at 192° C., likely associated with material melt.
7. KF analysis was carried out using a direct addition method on two samples of the solid. An average moisture content of 0.11 wt. % was determined.
8. GC analysis of the dried solid returned a residual 1-propanol value of 401 ppm.
9. Particle size analysis of the material was carried out and the following PSD values were obtained:
   $D_{10}$=11.9 µm
   $D_{50}$=48.3 µm
   $D_{90}$=119.9 µm All of the U.S. patents, U.S. patent application publications, U.S. patent applications, foreign patents, foreign patent applications, and non-patent publications referred to in this specification are incorporated herein by reference in their entireties, including U.S. provisional application No. 62/913,574 filed Oct. 10, 2019.

Although the foregoing disclosure has been presented in some detail to facilitate understanding, it will be apparent that certain changes and modifications may be practiced within the scope of the appended claims. Accordingly, the described embodiments are to be considered as illustrative and not restrictive, and the claimed invention is not to be limited to the details given herein, but may be modified within the scope and equivalents of the appended claims.

What is claimed is:

1. A crystalline form of Compound A, wherein Compound A is N-(4-(6-fluoro-3,4-dihydroisoquinolin-2 (1H)-yl)-2,6-dimethylphenyl)-3,3-dimethylbutanamide, and wherein the crystalline form is characterized by three or more peaks in an XRPD pattern selected from 13.62, 14.16, 14.61, 18.44, 19.92, and 22.97 degrees 2θ±0.3 degrees 2θ.

2. The crystalline form according to claim 1, wherein the crystalline form is characterized by four or more peaks in an XRPD pattern selected from 13.62, 14.16, 14.61, 18.44, 19.92, 22.97, and 23.73 degrees 2θ±0.3 degrees 2θ.

3. The crystalline form according to claim 1, wherein the crystalline form is characterized by five or more peaks in an XRPD pattern selected from 13.62, 14.16, 14.61, 18.44, 19.92, 22.97, and 23.73 degrees 2θ±0.3 degrees 2θ.

4. The crystalline form according to claim 1, wherein the crystalline form is characterized by six or more peaks in an XRPD pattern selected from 13.62, 14.16, 14.61, 18.44, 19.92, 22.97, and 23.73 degrees 2θ±0.3 degrees 2θ.

5. The crystalline form according to claim 1, wherein the crystalline form is characterized by the following peaks in an XRPD pattern: 13.62, 14.16, 14.61, 18.44, 19.92, 22.97, and 23.73 degrees 2θ±0.3 degrees 2θ.

6. The crystalline form according to claim 1, wherein the crystalline form is characterized by the following peaks in an XRPD pattern: 13.62, 14.61, and 22.97 degrees 2θ±0.3 degrees 2θ.

7. The crystalline form according to claim 6, wherein the crystalline form is characterized by the following peaks in an XRPD pattern: 13.62, 14.61, and 22.97 degrees 2θ±0.1 degrees 2θ.

8. The crystalline form according to claim 1, wherein the crystalline form is characterized by the following peaks in an XRPD pattern: 13.62, 14.16, and 19.92 degrees 2θ±0.3 degrees 2θ.

9. The crystalline form according to claim 1, wherein the crystalline form is characterized by three or more peaks in an XRPD pattern selected from 13.62, 14.16, 14.61, 18.44, 19.92, and 22.97 degrees 2θ±0.2 degrees 2θ.

10. A crystalline form of Compound A, wherein Compound A is N-(4-(6-fluoro-3,4-dihydroisoquinolin-2(1H)- yl)-2,6-dimethylphenyl)-3,3-dimethylbutanamide, and wherein the crystalline form is form is characterized by at least the following three peaks in an XRPD pattern: 14.61, 18.44, and 22.97 degrees 2θ±0.3 degrees 2θ.

11. The crystalline form of claim 10, wherein the crystalline form is form is characterized by the following three peaks in an XRPD pattern: 14.61, 18.44, and 22.97 degrees 2θ±0.2 degrees 2θ.

12. A crystalline form of Compound A, wherein Compound A is N-(4-(6-fluoro-3,4-dihydroisoquinolin-2 (1/)-yl)-2,6-dimethylphenyl)-3,3-dimethylbutanamide, and wherein the crystalline form is characterized by the following peaks in an XRPD pattern: 13.62, 14.16, and 19.92 degrees 2θ±0.2 degrees 2θ.

13. A pharmaceutical composition comprising a pharmaceutically acceptable excipient and a therapeutically effective amount of a crystalline form of Compound A according to claim 1.

14. A pharmaceutical composition comprising a pharmaceutically acceptable excipient and a therapeutically effective amount of a crystalline form of Compound A according to claim 12.

15. A pharmaceutical composition comprising a pharmaceutically acceptable excipient and a therapeutically effective amount of a crystalline form of Compound A according to claim 12.

16. A method of treating a seizure disorder in a human, wherein the method comprises administering to the human in need thereof a therapeutically effective amount of a crystalline form of Compound A according to claim 1.

17. The method of claim 16, wherein the crystalline form of Compound A is orally administered to the human.

18. The method of claim 16, wherein the seizure disorder is partial onset (focal) seizures.

19. The method of claim 16, wherein 5-50 mg of the crystalline form of Compound A is administered.

20. The method of claim 16, wherein 10, 15, 20, 25, or 30 mg of the crystalline form of Compound A is administered.

21. The method of claim 16, wherein 10-30 mg of the crystalline form of Compound A is administered per day as a single dose.

22. A method of treating a seizure disorder in a human, wherein the method comprises administering to the human in need thereof a therapeutically effective amount of a crystalline form of Compound A according to claim 10.

23. The method of claim 22, wherein the seizure disorder is partial onset (focal) seizures.

24. The method of claim 22, wherein 10-30 mg of the crystalline form of Compound A is administered.

25. The method of claim 23, wherein 10-30 mg of the crystalline form of Compound A is administered.

26. The method of claim 23, wherein 10-30 mg of the crystalline form of Compound A is orally administered per day as a single dose.

27. A method of treating a seizure disorder in a human, wherein the method comprises administering to the human in need thereof a therapeutically effective amount of a crystalline form of Compound A according to claim 12.

28. The method of claim 27, wherein the seizure disorder is partial onset (focal) seizures.

29. The method of claim 27, wherein 10-30 mg of the crystalline form of Compound A is administered.

30. The method of claim 28, wherein 10-30 mg of the crystalline form of Compound A is administered.

* * * * *